US012697140B2

(12) United States Patent
Lee et al.

(10) Patent No.: US 12,697,140 B2
(45) Date of Patent: Aug. 4, 2026

(54) METHODS FOR USING CERVICAL CONTROL SYSTEMS AND CERVICAL CONTROL DEVICES

(71) Applicant: Novocuff, Inc., Mountain View, CA (US)

(72) Inventors: Donald J. Lee, Santa Clara, CA (US); Amelia M. Degenkolb, Birmingham, AL (US); Don Hannula, San Luis Obispo, CA (US)

(73) Assignee: Novocuff, Inc., Mountain View, CA (US)

( * ) Notice: Subject to any disclaimer, the term of this patent is extended or adjusted under 35 U.S.C. 154(b) by 0 days.

(21) Appl. No.: 19/222,963

(22) Filed: May 29, 2025

(65) Prior Publication Data

US 2025/0288456 A1     Sep. 18, 2025

Related U.S. Application Data

(63) Continuation of application No. PCT/US2024/018224, filed on Mar. 1, 2024.

(Continued)

(51) Int. Cl.
*A61B 17/42*        (2006.01)
*A61F 2/00*         (2006.01)
(Continued)

(52) U.S. Cl.
CPC .......... *A61B 17/42* (2013.01); *A61B 17/4241* (2013.01); *A61F 2/0027* (2013.01);
(Continued)

(58) Field of Classification Search
CPC .... A61F 6/08; A61F 6/14; A61F 2/004; A61F 2/0027; A61F 2/0045; A61F 6/146;
(Continued)

(56) References Cited

U.S. PATENT DOCUMENTS

| | | | |
|---|---|---|---|
| 15,897 | A | 10/1856 | Provines |
| 2,365,296 | A | 12/1944 | Schimpf |

(Continued)

FOREIGN PATENT DOCUMENTS

| | | |
|---|---|---|
| CN | 108498146 A | 9/2018 |
| CN | 108836453 A | 11/2018 |

(Continued)

OTHER PUBLICATIONS

Novocuff, Inc.; International Application No. PCT/US2024/018224 filed Mar. 1, 2024; International Search Report and Written Opinion; ISA/US; Aug. 23, 2024; 14 pp.

(Continued)

*Primary Examiner* — Camtu T Nguyen
(74) *Attorney, Agent, or Firm* — Cooley LLP

(57)                    ABSTRACT

Systems, devices, and methods are provided that control, support, and/or elongate a cervix to treat pregnancy complications and/or delay an onset of labor so that a gestational period for a fetus may be extended, thereby preventing preterm labor and delivery of the fetus. The cervical control systems may include a main body configured for placement in a vagina. The main body has in internal passageway configured for acceptance of a cervix therein and an inflatable and/or expandable inner cuff extends from portion of the internal passageway. The inner cuff may be expandable inward toward the cervix, or downward away from the uterus, or both inward and downward so that the inner cuff may engage, or grip, the cervix thereby holding the cervical control system in place while compressing the cervix closed, elongating the cervix, and/or adjusting an angle of orientation of the cervix.

30 Claims, 75 Drawing Sheets

Related U.S. Application Data

(60) Provisional application No. 63/617,030, filed on Jan. 2, 2024, provisional application No. 63/487,802, filed on Mar. 1, 2023.

(51) Int. Cl.

| | | |
|---|---|---|
| *A61F 6/08* | (2006.01) | |
| *A61B 17/00* | (2006.01) | |
| *A61B 90/00* | (2016.01) | |

(52) U.S. Cl.
CPC ...... *A61F 6/08* (2013.01); *A61B 2017/00022* (2013.01); *A61B 2017/00557* (2013.01); *A61B 2017/00849* (2013.01); *A61B 2017/4225* (2013.01); *A61B 2090/065* (2016.02); *A61F 2250/0001* (2013.01)

(58) Field of Classification Search
CPC ....... A61F 6/16; A61B 17/4241; A61B 17/42; A61B 2017/4225; A61B 2017/4216; A61B 17/12099; A61B 2017/00805
See application file for complete search history.

(56) References Cited

U.S. PATENT DOCUMENTS

| | | | | |
|---|---|---|---|---|
| 2,638,093 | A * | 5/1953 | Kulick | A61F 5/485 |
| | | | | 128/DIG. 25 |
| 3,741,216 | A * | 6/1973 | Yosowitz | A61B 17/42 |
| | | | | 446/224 |
| 4,381,771 | A * | 5/1983 | Gabbay | A61F 6/08 |
| | | | | 128/836 |
| 4,823,814 | A | 4/1989 | Drogendijk et al. | |
| 5,947,991 | A | 9/1999 | Cowan | |
| 6,350,463 | B1 | 2/2002 | Herman et al. | |
| 7,153,280 | B2 | 12/2006 | Welch | |
| 8,308,657 | B2 | 11/2012 | Park et al. | |
| 8,408,212 | B2 | 4/2013 | O'Brien et al. | |
| 8,550,088 | B1 | 10/2013 | Booher, Sr. | |
| 9,610,099 | B2 | 4/2017 | Jones et al. | |
| 10,307,236 | B2 | 6/2019 | Snow | |
| 10,463,530 | B2 | 11/2019 | Booher, Sr. | |
| 10,499,926 | B2 | 12/2019 | Tsur et al. | |
| 10,729,464 | B1 | 8/2020 | Booher, Sr. | |
| 10,918,414 | B2 | 2/2021 | Yang et al. | |
| 11,311,409 | B2 | 4/2022 | Crafton | |
| 11,497,647 | B2 | 11/2022 | Kelley et al. | |
| 11,607,248 | B1 | 3/2023 | Booher, Sr. | |
| 11,712,248 | B2 | 8/2023 | Tsur et al. | |
| 2004/0089308 | A1 | 5/2004 | Welch | |
| 2004/0092847 | A1 | 5/2004 | Welch | |
| 2005/0277948 | A1 | 12/2005 | Cedars et al. | |
| 2006/0058831 | A1 | 3/2006 | Atad | |
| 2007/0225744 | A1 | 9/2007 | Nobles et al. | |
| 2007/0249893 | A1 | 10/2007 | Krumme | |
| 2008/0287969 | A1 | 11/2008 | Tsonton et al. | |
| 2013/0012764 | A1 | 1/2013 | Herbowy et al. | |
| 2014/0364685 | A1 | 12/2014 | McClurg | |
| 2015/0371560 | A1 | 12/2015 | Lowe | |
| 2016/0022475 | A1 | 1/2016 | Honda | |
| 2017/0020529 | A1 | 1/2017 | Tsur et al. | |
| 2017/0087344 | A1 | 3/2017 | Ichim | |
| 2017/0301263 | A1 | 10/2017 | Souter et al. | |
| 2019/0008674 | A1 | 1/2019 | Myers et al. | |
| 2019/0110797 | A1 | 4/2019 | Melsheimer | |
| 2019/0160332 | A1 | 5/2019 | Beer et al. | |
| 2019/0321215 | A1 | 10/2019 | Kelley et al. | |
| 2020/0086110 | A1 | 3/2020 | Karsdon et al. | |
| 2020/0129179 | A1 | 4/2020 | Tsur et al. | |
| 2020/0398052 | A1 | 12/2020 | Gei et al. | |
| 2021/0177462 | A1 | 6/2021 | Gimovsky et al. | |
| 2021/0177645 | A1 | 6/2021 | Crafton | |
| 2021/0236170 | A1 | 8/2021 | Shashar et al. | |
| 2021/0280085 | A1 | 9/2021 | Krach et al. | |
| 2022/0071752 | A1 | 3/2022 | Choi | |
| 2022/0175573 | A1 | 6/2022 | Crafton | |
| 2022/0313947 | A1 | 10/2022 | Petros et al. | |
| 2023/0060850 | A1 | 3/2023 | Lee et al. | |
| 2023/0065828 | A1 * | 3/2023 | Forsell | A61N 1/0514 |
| 2023/0097495 | A1 | 3/2023 | Raygan et al. | |
| 2023/0329723 | A1 | 10/2023 | Tsur et al. | |
| 2025/0000547 | A1 | 1/2025 | Lee et al. | |
| 2025/0143748 | A1 | 5/2025 | Lee et al. | |

FOREIGN PATENT DOCUMENTS

| | | | |
|---|---|---|---|
| DE | 19816349 | A1 | 10/1999 |
| EP | 0663197 | B1 | 12/1998 |
| EP | 3307205 | B1 | 3/2021 |
| JP | 3772349 | B2 | 5/2006 |
| JP | 2017511214 | A | 4/2017 |
| KR | 101806732 | B1 | 12/2017 |
| RU | 2738548 | C1 | 12/2020 |
| RU | 2746437 | C1 | 4/2021 |
| WO | WO-1996011641 | A1 | 4/1996 |
| WO | WO-2001001899 | A1 | 1/2001 |
| WO | WO-2001013780 | A2 | 3/2001 |
| WO | WO-2010114577 | A1 | 10/2010 |
| WO | WO-2015159291 | A1 | 10/2015 |
| WO | WO-2016061690 | A1 | 4/2016 |
| WO | WO-2016199115 | A2 | 12/2016 |
| WO | WO-2016201085 | A1 | 12/2016 |
| WO | WO-2019226441 | A1 | 11/2019 |
| WO | WO-2020256791 | A1 | 12/2020 |
| WO | WO-2019244159 | A9 | 1/2021 |
| WO | WO-2023026109 | A1 | 3/2023 |
| WO | WO-2024182773 | A2 | 9/2024 |
| WO | WO-2025137719 | A1 | 6/2025 |

OTHER PUBLICATIONS

EP Application No. 22860702.4, Extended European Search Report mailed Jun. 6, 2025; Applicant Novocuff, Inc.; 8 pages.

PCT Application No. PCT/IB2022/056650, International Search Report and Written Opinion mailed Dec. 28, 2022; Applicant Novocuff, Inc.; 12 pages.

PCT Application No. PCT/US2024/061794, International Search Report and Written Opinion mailed Feb. 28, 2025; Applicant Novocuff, Inc.; 7 pages.

U.S. Appl. No. 17/813,454, Final Office Action mailed Oct. 23, 2025; Inventor Lee, Donald J.; 24 pages.

U.S. Appl. No. 17/813,454, Non-Final Office Action mailed Apr. 22, 2025; Inventor Lee, Donald J.; 20 pages.

U.S. Appl. No. 18/882,654, Final Office Action mailed Aug. 13, 2025; Inventor Lee, Donald J. et al.; 24 pages.

U.S. Appl. No. 18/882,654, Non-Final Office Action mailed Apr. 18, 2025; Inventor Lee, Donald J. et al.; 21 pages.

U.S. Appl. No. 18/882,654, Non-Final Office Action mailed Dec. 11, 2024; Inventor Lee, Donald J. et al.; 21 pages.

PCT Application No. PCT/US2025/044537, International Search Report and Written Opinion mailed Feb. 9, 2026, Applicant Novocuff, Inc.; 12 pages.

PCT Application No. PCT/US2025/044537, Invitation to Pay Additional Fees mailed Dec. 19, 2025, Applicant Novocuff, Inc.; 2 pages.

U.S. Appl. No. 18/882,654, Notice of Allowance mailed Mar. 9, 2026; Inventor Lee, Donald J et al.; 9 pages.

U.S. Appl. No. 18/882,671, Non-Final Office Action mailed May 7, 2026; Inventor Lee, Donald J. et al., 19 pages.

* cited by examiner

1301

1301

1301

1301

1301

1900

2060

2065

2075

2070

1901

2215

2210B

2210A

2000

2060

1900

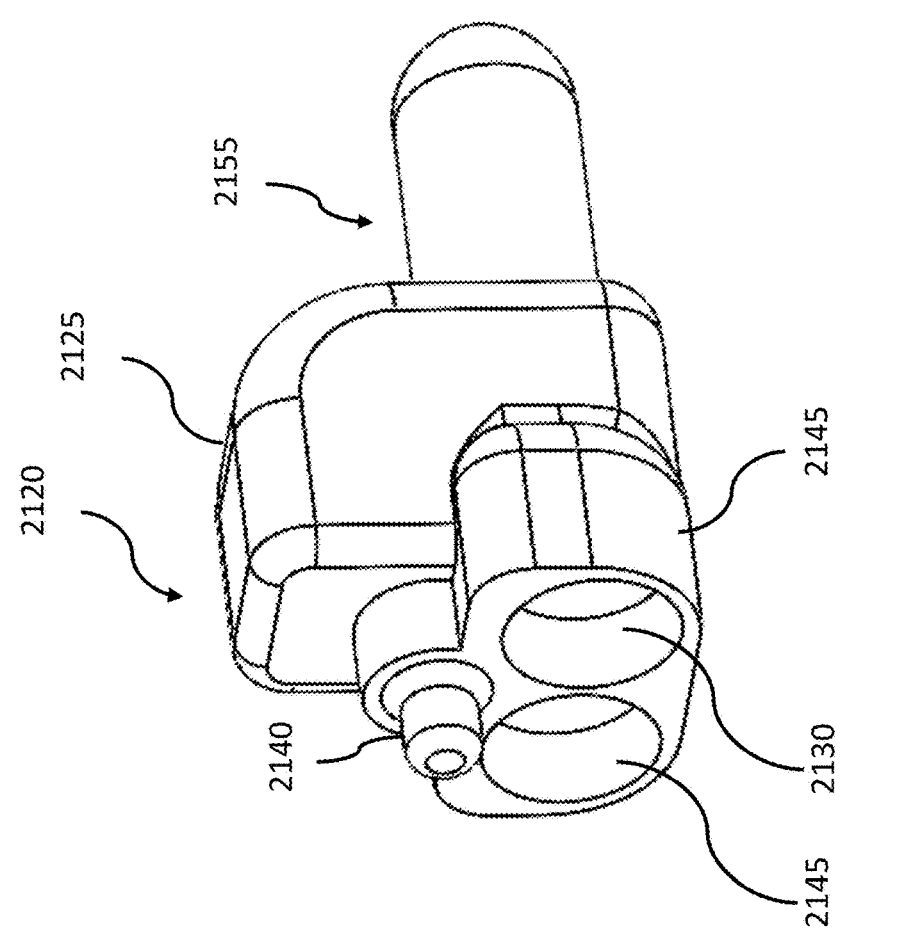
FIGURE 76B
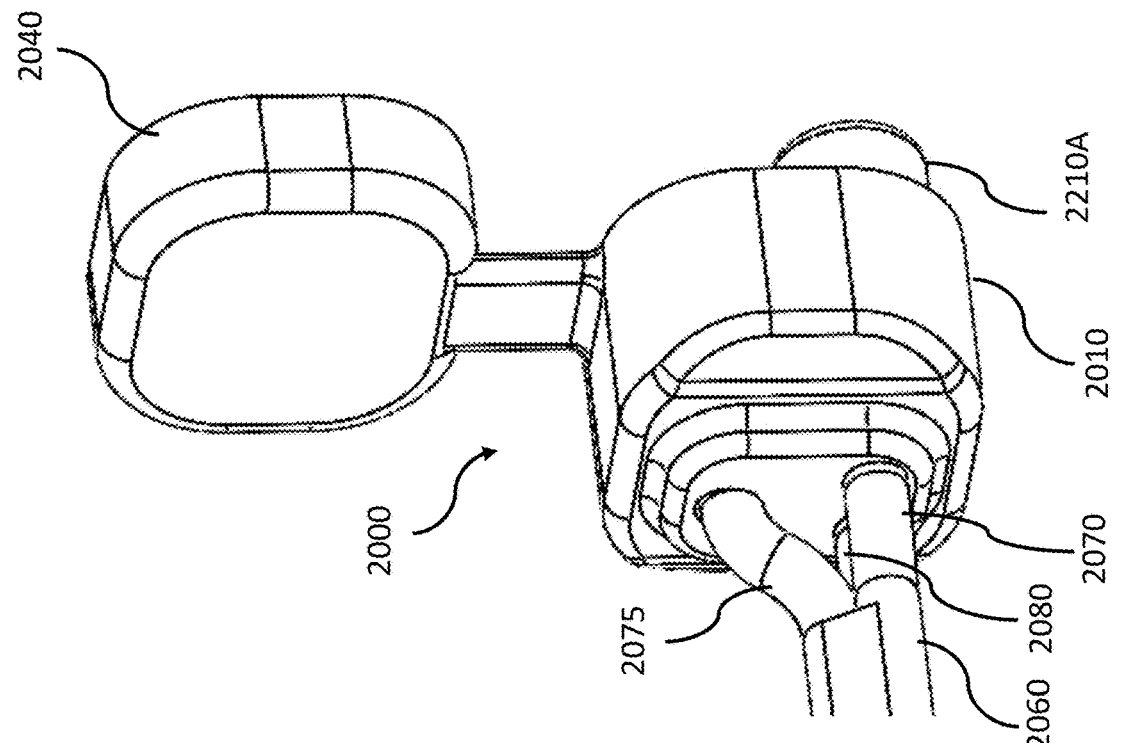

7801

7802

7700

7803

7805

7801

7802

2100

7803

7805

7700

7701

1908

Inflated inner cuff

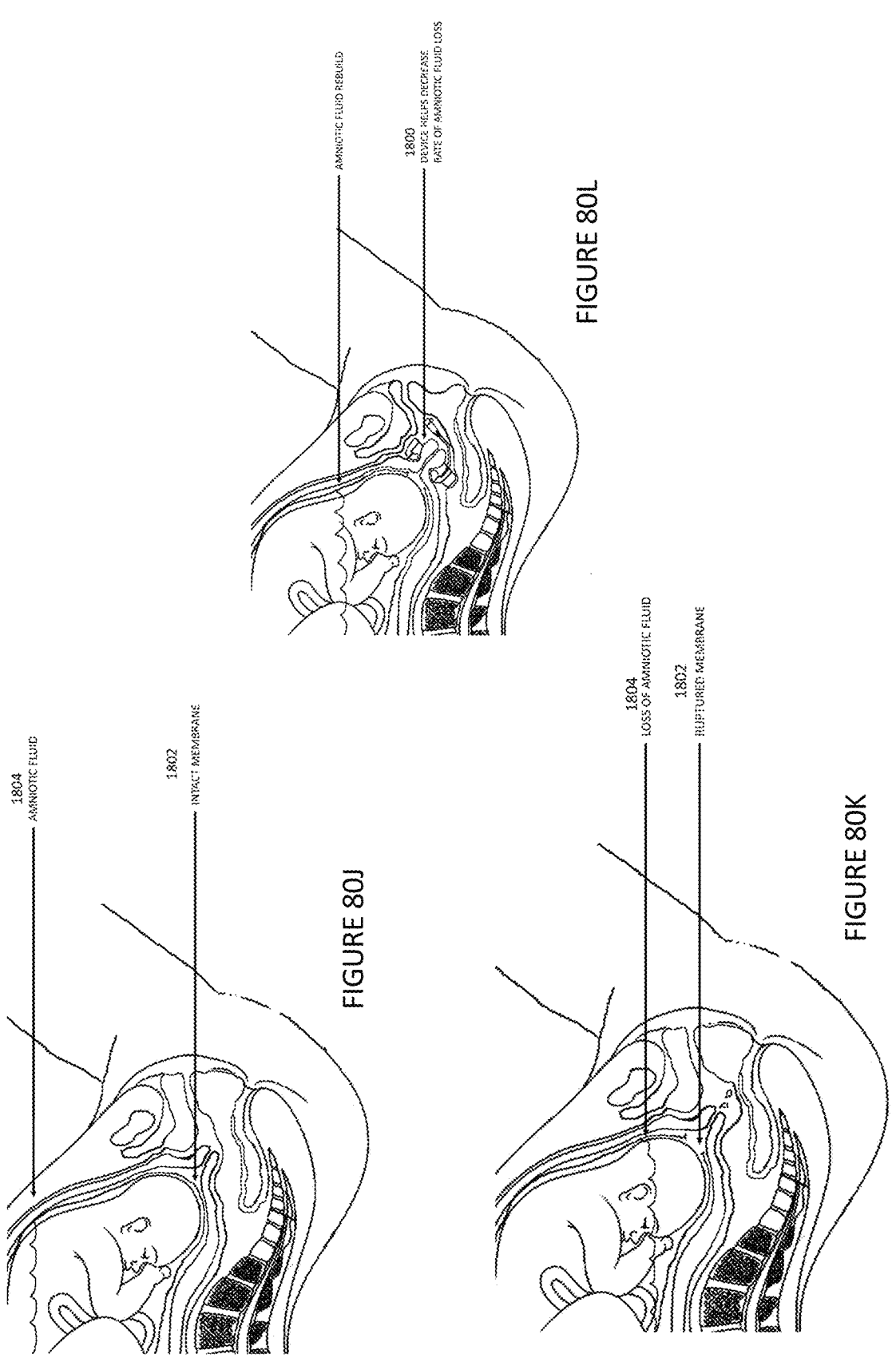

8100

| Cervical Control Device(s) and/or System(s) 8105 | Cervical Stabilization Device(s) 8120 | Tubes and/or Catheters 8135 |
| Inflation Media Container 8110 | Measurement Device 8125 | Speculum 8140 |
| Inflation Media Delivery Device 8115 | Valve Housing 8130 | Lubricant Container 8140 |

FIGURE 81

METHODS FOR USING CERVICAL CONTROL SYSTEMS AND CERVICAL CONTROL DEVICES

RELATED APPLICATIONS

This application is a CONTINUATION application of PCT application Number PCT/US2024/018224, filed 1 Mar. 2024 and entitled "CERVICAL CONTROL DEVICES, CERVICAL CONTROL SYSTEMS, AND METHODS FOR USE THEREOF" which is a PCT Application and claims priority to U.S. Provisional Patent Application No. 63/487,802, filed 1 Mar. 2023 and entitled "DEVICE FOR REDUCTION OR PREVENTION OF PRETERM LABOR" and U.S. Provisional Patent Application No. 63/617,030, filed 2 Jan. 2024 and entitled "SYSTEMS AND DEVICES FOR CERVICAL SUPPORT AND FLUID DELIVERY AND METHODS FOR USING SAME," both of which are incorporated herein in their entireties.

FIELD OF THE INVENTION

The present disclosure is directed to reproductive, gestational, and prenatal health, and for example, to devices, methods, and systems that control a cervix to, for example, prevent preterm birth, prevent and/or mitigate pregnancy complications, and/or treat pelvic organ prolapse.

BACKGROUND

The most common reason for infant mortality is complications due to preterm labor. Several factors contribute to early births, including most commonly, cervical insufficiency, otherwise referred to medically as a "short cervix". When a short cervix occurs in singleton pregnancies (i.e. single fetus pregnancies), a common intervention method includes a suture(s) placed in the cervix in attempts to delay birth, known as a cervical cerclage. Generally, interventions for cervical insufficiency in multiple gestations (i.e. multiple fetus pregnancies) are limited and may provide only limited efficacy.

Another intervention for a short cervix is the application of vaginal progesterone to the cervix so that it may maintain its length and structure. However, vaginal progesterone cannot remain in place for an extended period of time due to vaginal discharge flushing out the medication over time. Furthermore, application of vaginal progesterone to the cervix is an invasive procedure requiring transvaginal access by clinicians.

SUMMARY

Disclosed herein are cervical control devices, systems, and methods of their use to, for example, control and/or adjust anatomical and/or functional aspects of a pregnant mammal's (in most cases, a pregnant human woman and sometimes referred to herein as a "patient") cervix including but not limited to cervical length, degree of dilation, and orientation. For example, the systems, devices, and/or methods disclosed herein may disclosed herein may be used to compress a cervix, which may, or may not, be partially dilated, closed, which may delay the onset of labor and/or may allow a cervical mucus plug to regenerate. Additionally, or alternatively the systems, devices, and methods disclosed herein may be used the patient is associated with a risk factor for and/or indication of premature rupture of membranes (PROM) or preterm premature rupture of membranes (PPROM). In these instances, compression of the cervix via use of the systems, devices, and methods disclosed herein may act to hold the cervix closed so that the leaking of amniotic fluid from the membrane may be slowed or stopped and/or amniotic fluid that has been lost to a ruptured amniotic sac to be replaced.

Additionally, or alternatively the systems, devices, and methods disclosed herein may be used the patient is associated with a risk factor for and/or indication of pre-term labor and/or short cervix. Additionally, or alternatively, the systems, devices, and/or methods disclosed herein may also be used to support the patient's uterus and/or pelvic organs to avoid and/or mitigate effects of pelvic organ prolapse. Functions of the cervical control devices and/or systems disclosed herein include, but are not limited to, preventing pre-term labor and/or pre-term birth, thereby extending a gestational period for the patient's fetus.

Use of the systems, devices, and/or methods disclosed herein may be responsive to one or more factors and/or indications including, but not limited to, a patient's medical history, condition, age, and/or risk factors as may be determined via analysis of patient blood work and/or images (e.g., ultrasound) of the patient's uterus and/or cervix. In some cases, the systems, devices, and/or methods disclosed herein may be used in moderate and/or high-risk situations to prevent the onset of labor and/or pre-term birth even when no indications or symptoms associated with a condition that could trigger pre-term birth are present to prevent pre-term birth.

The cervical control devices and/or systems disclosed herein may include a body configured for insertion into a patient's vagina so that an inner passageway thereof may accept insertion of the patient's cervix. The body may be flexible and/or foldable to facilitate compression, deformation, and/or folding prior to insertion into the vagina and may be sized and/or shaped to occupy space within the vagina proximate to the anterior and/or posterior fornix. The interior passageway may be configured for acceptance of a patient's cervix therein and may be defined by a cylindrical aperture or orifice positioned within the body. The interior passageway may extend from one end of the body to the other. In some embodiments, a portion of the interior passageway and/or an exterior surface of the inner cuff may comprise and/or be coated with, for example, a medication, an anti-bacterial agent, a friction-increasing agent, and/or an adhesive.

The body may also include an inflation media conduit disposed within a sidewall thereof. A first end of the inflation media conduit may be open to and configured for fluid communication with an inner chamber defined by a flexible membrane of an inner cuff of the cervical control device and/or system. A second end of the inflation media conduit may comprise an inlet configured to accept fluid and/or inflation media (e.g., water, saline, hydrogel, fluid, gas, etc.) for communication to the inner chamber of the inner cuff via the first end of the inflation media conduit. For the purposes of discussion, the portion of the body proximate to the inner cuff may be referred to herein as a proximal, or upper, portion or side of the cervical control device and/or system and/or body and the portion of the body on the opposite side as the inner cuff may be referred to herein as a distal, or lower, portion or side of the cervical control device and/or system and/or body.

At times, the body may have a circular, ovoid, or irregular horizontal cross sectional shape. In some embodiments, a position of a radial center of the inner cuff and/or interior passageway may be offset from a position of a radial center of the body. Alternatively, a position of a radial center of the inner cuff and/or interior passageway may align with a position of a radial center of the body. In some embodiments, the body may include a relief notch configured to allow for at least one of bending the body and expanding the body. Additionally, or alternatively, the cervical control device and/or system may further include an annular ring positioned on a proximal edge of the body and proximate to a proximal side of the inner cuff, the annular ring including a tapered edge configured to guide the cervix into the interior passageway.

The inner cuff may comprise the flexible membrane, which defines the inner chamber therein. The flexible membrane may be configured to expand when inflation media may be added to the inner chamber via the first end of the inflation media conduit and/or may be otherwise pressurized. In some embodiments, the flexible membrane expands in a radially inward direction toward the inner passageway so that an exterior surface of the inner cuff contacts and compresses the cervix positioned within the inner passageway and as a volume inflation media added to the inner chamber increases, a compressive force exerted on the cervix by the expanding flexible membrane also increases.

Additionally, or alternatively, the flexible membrane may expand in a downward, or distal direction, thereby pulling the cervix further into the interior passageway and/or elongating the cervix within the interior passageway. Additionally, or alternatively, expansion of the flexible membrane may act to adjust an angle of orientation of the cervix, a degree of dilation of the cervix, and a length of the cervix. In some instances, when a volume inflation media added to the inner chamber increases, an elongation force exerted on the cervix by the expanding flexible membrane may also increase. In some embodiments, expansion of the flexible membrane may act to kink or otherwise bend the cervix.

In some embodiments, a thickness of the flexible membrane may be consistent, or uniform, across and/or throughout the flexible membrane and, in other embodiments, a thickness of the flexible membrane may be variable across the flexible membrane. For example, an apical portion of the flexible membrane may be thicker than an upper, or proximal, portion and/or a lower, or distal, portion of the flexible membrane when the inner cuff may be in a neutral, or uninflated, state. In this example, a thickness of an apical portion of the flexible membrane may decreases as the flexible membrane expands to facilitate expansion of the inner cuff. Additionally, or alternatively, a length of an upper, or proximal, portion of the flexible membrane may be greater than a length of the lower, or distal, portion of the flexible membrane when the inner cuff may be in a neutral state and, in this example, the flexible membrane may expand in a distal and/or downward direction due to the longer length of the proximal portion of the flexible membrane.

Additionally, or alternatively, the flexible membrane may include a buckle or other feature configured to assist with expansion of the flexible membrane when the inner chamber may be inflated.

In many cases, the flexible membrane of the inner cuff may be further configured to contract, or deflate, when inflation media is withdrawn from the inner chamber. A degree of expansion or contraction of the flexible membrane of the inner cuff may be controlled by the volume of inflation media present within the inner chamber and/or a degree of pressure within the inner chamber. The degree of expansion or contraction of the flexible membrane of the inner cuff may be responsive to, for example, patient comfort, a clinical need, an orientation of the cervix, an orientation of the patient's uterus, a degree of dilation of the cervix, a length of the cervix, a degree of softness of the cervix, and/or an indication of a status of the patient's amniotic sac membrane.

In some embodiments, the inner cuff may further include a plurality (e.g., two, three, four, or six) of a flexible membranes and each of the plurality of flexible membranes may define a separate inner chamber therein that may be in fluid communication with the inflation media conduit and configured to expand when inflation media is added to each respective inner chamber and contract when inflation media is withdrawn from each respective inner chamber.

In some embodiments, the flexible membrane may further include one or more expandable portions configured to expand when inflation media is added to the inner chamber and one or more recessed portions that are configured to minimally expand or not expand when the expandable portions are inflated. At times, the second recessed portion may be positioned approximately one hundred and eighty degrees in opposition to the first recessed portion. The one or more recessed portions may be sized, configured, and/or positioned within the flexible membrane to coincide with predicted positions of cervical blood vessels (e.g., arteries) so that when the flexible membrane is inflated, the recessed portion(s) do not expand as much as the expandable portions and compression of a blood vessel of the cervix is thereby avoided so that blood may flow throughout the cervix, which is particularly important for extended (e.g., hours or days) use of the devices and/or systems disclosed herein.

At times, there may be one or more cleats positioned on, and extending from, an exterior surface of the flexible membrane and/or expandable portions of the flexible membrane. In some instances, the cleats may not be positioned on the exterior surface of the recessed portion(s). The cleats may be configured to press into and hold the cervix and/or increase coefficient of friction between the cervix and the flexible membrane to, for example, effectively hold the cervix within the interior passageway and/or prevent unintended movement of the cervical control device and/or system (e.g., slipping off the cervix).

The one or more cleats may have a semi-circular, rectangular, parallelogram, triangular, ovoid, trapezoidal, hooked, curved, and irregular radial, cross sectional, and/or elevation profile. The cleats may be arranged in any manner including, but not limited to, at various points on one or more concentric row extending from the exterior surface of the flexible membrane, a plurality of columns, and an array of offset cleats.

In some embodiments, the cervical control devices and/or systems disclosed herein may include and/or be permanently or removably coupled to a valve and/or a valve housing. The valve may be configured for fluid communication with the second end of the inflation media conduit and indirect fluid communication with the inner chamber via. For example, the valve and/or valve housing may be configured to accept insertion of a source of inflation media therein. Inflation media may then be transferred from the source of inflation media to the inflation media conduit via passage through the valve. When the source of inflation media is removed from the valve, the valve may close thereby trapping the inflation media within the inflation media conduit and inner chamber and holding the flexible membrane in an inflated state. When deflation of the inner cuff/flexible membrane is desired, the valve may be opened so that some, or all, of the inflation may escape from the inflation media conduit and/or inner chamber. Exemplary sources of inflation media include, but are not limited to, syringes, pumps, and tubes.

Exemplary valves include, but are not limited to, one-way valves, duckbill valves, silicone valves, check valves, Halkey Roberts valves, luer activated check valves, check valves with a polycarbonate body, and check valves. In some embodiments, the valve and/or valve housing may be permanently or removably coupled to the second end of the inflation media conduit of the body. Additionally, or alternatively, the second end of the inflation media conduit may be permanently or removably coupled to a first end of a tube or catheter that may be permanently or removably coupled to the valve and/or valve housing.

In some embodiments, the valve housing may include a pressure sensor and/or a cap configured to cover the valve when not in use.

In some embodiments, the inflation media conduit may be configured (e.g., have a sufficient length) to extend outside the body so that it may be accessible outside the patients introitus. Alternatively, the second end of the inflation media conduit may be coupled to a tube or catheter that is configured (e.g., have a sufficient length) to extend outside the body so that it may be accessible outside the patients introitus when the cervical control device and/or system is in situ without disturbing or moving the cervical control device and/or system. At times, the valve and/or valve housing may be configured to be removed from the second end the inflation media conduit and/or tube coupled thereto following use so that the second end of the inflation media conduit and/or tube coupled thereto may be placed within the patient's vaginal canal and/or taped to her leg, which may decrease the weight of system comprising a cervical control device and/or system and a valve/valve housing, thereby decreasing a likelihood that gravity may pull the system away from its preferred position and/or increasing patient comfort when the cervical control device and/or system is in situ but the valve and/or valve housing is not being used.

In many embodiments, the cervical control devices and/or systems disclosed herein may include a positioning balloon positioned on an exterior surface of the body, the positioning balloon may be expandable when inflation media is positioned therein. In some embodiments, the positioning balloon may comprise a flexible membrane that defines an inner chamber configured for receipt of inflation media. As the inner chamber fills with inflation media, the flexible membrane of the positioning balloon may stretch and expand outwards away from the exterior surface of the body, thereby expanding an external circumference of a portion of the cervical control device and/or system. At times, the cervical control devices and/or systems disclosed herein may include a second, or positioning balloon, inflation media conduit disposed within a sidewall of the body. A first end of the positioning balloon inflation media conduit may be open to and configured for fluid communication with the positioning balloon inner chamber as defined by the flexible membrane of the positioning balloon. A second end of the positioning balloon inflation media conduit may comprise an inlet, or valve, configured to accept insertion of inflation media for communication to the positioning balloon inner chamber via the first end of the positioning balloon inflation media conduit. At times, the positioning balloon inflation media conduit may be in communication with the inner cuff inflation media conduit so that inflation media entering the inlet may be communicated to the inner cuff and/or positioning balloon.

Like the inflation media conduit for the inner cuff, the second end of the positioning balloon inflation media conduit may be permanently or removably coupled to a valve and/or valve housing. This valve and/or valve housing may be similar to the valve and/or valve housing permanently or removably coupled to the second end of the inner cuff inflation media conduit The positioning balloon may encircle all, or a portion (e.g., 20-75%) of a distal portion of the body's exterior surface. Additionally, or alternatively, the positioning balloon may be positioned on a distal end of the body. In some embodiments, the positioning balloon may be configured to adjust an orientation of the cervical control device and/or system when positioned within the vagina and inflated. Additionally, or alternatively, the positioning balloon may be configured to adjusts an angle of orientation of the cervix when inflated.

In some embodiments, the cervical control devices and/or systems disclosed herein may be manufactured and/or molded in one piece. In these embodiments, the flexible membrane may be molded with a first extension that encircles a proximal edge of the flexible membrane and a second extension that encircles a distal edge of the flexible membrane and the body may be molded with a first groove sized, positioned, and configured for acceptance the first extension and a second groove sized, positioned, and configured for acceptance the second extension, wherein the inner cuff may be formed when the first extension may be positioned within the first groove and the second extension may be positioned within the second groove.

Additionally, or alternatively, in some embodiments, the cervical control devices and/or systems disclosed herein may further comprise a liquid delivery device, conduit, or channel comprising at least one port configured to allow delivery and/or leaching of a liquid from the liquid delivery device onto the cervix. The liquid delivery device may be positioned proximate to the interior passageway and/or an exterior surface of the inner cuff and/or flexible membrane thereof and may be in liquid communication with a liquid conduit. The liquids leaching from and/or delivered by liquid delivery device include, but are not limited to medications, anti-bacterial agents, and hormones. At times, the liquid conduit may be in communication with the inflation media conduit and/or the inner chamber of the inner cuff. In these embodiments, the inflation media may be the fluid intended for delivery to the cervix via the liquid delivery device so that the inner chamber of the inner cuff and/or positioning balloon are inflated using this fluid.

Also disclosed herein are kits the comprise one or more of the cervical control devices and/or systems disclosed herein along with, for example, a source of inflation media, a speculum, a measurement device configured to, for example, measure a length and/or degree of structural integrity of a cervix, forceps, cervical stabilization device, a tenaculum, and/or a sensor. In some embodiments, the kit may also include a valve housing configured for fluid communication with an inflation media conduit (e.g., inner cuff and/or positioning balloon inflation media conduit(s)) of the cervical control device(s) and/or systems included in the kit. Exemplary sources of inflation media include, but are not limited to, a syringe, a pump, and a container of inflation media.

In some embodiments, the cervical control devices and/or systems disclosed herein may provide selectively adjustable or customizable support and/or control for a patient's cervix and may aid in delaying labor with both singleton and multiple gestation pregnancies in, for example, individuals experiencing an insufficient cervix. In some embodiments, the cervical control devices and/or systems disclosed herein may be utilized to support or reduce the effects of pelvic organ prolapse. The cervical control devices and/or systems disclosed herein may include one or more inflatable portions, balloons, cuffs, or bladders (at times, collectively referred to herein as "cuffs"), which may be individually and/or collectively selectively inflatable and deflectable to provide a desired amount of cervical control, cervical compression, and/or position correction to the cervix. The cervical control devices and/or systems disclosed herein may include a proximal or inner cuff configured and positioned to engage, control and/or support the cervix, uterus, and/or fetus, and an outer when inflated and/or a positioning balloon configured and/or positioned to engage the patient's vaginal wall to support the cervical control devices and/or systems disclosed herein in proximity to the cervix when inflated. The inner cuff may be utilized to provide a constricting, compressive force to the exterior of the cervix at the top of the fornix, in an attempt to close and/or hold the cervix in a closed state.

The inner and/or positioning balloons may include one or more individually addressable (e.g., inflatable/deflatable) bladders that comprise a flexible membrane and inner chamber. Inner cuff bladder(s) may be configured to cooperate with one another to inflate and compress the cervix. At times, the inner cuff may be configured to permit blood/fluid perfusion in the cervix (such as by inflating expandable portions of inner cuff), while providing a sufficient amount of compressive pressure to the cervix.

The anatomy of the cervix may vary in its nominal external dimension from patient to patient, and an insufficient cervix may (and is likely to) continue to shrink as the gestation progresses. As such, the adjustable functionality of the cervical control devices and/or systems disclosed herein may permit a care provider (e.g., medical provider such as a physician, midwife, or nurse) to customize the cervical support and/or control to a particular patient's cervix by directing and/or adjusting the inflation/deflation of inner cuff(s).

At times, the positioning balloon may be utilized to adjust the position of one or more of cervical control devices and/or systems disclosed herein when positioned within the patient's vagina and these adjustments may adjust an orientation of respective cervical control device and/or system relative to the cervix, which may redirect and/or kink the cervix.

Optionally, the cervical control devices and/or systems disclosed herein may be inverted such that the distal opening is positioned proximate to the vaginal fornix (i.e., faces towards the cervix) and the inner cuff is positioned proximate to the external cervical os. In this orientation, the cervical control devices and/or systems disclosed herein may provide support to the pelvic organs (e.g., bladder and uterus) (without directly contacting the lower portion of the cervix) in cases of prolapse (e.g., uterine, or cervical prolapse).

Use of the cervical control devices and/or systems disclosed herein may also be beneficial in reducing or limiting the risk of infection and/or extending fetal development in instances of premature rupture of membranes (PROM) and preterm premature rupture of membranes (PPROM) because they act to hold the cervix closed, thereby preventing migration of bacteria and foreign material into the cervix and/or uterus (which may cause an infection). In addition, the compression of the cervix provided by the cervical control devices and/or systems disclosed herein provides an opportunity for the regrowth of the cervical mucus plug, which also assists with prevention of migration of bacteria into the cervix and uterus. This is particularly advantageous because traditionally there are no treatments for patients who have experienced PROM or PPROM. Cerclages are contraindicated due to the risk of introducing infection or resulting in cervical lacerations caused during labor.

In addition, the cervical control devices and/or systems disclosed herein may be configured to contact/engage the outside of the cervix while not coming into (or coming in minimal) contact with the cervical os. Thus, the cervical control devices and/or systems disclosed herein may provide support control of the cervix without introducing infection to the uterus. Mechanical closure and angling of the cervix can increase amniotic fluid retention and improve fetal outcomes. In addition, since the cervical control devices and/or systems disclosed herein may not cover the os of the cervix (like a cervical cap) during use, the cervical control devices and/or systems do not create an environment in which anaerobic bacteria could flourish and, therefore, use of the cervical control devices and/or systems disclosed herein may be safer than use of a cervical cap, which covers the os, thereby creating an environment in which bacteria may flourish.

According to some embodiments, the cervical control devices and/or systems disclosed herein can comprise a body defining an interior passageway for receiving a cervix, the body may comprise upper and lower portions defining proximal and distal openings to the interior passageway, respectively, and an exterior surface for engaging a vaginal wall. An inner cuff may be coupled to and/or extend from the body at, or near, the proximal opening. The inner cuff may be configured to accept insertion of a cervix therein when in an unexpanded state and surround at least a portion of the cervix. Once in position, the inner cuff may be configured expand from the neutral state to an expanded state so that it may contact and/or engage at least a portion of the cervix. Once the cervix is secured by the inner cuff, the positioning balloon may be inflated so that it expands away from an axial center of the distal opening toward, and into, the vaginal wall.

The cervical control devices and/or systems disclosed herein may include one or more of the following features. In one embodiment, the positioning balloon can comprise a minor arc shape disposed around less than 180 degrees of the circumference of an exterior or lower (distal) surface of the body. In another embodiment, the positioning balloon can comprise a major arc shape disposed around more than 180 degrees of the circumference of an exterior or lower (distal) surface of the body. In some embodiments, in the expanded state a radius of the cervical control devices and/or systems disclosed herein as measured from an axial center of a distal opening to an exterior perimeter of the positioning balloon can be larger than a radius of the device from the axial center of the distal opening to an exterior perimeter of the body in a portion of the circumference of the body without the positioning balloon. In some embodiments, the positioning balloon can comprise a varying or a non-uniform wall thickness (and/or resilience or flexibility) configured to control expansion of the positioning balloon away from the axial center of the distal opening to expand toward and into the vaginal wall. In some embodiments, the positioning balloon can comprise a first wall thickness on a proximal side of the device, a second wall thickness on the distal side of the device, and a third wall thickness on the exterior perimeter of the positioning balloon extending between the first wall and the second wall. In some embodiments, the first wall thickness and the second wall thickness can be substantially the same and wherein the third wall thickness is larger than the first wall thickness and the second wall thickness. In some embodiments, the first and second wall can be different lengths. In some embodiments, the body can comprise a semi-spheroid or otherwise curved shape and the proximal opening defines a smaller area than the distal opening. In one embodiment, the cervical control devices disclosed herein can further comprise one or more cleat(s) disposed along an interior perimeter of the inner cuff for gripping an exterior of the cervix and holding the cervical control device in place relative to the cervix.

In some embodiments, the inner cuff, upon expansion, is configured to expand substantially radially inward toward the axial center of the proximal opening and/or downward away from a transverse plane of the proximal opening and away from a uterus as the inner cuff expands around the cervix.

Additionally, or alternatively, the inner cuff and/or a flexible membrane thereof can comprise a non-uniform wall thickness. For example, the flexible membrane of the inner cuff can comprise a first wall thickness on a proximal side of the device, a second wall thickness on the distal side of the device, and a third wall thickness on an interior surface of the inner cuff extending between the first wall and the second wall. In some embodiments, the first wall thickness and the second wall thickness can be substantially the same and the third wall thickness can be larger than the first wall thickness and/or the second wall thickness.

Additionally, or alternatively, the inner cuff can comprise an inner wall configured to be angled with respect to the axial center of the proximal opening. Additionally, or alternatively, the inner cuff can comprise an inner wall opposite the wall on the interior surface of the inner cuff, wherein the inner wall can be configured to be parallel to the axial center of the proximal opening.

Additionally, or alternatively, the inner cuff can comprise an expandable portion adjacent a recessed portion, wherein the expandable portion can be selectively extendable further into the interior passageway than the recessed portion. In some embodiments, the inner cuff can comprise a non-uniform wall thickness, wherein the recessed portion can comprise a thicker wall thickness than the expandable portion, wherein the thicker wall thickness of the recessed portion constricts expansion of the recessed portion relative to the expandable portion when inflated. In some embodiments, the inner cuff can comprise at least two of the recessed portions and at least two of the expandable portions alternatingly spaced with the recessed portions.

Additionally, or alternatively, the cervical control devices disclosed herein can further comprise one or more inflation media conduits sized, shaped, and configured to be in fluid communication with the inner and/or positioning balloon and facilitate the communication of inflation media into and out of the inner cuff and/or positioning balloon. At times, the inflation media conduits may be configured to accept insertion and/or withdrawal of inflation media via an inlet, port, and/or valve. In some embodiments, the valve can be operable to removably receive a portion of an inflation device operable to inflate the first and/or positioning balloon without removal of the device from a patient's vagina.

In some embodiments, the cervical control device can further comprise a pump and a fluid reservoir disposed in the body. The pump may be in fluid communication with the fluid reservoir and the fluid reservoir may be in fluid communication with the inner cuff and/or positioning balloon and may be configured to move or move inflation media between the fluid reservoir and the inner cuff and/or positioning balloon for inflation and/or deflation thereof. In some embodiments, the cervical control device can further comprise a wireless control device for remotely controlling the pump.

In another embodiment, one or more of the cervical control devices disclosed herein may comprise a semi-spheroid or otherwise curved body defining an interior passageway for receiving a cervix, the body comprising upper and lower portions defining proximal and distal openings, respectively, and an exterior surface for engaging a vaginal wall to support the device proximate the cervix, the body (e.g., semi-spheroid body) can comprise a inner cuff coupled to the body at the proximal opening and configured to surround at least a portion of the cervix, and a positioning balloon disposed at one or both chosen from the exterior portion of the body and the lower portion of the body proximate the distal opening, the positioning balloon configured to expand away from an axial center of the distal opening to expand toward and into the vaginal wall, the positioning balloon expandable from a neutral state to an expanded state in which an exterior perimeter of the positioning balloon is enlarged as compared to its exterior perimeter when in the neutral state, a inflation media conduit comprising a first end configured to be in fluid communication with the first and/or positioning balloon and a second end opposite the first end, a valve comprising a first end configured to be in fluid communication with the second end of the inflation media conduit and a second end opposite the first end configured to receive a portion of an inflation device operable to inflate the first and/or positioning balloon without removal of the device from a patient's vagina, and a valve housing comprising a first end configured to receive the inflation media conduit and a second end comprising an opening configured to surround the first end of the valve. Multiple valves are used in some embodiments.

In some embodiments, the cervical control devices disclosed herein may be permanently, or removably, coupled to a valve and/or valve housing that may comprise a senor and/or pressure gauge configured to provide tactile and/or visual indication of the pressure within the inner cuff and/or positioning balloon. In some embodiments, the pressure gauge can comprise a pressure balloon configured to be incrementally inflated to indicate how much pressure has increased in within the device. In some embodiments, the pressure balloon can have varying wall thicknesses and/or be color coded that can be configured to indicate different levels of pressure within the first and/or positioning balloon.

Although the devices described herein are described as "cervical control devices," such devices, in some embodiments, may also be used to support other tissue instead of, or in addition to, the cervix, such as the uterus or bladder as may happen with pelvic organ prolapse. In the case of pelvic organ prolapse (POP), the cervical control devices disclosed herein may be used to support the tissues or organs that have prolapsed and/or are out of position or causing discomfort to the patient. For example, when the cervical control devices disclosed herein are used to treat bladder prolapse, the cervical control device may be positioned within the vaginal canal to keep the bladder lifted higher in the pelvis. For uterine prolapse, the cervical control devices disclosed herein may be used to keep the uterus higher in the pelvis and prevent it from descending into the vaginal canal or out of the vaginal opening.

In several embodiments described herein, the cervical control devices disclosed herein may be configured to expand from a neutral state to an expanded state. This includes, for example, expansion from an expanded or lesser expanded state to a more expanded state. In some embodiments, expansion may occur gradually over time or at one time and a degree of expansion of the inner and/or positioning balloon(s) may be responsive to, for example, a physiological condition of the patient and/or patient comfort.

In some embodiments, the devices described herein are coated with, embedded with, and/or otherwise include one or release or more active or inactive agents such as medication, hormones, anti-irritants, lubricants, progesterone, tocolytics, antimicrobial APIs (active pharmaceutical ingredients) or silver nitrate (non-active pharmaceuticals can be used.

In several embodiments, the devices and methods described herein work synergistically with drugs (such as oral and intravenous drugs) that delay preterm labor (such as drugs that can slow or stop contractions of the uterus). In some embodiments, such drugs may be needed for a shorter time, at a lower dose or not at all if one of the cervical control devices disclosed herein is used to control the cervix according to one or more embodiments described herein, thus reducing undesired side effects.

In another embodiment, a method of supporting and reinforcing tissue (such as a cervix) is provided wherein the method can comprise positioning a cervical control device around the tissue (e.g., cervix) of a patient. The cervical control device can comprise a body defining an interior passageway for receiving the tissue (e.g., cervix), upper and lower portions defining proximal and distal openings to the interior passageway, respectively, and an exterior surface (e.g., for engaging a vaginal wall or other structure). An inner cuff may be coupled to and/or extend from the body at, or near, the proximal opening. The inner cuff may be configured to surround at least a portion of the tissue (e.g., cervix). The cervical control device may further include a positioning balloon disposed on an exterior portion of the body and/or lower portion of the body proximate the distal opening, wherein the positioning balloon is disposed around a portion of a circumference of the body. Once in position, the inner cuff may be inflated to expand the inner cuff from a neutral state to an expanded state so that the inner cuff contacts and/or engages at least a portion of the tissue (e.g., cervix). The positioning balloon may also be inflated and, when it inflates, it may expand away from an axial center of the distal opening to expand toward a desired region (such as toward and into the vaginal wall), the positioning balloon expandable from a neutral state to an expanded state in which an exterior perimeter of the positioning balloon is enlarged as compared to its exterior perimeter when in the neutral state.

In some embodiments, the cervical control device can further comprise an inflation media conduit in fluid communication with the first and/or positioning balloon, and a valve in fluid communication with the inflation media conduit. In some embodiments, the method can further comprise connecting an inflation device to the valve to inflate the inner cuff and/or positioning balloon in situ without removal of the cervical control device from the patient's vagina and/or disengagement with the cervix. In some embodiments, the positioning balloon can comprise a minor arc shape disposed around less than 180 degrees of the circumference of the body. In some embodiments, the positioning balloon can comprise a major arc shape disposed around more than 180 degrees of the circumference of the body. In some embodiments, the positioning balloon can comprise a non-uniform wall thickness configured to control expansion of the positioning balloon away from the axial center of the distal opening to expand toward and into the vaginal wall when in situ.

According to another embodiment, a method of treating prolapse can comprise positioning a cervical control device like the cervical control devices disclosed herein around the cervix of a patient, the cervical control device can comprise a body defining an interior passageway for receiving a cervix, upper and lower portions defining proximal and distal openings to the interior passageway, respectively, and an exterior surface for contacting, engaging, and/or wedging against a vaginal wall. The cervical control device may further comprise a positioning balloon disposed on an exterior and/or lower (or distal) edge of the body proximate to the distal opening. When the positioning balloon is disposed around a portion of an exterior circumference of the body, inflation of the positioning balloon may act to expand it in a desired direction (e.g., away from an axial center of the distal opening and toward and into the vaginal wall).

According to another embodiment, a cervical control device can comprise a body defining an interior passageway for receiving a cervix, the body comprising upper and lower portions defining proximal and distal openings to the interior passageway, respectively, and an exterior surface for engaging a vaginal wall, and an inner cuff coupled to and/or extending from the body at, or near, the proximal opening. The inner cuff may be configured to surround at least a portion of the cervix and expand from a neutral state to an expanded state in which the inner cuff is configured to engage at least a portion of the cervix. At times, the inner cuff may comprise a non-uniform wall thickness configured to control expansion of the inner cuff in a desired direction such as radially inward and/or downward away from a transverse plane of the proximal opening and away from a uterus as the inner cuff expands around and engages the cervix. The cervical control device may further include a positioning balloon disposed on the exterior portion of the body and/or lower (distal) edge of the body proximate the distal opening. The positioning balloon may be disposed around a portion of a circumference of the body and configured to be inflated and expand away from an axial center of the distal opening toward and into the vaginal wall. When the positioning balloon expands from a neutral state to an expanded state, an exterior perimeter of the positioning balloon is enlarged as compared to its exterior perimeter when in the neutral state. The positioning balloon may comprise a minor arc shape disposed around less than 180 degrees of the circumference of the body and/or a non-uniform wall thickness configured to control expansion of the positioning balloon away from the axial center of the distal opening to expand toward and into the vaginal wall without, for example, expanding toward the distal or proximal opening.

According to some embodiments, a cervical control device is provided for supporting and/or controlling a patient's cervix and includes a main body dimensioned and shaped for placement in the patient's vagina. The main body defines an interior passageway having a proximal opening at an upper portion of the body and a distal opening at a lower portion of the body. A portion of the exterior perimeter of the body is provided for engaging and pressing or partially embedding into the vaginal wall to anchor the device near the cervical opening in one embodiment. An expandable inner cuff is provided, in one embodiment, around an interior of the body proximate the proximal opening such that the inner cuff defines at least a portion of the proximal opening. The inner cuff may be expandable toward the axial center of the proximal opening to circumscribe an exterior portion of the lower cervix. The inner cuff may be expandable from a neutral state to an expanded state, which decreases the area of the proximal opening. In other words, when inflated, the inner cuff can expand inward to constrict the exterior of the cervix. The inner cuff may include one or more recessed or minimally inflatable portions and one or more enlarged or enlargeable portions that are adjacent the recessed portion (s). The expandable portions are expandable, for example, toward the axial center of the proximal opening to constrict the cervix and the recessed portion of the inner cuff remains generally uninflated or unexpanded to permit blood flow between the upper cervical tissue and the lower (below the inner cuff) cervical tissue. Optionally, the cervical control device may include one, two or more ridges (such as an annular ridge) along an interior perimeter of the inner cuff for gripping or engaging the exterior of the cervix, such as providing improved grip around the cervix as the inner cuff is inflated.

In some embodiments, the main body of the cervical control devices disclosed herein may be a semi-spheroid body formed with a semi-spheroid shape defining a proximal opening at an upper portion of the semi-spheroid body and a distal opening at a lower portion of the semi-spheroid body. The proximal opening may have a smaller diameter and/or area than the distal opening. The exterior portion of the body at, or near, the distal opening may be dimensioned and shaped for engaging the vaginal wall to support the cervical control device within the vagina proximate to the fornix and/or cervical opening. In other embodiments, the main body of the device is curved or arced with angles in the range of 7 mm radius to 15 mm radius where the inner cuff transitions to the main body. The outer walls of the main body can be vertical or have a curved arc ranging from 20 mm radius to 50 mm radius. The height of the main body may be, for example, 15-30 mm. In other embodiments, the main body may have a partial cube shape, a pyramid shape, a partial egg shape with an oval or partially oval cross section, an irregular three-dimensional shape with non-symmetrical cross section, or any other shape suitable for placement around the cervix and for engaging the vaginal wall.

Additionally, or alternatively, the inner cuff of the cervical control devices disclosed herein may be expandable radially inward toward the axial center of the proximal opening, as well as downward away from the transverse plane of the proximal opening and away from the uterus as inner cuff expands around the cervix. The inward, radial expansion of the inner cuff acts, for example, to constrict an exterior portion of the cervix, while the downward expansion acts to pull or push the cervix downward away from the uterus.

Additionally, or alternatively, the inner cuff may include two or more adjacent bladders that are positioned, shaped, and dimensioned in a manner such that, upon inflation of one or more of the inflatable bladders, the inner cuff expands radially inward and/or downward away from the transverse plane of the proximal opening. For example, the inner cuff may include a first inflatable bladder that is coaxial with the proximal opening and a second inflatable bladder that is coaxial with the first inflatable bladder and the proximal opening. In one embodiment, the inner cuff is expandable from a neutral state to an expanded state in which some portion of the inner cuff may expand both radially inward toward the axial center of the proximal opening, as well as downward away from the transverse plane of the proximal opening and away from the uterus, to thereby apply a downward force to the exterior of the cervix.

Additionally, or alternatively, a radial cross section of the inner cuff of one or more of the cervical control devices disclosed herein may be formed to have a non-uniform wall thickness such that, upon expansion, the arrangement of the non-uniform wall cuff causes inner cuff to expand both radially inward, as well as downward away from the transverse plane of the proximal opening.

Additionally, or alternatively, the cervical control devices disclosed herein may include an annular rim positioned proximate to an upper (proximal) portion of the main body. The annular rim may extend upward away from the transverse plane of the proximal opening. Upon placement of the device in the patient's vagina, the annular rim may be configured to initially receive the lower end of the cervix and then guides the cervix into the proximal opening and inner passageway, which may aid a provider is properly positioning the device proximate to, and around, the cervix.

The valve(s) disclosed herein may removably receive a portion of an inflation device (e.g., a pump and/or syringe needle) that is operable to inflate the inner and/or positioning balloon(s) without removal of the cervical control device from the patient's vagina and/or dislodging it from the cervix. The valve(s) may be configured to minimize backflow of fluid after it is directed into an inner and/or positioning balloon(s).

In still another embodiment, the cervical control devices disclosed herein may include second expandable annular cuff (also referred to herein as a "positioning balloon") positioned near the lower portion and/or outer (convex) curvature of the main body, such as proximate the distal opening. The positioning balloon may be outwardly expandable, away from the axial center of the distal opening such that it expands toward and into contact with the vaginal wall. The positioning balloon may be expandable from a neutral state to an expanded state in which the exterior perimeter of the positioning balloon is increased (as compared to its exterior perimeter when in the neutral state), to expand into contact with the vaginal wall and to anchor the device at the vaginal wall. The positioning balloon may be in fluid communication with an inflation media conduit, such as that described herein, in order to receive or release fluid to/from the positioning balloon. A single inflation media conduit may be provided in communication with the distal and inner cuffs of the device, or dedicated inflation media conduits may be provided for the positioning balloon and inner cuff separately, and/or each individually addressable bladder of the inner and/or positioning balloon(s).

In several embodiments, a cervical control device and/or system may be provided for supporting a patient's cervix and may include a main body dimensioned and shaped for placement in the patient's vagina. The main body has an upper portion defining a proximal opening and a lower portion defining distal opening. An exterior portion of the body is configured for engaging the vaginal wall to support or anchor the cervical control device and/or system proximate the cervical opening.

The cervical control devices and/or systems disclosed herein may include, for example, one or more expandable annular cuffs at an interior of the body, near the proximal opening, and inner cuff defines at least a portion of the proximal opening. At least a portion of inner cuff is expandable, in one embodiment, from a neutral state to an expanded state in which inner cuff is expanded both (i) radially inward, toward the axial center of the proximal opening to constrict an exterior portion of the cervix, and (ii) downward away from the transverse plane of the proximal opening and away from the uterus to apply a downward force to the exterior of the cervix.

In some embodiments, the inner cuff may include one or more recessed portions and one or more expandable portions in spaced arrangement with one another around the circumference of the inner cuff. The expandable portions may be expandable toward the axial center of the proximal opening, as well as downward away from the transverse plane of the proximal opening. The recessed portion(s) of inner cuff may permit blood flow from the upper cervical tissue to the lower cervical tissue that extends through the inner cuff.

In another embodiment, a radial cross section of the inner cuff has a non-uniform wall thickness, such that based on the material characteristics of the non-uniform wall thickness, upon expansion, the inner cuff is expandable both radially inward and downward away from the transverse plane of the proximal opening.

In yet another embodiment, the inner cuff may include a plurality of inflatable bladders adjacent and co-axial with one another. The plurality of inflatable bladders may be arranged such that, upon inflation of one or more of the bladders, inner cuff expands radially inward, toward the axial center of the proximal opening and/or downward away from the transverse plane of the proximal opening.

The cervical control systems, cervical control devices, and/or methods disclosed herein may be used to, for example, delay labor, control a cervix, support a weak cervix, treat cervical insufficiency, treat pelvic organ prolapse, treat incontinence, treat pelvic organ pain or pressure, bleeding, and/or bladder conditions.

Disclosed herein are kits comprising one or more of the cervical control devices and/or systems disclosed herein and an inflation device.

Accordingly, the cervical control devices and/or systems disclosed herein provide a customizable and adjustable device for supporting and/or controlling a cervix of a patient with a high-risk pregnancy and/or a patient experiencing pregnancy complications that may progress to a pre-term labor such as an insufficient cervix, PROM, PPROM, and/or an insufficient cervical mucus plug. The cervical control devices and/or devices disclosed herein include an inner cuff and/or individually addressable inflatable bladders the permit a care provider to direct a compressive force at desired locations around the patient's cervix at the top of the fornix. The adjustable nature of the cervical control devices and/or devices disclosed herein permits a provider or user to, for example, adjust the amount of pressure applied to the cervix, compress a cervix closed, and/or or adjust an orientation of the cervix and/or the cervical control device and/or system relative to the cervix and vagina, all without removal or direct, manual manipulation of the cervical control device and/or system through the vagina. The inner and/or positioning balloons disclosed herein may include various dimensional features or structural aspects that cause the inner and/or positioning balloon to expand radially inward toward the cervix and/or downward away from the uterus to apply an oblique, inward downward force to the cervix.

These and other objects, advantages, purposes, and features of this disclosure will become apparent upon review of the following specification in conjunction with the drawings.

BRIEF DESCRIPTION OF THE DRAWINGS

The following drawings are for illustrative (example) purposes only and show non-limiting embodiments. Features from different figures may be combined in several embodiments.

FIG. 76B illustrates a front perspective exploded view of the triple port valve housing and micropump assembly of FIG. 76A with the reservoir positioned within the micropump assembly, in accordance with some embodiments of the present invention;

FIG. 78J is a cross section view of the exploded assembly and molded cervical control system of FIG. 78I, in accordance with some embodiments of the present invention;

FIG. 78K illustrates a bisecting cross sectional view of the cervical control system of FIG. 78I, in accordance with some embodiments of the present invention;

FIG. 78L illustrates an angled sectional view of the cervical control system of FIG. 78I, in accordance with some embodiments of the present invention;

FIG. 78M illustrates a bisecting cross sectional view of a cervical control system in which the inner cuff fully assembled, in accordance with some embodiments of the present invention;

FIG. 79 illustrates a flow chart illustrating a process for using a cervical control system, the systems, and/or devices disclosed herein, in accordance with some embodiments of the present invention;

FIG. 80A illustrates a sagittal view of a patient with an intact membrane and normal level of amniotic fluid, in accordance with some embodiments of the present invention;

FIG. 80B illustrates a sagittal view of a patient that has experienced PPROM, in accordance with some embodiments of the present invention;

FIG. 80C illustrates a sagittal view of a patient and shows how a cervical control system may be digitally placed around a cervix of the patient, in accordance with some embodiments of the present invention;

FIG. 80D illustrates a sagittal view of a patient and shows how a cervical control system may be positioned within the patient's vagina and around her cervix using forceps, in accordance with some embodiments of the present invention;

FIG. 80E illustrates a sagittal view of a patient and shows how an inner cuff and/or positioning balloon of cervical control system in situ may be inflated and/or deflated using a source of inflation media in the form of a syringe, in accordance with some embodiments of the present invention;

FIG. 80F illustrates a sagittal view of the patient of FIG. 80E with the inner cuff inflated so that it engages the cervix and presses it closed, in accordance with some embodiments of the present invention;

FIG. 80G illustrates a sagittal view of the patient of FIG. 80F with the inner cuff inflated so that it engages and tilts, or redirects and angle of, the cervix and presses it closed, in accordance with some embodiments of the present invention;

Figures 80A, 80B:
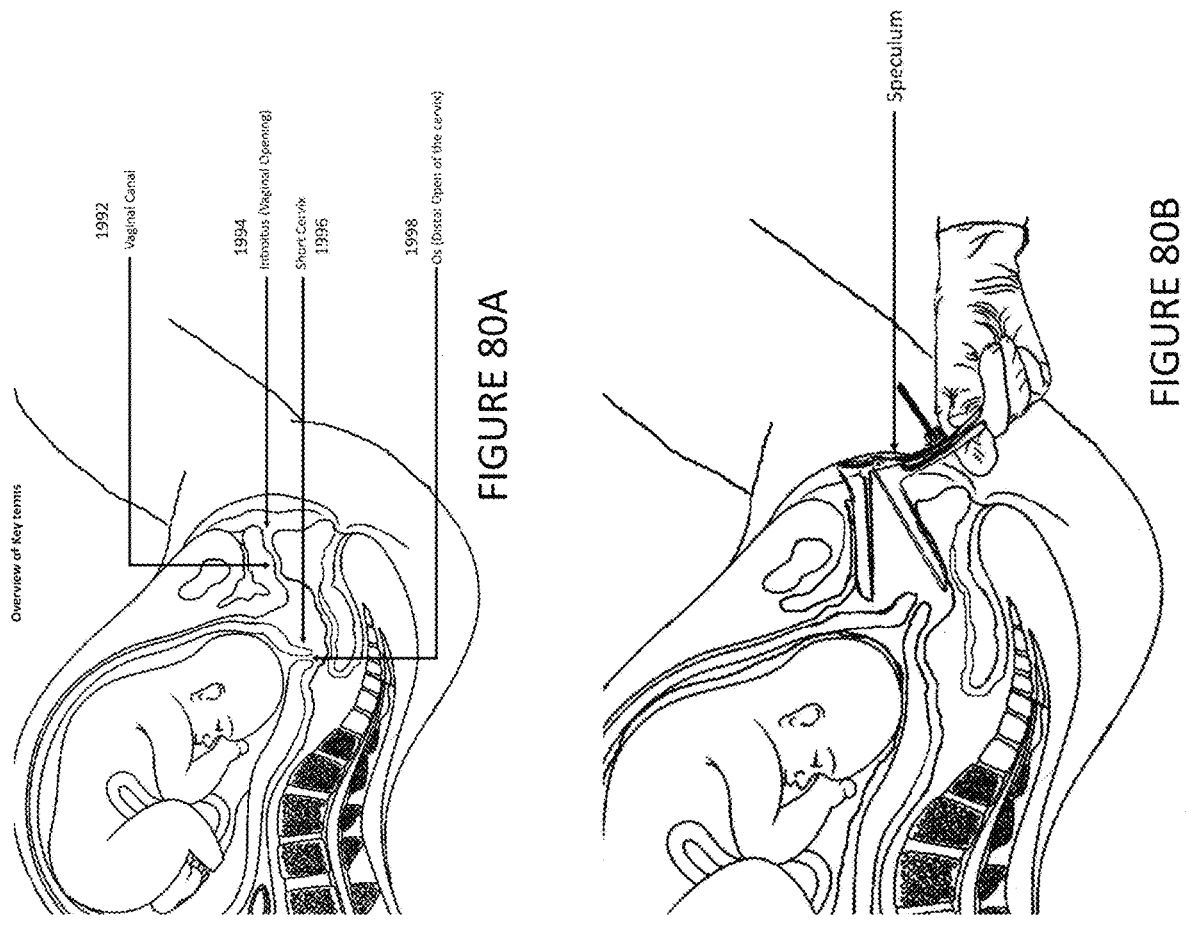
Figures 80C, 80D:
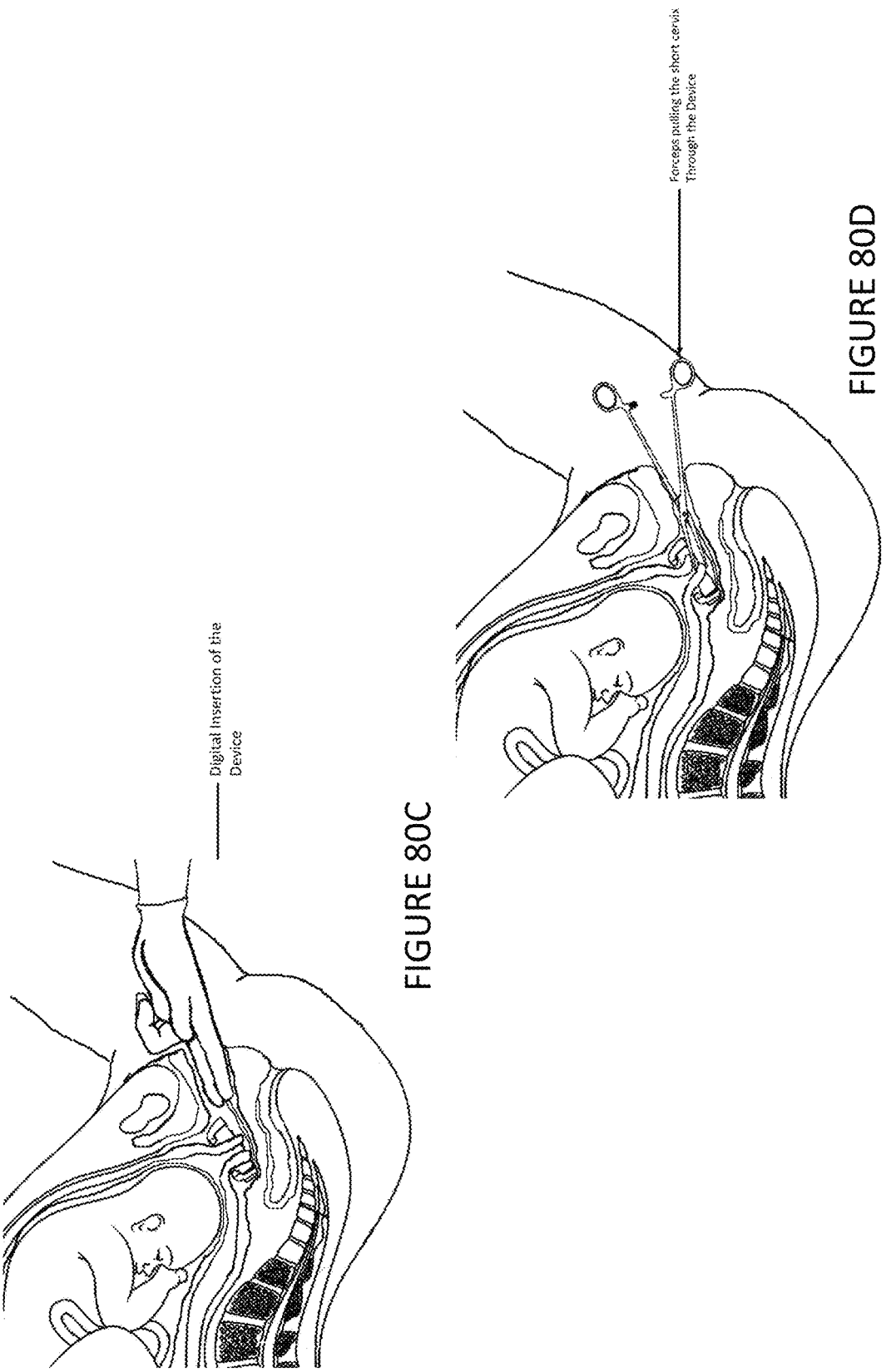
Figure 80E:
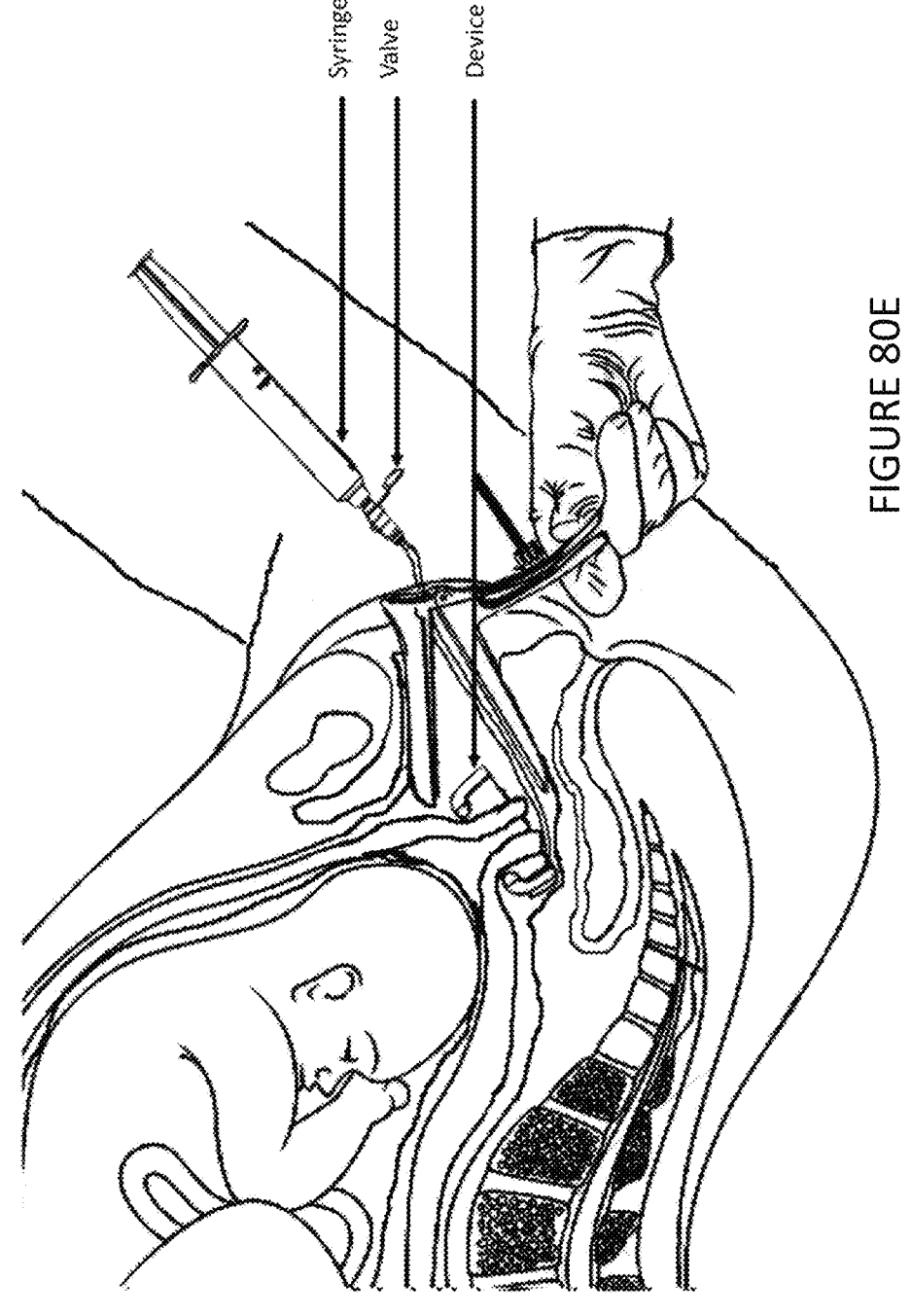
Figure 80F:
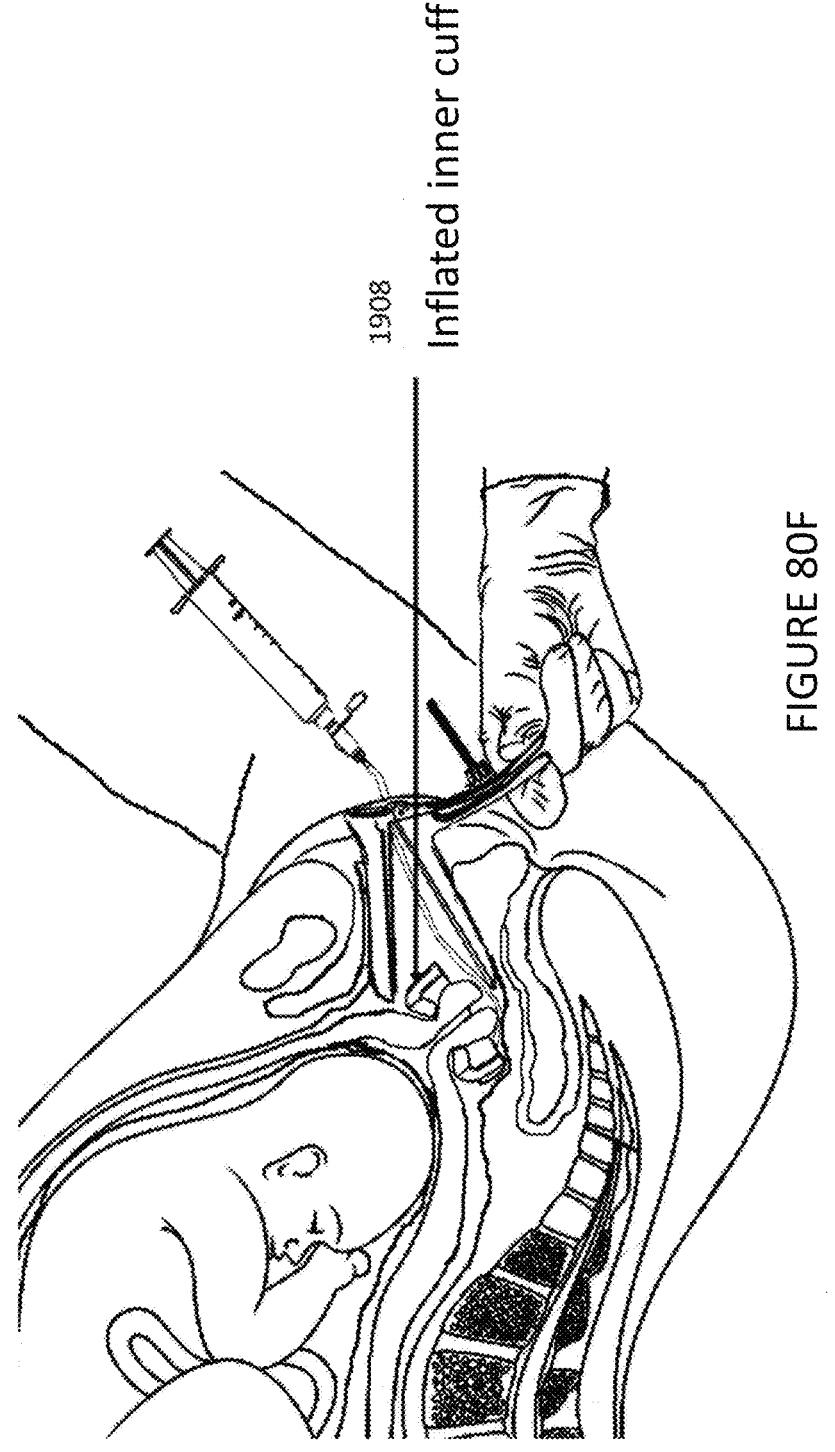
Figure 80G:
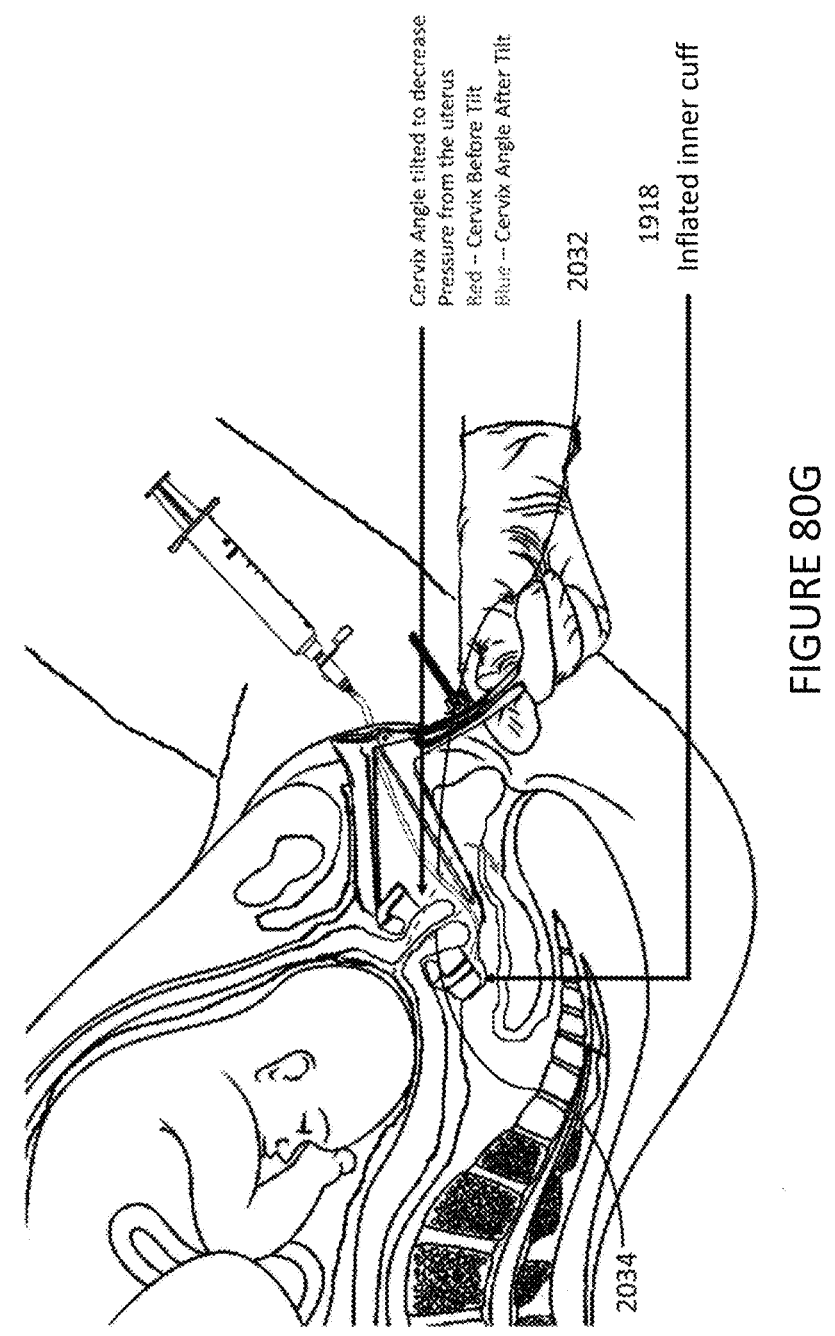
Figure 80H:
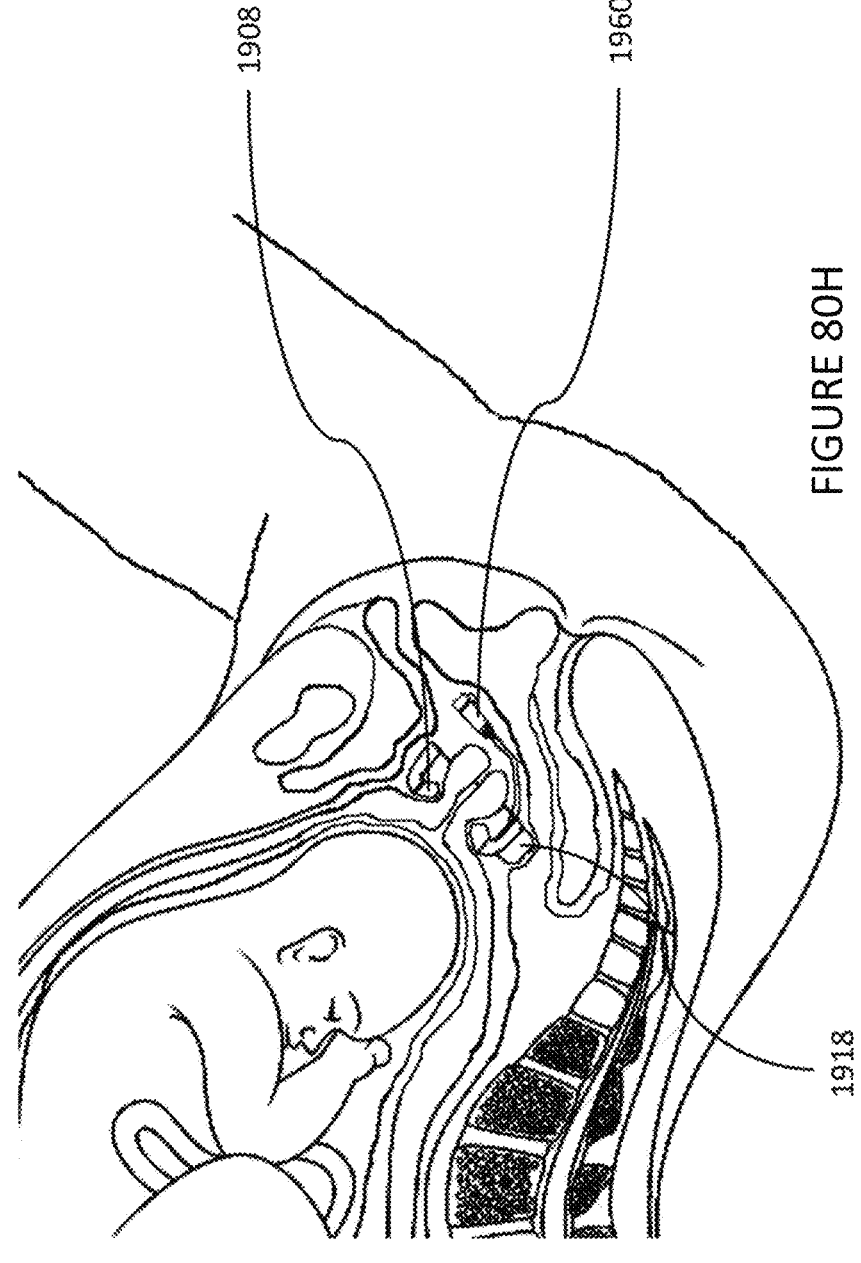
Figure 80I:
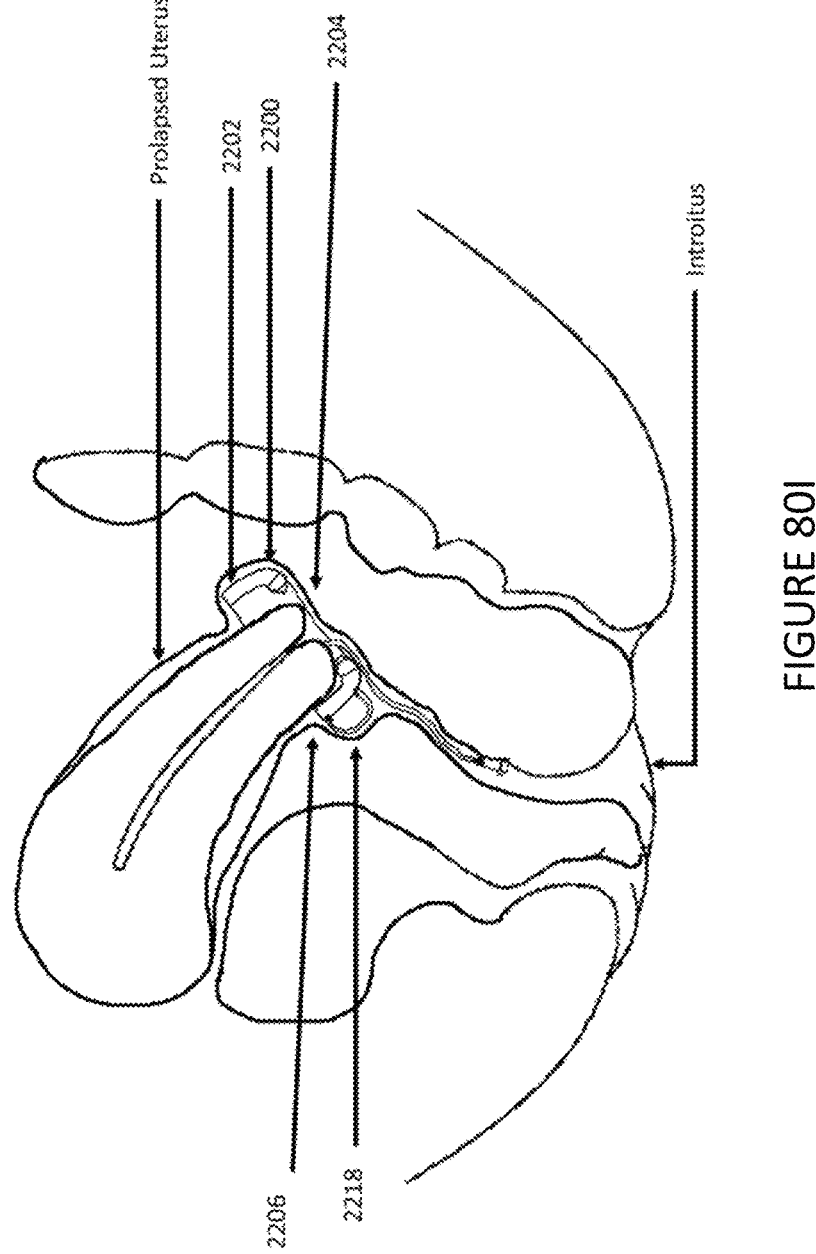

FIG. 80H illustrates a sagittal view of the patient of FIG. 80E with a fluid conduit and valve housing positioned within the patient's vagina, in accordance with some embodiments of the present invention;

FIG. 80I illustrates a sagittal view of a patient with a cervical control system placed around her cervix in an inverted position to that shown in FIG. 80H, in accordance with some embodiments of the present invention;

FIG. 80J illustrates a sagittal view of a patient with an intact amniotic membrane and a normal amniotic fluid level, in accordance with some embodiments of the present invention;

FIG. 80K illustrates a sagittal view of a patient of with a ruptured amniotic membrane who has lost some amniotic fluid level, in accordance with some embodiments of the present invention;

FIG. 80L illustrates a sagittal view of the patient of FIG. 80K once a cervical control system has been fit around her cervix so that leaking of amniotic fluid from the ruptured amniotic membrane is slowed and has been restored, in accordance with some embodiments of the present invention; and FIG. 81 illustrates a block diagram of a kit that includes a cervical control system, in accordance with some embodiments of the present invention.

WRITTEN DESCRIPTION

Referring now to the drawings and the illustrative embodiments depicted therein, various embodiments of cervical control devices, systems, and methods of use are provided for reduction or prevention of preterm labor caused by, for example, cervical insufficiency (for example, shortened or incompetent cervix), prolapse, cervical support, etc. The cervical control devices are, in some embodiments adjustable to apply a compressive force around the exterior of the cervix and may function to alter the angle of the cervix, which may promote an extended gestation of a fetus in patients who experience cervical insufficiency. The cervical control devices disclosed herein may include one or more expandable (e.g., inflatable) cuffs, which when expanded apply a compressive force to the exterior of the cervix. The cervical control devices may be adjusted by an operator or user (e.g., medical care provider) without removing the cervical control system and/or device from inside the patient. In some instances where the cervix is partially dilated, opened to the point the cervical mucus plug has fallen out, the cervical control system can be utilized to compress the cervix to facilitate mucus plug regeneration, which may prevent infection from traveling up the cervix into the uterus. In instances of PROM or PPROM, the cervical control system can be utilized to compress the cervix to decrease the rate of amniotic fluid loss, to help promote fetal lung development. The cervical control systems disclosed herein may be utilized in a minimally invasive manner to provide support around the lower cervix to support the weight of the uterus and fetus, preferably (in one embodiment) with little or no stimulation or irritation to the cervix. In other words, the inner and/or positioning balloon(s) may be left in a neutral or uninflated state. In the event that the patient's cervix continues to shorten and dilate and the minimally invasive approach is not adequate, inner and/or positioning balloon(s) may be inflated, or inflated further, to decrease the proximal opening diameter to supply additional support to the external cervix and provide external compressive force around the exterior of the cervix in effort to keep the cervix from opening or dilating further. The term "cuff" and "bladder" are used herein to refer to the expanding components of some illustrative embodiments of the present disclosure, which may partially or fully annular, including "inner cuffs", "positioning balloons", and "inflatable bladders", for example. Optionally, inner and/or positioning balloon(s) may be continuous around an inner and/or outer circumference of the cervical control system, intermittently spaced around an inner and/or outer circumference of the cervical control system, may expand to define non-circular or non-uniform openings, and/or may be expandable in lateral (e.g., radial) and/or oblique (e.g., non-radial) directions. In some embodiments, the cervical control systems disclosed herein may be utilized to support the cervix, uterus, and fetus, even with inner and/or positioning balloon(s) in a neutral or uninflated state.

Disclosed herein are cervical control devices and systems configured to topically dispense substances to cervical tissue, in situ, on a continuous, as-needed, and/or periodic basis so that the substances may be in contact with (through, for example, reapplication) the cervical tissue regardless of vaginal discharge flushing, or otherwise cleaning, the cervix and vagina. Substances dispensed via the cervical control devices and systems disclosed herein include, but are not limited to medication such as progesterone, saline, disinfectant, antibiotics, lubricant, water, chlorhexidine, betadine, analgesics, and/or lubricant. Use of the systems and devices disclosed herein may allow clinicians to deliver substances to the cervix without the need to remove and reinsert the device and/or system or disturb the cervix.

The discussion of the cervical control systems, cervical control devices, and methods disclosed herein uses the terms proximal, top, distal, and/or bottom to refer to portions of the respective systems, devices, and methods as oriented in the respective figures, wherein in many embodiments, the top and/or proximal portion of the systems and/or devices disclosed herein is intended to be positioned proximate to a patient's fornix with an inner cuff surrounding a portion of a cervix that is proximate to the patient's uterus and bottom and/or distal portions of the cervical control devices and/or systems disclosed herein may refer to portions thereof configured to be oriented away from a patient's uterus and/or have a side and/or edge proximate to the patient's introitus It will be understood that the systems and devices disclosed herein may be used in a variety of orientations (i.e., orientations not necessarily shown in the figures) and, in some cases, a portion of the systems and/or devices labeled as a proximal or top side may, in fact be distally placed within a patient when inverted to, for example, treat pelvic organ prolapse.

Components (e.g., inner cuffs and/or positioning balloons) of the cervical control systems described and illustrated herein may include one or more flexible membranes (also referred to herein as "walls") that define one or more inner chambers configured to accept insertion of inflation media therein. As the inner chambers of the inner cuffs disclosed herein fill with inflation media, their respective flexible membrane(s) expand in one or more directions (e.g., radially, orthogonally, tangentially, obliquely, and/or in a downward (i.e., away from the uterus)) direction to, for example, contact and/or engage, elongate, compress, or otherwise support and/or control a cervix. As the inner chambers of the positioning balloons disclosed herein fill with inflation media, the flexible membranes defining their respective inner chambers expand in one or more preferred directions (e.g., orthogonally to a main body of the cervical control system and/or into the vagina) to, for example, secure the cervical control system within the vagina and/or adjust a position and/or orientation of the cervical control system relative to a patient's cervix, uterus, and/or vagina. Additionally, or alternatively, the flexible membranes of the inner cuffs and positioning balloons disclosed herein may be selectively inflatable and/or deflatable to, for example, adjust a degree of compression and/or elongation of a cervix, an angle of orientation of the cervix and/or cervical control system, and/or a position and/or orientation of the cervical support device within the vagina as desired and/or required by physician, clinical, and/or patient needs and/or preferences.

Figure 1:
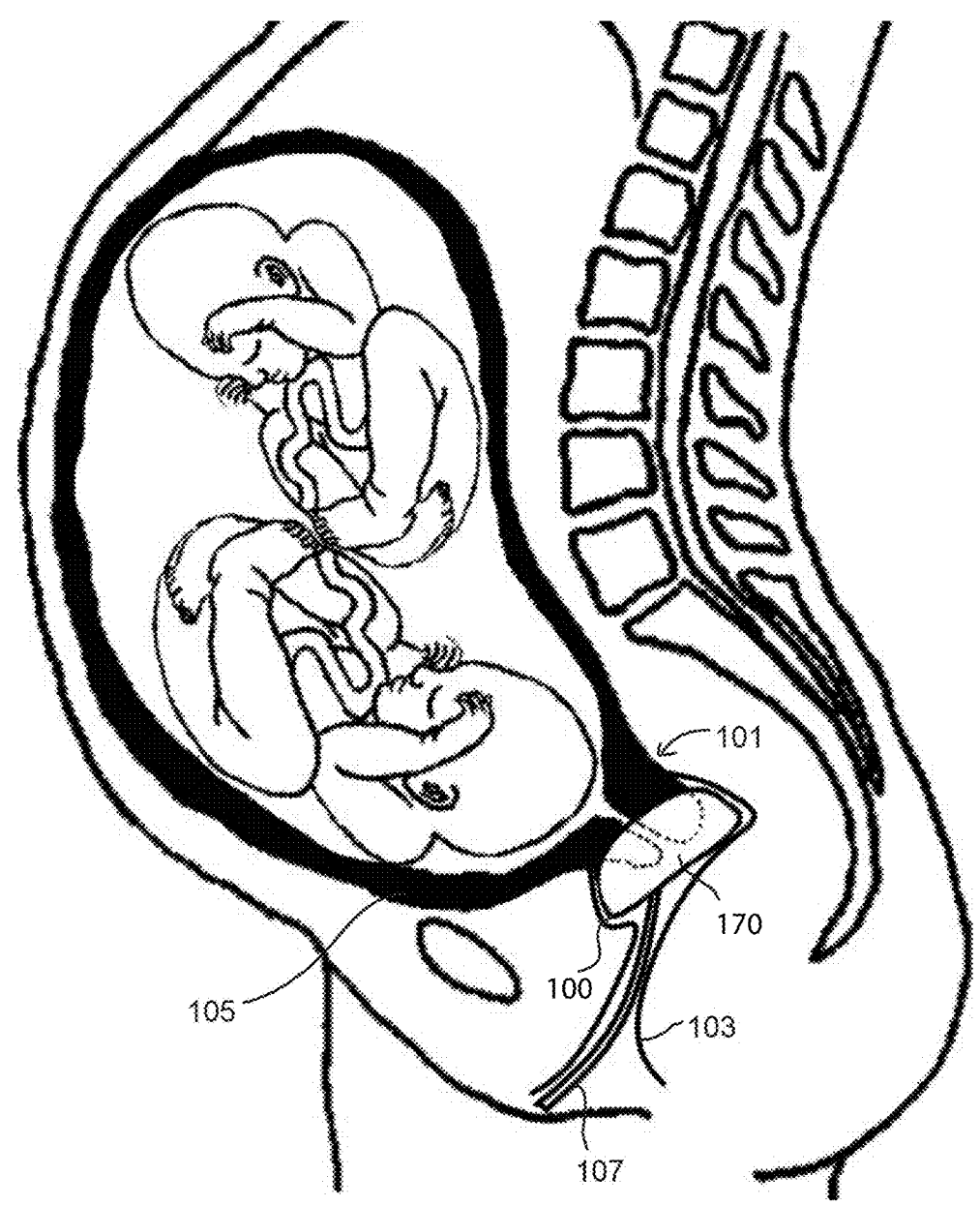
FIG. 1 illustrates a sagittal view of a patient with multiple gestations, illustrating placement of an exemplary cervical control system, in accordance with some embodiments of the present invention.
Figure 2:
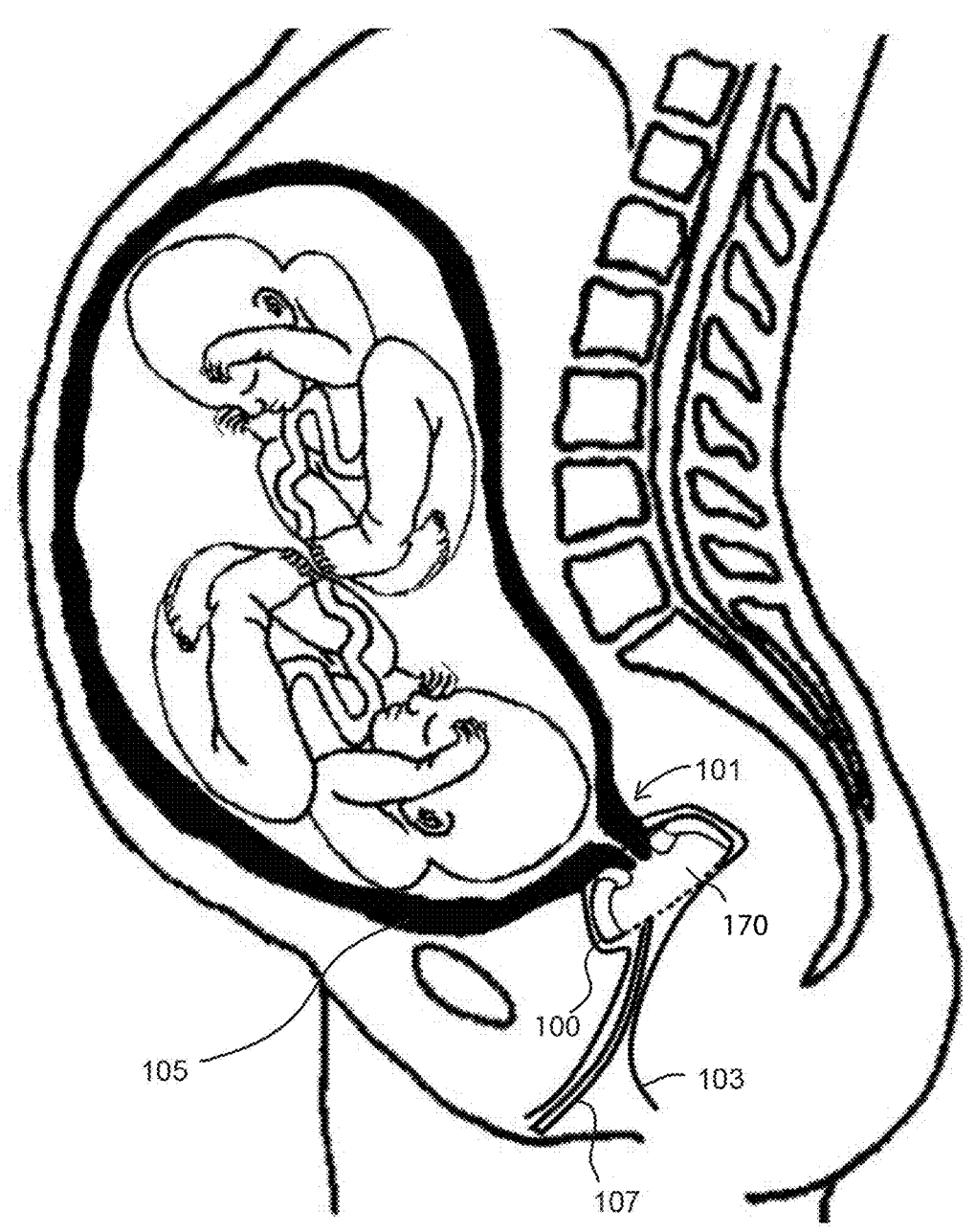
FIG. 2 illustrates another sagittal view of the patient of FIG. 1, with the cervical control system shown in a sectional side view with an inner cuff in an inflated or expanded state, in accordance with some embodiments of the present invention.
Figures 3, 4:
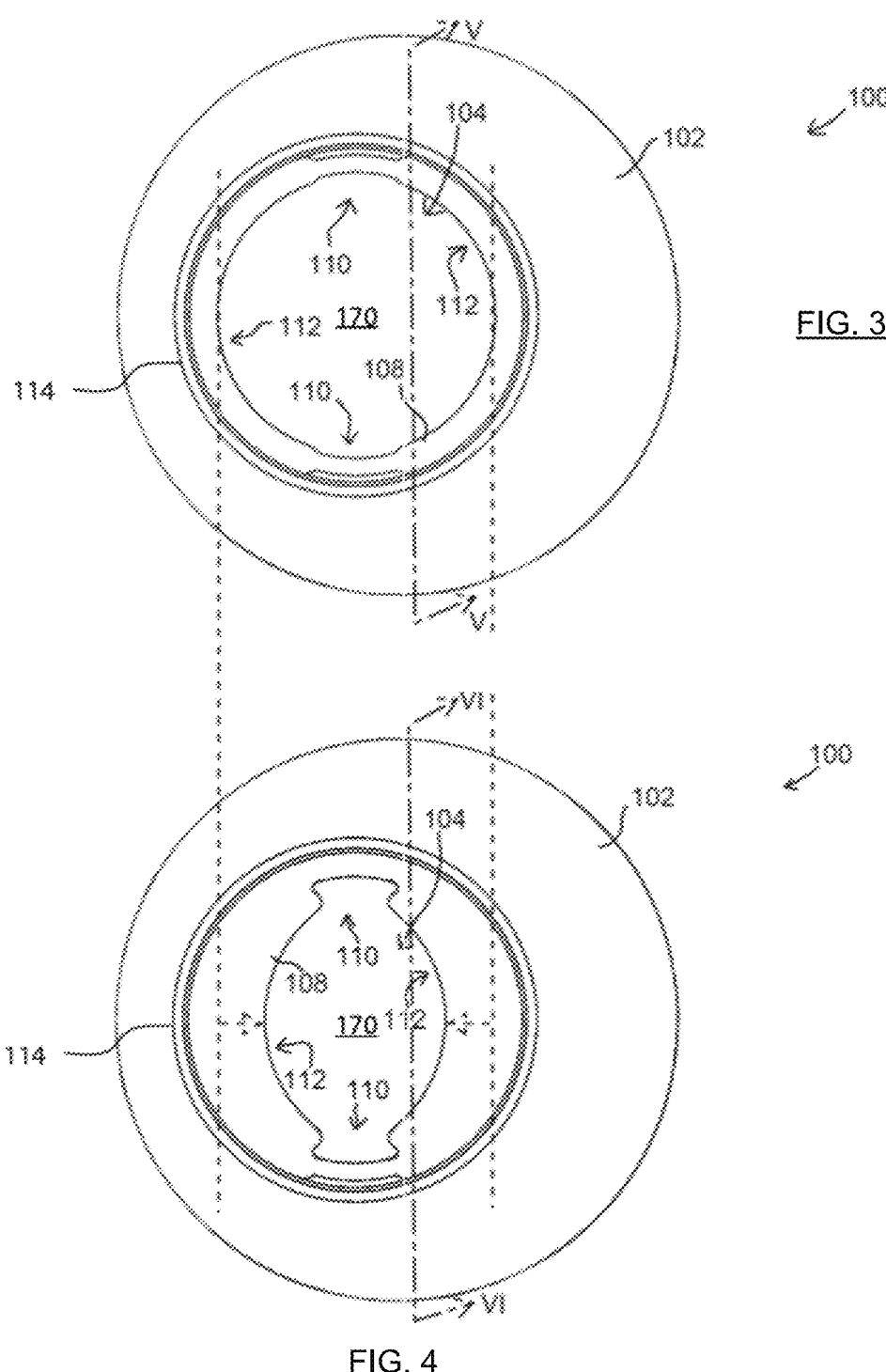
FIG. 3 illustrates a top perspective view of the cervical control system of FIG. 1, depicted with an inner cuff in a deflated or neutral state, in accordance with some embodiments of the present invention.
FIG. 4 illustrates top perspective view of the cervical control system of FIG. 1, depicted with the inner cuff in the inflated state, in accordance with some embodiments of the present invention.

Turning now to the figures, FIGS. 1 and 2 are sagittal views of a pregnant woman with an exemplary cervical control system 100 (also referred to herein as "system 100") positioned within the woman's vagina 103 so that a portion of the woman's cervix 101 is positioned within, and supported by, system 100 in an effort to, for example, treat PPROM, short cervix, and/or prevent preterm labor according to, for example, one or more methods disclosed herein. An inner cuff of system 100 may be configured to translate between a neutral, or deflated, state (e.g., when positioning cervix 101 therein) and an inflated state (e.g., when cervix 101 is positioned therein and being supported and/or reinforced by system 100). FIG. 3 is a top perspective view of system 100 when inner cuff is in the deflated or neutral state and FIG. 4 is a top perspective view of system 100 when inner cuff in the inflated state.

Figures 5, 6:
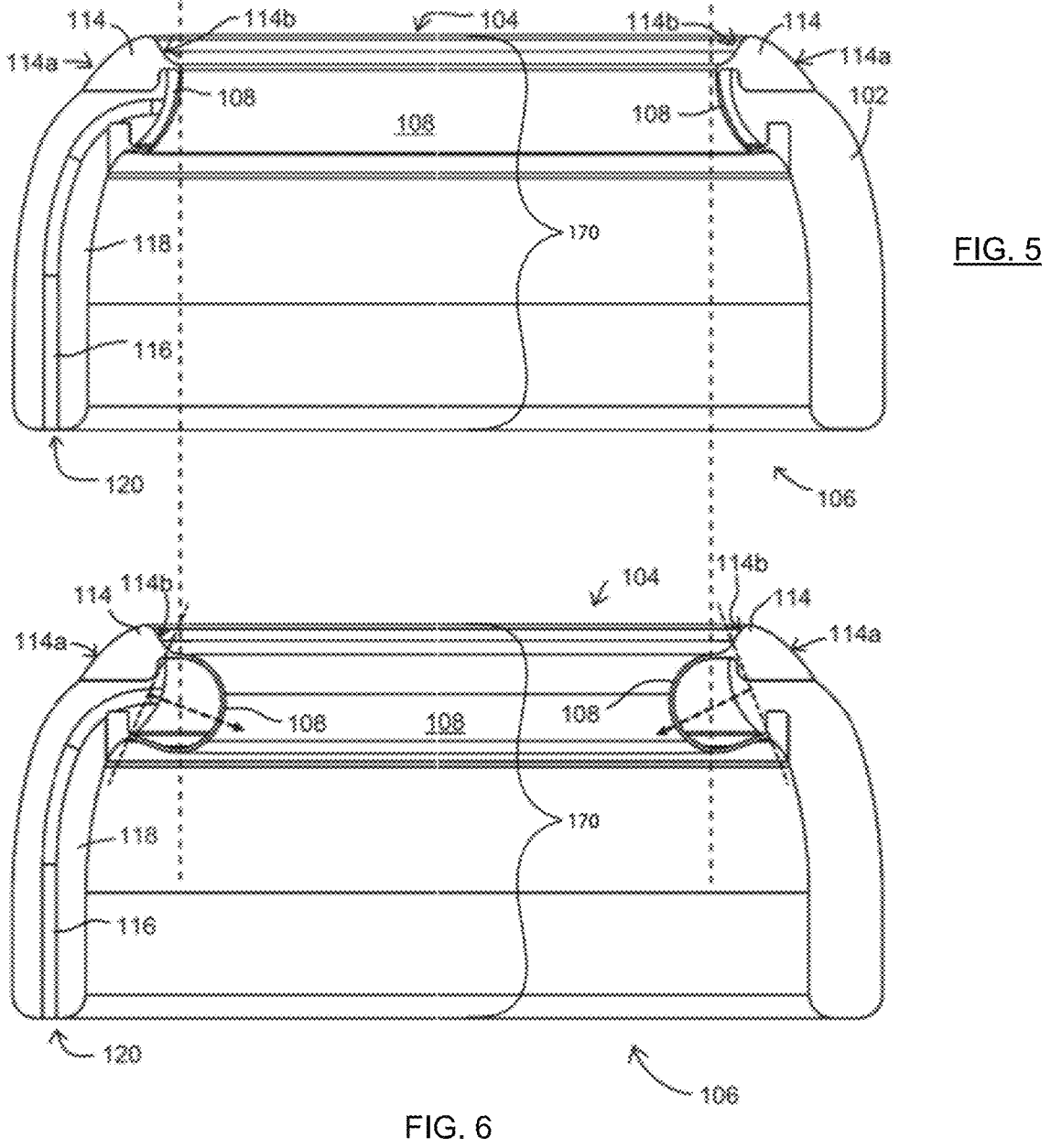
FIG. 5 illustrates a sectional side elevation view of the cervical control system of FIG. 1 taken along line V-V of FIG. 3, depicted with the inner cuff in the deflated state, in accordance with some embodiments of the present invention.
FIG. 6 illustrates another sectional side elevation view of the cervical control system of FIG. 1 taken along line VI-VI of FIG. 4, depicted with the inner cuff in the inflated state, in accordance with some embodiments of the present invention.
Figures 16, 17, 18:
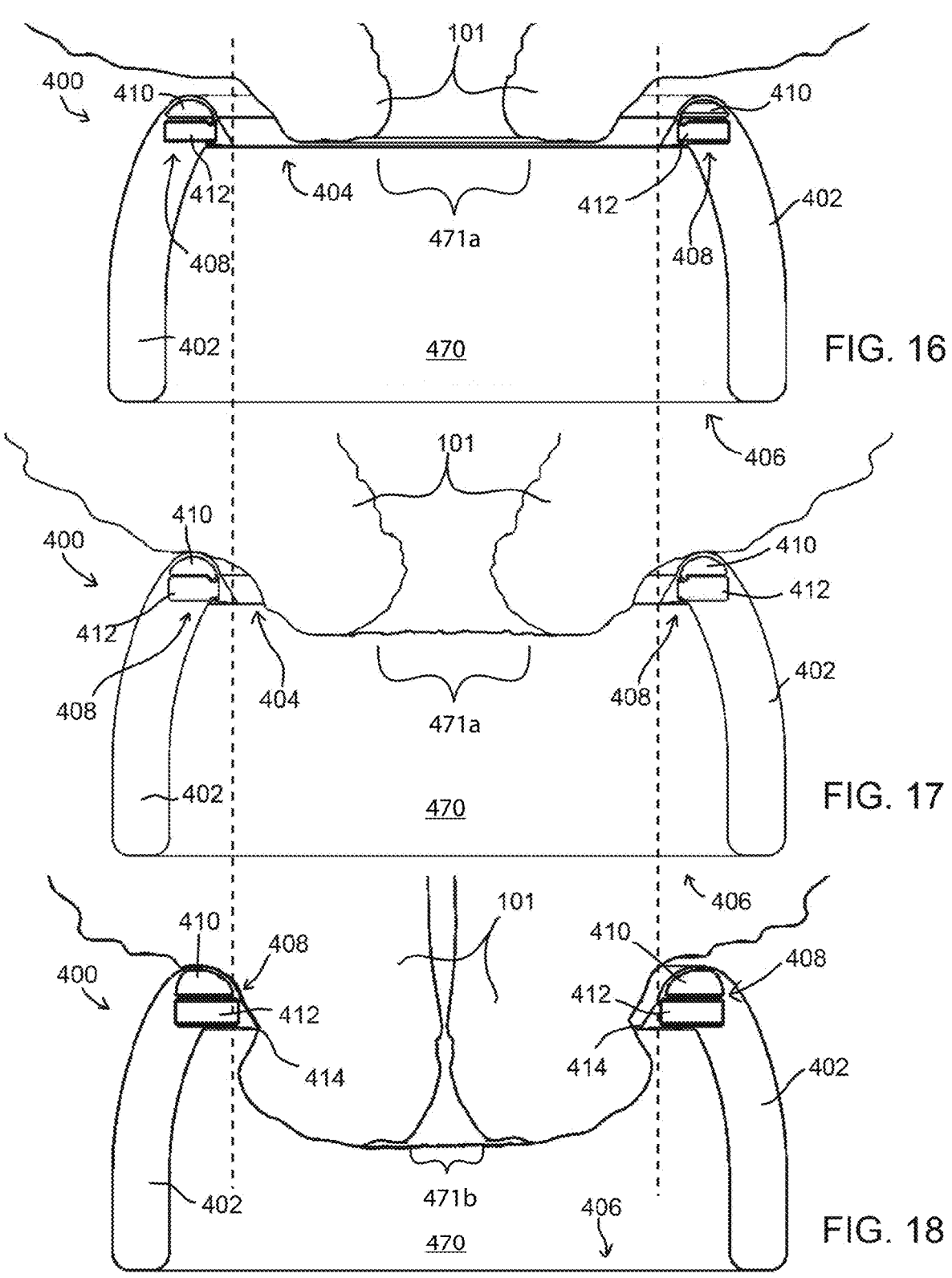
FIG. 16 illustrates a sectional side elevation view of the cervical control system of FIG. 14, shown in position around a patient's cervix at the top of the fornix, and depicted with the inner cuff in the deflated state, in accordance with some embodiments of the present invention.
FIG. 17 illustrates a sectional side elevation view of the cervical control system of FIG. 16, depicting the patient's cervix at the top of the fornix extending into the opening formed by the inner cuff, in accordance with some embodiments of the present invention.
FIG. 18 illustrates a sectional side elevation view of the cervical control system of FIG. 17, depicted with the inner cuff in the inflated state and engaging or impinging on the exterior of the patient's cervix at the top of the fornix, in accordance with some embodiments of the present invention.

System 100 includes a flexible body 102 that may have a semi-spheroid or semi-sphere-like shape and an interior passageway 170 with an upper, or proximal, opening 104 positioned proximate to an upper (as oriented in FIGS. 3-6) portion of the body 102/interior passageway 170 and a lower (as oriented in FIGS. 3-6), or distal, opening 106 positioned proximate to a lower (as oriented in FIGS. 3-6) portion of the body 102/interior passageway 170 as shown in, for example, FIGS. 5 and 6. In the illustrative embodiment, proximal opening 104 is smaller in diameter than distal opening 106 and is dimensioned to receive and encircle the lower, exterior portion of the patient's cervix 101 when system 100 is placed in the patient's vagina 103 proximate the base of the cervix as shown in, for example, FIGS. 1 and 2. For reference purposes, FIGS. 16-18 provide a sequential illustration of the positioning of cervix 101 within an interior passageway 470 (which is similar to interior passageway 170) of another exemplary cervical control system 400 and interaction between cervical control system 400 and cervix 101 as the system 400 is placed around, and engages with, cervix 101. An exterior surface of a portion of body 102 (e.g., a lower portion of the body 102 proximate to distal opening 106) may be dimensioned to engage, press against, and/or interact with interior walls of the patient's vagina 103 (see e.g., FIGS. 1 and 2) to, for example, hold system 100 in place and/or assist with holding a portion of cervix 101 positioned within interior passageway 170 closed.

System 100 includes an inner cuff or bladder 108 that may be positioned around the circumference of the proximal opening 104 as shown in, for example, FIGS. 5 and 6. An exterior (e.g., interior passageway facing) surface of inner cuff 108 is expandable (e.g., inflatable with a fluid such as saline or air) so that when cervix 101 is in position within internal passageway 170 (see e.g., FIGS. 1 and 2) inner cuff 108 may expand to engage with, constrict, and/or circumscribe a portion (for example, a top of the fornix and/or the lower portion of the cervix 101) of an exterior surface of cervix 101. Inner cuff 108 is shown in a normal, neutral, or deflated state in FIGS. 3 and 5 and shown in an expanded or inflated state in FIGS. 4 and 6, in which portions of inner cuff 108 have been expanded toward a center of the proximal opening 104. In the inflated state, the inner cuff 108 expands and encroaches or impinges on the exterior of cervix 101 (or a portion thereof) and thereby applies an external force or pressure to cervix 101 which may assist in closing, and/or maintaining a sufficiently closed cervical opening or OS, thereby delaying labor and delivery of a fetus, and permitting the fetus to remain in utero for a longer duration (i.e., preventing pre-term labor). The area of the proximal opening 104 is significantly reduced when the inner cuff 108 is inflated. A pair of phantom lines are provided between sequential FIGS. 3 and 4 and sequential FIGS. 5 and 6 to highlight the relative expansion of the inner cuff 108 from its neutral state in FIGS. 3 and 5 to its expanded state in FIGS. 4 and 6, which decreases a size or area of proximal opening 104 and increases a prominence of two recessed portions 110 as shown. Inner cuff 108 may be affixed (e.g., chemically, vibrationally, or thermally bonded) to, integrated into (e.g., via a unitary molding process or an over-molding process), and/or coupled to the proximal end of interior passageway 170 via, for example, a mechanical coupling like a tongue-and-grove or dovetail fit arrangement. Further details regarding the manufacturing of system 100 and/or inner cuff 108 are shown in, for example, FIGS. 1-6 and discussed herein.

As illustrated in FIGS. 3 and 4, inner cuff 108 includes two recessed portions 110 at opposing sides of the proximal opening 104 and two expandable portions 112 at other opposing sides of the proximal opening 104 and formed between the recessed portions 110. In the neutral state, the inner cuff 108 defines a generally circular shape (see e.g., FIG. 3). As the inner cuff 108 expands, the expandable portions 112 expand toward the axial center of the proximal opening 104 and the recessed portions 110 remain substantially static, unchanged, or unexpanded as shown in, for example, FIG. 4. As such, in the expanded state, recesses 110 and expandable portions 112 cooperate to form a non-circular inner perimeter of the inner cuff 108 (FIG. 4). With the inner cuff 108 in the expanded state, the area of the proximal opening 104 is decreased as compared to its area with the inner cuff 108 in the neutral state. Recessed portions 110 are positioned within inner cuff 108 to receive portions of cervix 101 containing the major blood vessels that supply blood to cervical tissue (e.g., the end of the cervix), and are configured to minimally constrict cervical tissue so that blood flow through these blood vessels is not compromised while other cervical tissue is compressed via inflation of inner cuff 108.

As sequentially illustrated in FIGS. 5 and 6, as the inner cuff 108 expands, it does so both radially inward toward the center of the proximal opening 104 as well as downward (as oriented in FIG. 6) in relation to a transverse plane of proximal opening 104. In other words, when system 100 is placed in the vagina so that cervix 101 is positioned within interior passageway and inner cuff 108 expands, expansion of inner cuff 108 may constrict a portion of the exterior surface of cervix 101 while applying a downward force (e.g., away from the uterus 105) on cervix 101. The downward angle of expansion of the inner cuff 108 may act to pull or push the cervix 101 downward, away from the uterus 105, which may assist with holding inner cuff 108 in place (e.g., mitigate or prevent the cervix from slipping out of inner cuff 108) during use, which may be caused by, for example, inner cuff's increasing volume during expansion and/or cervical shortening over time. In other words, the combination of transverse and downward constricting forces on cervix 101 may more effectively engage and constrain the exterior of the cervix 101, as compared to if the constricting force was applied only in the transverse or downward direction alone. The angle of expansion of the inner cuff 108 away from the transverse plane of proximal opening 104 may be selected from a range of between one-half degree (0.5°) and eighty-nine and a half degrees (89.5°).

In some embodiments, the entirety of the inner cuff 108 may be formed of the same material (e.g., flexible silicone)

that, on some occasions may have varying thicknesses (e.g., the flexible silicone of recessed portions 110 is thicker than the flexible silicone of expandable portions 112). Alternatively, different portions of inner cuff 108 (e.g., recessed portions 110 and expandable portions 112) may be formed from different materials (e.g., expandable portions 112 may comprise flexible silicone and recessed portions 110 may comprise medical grade plastic), and/or the different portions 110 and 112 of inner cuff 108 may be formed of differing compositions of a material (e.g., the expandable portions 112 may comprise flexible silicone and the recessed portions 110 may comprise semi-rigid silicone having a higher durometer than the silicone of the expandable portions 112).

In some embodiments, system 100 includes a raised, annular rim, ridge, or lip 114 (referred to herein as rim 114) positioned proximate to the upper (as oriented in FIGS. 3-6) or proximal portion of the body 102. Rim 114 may extend upward above or proud of the inner cuff 108 (see e.g., FIGS. 5 and 6) and may be configured to be positioned toward uterus 105 when system 100 is in situ; see FIGS. 1 and 2). Rim 114 may define the uppermost or most proximal edge of system 100 and may include a sloped exterior wall 114a extending from the top (as oriented in FIGS. 5 and 6) of the rim 114 toward an interface with the exterior of body 102 and a sloped interior wall 114b extending from the top of the rim 114 toward an upper (as oriented in FIGS. 5 and 6) edge of inner cuff 108. Sloped interior wall 114b may be configured, sized, and/or shaped to facilitate entry of the cervix 101 into the proximal opening 104 and interior passageway 170 by funneling, or guiding, the end of cervix 101 along sloped interior wall 114b during placement of system 100 around cervix 101 in vagina 103. Sloped interior wall 114b may be angled by, for example, 20-85 degrees (20-85°) or between about five degrees (5°) and about sixty degrees (60°) in relation to a longitudinal axis (represented as a vertically-oriented dashed line superimposed on FIGS. 5 and 6) of system 100 to, for example, guide cervix 101 into internal passageway 170 when placing system 100 in situ (see FIGS. 1 and 2). In some embodiments, the rim 114 may extend 1-1-mm above an upper (as oriented in FIGS. 3-6), or proximal, edge of the inner cuff 108.

Figures 29, 30, 31:
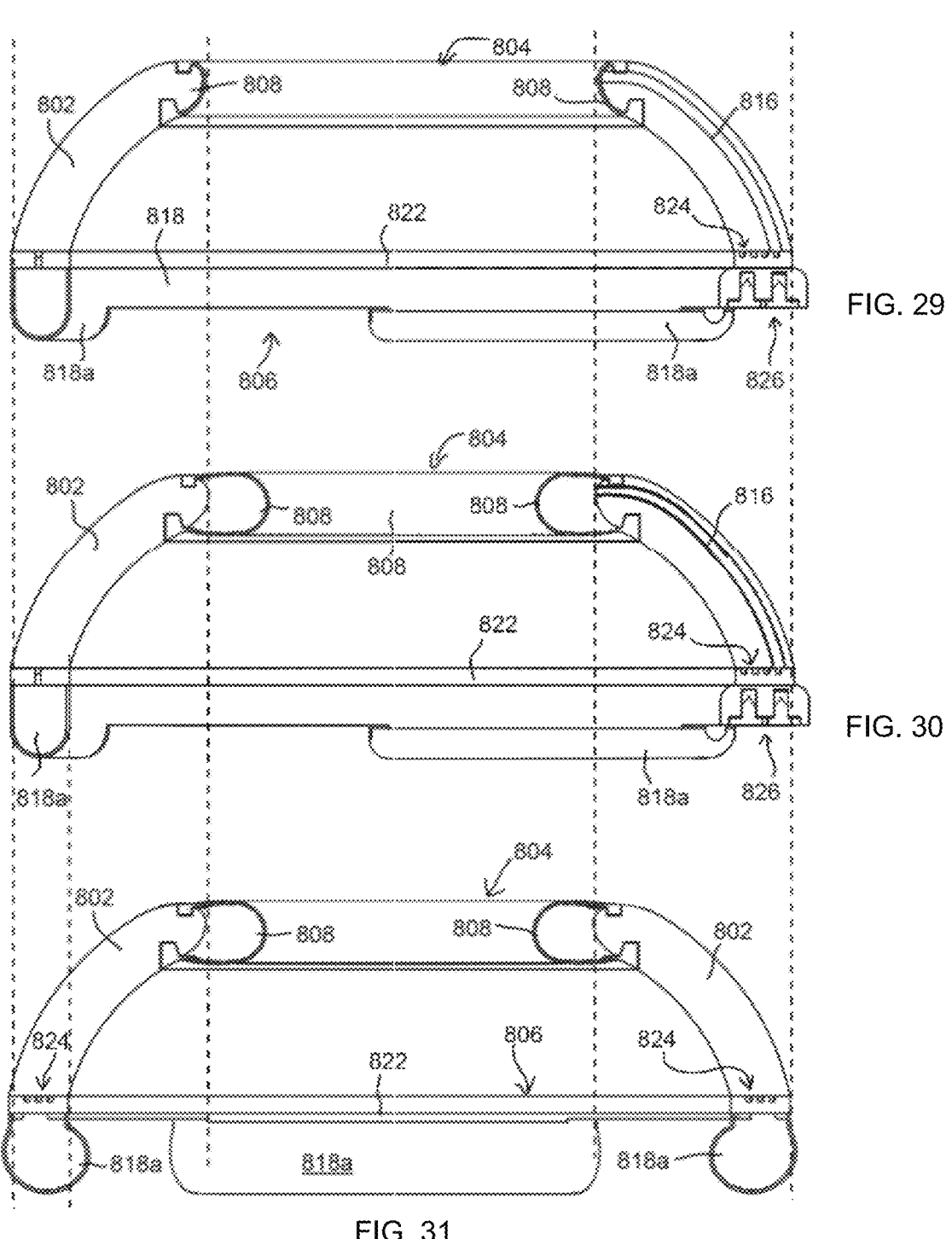
FIG. 29 illustrates a sectional side elevation view taken along sectioning line XXVI-XXVI of FIG. 25, depicted with the inner cuff and the positioning balloon each in the deflated state, in accordance with some embodiments of the present invention.
FIG. 30 illustrates another sectional side elevation view taken along sectioning line XXVI-XXVI of FIG. 25 depicted with the inner cuff in an inflated state and the positioning balloon in a deflated state, in accordance with some embodiments of the present invention.
FIG. 31 illustrates a sectional side elevation view taken along line XXXI-XXXI of FIG. 25, depicted with the inner cuff and the positioning balloon each in the inflated state, in accordance with some embodiments of the present invention.

In some embodiments, system 100 may include an inflation media conduit 116 configured to be in fluid communication with inner cuff 108 via an inlet 120. Conduit 116 may be positioned on an exterior surface of body 102 and/or embedded within a wall 118 of the body 102 as shown in FIGS. 5 and 6. Fluid introduced to conduit 116 via inlet 120 may be communicated to and inflate inner cuff 108 and fluid extracted from inner cuff 108 via conduit 116 and inlet 120 may deflate inner cuff 108 during use according to one or more methods disclosed herein. Inlet 120 may be positioned on an exterior portion or surface of the body 102 so that it may be accessed by and/or removably coupled to an inflation device (e.g., syringe or tube) (not shown) for the purpose of adding and/or removing fluid from conduit 116 and/or inner cuff 108. In this way inner cuff 108 may be inflated and/or deflated in situ, without the need to remove system 100 from vagina 103 during treatment. Optionally, a valve (not shown) may be provided at or near the inlet 120 to regulate the flow of fluid into and out of the conduit 116. For example, a y-valve system, such as y-valve system 826 as illustrated in FIGS. 29 and 30 and discussed below may be used as a valve for inlet 120. Additionally, or alternatively, an inflation/deflation device such as inflation/deflation device 827, which includes a tube 828 and valves 830 as illustrated in FIG. 32, which are described in further detail below may be used to inflate and/or deflate inner cuff 108.

In some of the illustrated embodiments inner cuff 108 expands downward or away from the transverse plane of the proximal opening. Additionally, or alternatively, inner cuff 108 may expand substantially along the transverse plane of the proximal opening as, for example, depicted in the illustrative embodiments of cervical control systems 400 and 800 shown in FIGS. 14-18 and 29-30, respectively, and described in further detail below. For example, an inner cuff 808 may be configured to expand in a purely radial and concentric manner as sequentially depicted for system 800 in FIGS. 29 and 30.

Figures 7, 8:
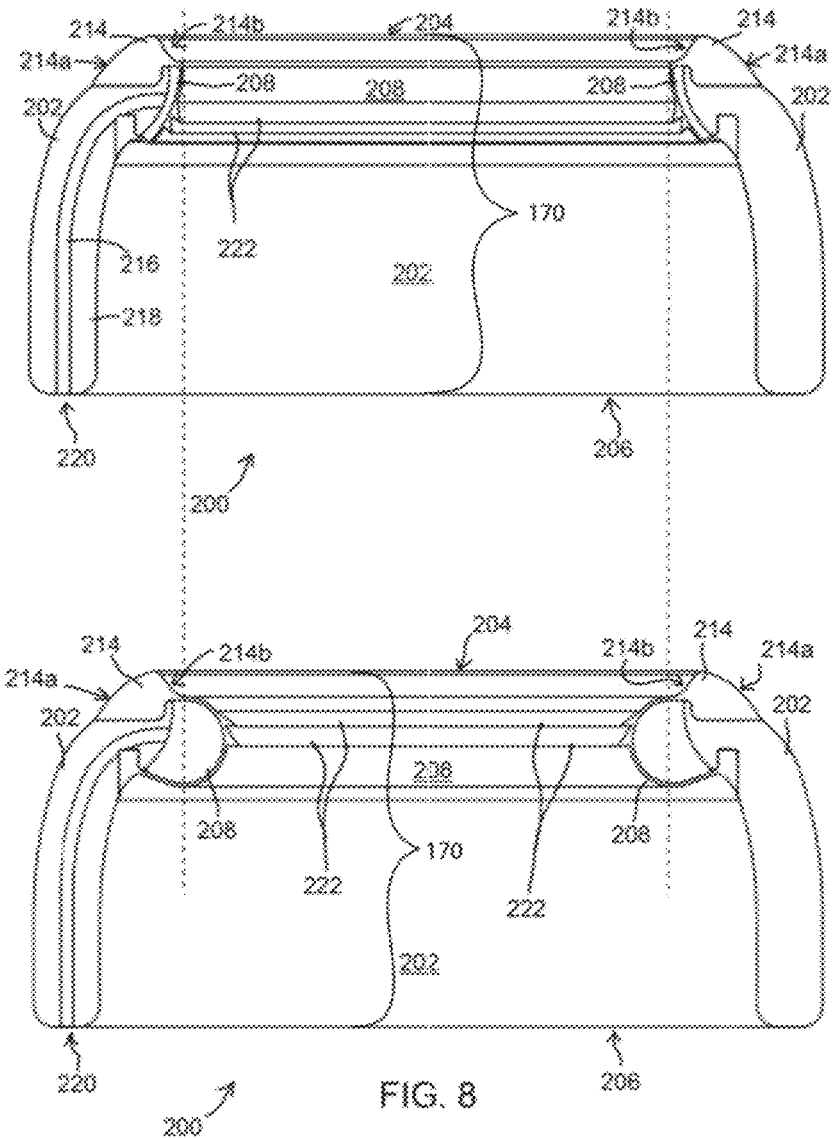
FIG. 7 illustrates a sectional side elevation view of another exemplary cervical control system depicted with an inner cuff in a deflated or neutral state, in accordance with some embodiments of the present invention.
FIG. 8 illustrates sectional side elevation view of the cervical control system of FIG. 7, depicted with the inner cuff in an inflated or expanded state, in accordance with some embodiments of the present invention.

FIGS. 7 and 8 provide cross section views of another cervical control system 200 that is similar to system 100 described above but includes some alternative and/or additional components and functions. Similar to the components of system 100, system 200 includes a main body 202, a proximal opening 204, a distal opening 206, an inner cuff 208, a raised, annular rim 214, an interior passageway 270, and an inflation media conduit 216 in a body wall 220. In addition, cervical control system 200 includes a plurality of mechanical engagement elements 222 in the form of, for example, one or more annular ridges, cleats, and/or teeth, positioned along an interior surface, or perimeter, of the inner cuff 208 that may extend into interior passageway 270. Mechanical engagement elements 222 may be configured to engage with cervical tissue to assist with holding cervical control system in place and/or prevent unintentional movement of cervical control system 200 (e.g., disengagement with cervix 101) caused by, for example, a low coefficient of friction between cervical control system 200 and cervix 101, which may be caused by, for example, bodily fluids present (e.g., discharge and mucus) on and around cervix 101 and vagina 103. In some embodiments, mechanical engagement elements 222 may be configured to grip the exterior of cervix 101, which may assist with holding cervix 101 in an elongated and/or closed state and/or mitigate or prevent cervix 101 from slipping out of inner cuff 208. In some embodiments, cervical control system 200 may include multiple rows of mechanical engagement elements 222 configured so that as inner cuff 208 expands, compressive force is directed onto cervix 101 by the inflated inner cuff 208 is substantially focused on the edge of one or more of the mechanical engagement elements 222 to encourage engagement between mechanical engagement elements 222 and cervix 101 so that, for example, inner cuff 208 may be held in place regardless of a coefficient of friction between cervix 101 and inner cuff 208.

In some embodiments one or more mechanical engagement elements 222 may include a ridge or extension that continuously encircles an entire interior perimeter of the inner cuff 208. Additionally, or alternatively, one or more mechanical engagement elements 222 may include individual segments or extensions that are positioned along and extend from and/or depress into the outer surface of inner cuff 208 such as segmented cleats provided by cervical control systems 1000 and 1100 of FIGS. 36-37 and 51-54 and discussed herein. When mechanical engagement elements 222 include segmented ridges, an end of each ridge segment may be chamfered, or tapered, for comfort and/or to concentrate more of the compressive force from interior cuff 208 to a smaller surface area in contact with cervix 101.

Mechanical engagement elements 222 may extend from and/or be depressed into an exterior surface of inner cuff 208 by approximately 0.1 mm-10 mm and, in many embodiments may extend from and/or be depressed into an exterior surface of inner cuff 208 by approximately 1.5-6 mm or 3 mm. At times, mechanical engagement elements 222 may be formed during a process for manufacturing inner cuff 208 and/or may be made from a similar material as inner cuff 208 (e.g., flexible silicone) by being integrally formed or molded with inner cuff 208. Additionally, or alternatively, mechanical engagement elements 222 may be formed of different material than inner cuff 208, such as a rigid polymer (e.g., polyether ether ketone (PEEK), a higher durometer silicone than that used for inner cuff 208, and/or a semi-flexible metal (e.g., 316L stainless steel), for example. In these embodiments, mechanical engagement elements 222 may be affixed to an exterior surface of inner cuff 208 and/or may be formed when inner cuff 208 is formed as part of the manufacturing process for inner cuff 208 and/or mechanical engagement elements 222. When mechanical engagement elements 222 are formed separately from inner cuff 208, they may be adhered to the external surface of inner cuff 208 via, for example, an over-molding process, a bonding (e.g., chemical, thermal, and/or vibrational), and/or a fixation process that may use a mechanical fastener (e.g., a clip or snap).

Figures 12, 13:
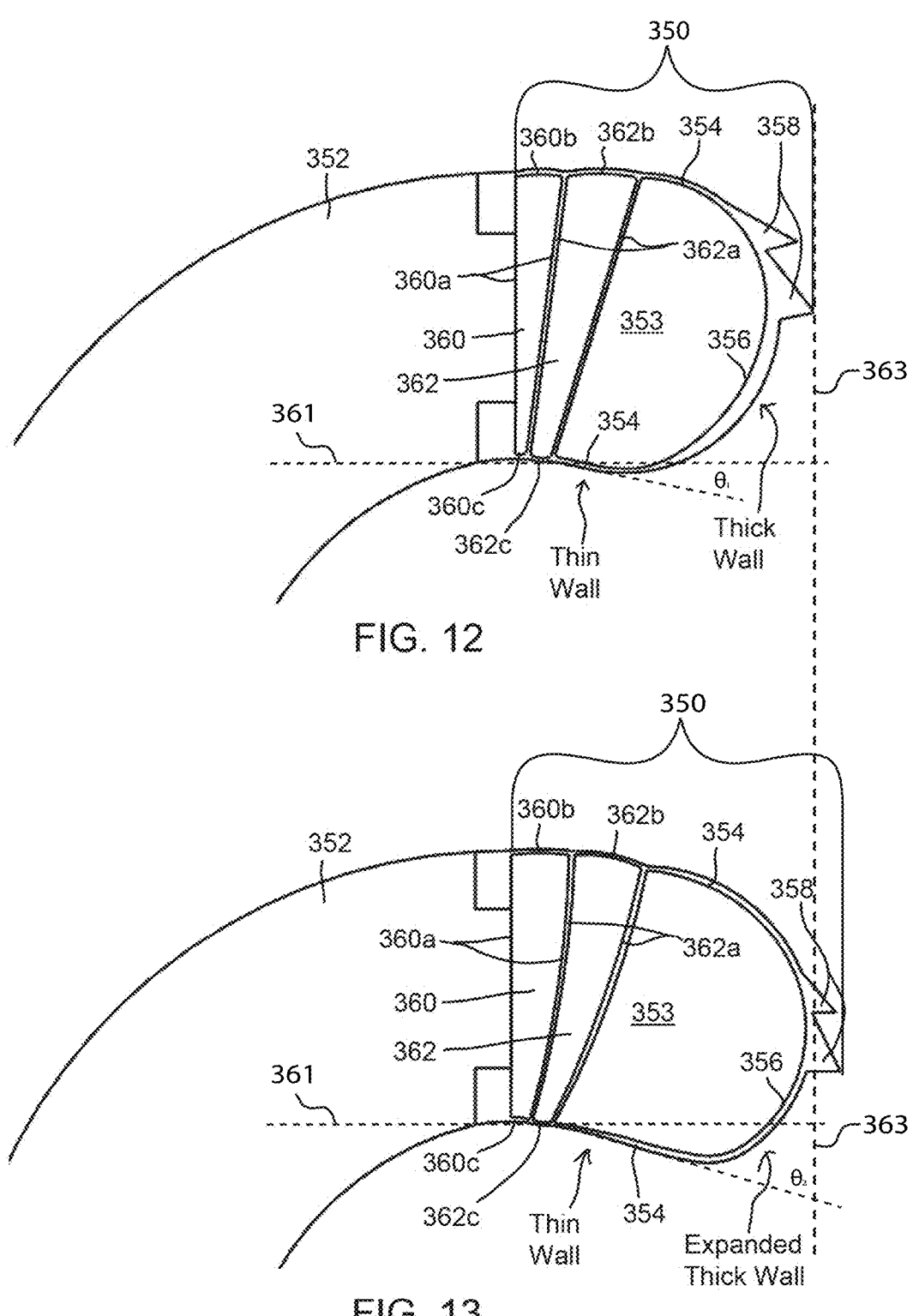
FIG. 12 illustrates a radial, sectional side elevation view of a portion of another inner cuff for a cervical control system, depicted in a deflated or neutral state, in accordance with some embodiments of the present invention.
FIG. 13 illustrates radial, sectional side elevation view of the portion of inflatable cuff of FIG. 12, depicted in an inflated or expanded state, in accordance with some embodiments of the present invention.

In some embodiments, one or more of the cervical control systems disclosed herein may include inner cuffs that utilize various structural and/or geometrical features to achieve expansion in a desired (e.g., downward) direction relative to a transverse plane of their respective proximal openings, as will be discussed in further detail below. For example, in some embodiments (see e.g., FIGS. 9-13 and the discussion below), the inner cuff may be formed with a non-uniform wall thickness along a radial cross section thereof and, upon expansion, this inner cuff may expand in the direction of the thickest portion of the wall (i.e., the desired expansion direction). Continuing with this example, sequential FIGS. 12 and 13 depict an exemplary inner cuff expansion along a desired expansion direction wherein inner cuff expands at the thickest portion of inner cuff wall in a downward (as oriented in FIGS. 9-13). In embodiments having an inner cuff that forms a non-circular proximal opening, expanded portions of an inflated inner cuff may utilize a non-uniform wall thickness, while the recessed portions may have generally uniform wall thickness, for example.

Figures 9, 10A, 10B, 11:
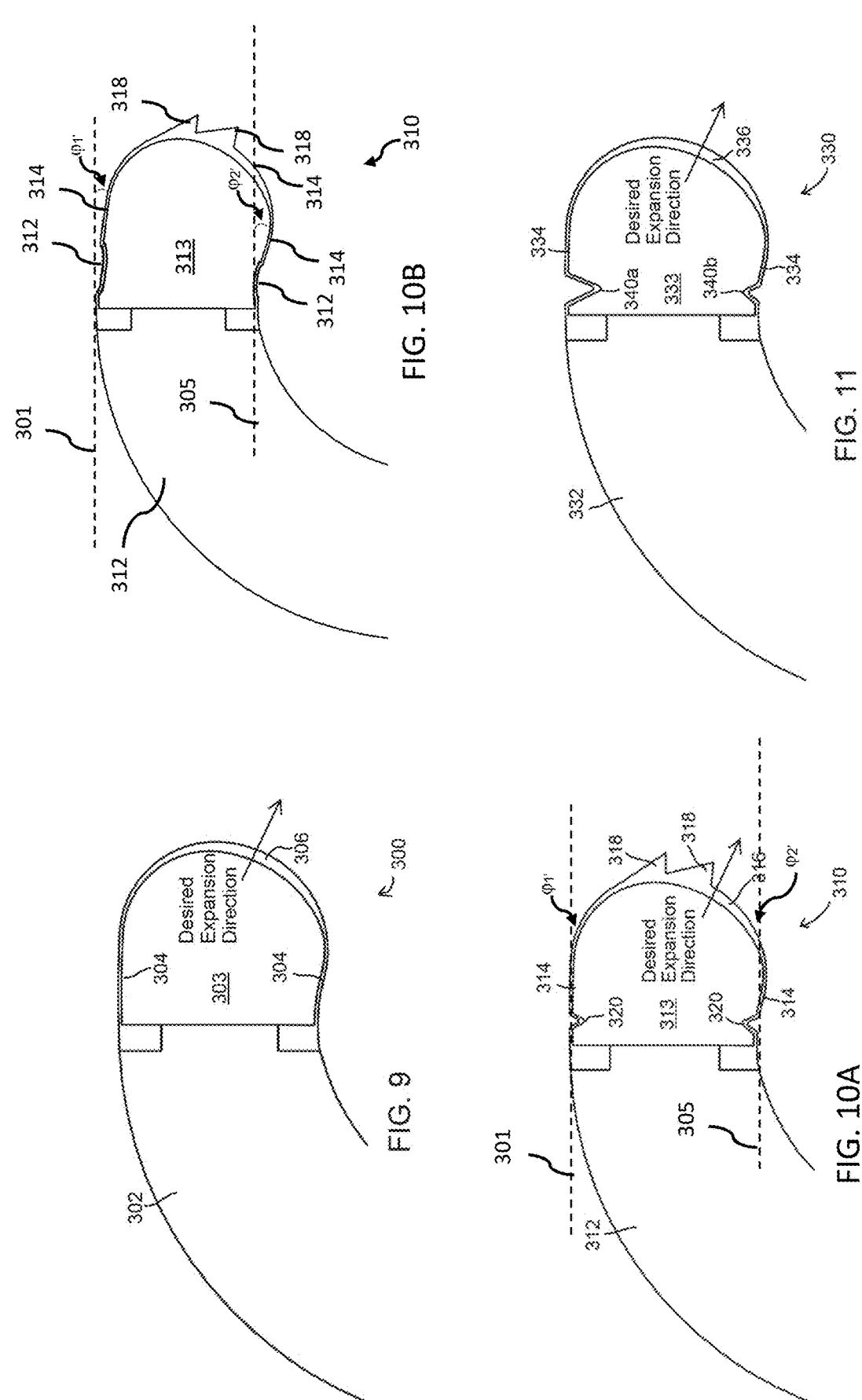
FIG. 9 illustrates a radial, sectional side elevation view of a portion of another inner cuff for a cervical control system, in accordance with some embodiments of the present invention.
FIG. 10A illustrates a radial, sectional side elevation view of a portion of another inner cuff for a cervical control system in a neutral state, in accordance with some embodiments of the present invention.
FIG. 10B illustrates a radial, sectional side elevation view of the portion of the inner cuff of FIG. 10A when in an expanded state, in accordance with some embodiments of the present invention.
FIG. 11 illustrates a radial, sectional side elevation view of a portion of another inner cuff for a cervical control system, in accordance with some embodiments of the present invention.

FIG. 9 is a cross section view of a portion of a cervical control system like cervical control systems 100 or 200 that includes an exemplary inner cuff with varying wall thickness 300 coupled to a proximal portion of a wall 302 of a cervical control system (such as systems 100 or 200 described above) is illustrated in the cross section view of FIG. 9. Inner cuff 300 includes a main inflatable bladder or chamber 303 that is defined by upper and lower thin-walled portions 304 and a thicker wall or thick-walled portion 306 between the thin-walled portions 304 at a proximal portion of inner cuff 300. Upper and lower thin-walled portions 304 may be generally parallel with one another and a transverse plane of the proximal opening formed by inner cuff 300 (not shown) like proximal openings 104 and 204. When inner cuff 300 comprises flexible silicone thick-walled portion 306 will expand more upon inflation of inner cuff 300 than the thin-walled portions 304 due to the expansion properties of the flexible silicone and, this differing degree of expansion may effectively expand cuff 300 in a desired expansion direction both radially toward the center of the proximal opening and downward away from the transverse plane of the proximal opening.

Stated differently, during inflation, thin-walled portions 304 may expand more quickly initially than the thick-walled portion 306, until the thin-walled portions 304 each reach maximum expansion, at which point they will no longer expand, and the remaining expansion of inner cuff 300 will occur at the thick-walled portion 306. Example wall thicknesses for inner cuff 300 include thin-walled portions 304 ranging between about 0.004 inches and 0.060 inches thick (e.g., 0.004-0.008, 0.005-0.010, 0.010-0.015, 0.015-0.020 inches, 0.020-0.040 inches, 0.020-0.060 inches and overlapping ranges therein), and thick-walled region 306 ranges between about 0.010 inches to 0.100 inches thick (e.g., 0.01-0.03, 0.03-0.07, 0.07-0.1 inches and overlapping ranges therein). In one embodiment the different portions, e.g., thin-walled portions 304 and thick-walled portion 306, may be formed of silicones having different durometers, which may further facilitate expansion of cuff 300 in the desired direction. In some cases, the selected wall thickness for thin-walled portions 304 and/or thick-walled portion 306 may be dependent on the material hardness level or durometer of the material being used to manufacture inner cuff 300. For example, when inner cuff 300 comprises silicone, the selected wall thickness may be dependent on the silicone durometer.

FIGS. 10A and 10B are cross section views of a portion of a cervical control system like cervical control systems 100 or 200 that includes another exemplary inner cuff with varying wall thicknesses 310 and is shown coupled to a proximal portion of a wall 312 of the body of the cervical control system when inner cuff 310 is in a neutral state (FIG. 10A) and an expanded state (FIG. 10B). Inner cuff 310 has a similar structure to cuff 300 and includes a main inflatable bladder or chamber 313, thin-walled portions 314, and a thick-walled portion 316, which function in substantially the same manner as the corresponding features of inner cuff 300. In addition, inner cuff 310 also includes a pair of ridges, cleats, or teeth 318, which are similar in structure and function to the mechanical engagement element 222 described above for cervical control system 200 and illustrated in FIGS. 7 and 8. Inner cuff 310 also includes a pair of buckled wall segments 320 in respective thin-walled portions 314 (FIG. 10). In the neutral, unexpanded state (see FIG. 10A), the buckled wall segments 320 of inner cuff 310 retain their buckled shape, as illustrated in FIG. 10A. As inner cuff 310 is inflated, buckled wall segments 320 extend and flatten to provide the initial expansion of inner cuff 310 as shown in FIG. 10B, which permits inner cuff 310 to expand both radially toward the center of the proximal opening and in a downward (as oriented in FIGS. 10A and 10B) direction, which is illustrated with regard to an upper 301 and a lower 305 (as oriented in FIGS. 10A and 10B) reference line. When in a neutral state an angle $\varphi_1$ between upper reference line 301 and upper thin-walled portion 314 may be approximately 0-6 degrees and an angle $\varphi_2$ between lower reference line 305 and lower thin-walled portion 314 may be approximately 0-6 degrees.

Once inner cuff 310 expands due to inflation media entering and/or being pushed into inner chamber 313, buckled wall segments 320 may extend and/or substantially flatten out (or unbuckle), the remainder of the expansion of inner cuff 310 may occur at thick-walled portion 316. Additionally, or alternatively, when inner cuff 310 expands, an angle $\varphi_{1'}$ or between upper reference line 301 and upper thin-walled portion 314 may increase to approximately 3-20 degrees or 10 degrees and an angle $\varphi_{2'}$ between lower reference line 305 and lower thin-walled portion 314 may In one embodiment multiple buckled wall segments may be provided at the upper and/change to 2-30 (negative 2-30) degrees so that inner cuff 310 extends in a downward desired direction and/or through a desired displacement as shown. In some embodiments, multiple (e.g., 3, 4, 5, 6, or 8) buckled wall segments may permit extended expansion of inner cuff 310 without inner cuff 310 reaching a limit of elastic deformation. It will also be appreciated that a buckled wall segment 320 may be provided at only the upper or lower portion of inner cuff, to permit the inner cuff to expand in a desired direction and/or through a desired displacement.

FIG. 11 is a cross section view of a portion of a cervical control system like cervical control systems 100 or 200 that includes another embodiment of an inner cuff 330 coupled to a proximal portion of a wall 332 of the cervical control system. Inner cuff 330 includes features similar to inner cuffs 300 and 310 such as a main inflatable bladder or chamber 333, thin-walled portions 334, and a thick-walled portion 336 and these features function in substantially the same manner as the corresponding features of inner cuffs 300 and 310. In addition, inner cuff 330 also includes a first, relatively large, buckled wall segments 340_a_ positioned within an upper (as oriented in FIG. 11) first thin-walled portion 334 and a second, relatively small, buckled wall segment 340_b_ positioned within a lower thin-walled segment 334. In the neutral, unexpanded state, first and second buckled wall segments 340_a_ and 340_b_ of inner cuff 330 retain their buckled shape, as illustrated in FIG. 11 and, as inner cuff 330 is inflated, the buckled wall segments 340_a_ and 340_b_ extend and flatten. Because first buckled wall segment 340_a_ is larger than second buckled wall segment 340_b_, it is extendable to a longer length than second buckled wall segment 340_b_, thus permitting inner cuff 330 to expand both radially toward the center of the proximal opening and downward away from the transverse plane of the proximal opening in a desired expansion direction as shown in FIG. 11.

FIGS. 12 and 13 are cross section views of yet another embodiment of a portion of a cervical control system like cervical control systems 100 or 200 that includes an inner cuff 350 in a neutral, or unexpanded, configuration and in an expanded configuration, respectively. Inner cuff 350 that is coupled to a proximal portion of a wall 352 of the cervical control system. Inner cuff 350 includes some features that are similar to inner cuff(s) 300 and 310, such as a main inflatable bladder or chamber 353, thin-walled portions 354, a thick-walled portions 356, and a pair of ridges, cleats, or teeth 358 (like teeth 318 of FIG. 10), which each function in substantially the same manner as the corresponding features of cuffs 300 and 310. Inner cuff 350 does not include buckled wall segments but does include a first inflatable bladder, or chamber, 360 and a second inflatable bladder, or chamber, 362. Second inflatable bladder 362 is positioned between first inflatable bladder 360 and main inflatable chamber 353 and first inflatable bladder 360 is positioned between second inflatable bladder 362 and wall 352. First and second inflatable bladders 360 and 362 are adjacent to and substantially co-axial with one another and the main chamber 353, wherein first inflatable bladder 360 is defined as an elongated trapezoidal cross sectional shape with two elongated side walls 360_a_, an upper (as oriented in FIG. 12) wall 360_b_, and a bottom wall 360_c_ that is shorter than upper wall 360_b_. Second inflatable bladder 362 is defined as an elongated trapezoidal cross sectional shape with two elongated side walls 362_a_, an upper (as oriented in FIG. 12) wall 362_b_, and a bottom wall 362_c_ that is shorter than upper wall 360_b_. The relatively longer length of upper walls 360_b_ and 362_b_ when compared with lower walls 360_c_ and 362_c_ act to collectively orient inner cuff 350 at an initial downward (as oriented in FIG. 12) facing angle θ1 of approximately 0.5-50 degrees relative to a lower (as oriented in FIG. 12) edge of inner cuff 350, which is represented by a horizontal dashed line 361 superimposed on FIG. 12 and may facilitate a downward expansion of inner cuff 350. Horizontal dashed line 361 may be parallel to a transverse plane of a proximal opening for a cervical control system incorporating inner cuff 350.

As inner cuff 350 is inflated, first and second bladders 360 and 362 may extend toward the radial center of the proximal opening (represented by a vertically-oriented dashed phantom line 363 superimposed on FIGS. 12 and 13 that is approximately parallel to the radial center of the proximal opening) or may remain substantially unchanged or uninflated. During inflation, main chamber 353 extends both radially inward toward vertically-oriented dashed phantom line 363 (i.e., the axial center of the proximal opening) and downward at an angle θ2 (e.g., 3-50 degrees) relative to the transverse plane of the proximal opening, which is represented by horizontally-oriented dashed phantom line 361. The relative radial and downward movements between inner cuff 350 when in a neutral and inflated state can be seen with reference to vertically- and horizontally-oriented phantom lines 363 and 361, which are in the same positions for both FIGS. 12 and 13 so that relative changes in position and orientation of inner cuff between the inflated and deflated states may be observed. In some embodiments, first and second bladders 360 and 362 and/or main chambers 353 may be in fluid communication with one another such that any inflation of inner cuff 350 inflates all three chambers together. Alternatively, first and second bladders 360 and 362 and/or main chambers 353 may be individually sealed and in fluid connection with a dedicated inflation media conduit such that first and second bladders 360 and 362 and/or main chambers 353 are individually addressable (e.g., inflatable or deflatable) by a provider.

In another embodiment, an inner cuff may have a first and second bladder that are oriented in a manner different from what is shown in FIGS. 12 and 13. For example, in some embodiments, an orientation of second bladder 362 may be reversed by 180 degrees so that may have upper wall 362b is positioned on a lower (as oriented in FIG. 12) edge of the inner cuff and lower wall 362c is positioned on an upper edge of the inner cuff. In such an embodiment, as the first and second bladders of the inner cuff are inflated, the two adjacent upper and lower walls of first and second bladders may extend in a manner similar to a sinusoidal wave, which may allow for greater capability to effect minor adjustments to the angle θ of the inner cuff relative to horizontally-oriented phantom line 361 so that a direction of application of compressive force applied to a cervix may be adjusted for a better and/or more secure fit. In yet another embodiment, first bladder 360 may have equal upper and lower wall lengths, while second bladder 362 has non-uniform upper and lower wall lengths as illustrated in FIGS. 12 and 13. In this embodiment, when first bladder 360 is inflated, it may expand substantially radially toward vertically-oriented phantom line 363 and second bladder may expand both radially inward toward vertically-oriented phantom line 363 (i.e., the axial center of the proximal opening) and downward relative to horizontally-oriented phantom line 361 (i.e., the transverse plane of the proximal opening).

Figures 14, 15:
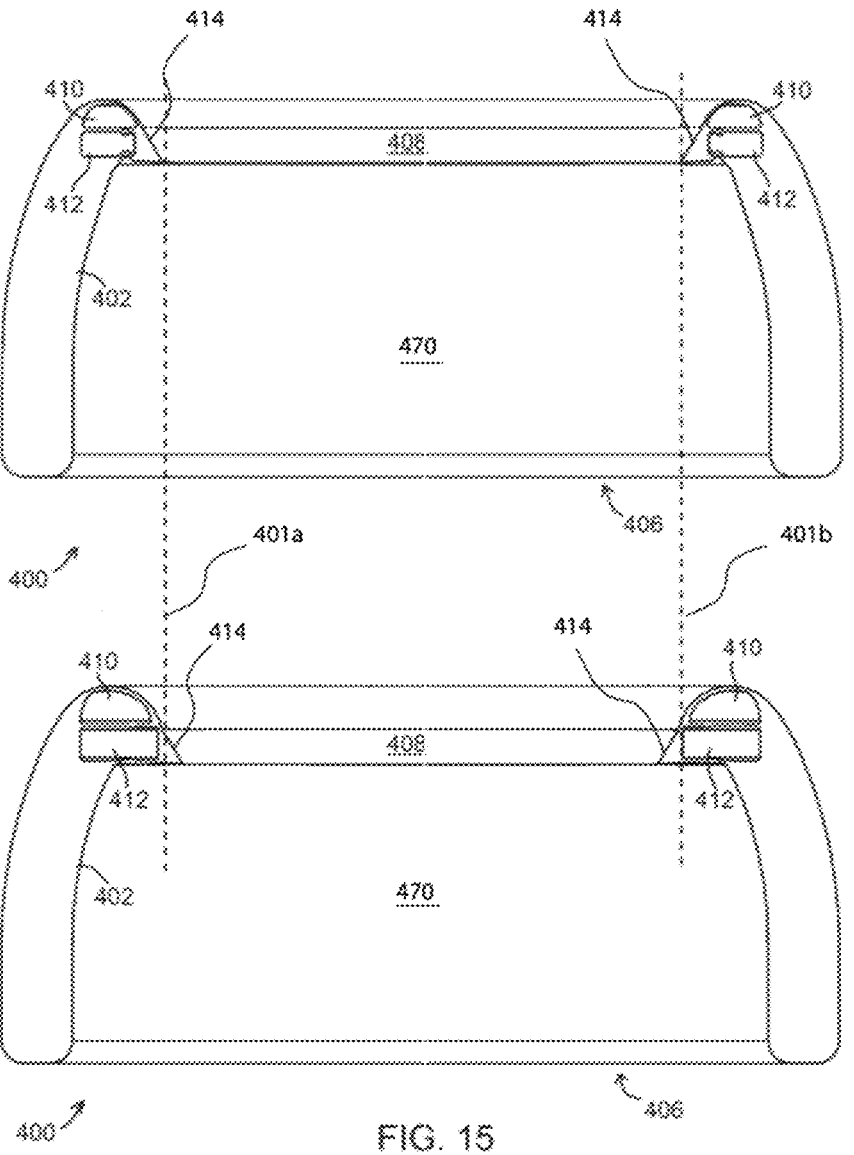
FIG. 14 illustrates a sectional side elevation view of another cervical control system, depicted with an inner cuff in a deflated or neutral state, in accordance with some embodiments of the present invention.
FIG. 15 illustrates another sectional side elevation view of the cervical control system of FIG. 14, depicted with the inner cuff in an inflated or expanded state, in accordance with some embodiments of the present invention.

FIGS. 14 and 15 provide cross sectional views of another cervical control system 400 (also referred to herein as "system 400") in a neutral, or deflated, state and an inflated state, respectively. Cervical control system 400 is similar to systems 100 and 200 described above but includes some alternative and/or additional components and capabilities. Similar to the components of systems 100 and 200, system 400 includes a main body 402, a proximal opening 404, a distal opening 406, an inner passageway 470, and an expandable annular inner cuff 408 that may be placed within a vagina like vagina 103 around a cervix like cervix 101 as shown in the cervical control system placement examples of FIGS. 1 and 2. In addition, inner cuff 408 includes a first annular bladder 410 positioned above (as oriented in FIG. 14) a second annular bladder 412 and mechanical engagement element(s) 414 (e.g., an annular ridge, tooth, or cleat) positioned on an exterior surface of both first and second annular bladders 410 and 412 as shown. Mechanical engagement elements 414 may be similar to mechanical engagement elements 222. Mechanical engagement elements 414, first annular bladder 410, and/or second annular bladder 412 may be integrally formed (e.g., over-molded) into an upper or proximal portion of main body 402 and/or unitarily formed with the proximal portion of main body 402.

First and/or second annular bladders 410 and 412 may be individually or collectively addressable and/or inflatable and, in some embodiments, may be configured to inflate in a proximal (e.g., toward uterus 105), radial (e.g., toward internal passageway 470), and/or distal (e.g., away from uterus 105). As shown in FIG. 14, when in a neutral, or uninflated state, first and second annular bladders 410 and 412 are recessed away from a first and second vertically-oriented phantom lines 410a and 401b and, when inflated both first and second annular bladders 410 and 412 expand radially toward first and second vertically-oriented phantom lines 410a and 401b as shown in FIG. 15. In one example, first annular bladder 410 is inflated first and second annular bladder 412 is inflated after inflation of first annular bladder 410, inner cuff 408 may expand in a generally proximal (e.g., toward the uterus 105) direction. In another example, second annular bladder 412 is inflated before first annular bladder 410 and inner cuff 408 may expand in a generally radially inward direction toward the axial center of the proximal opening 404.

Having two independently inflatable annular bladders like first and second annular bladders 410 and 412 allows for greater flexibility in tailoring how inner cuff 408 is inflated, oriented, positioned, and/or engages with a patient's cervix 101 so that, for example, it may be adapted to patient anatomy or her vaginal environment (e.g., accommodate varying levels of friction within vagina 103) without the need to manually adjust system's 400 position intravaginally and risk potential irritation and/or introduction of pathogens to cervix 101 or vagina 103.

FIGS. 16-18 provide sectional views an exemplary time series for how system 400 may be positioned within a patient's vagina 103 (see e.g., FIGS. 1 and 2) and cervix 101 may be positioned within interior passageway 470 of system 400 and inner cuff 408 may be inflated to engage cervix 101 to, for example, control, compress, and/or support, cervix 101 by reducing a size of a cervical opening 471. FIGS. 16-18 include first and second vertically-oriented phantom lines 401a and 410b in the same positions as that shown in FIGS. 15 and 16 so that a comparison between the figures may be easily observed. In particular, FIG. 16 is a sectional view of a portion cervix 101 that is dilated with an opening 471a being positioned within a proximal opening 404 so that a lower (as oriented in FIG. 16) of cervix 101 is in line with a lower edge of inner cuff 408. As the system 400 fitting procedure continues, cervix 101 is further inserted into interior passageway 470 as shown in FIG. 17. Inner cuff 408 is in a neutral, or uninflated, state in FIGS. 16 and 17. When cervix 101 is in position (e.g., fully inserted into interior passageway 470), first and second annular bladders 410 and 412 may be inflated (as described above with regard to FIG. 15) to extend to first and second vertically-oriented phantom lines 401a and 401b to apply a constrictive, compressive force around cervix 101 to begin to close and/or reduce a size of cervical opening to a closed configuration 471b as shown in FIG. 18. On some occasions, first annular bladder 410 may be inflated before second annular bladder 412 and this initial inflation of first annular bladder 410 may apply a force to cervix 101 that is normal to the transverse plane of the proximal opening 404, or in other words, apply a force to cervix 101 that is directed substantially upward toward the uterus 105, which may act to displace more of the cervical tissue and thereby urge it into the proximal opening 404 and descend into interior passageway 470 as shown in FIG. 18. Additionally, or alternatively, when first and second annular bladder 410 and 412 are inflated as shown in FIG. 18, mechanical engagement elements 414 may encroach onto and engages the exterior of the cervix 101 as shown, thereby holding system 400 in place.

In some embodiments, a cervical control system may include an external expandable positioning balloon configured to expand into and/or engage with vaginal walls when inflated and in situ. These external expandable positioning balloons may assist with, for example, orienting the cervical control system within the vagina to properly and/or optimally accept insertion of and/or engagement with the cervix and/or holding a cervical control system in place around the cervix within the vagina.

Figures 19, 20:
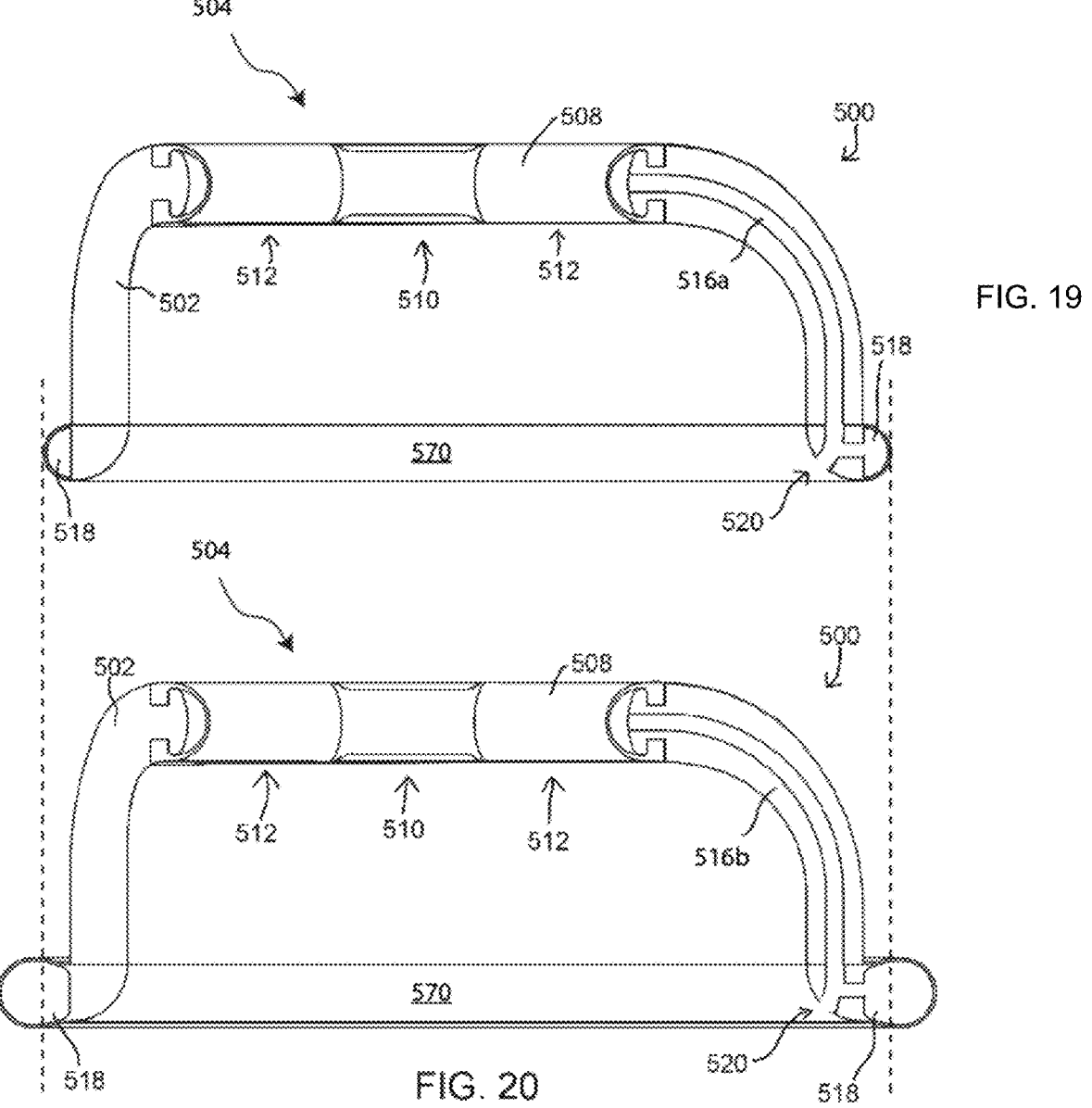
FIG. 19 illustrates a sectional side elevation view of another exemplary cervical control system, the cervical control system being depicted with a positioning balloon in a deflated or neutral state, in accordance with some embodiments of the present invention.
FIG. 20 illustrates a sectional side elevation view of the cervical control system of FIG. 19, depicted with the positioning balloon in an inflated or expanded state, in accordance with some embodiments of the present invention.

FIGS. 19 and 20 provide cross section views of another exemplary cervical control system 500 with an expandable annular inner cuff 508 (also referred to herein as "inner cuff 508") that includes components and functionality that may be similar to systems 100, 200, and 400 described above. System 500 includes a main body 502, a proximal opening 504, a distal opening 506, and an interior passageway 570. In addition, system 500 inner cuff 508 includes recessed portions 510, expandable portions 512, and a first inflation media conduit 516a configured to be in fluid communication with inner cuff 508 via a port 520 as, for example, described herein. Port 520 is also in fluid communication with an exterior, distal, cuff 518 (also referred to as "positioning balloon 518") via a second inflation media conduit 516b. Recessed portions 510 may be similar to recessed portions 110 and expandable portions 512 may be similar to expandable portions 112 (see e.g., FIGS. 3 and 4). Positioning balloon 518 may be sized, positioned, and/or configured to expand into and engage the wall of vagina 103 to hold system 500 in a desired position and/or orientation around cervix 101 and/or vaginal 103. In one embodiment the positioning balloon 518 may include similar structures and functions to inner cuffs 108, 208, 300, 310, 330, 350, and/or 408, described above, such as buckled wall portions 320, 304a, or 340b (FIGS. 10 and 11), non-uniform wall thickness as illustrated with inner cuffs 300, 310, 330, and 350 (FIGS. 9-13), and/or two or more bladders as illustrated with inner cuff 350 (FIGS. 12 and 13), and inner cuff 408 (FIGS. 14-18), for example. During inflation, positioning balloon 518 expands outward, away from the axial center of the distal opening 506, and therefore toward the vaginal wall 103. The outward expansion of positioning balloon 518 is illustrated in sequential FIGS. 19 and 20, with phantom lines added to more clearly show the relative movement of positioning balloon 518 in an expanded state depicted in FIG. 20 relative to its neutral state depicted in FIG. 19.

Figures 21, 22, 23, 24:
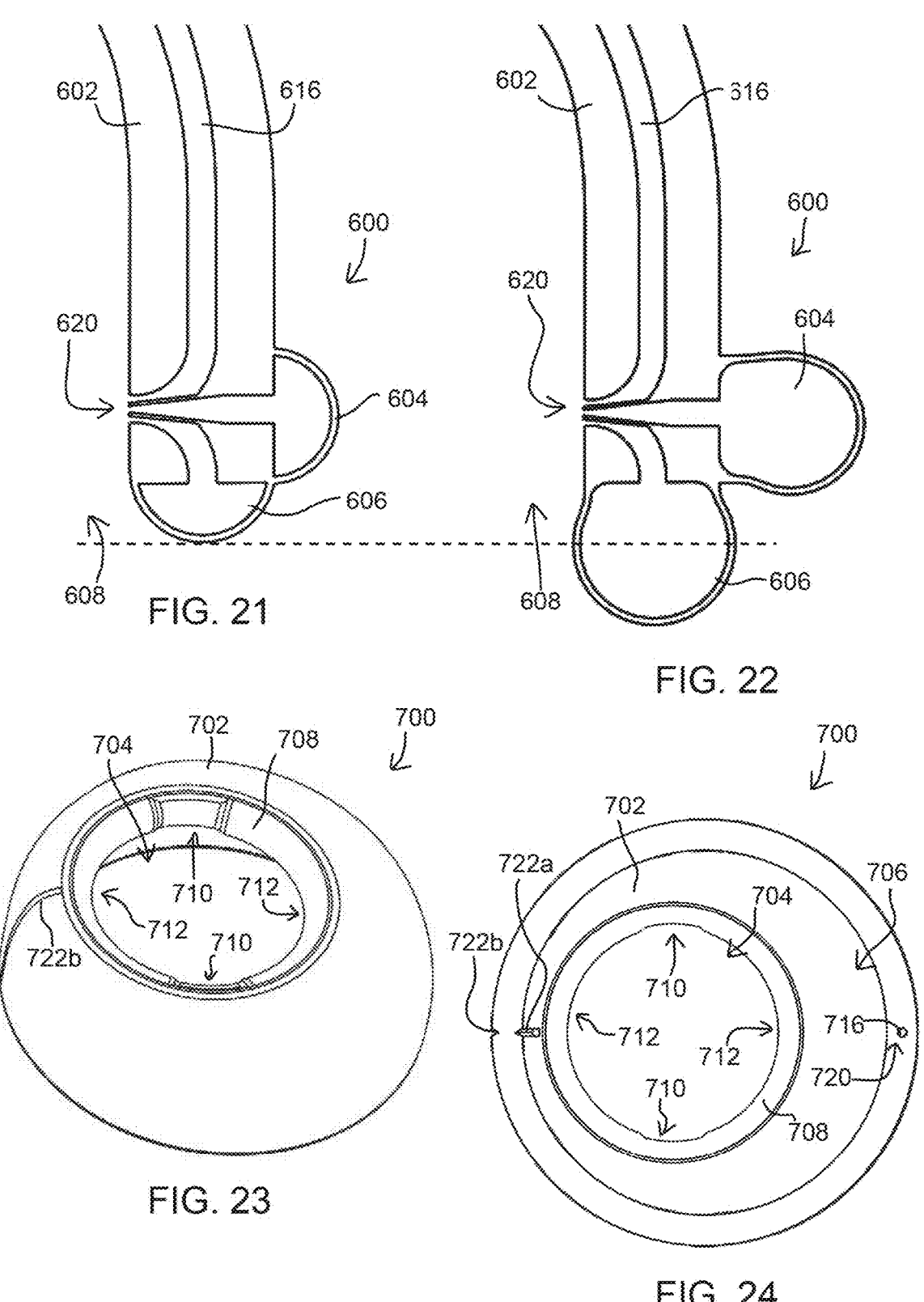
FIG. 21 illustrates a radial, sectional side elevation view of a portion of an exemplary cervical control system that includes a pair of positioning balloons, depicted in a deflated or neutral state, in accordance with some embodiments of the present invention.
FIG. 22 illustrates a radial, sectional side elevation view of the positioning balloons of FIG. 21, depicted in an inflated or expanded state, in accordance with some embodiments of the present invention.
FIG. 23 illustrates a top perspective view of another cervical control system depicted with an inner cuff and a positioning balloon each in a deflated or neutral state, in accordance with some embodiments of the present invention.
FIG. 24 illustrates bottom plan view of the cervical control system of FIG. 23, in accordance with some embodiments of the present invention.

An embodiment of an expandable cuff system or portion of a cervical control system 600 is illustrated in FIGS. 21 and 22 and is coupled to a distal portion and/or exterior of a wall 602 of a cervical control system (such as systems 100, 200, 400, or 500 described above). Inner cuff system 600 includes a pair of inflatable, annular bladders, or chambers, including a first or radial bladder 604 and a second or transverse bladder 606. The radial bladder 604 is positioned around an exterior perimeter of the distal portion of the body 602, and the transverse bladder is positioned along a distal end of the body 602. Upon inflation, the radial bladder 604 expands outward, away from the axial center of the distal opening 608 of system 600 in order to extend into the vaginal wall when in situ. Upon inflation, the transverse bladder 606 expands downwardly away from the distal end of body 602. In other words, the transverse bladder 606 expands in the direction opposite uterus 105. A phantom line is provided between sequential FIGS. 21 and 22 to more clearly show the relative expansion of the transverse bladder 606 from its neutral state in FIG. 21 to its expanded state in FIG. 22. In its expanded state, the transverse bladder 606 provides an increase in the overall length of system 600, which may permit a provider to accommodate patient anatomy and/or further engage the cervix 101 via an inner cuff (like the inner cuffs disclosed herein) positioned at an upper or proximal end of wall 602 and/or provide additional control of and/or support to cervix 101 and/or uterus 105.

In some embodiments, either or both of the radial bladder 604 or the transverse bladder 606 may include similar structures and functions to cuffs 108, 208, 300, 310, 330, 350, 408, 508 and/or 518, described above, such as buckled wall portions 320, 304a, or 340b (FIGS. 10 and 11), non-uniform wall thickness as illustrated with inner cuffs 300, 310, 330, and 350 (FIGS. 9-13), and/or two or more smaller bladders as illustrated with inner cuffs 350 and 408 (FIGS. 12-13 and 14-18, respectively), for example. While cuff system 600 is illustrated as having two bladders 604 and 606, in one embodiment, a single bladder or chamber may provide sufficient vaginal wall engagement while also increasing the overall length of system 600. For example, expansion elements may be provided along particular walls of the single bladder to provide the desired directional expansion. It is contemplated that system 600 (as well as any of the previous or following embodiments of a cervical control system) may be placed in the patient in an inverted manner in which the distal end faces and engages with the cervix 101 to support the cervix and the uterus 105. In an inverted orientation, the positioning balloon of the cervical control device is positionable in contact with the upper vaginal walls and the fornix region (e.g., the upper portions of the vagina, which extend into recesses created between the vaginal wall and the exterior of the lower portion of cervix) such that as the positioning balloon expands, it may provide support to the uterus 105 at the location where a prolapse would typically occur. In an embodiment where the positioning balloon expands in the transverse direction, the positioning balloon would distribute the load of the uterus 105 to a larger surface area along the vaginal wall (relative to the cervical control system oriented in a standard orientation with the inner cuff toward the uterus), which may reduce the risk of medical complications, such as from pressure sores and/or necrosis. In an embodiment where the positioning balloon expands both in the transverse direction and away from the main body (e.g., toward the uterus 105), the positioning balloon may provide upward support (which may be customized as needed) to the uterus while distributing the load of the uterus 105 to a larger surface area.

FIGS. 23 and 24 provide a top perspective and bottom view, respectively, of another embodiment of a cervical control system 700 that includes a body that is similar or substantially identical to cervical control system 100 described herein and illustrated in FIGS. 1-6. Like system 100, system 700 includes a body 702, a proximal opening 704, a distal opening 706, an inner cuff 708, recessed portions 710, expandable portions 712, a inflation media conduit 716, and an inlet 720 that may be configured and/or function in a manner corresponding to, for example, body 102, proximal opening 104, distal opening 106, inner cuff 108, recessed portions 110, expandable portions 112, inflation media conduit 116, and inlet 120, respectively, of system 100. In addition, system 700 includes interior and exterior relief notches 722a and 722b positioned within respective interior and exterior surfaces of body 702. Interior and exterior relief notches 722a and 722b extend substantially between the distal end of body 702 and inner cuff 708 and may be configured to expand and/or provide increased flexibility of body 702, which may facilitate collapsing or folding system 700 prior to insertion into, and/or upon extraction from the patient's vagina. For example, a provider may be able to fold the cervical control system such that it forms a leading edge or point with reduced cross sectional area to project through the vaginal opening more easily. In addition to aiding in insertion, the notches 722a and 722b may also provide a visual indication of which side is intended for initial insertion into the patient.

Figures 25, 26:
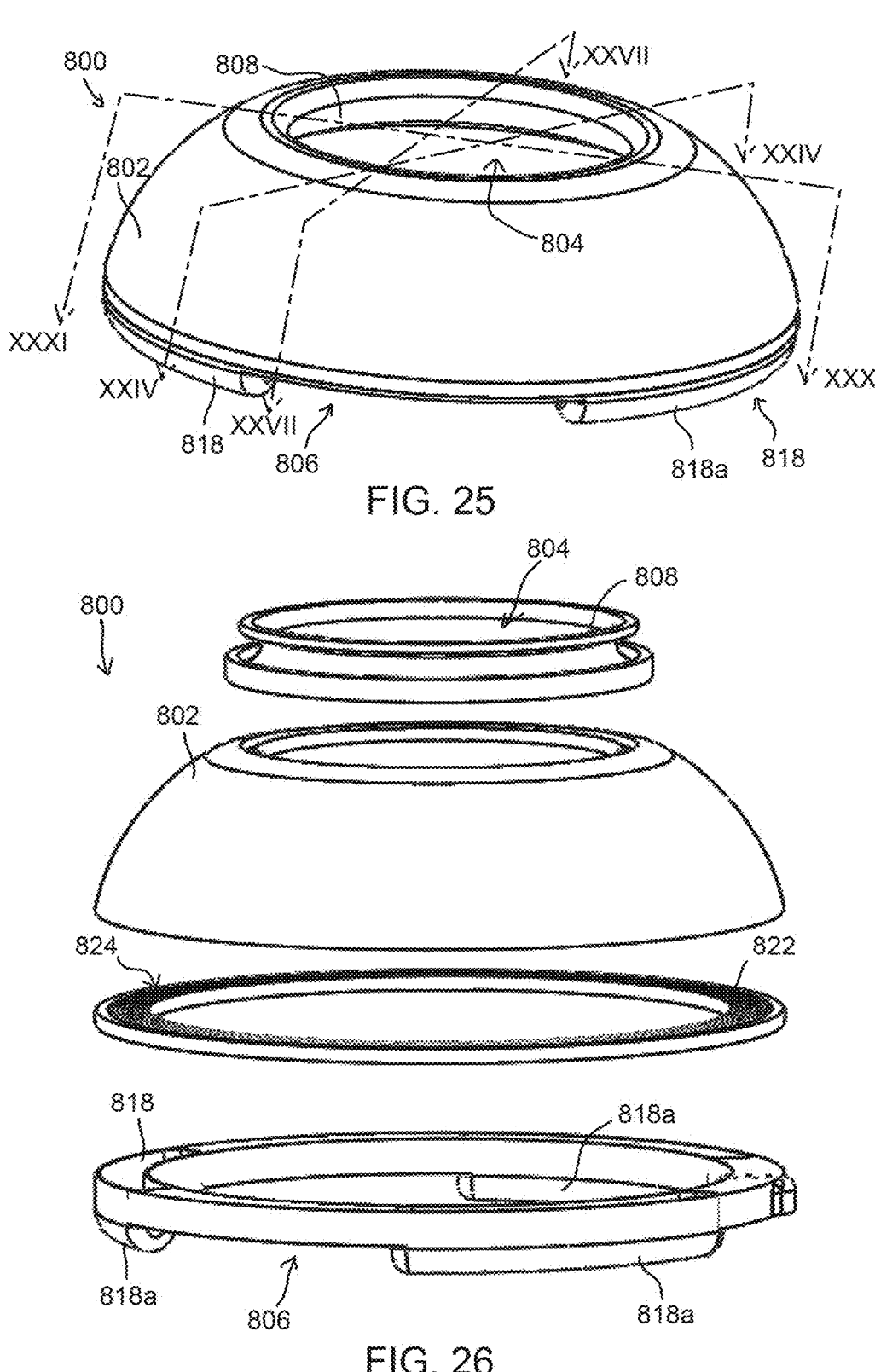
FIG. 25 illustrates a top perspective view of another cervical control system depicted with an inner cuff and a positioning balloon each in a deflated or neutral state, in accordance with some embodiments of the present invention.
FIG. 26 illustrates an exploded side perspective view of the cervical control system of FIG. 25, in accordance with some embodiments of the present invention.
Figure 27:
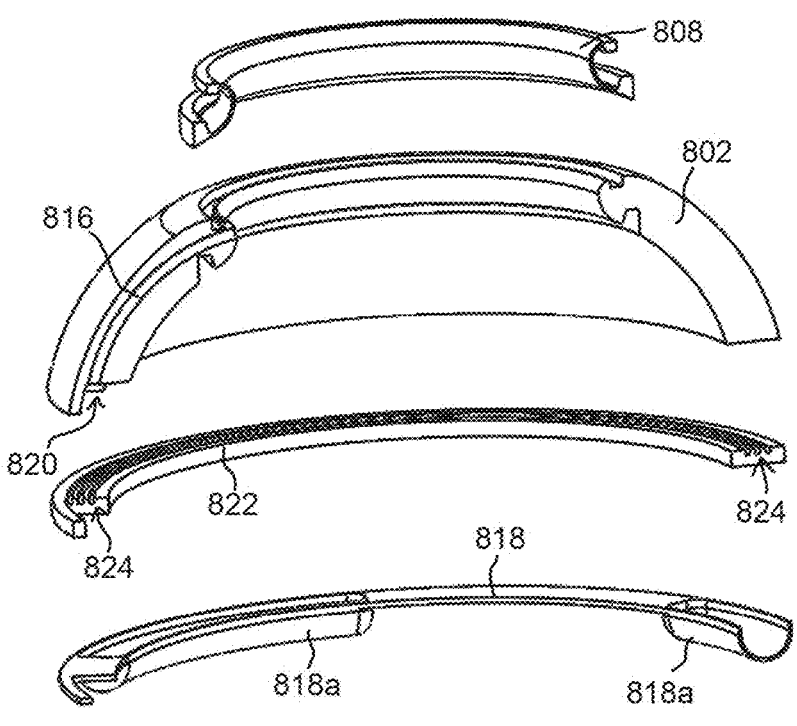
FIG. 27 illustrates an exploded sectional view of the components of the cervical control system of FIG. 25, viewed along sectioning line XXVII-XXVII of FIG. 25, in accordance with some embodiments of the present invention.
Figure 28:
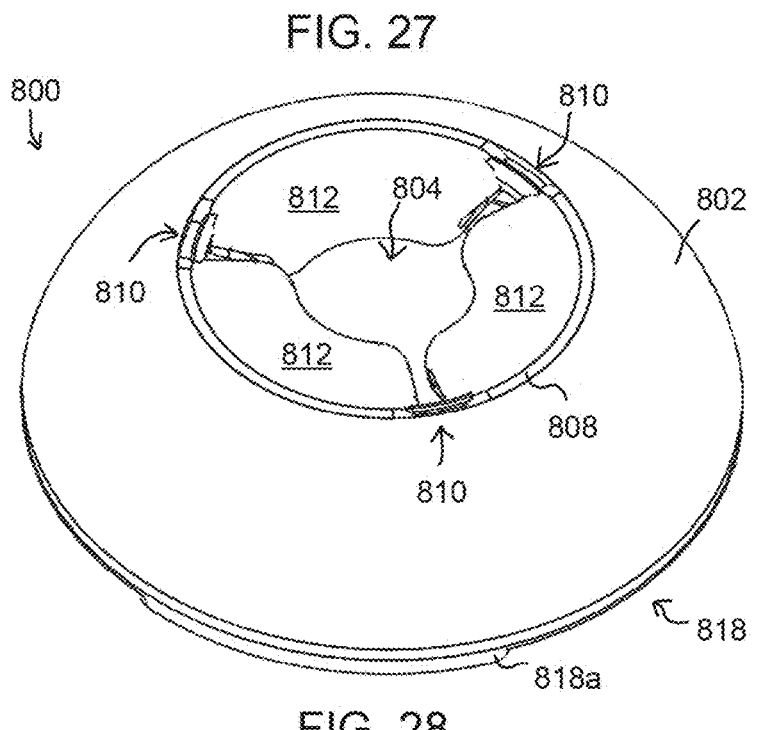
FIG. 28 illustrates another top perspective view of the cervical control system of FIG. 25, depicted with the inner cuff in an inflated or expanded state, in accordance with some embodiments of the present invention.
Figure 32B:
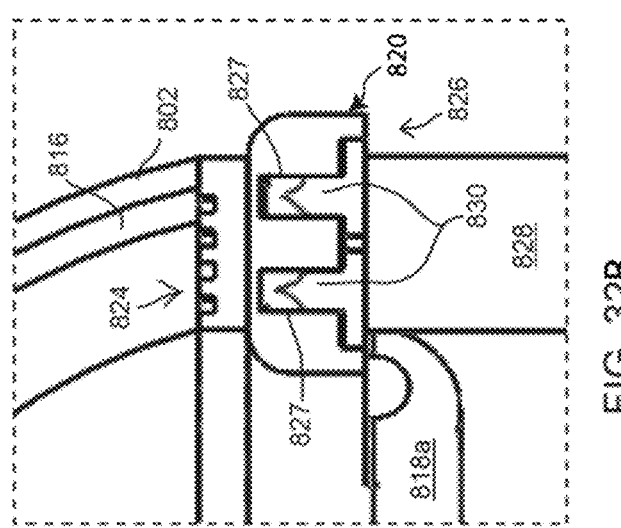
FIG. 32B illustrates an enlarged view of the region designated XXXIIA in FIG. 32A, in accordance with some embodiments of the present invention.
Figure 32A:
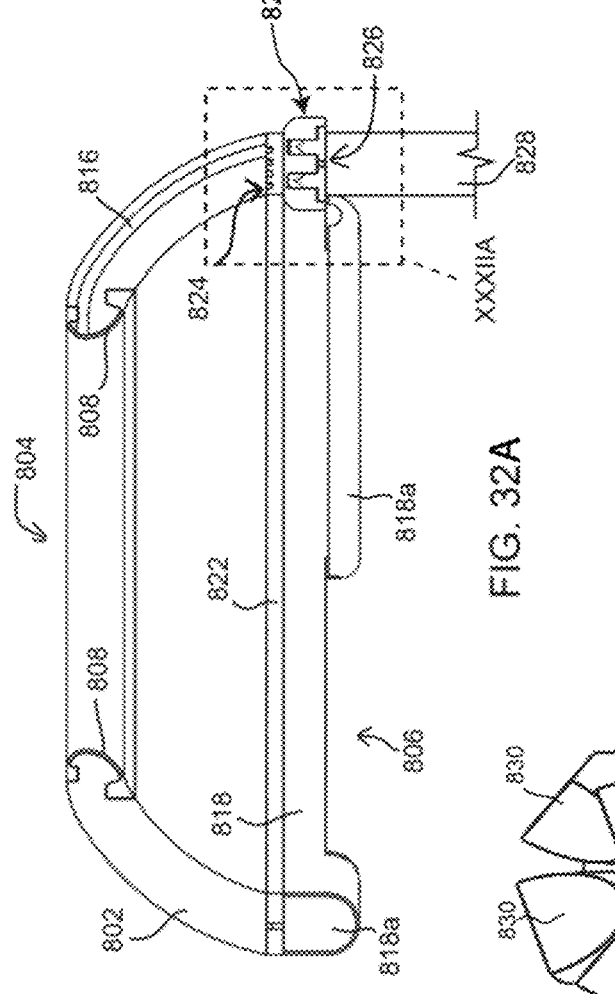
FIG. 32A illustrates another sectional side elevation view of the cervical control system of FIG. 29 and a quad lumen inflation system coupled with a valve system for inflating inner and/or positioning balloon(s) of the system inserted therein, in accordance with some embodiments of the present invention.
Figure 32C:
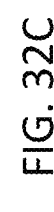
FIG. 32C illustrates a side perspective view of the quad lumen of FIG. 32A, in accordance with some embodiments of the present invention.
Figure 33:
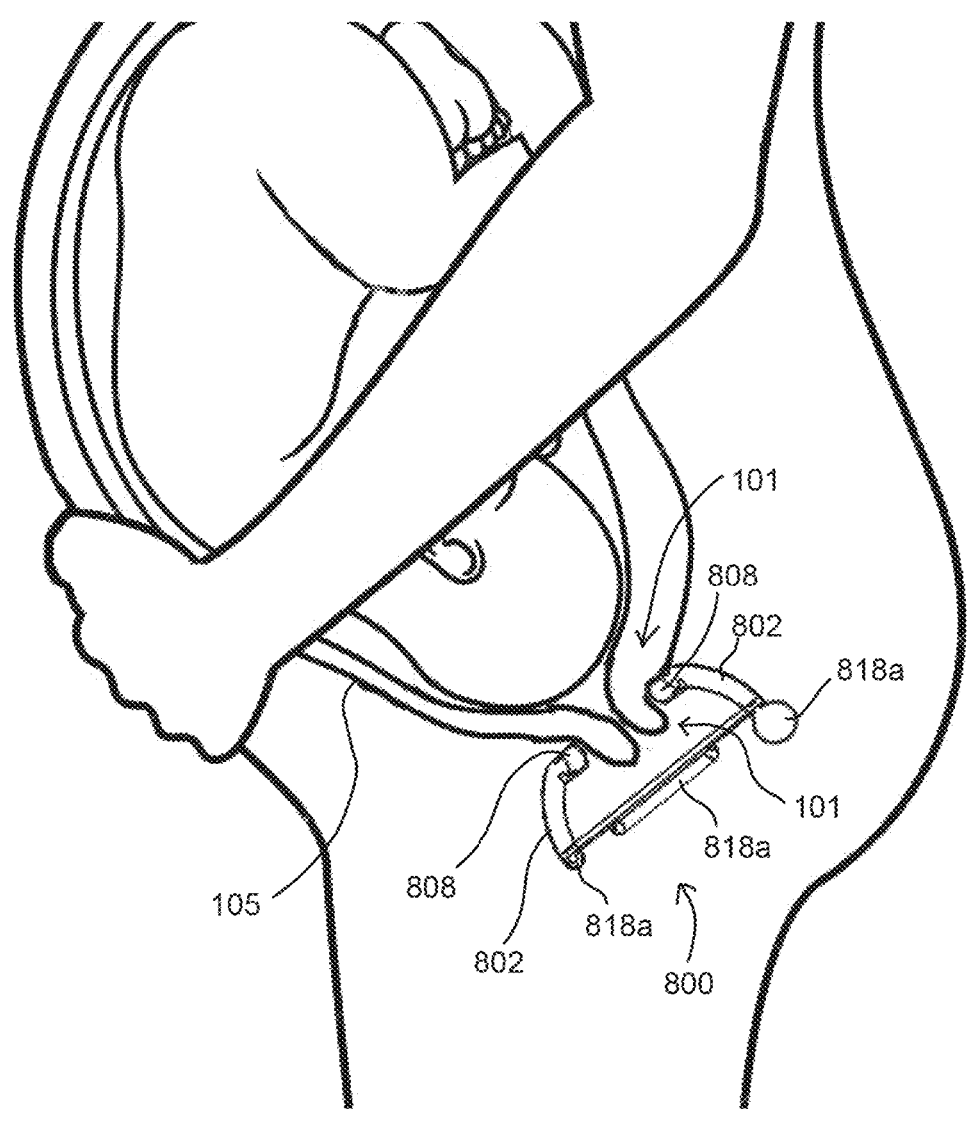
FIG. 33 illustrates a sagittal view of a patient with a single gestation, including a sectional side view of the cervical control system of FIG. 25 in the vagina of the patient to support the patient's cervix, in accordance with some embodiments of the present invention.
Figure 34:
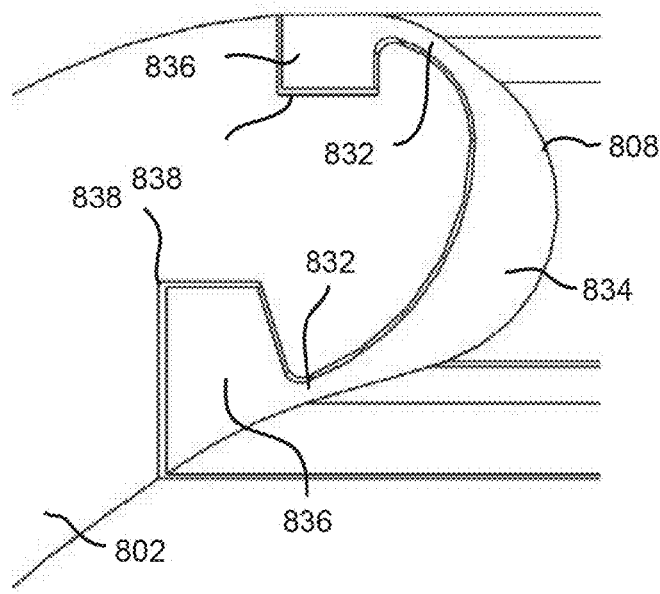
FIG. 34 illustrates a radial, sectional side elevation view of an inner cuff of the cervical control system of FIG. 25, in accordance with some embodiments of the present invention.

FIGS. 25-34 provide various views of another exemplary cervical control system 800 (also referred to herein as "system 800") that may have some features, components, and/or functionality with one or more of the cervical control systems and/or cervical control system components disclosed herein. In particular, FIG. 25 provides a perspective view of system 800 when in a neutral state; FIG. 26 provides an exploded view of system 800; FIG. 27 provides an exploded cross section view of system 800; FIG. 28 provides a top perspective view of system 800 when in an expanded state; FIG. 29 is a cross section view of system 800 with an inner cuff 808 and a positioning balloon 818 in a neutral, unexpanded state; FIG. 30 is a cross section view of system 800 with inner cuff 808 in an expanded, or inflated, state and a positioning balloon 818 in a neutral, unexpanded state; FIG. 31 is a cross section view of system 800 with inner cuff 808 and positioning balloon 818 in an expanded, or inflated, state; FIG. 32A is a cross section view of system 800 coupled to a source of inflationary media; FIG. 32B is a detailed view of a portion of FIG. 32A; FIG. 32C is a close up view of a portion of source of inflationary media; FIG. 33 is sagittal view of a pregnant woman with system 800 in situ; and FIG. 34 is a close up view of a portion of system 800.

System 800 includes a main body 802, a proximal opening 804, a distal opening 806, an internal passageway 870, an expandable annular inner cuff 808 (also referred to herein as "inner cuff 808") positioned proximate to proximal opening 804, and an inflation media conduit 816 (FIGS. 29 and 30). Inner cuff 808 includes three recessed portions 810 and three expandable portions 812, which are uniformly distributed around the proximal portion of the body 802 and define the proximal opening 804, which may be best seen in FIG. 28.

System 800 also includes an exterior expandable annular cuff or cuff system 818 (also referred to herein as "positioning balloon 818") positioned proximate to distal opening 806. Positioning balloon 818 may be configured and/or operable to expand distally away from the distal end of the body 802 and away from uterus 105 when inflated in situ. Positioning balloon 818 may include one or more inflatable bladders or bladder segments. In the embodiment of FIGS. 25-33, positioning balloon 818 includes three inflatable bladder segments 818a that are evenly spaced around the circumference of the distal end of the body 802 (see e.g., FIG. 26) but this need not always be the case. For example, positioning balloon 818 may include more (e.g., 4-8) or fewer (e.g., 2) inflatable bladder segments or the positioning balloon 818 may be formed of a single, continuous, uninterrupted bladder. FIG. 29 depicts the system 800 with the inner cuff 808 and the positioning balloon 818 each in a neutral or uninflated state, FIG. 30 depicts the system 800 with the inner cuff 808 in an inflated or expanded state and the positioning balloon 818 in a neutral or uninflated state, and FIG. 31 depicts the system 800 with the inner cuff 808 and the positioning balloon 818 each in an inflated or expanded state. Each of inflatable bladder segments 818a may be selectively and/or individually inflatable and an example of selective inflation of the bladders 818a is depicted in FIG. 33, in which one of the bladders 818a (positioned toward the patient's posterior) Of the positioning balloon 818 is inflated more than the other two bladders 818a.

During inflation, inner cuff 808 expands substantially inward, toward the axial center of the proximal opening 804 as shown in, for example, FIGS. 30 and 31, with phantom lines added to more clearly show the relative expansion of inner cuff 808 as it transitions from a neutral state (FIG. 29) to the expanded state depicted in FIG. 30. During inflation, the positioning balloon 818 and/or inflatable segments 818a expand both inwardly toward the axial center of the distal opening 806 and outwardly away from the axial center of the distal opening 806, and therefore toward vagina when in situ as sequentially illustrated in FIGS. 30 and 31, with phantom lines added to more clearly show the relative change in size when in an expanded state depicted as in FIG. 31 relative to its neutral state as depicted in FIG. 30.

As may be seen in, for example, FIGS. 26, 27, and 29-32, system 800 includes a lumen ring 822 positioned between the distal end of main body 802 and the positioning balloon 818. Lumen ring 822 includes a plurality of channels 824 open to and configured to provide fluid communication between bladder segments 818a, inflation media conduit 816, and an inlet 820. When system 800 is fully assembled with lumen ring 822 positioned between body 802 and positioning balloon 808, channels 824 form a plurality of closed lumens (as shown in, for example, FIGS. 29-32) with a distal side of body 802 forming the roof of the closed lumens. Each of the plurality of channels may be in fluid communication with an open port 827 of inlet 820 (see FIG. 32B) and an inflatable segment 818a of positioning balloon 810 so that, in some embodiments, individual inflatable bladders 818a may each be ported to a single lumen with the other end of the lumen being ported to an individual port 827 and, in this way, inflation and deflation of each inflatable bladder segment 818a may be individually controlled via insertion and/or extraction of fluid from a lumen and/or port 827.

Inlet 820 may be configured to cooperate with a multi-lumen inflation media delivery device 801, an example of which is shown in FIGS. 32A-32C. Multi-lumen inflation media delivery device 801 includes a multi-lumen tube 828 and an endcap 829 that includes four one-way valves 830 (e.g., check valves, one-way duck-bill valves, etc.) extending therefrom. One-way valves 830 may be sized, configured, and positioned on endcap so that they may be inserted into a respective port 827 of inlet 820 for the delivery and/or extraction of inflation media to/from a channel 824, inflatable bladder segment 818a, inner cuff 808, and/or positioning balloon 818 so that inflation/deflation of each inflatable bladder segment 818*a*, inner cuff 808, and/or positioning balloon 818 may be individually controlled to inflate and/or deflate these components as desired to properly fit and secure system 800 in the patient's vagina 103 and around cervix 101 so that cervix 101 may be controlled. The ability to address each of the bladders 808 and 818*a* may enable a care provider to redirect or reposition cervix 101 in a particular manner to, for example, close cervix 101, keep cervix 101 closed, alleviate pressure exerted on cervix, and/or and stabilize the cervix 101. For example, the provider may change the orientation of the system 800 by selectively inflating one or more of the positioning balloon bladders 818*a*. For example, in FIG. 33, bladder segment 818*a* positioned on the posterior side of the patient is more inflated than bladder segment 818*a* positioned on an anterior side of the patient so that, for example, system 800 may be pushed toward the patient's anterior side.

It is contemplated that the lumens within tube 828 may provide passageways for items to be delivered to the system 800, for example, nitinol wires, springs, electrical wiring, or pharmaceuticals/medications may be passed through the tube 828 to the system 800. The tube 828 may be removably coupled to the system 800, which may provide easier movement for the patient, or the tube 828 may be permanently bonded to the cervical delivery system with the tube remaining inside the patient and/or extending to the exterior of the vagina 103.

In some embodiments, inner cuff 808 includes variable wall thicknesses with upper and lower thin-walled portions 832 and a thicker wall or thick-walled portion 834 at a proximal portion of inner cuff 808 between the upper and lower thin-walled portions 832, which may be most clearly seen in FIG. 34. In these embodiments, inner cuff 808 is coupled to the proximal end of body 802 with teeth 836 that engage grooves 838 formed in the proximal end of body 802. The thin-walled portions 832 and thick walled portion 834 function in similar fashion to portions 304 and 306 of inner cuff 300 illustrated in FIG. 9 and described above.

Figure 35:
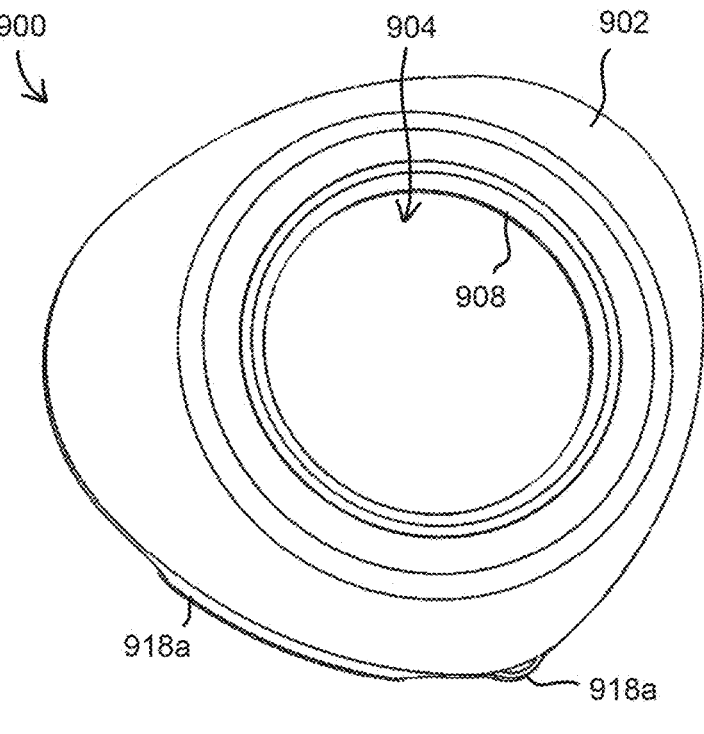
FIG. 35 illustrates a top view of another cervical control system depicted with an inner cuff and a positioning balloon each in a deflated or neutral state, in accordance with some embodiments of the present invention.

FIG. 35 provides a top view of another exemplary cervical control system 900 that is similar to systems 100, 200, 400, 500, 700, and 900 described above, but has a body 902 that asymmetric and non-circular or non-spherical. Like systems 100, 200, 400, 500, 700, and 800, system 900 includes a main body 902, a proximal opening 904, a distal opening (not shown), an expandable annular inner cuff 908 positioned proximate proximal opening 904, and an expandable annular positioning balloon 918 positioned proximate the distal opening, with two or more inflatable bladders segments 918*a* defining the positioning balloon 918. The asymmetrical shape of main body 902 may, for example, provide improved engagement with vagina 103 by, for example, occupying space in a correspondingly asymmetrically shaped vagina 103 proximate to cervix 101 to, for example, limit, or prohibit rotation of the system 900 inside the vagina 103.

Figure 36:
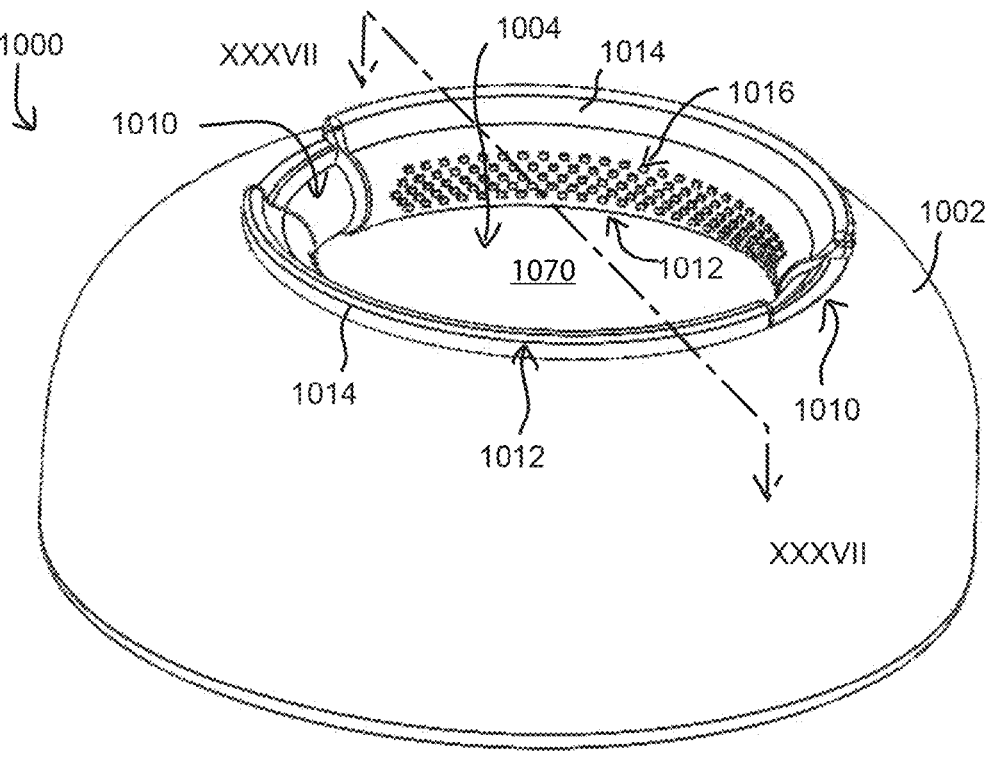
FIG. 36 illustrates a side perspective view of another cervical control system depicted with an inner cuff in a deflated or neutral state, in accordance with some embodiments of the present invention.
Figure 37:
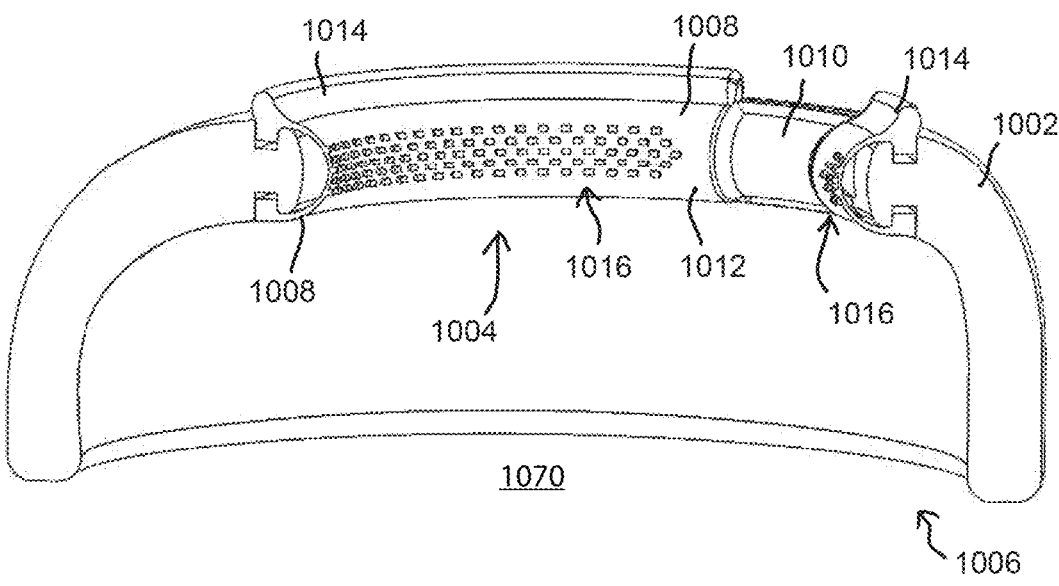
FIG. 37 illustrates a sectional side perspective view of the cervical control system of FIG. 36 taken along line XXXVII-XXXVII of FIG. 36, in accordance with some embodiments of the present invention.

FIGS. 36 and 37 provide a top-perspective and cross section view, respectively, of another cervical control system 1000. System 1000 is similar to systems 100 and 200 described above and illustrated in FIGS. 1-6 and 7-8, respectively, and includes a main body 1002, a proximal opening 1004, a distal opening 1006, an expandable annular cuff 1008 with recessed portions 1010 and expandable portions 1012, an internal passageway 1070, and a pair of raised, annular rim segments 1014. In addition, cervical control system 1000 includes an array of mechanical engagement mechanisms 1016 in the form of, for example, ridges, cleats and/or teeth (sometimes collectively referred to herein as "cleats") that may be similar to cleats 222 positioned on an exterior surface of expandable portions 1012. Cleats 222 may be arranged in rows, columns, offset rows, and/or offset columns along a portion of an interior surface of expandable portions 1012 of inner cuff 1008. Cleats 1016 may be configured for gripping the exterior of cervix 101 when system 1000 is in situ to enhance engagement of system 1000 with cervix when positioned within internal passageway 1070 and/or provide additional grip to retain cervix 1000 in an elongated and closed state and mitigate or prevent unintentional movement between system 1000 and cervix 101 (e.g., cervix 101 from slipping out of the inner cuff 1008). Cleats 1016 may be formed along with the exterior wall of inner cuff 1008 and/or expandable portions 1012 by, for example, an extruding, molding, and/or over-molding process. It is contemplated that the wall thickness of inner cuff 1008 at or adjacent to each cleat 1016 may be varied to permit them to extend outwardly relative inner cuff 1008 such that a cleat 1016 sits prouder of an exterior surface of inner cuff wall when inner cuff 1008 is in the inflated state as compared to when inner cuff 1008 is in the neutral state. Annular rim segments 1014 may be sized and positioned so that the extend from portions of a proximal side of body 1002 that correspond to and/or are proximate to expandable portions 1012 and do not extend from portions of the proximal side of body 1002 that that correspond to and/or are proximate to recessed portions 1010 as shown. In this way, annular rim segments 1014 may be sized and positioned so they do not correspond to a position of blood vessels within a cervix positioned within internal passageway 1070 and, therefore do not constrict these blood vessels or inhibit the flow of blood through them.

Figures 38, 39, 40, 41, 42, 43, 44, 45, 46, 47, 48, 49, 50:
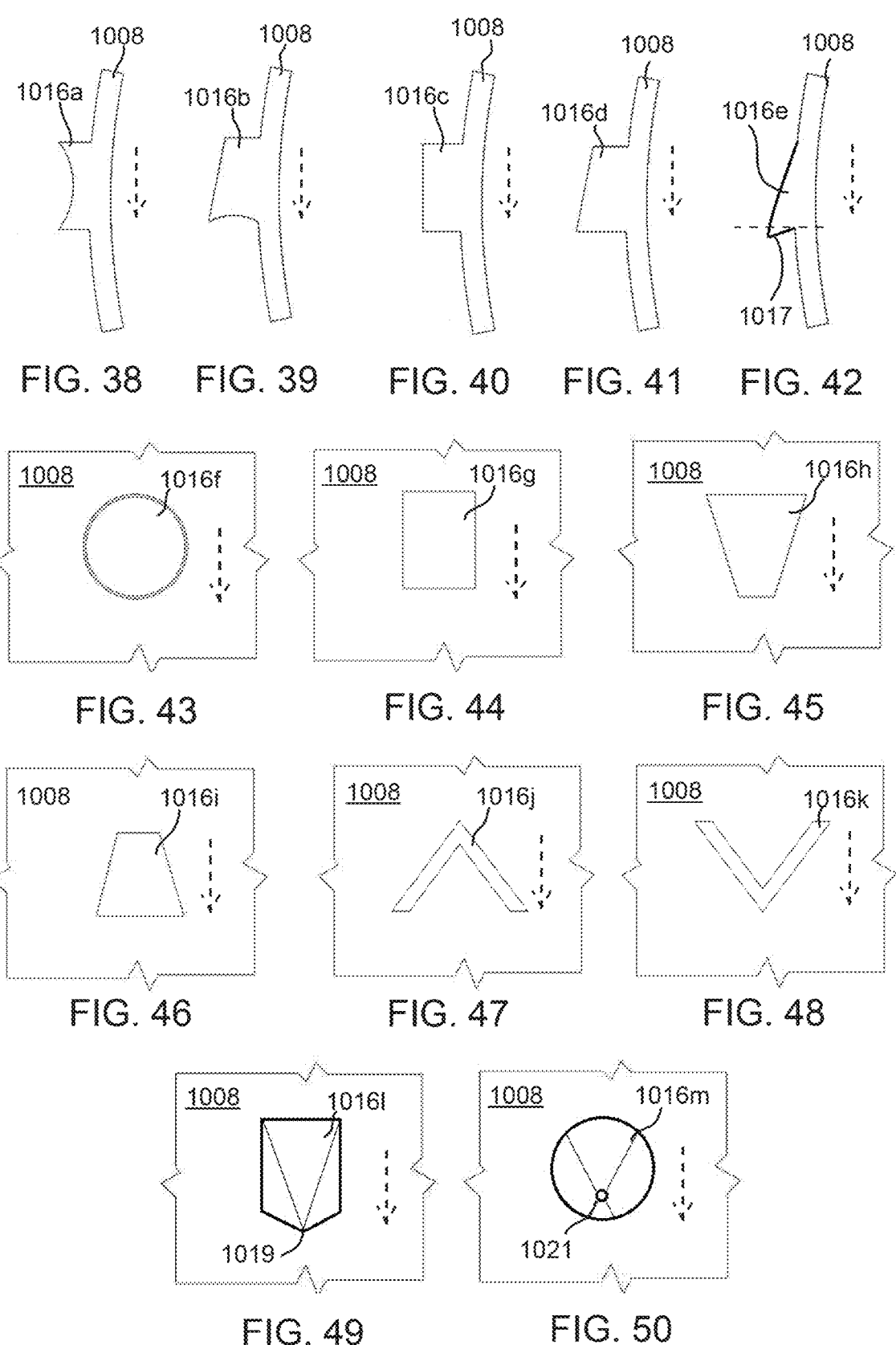
FIG. 38 illustrates a radial, sectional side elevation views of a first exemplary cleat, in accordance with some embodiments of the present invention.
FIG. 39 illustrates a radial, sectional side elevation views of a second exemplary cleat, in accordance with some embodiments of the present invention.
FIG. 40 illustrates a radial, sectional side elevation views of a third exemplary cleat, in accordance with some embodiments of the present invention.
FIG. 41 illustrates a radial, sectional side elevation views of a fourth exemplary cleat, in accordance with some embodiments of the present invention.
FIG. 42 illustrates a radial, sectional side elevation views of a fifth exemplary cleat, in accordance with some embodiments of the present invention.
FIG. 43 illustrates a front elevation view of a sixth exemplary cleat, in accordance with some embodiments of the present invention.
FIG. 44 illustrates a front elevation view of a seventh exemplary cleat, in accordance with some embodiments of the present invention.
FIG. 45 illustrates a front elevation view of an eighth exemplary cleat, in accordance with some embodiments of the present invention.
FIG. 46 illustrates a front elevation view of a ninth exemplary cleat, in accordance with some embodiments of the present invention.
FIG. 47 illustrates a front elevation view of a tenth exemplary cleat, in accordance with some embodiments of the present invention.
FIG. 48 illustrates a front elevation view of an eleventh exemplary cleat, in accordance with some embodiments of the present invention.
FIG. 49 illustrates a front elevation view of a twelfth exemplary cleat, in accordance with some embodiments of the present invention.
FIG. 50 illustrates a front elevation view of a thirteenth exemplary cleat, in accordance with some embodiments of the present invention.

FIGS. 38-42 illustrate provide a radial profile view of various exemplary cleats 1016*a*-1016*e*, respectively. For references purposes, FIGS. 38-42 also provide a phantom arrow alongside each radial cleat profiles 1016*a*-1016*e* to indicate a direction for a distal side of a cervical control system in which the respective cleat 1016 may be resident. In some embodiments, a cleat 1016 height (e.g., the distance that a cleat 1016 is proud of an inner cuff wall) may range from, for example, between about 100 micrometers (100 um) to 1500 micrometers (1500 um. Exemplary cleat 1016 lengths (e.g., a distance between a top and bottom (as oriented in FIGS. 38-42) edge of a cleat 1016) may range from between about 100 micrometers (100 um) to 1500 micrometers (1500 μm). In some embodiments, the various forms of cleat profiles 1016*a*-1016*e* of FIGS. 38-42 may be molded or formed of the same material as inner cuff 1008, or the cleats may be formed of a different material or different hardness of material, such as a silicone or plastic that is more rigid than the silicone of inner cuff 1008 and later affixed to inner cuff 1008 via any appropriate means (e.g., chemical and/or thermal bonding). For manufacturing purposes, it may be more preferred that cleats 1016 are formed of the same elastic material as inner cuff 1008. Cleats 1016 may be individually configured to act or function as suction cups (see e.g., cleat 1016*a* of FIG. 38) to form a vacuum engagement with the tissue of the exterior of the cervix 101 and/or projections configured to projected into and engage the exterior of cervix 101. As illustrated in FIGS. 38-42, the cleat profiles 1016*a*, 1016*b*, 1016*c*, 1016*d*, and 1016*e* are illustrated as solid bodies. However, in one embodiment cleats 1016 may be formed with voids between their perimeters and inner cuff wall, or cleats 1016 may be formed with voids that open into inner cuff 1008 such that as inner cuff is inflated, the voids in cleats 1016 may be inflated or expanded to expand a size and/or shape of the respective cleats 1016. As illustrated in FIG. 39, cleat 1016*b* has an extension with a curved lower profile configured to project into and hook cervical tissue; as illustrated in FIG. 41, cleat 1016*c* has a projection with a rectangular profile; as illustrated in FIG. 42, cleat 1016*d* has a projection with a truncated trapezoidal profile; and as illustrated in FIG. 42, cleat 1016*e* may be formed such that the downward edge/tip 1017 forms an acute angle with the exterior wall of inner cuff 1008. This configuration may effectively function as a hook to grab and hold cervical tissue and thus provide improved engagement with the cervical tissue.

FIGS. 43-50 illustrate various shapes in which the front, elevation shape of various cleats 1016*f*-1016*m*. For references purposes, FIGS. 43-50 also provide a phantom arrow alongside each cleat 1016*f*-1016*m* to indicate a direction for a distal side of a cervical control system in which the respective cleat 1016*f*-1016*m* may be resident. Any of the cleat shapes 1016*f*-1016*m* (in addition to other suitable cleat shapes) may be utilized with any of the cleat profiles 1016*a*-1016*e* (in addition to other suitable cleat profiles) to form a desired cleat 1016 for inclusion in a cervical control system and/or inner cuff such as the cervical control devices and/or inner cuffs disclosed herein and/or engaging the cervix 101. The cleat shape 1016*f* depicted in FIG. 43 is circular and may have a diameter that ranges between about 50 micrometers (50 um) to 2000 micrometers (2000 um), for example. FIGS. 44-49 illustrate non-circular cleat shapes 1016*g*-10161, respectively which may have overall height and width dimensions that range between 25 micrometers (25 um) to 2500 micrometers (2500 um), for example. In particular, FIG. 44 illustrates a rectangularly-shaped cleat 1016*g*, FIG. 45 illustrates a trapezoidal-shaped cleat 1016*h*, FIG. 44 illustrates an inverted trapezoid-shaped cleat 1016*i*, FIG. 47 illustrates a truncated triangularly-shaped cleat 1016*j*, and FIG. 48 illustrates an inverted truncated triangularly-shaped cleat 1016*k*. FIGS. 49 and 50 depict additional geometric cleat shapes 10161 and 1016*m* that each extend outward from inner cuff wall 1008 to a pointed end or tip 1019 and 1021, respectively. Cleat shape 10161 of FIG. 49 is a generally pyramidal shape, and in the illustrated embodiment is an oblique pyramid with the tip 1019 offset toward its lower side. Cleat shape 1016*m* is a generally conical shape, and in the illustrated embodiment is an oblique cone with the tip 1019 offset toward its lower side.

Figure 51:
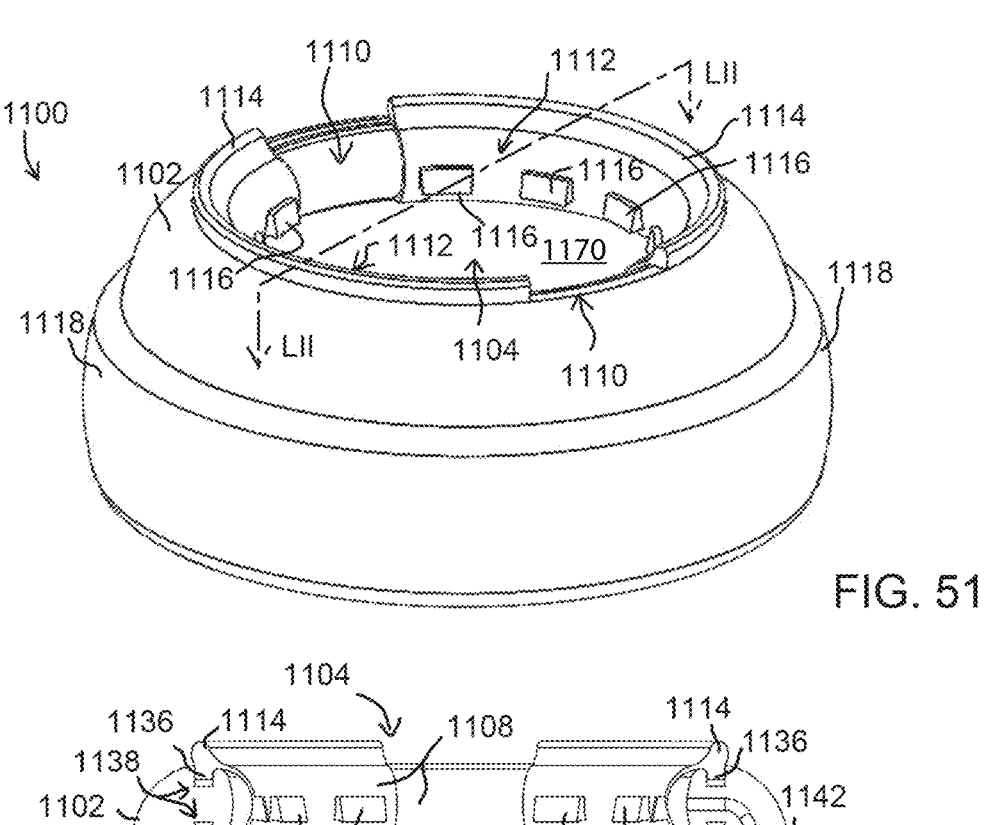
FIG. 51 illustrates a side perspective view of another cervical control system depicted with an inner cuff and a positioning balloon each in a deflated or neutral state, in accordance with some embodiments of the present invention.
Figure 52:
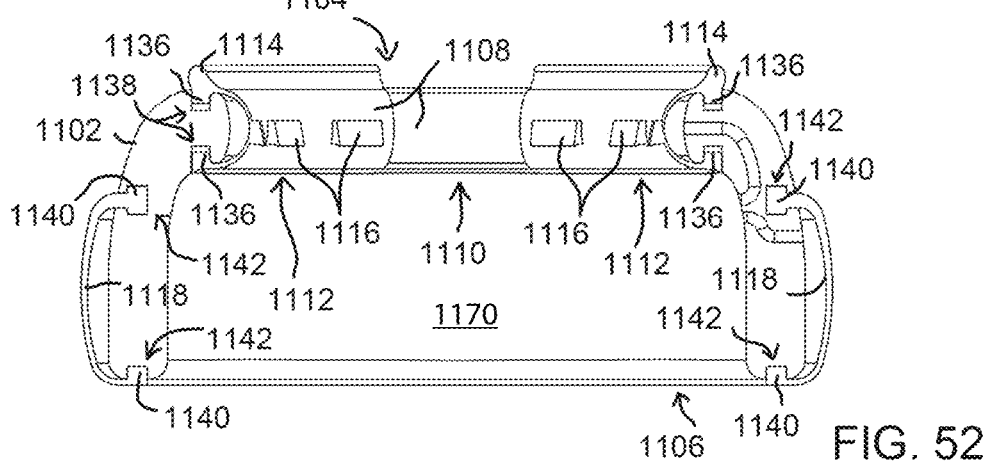
FIG. 52 illustrates a sectional side perspective view of the cervical control system of FIG. 51 taken along line LII-LII of FIG. 51, in accordance with some embodiments of the present invention.
Figure 53:
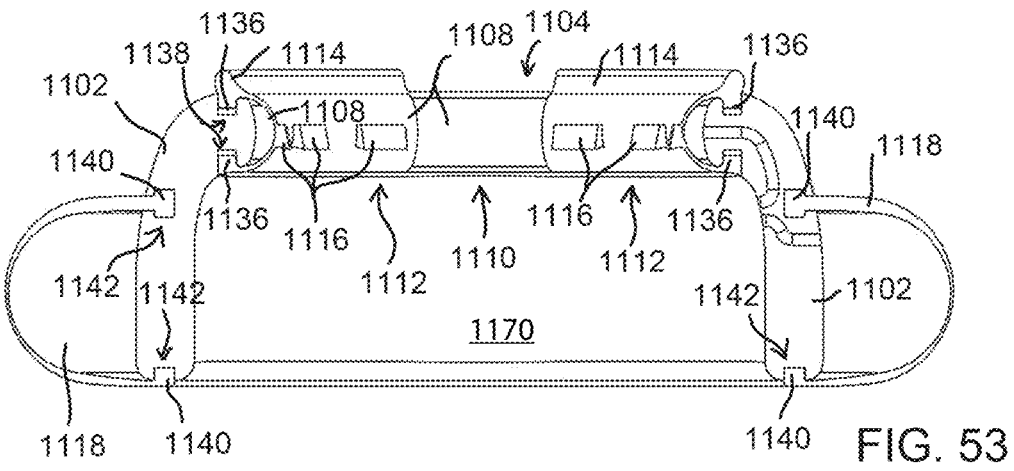
FIG. 53 illustrates sectional side perspective view of the cervical control system of FIG. 52, depicted with the inner cuff in the deflated state and the positioning balloon in an inflated or expanded state, in accordance with some embodiments of the present invention.
Figure 54:
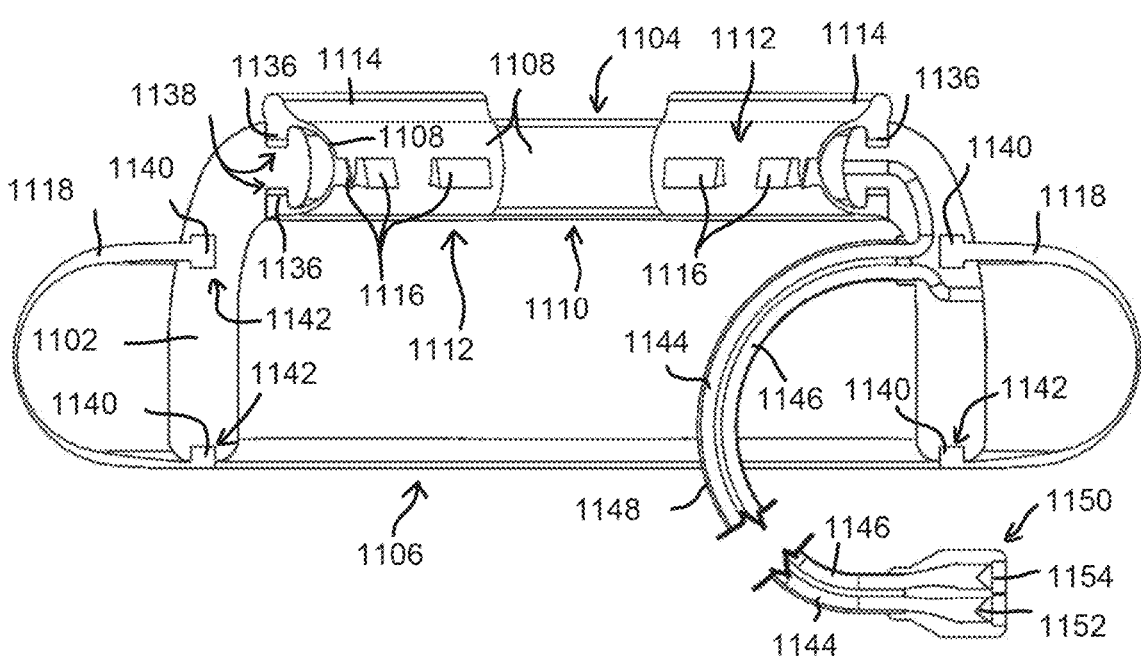
FIG. 54 illustrates another sectional side perspective view of the cervical control system of FIG. 53, depicting a tube and valve assembly for inflating the top and positioning balloons, in accordance with some embodiments of the present invention.

FIGS. 51-54 provide various views of another cervical control system 1100 (also referred to herein as "system 1100"). In particular, FIG. 51 provides a top perspective view of system 1100; FIG. 52 provides a cross section view of system 1100 when a positioning balloon 1118 is in a neutral state; FIG. 53 provides a cross section view of system 1100 when positioning balloon 1118 is in an inflated state; and FIG. 54 provides a cross section view of system 1100 when positioning balloon 1118 is in an inflated state and system 1100 is coupled to and/or integrated with a source of inflation media. Similar to the components of systems 100, 500, and 1000 described above and illustrated in FIGS. 1-6, 19-20, and 36-37, respectively, system 1100 includes a main body 1102, a proximal opening 1104, a distal opening 1106, an expandable annular inner cuff 1108 (also referred to herein as "inner cuff 1108") with recessed portions 1110 and expandable portions 1112, an internal passageway 1170, and a raised, annular rim 1114. In further similarity to the components of system 500, system 1100 includes an external, or distal, expandable annular cuff 1118 (also referred to herein as "positioning balloon 1118") positioned proximate the distal opening 1106 on an exterior of body 1102. In further similarity to the components of system 1000, system 1100 includes an array of cleats or teeth 1116 arranged around, and extending from, an exterior surface of expandable portions 1112 of the inner cuff 1108. Cleats 1116 may be similar in shape and/or function to cleats 1016 shown in FIGS. 38-50 and discussed herein. As compared to system 500, positioning balloon 1118 of cervical control system 1100 is relatively larger than positioning balloon 518 and extends further up the wall of the body 1102 of the system 1100 than positioning balloon 518 extends up body 502.

Various embodiments of positioning balloon 1118 may extend halfway up the exterior wall of the body 1102, or substantially the entire length of the exterior wall of the body 1102, for example. The increased size of positioning balloon 1118 increases the contact area between positioning balloon 1118 and a patient's vagina 103 to, for example, provide greater stability for system 1100 when in situ as well as improved support to, and/or control of, the patient's cervix 101 and/or uterus 105. Positioning balloon 1108 may comprise a single bladder or a plurality (e.g., 2-8) bladders such as bladders 818*a* of positioning balloon 818 described above and illustrated in FIGS. 25-31.

Further, as compared to system 1000, the cleats 1116 of cervical control system 1100 are significantly larger than cleats 1016 of system 1000 and fewer cleats 1116 are provided around the interior perimeter of the expandable portions 1112. Like cleats 1016, cleats 1116 may be configured to engage with (e.g., press into and/or adhere to) cervical tissue following insertion of cervix 101 into internal passageway 1170 and inflation of inner cuff 1108 and/or expandable portions 1112 to attempt to provide additional grip to pull and/or retain cervix 101 in an elongated and closed state (see e.g., FIG. 18) and mitigate or prevent cervix 101 from slipping out of inner cuff 1108. Cleats 1116 may be formed along with the exterior wall of inner cuff 1108, such as by extruding, molding, or an over-molding process, for example. At times, a wall thickness of inner cuff 1108 at, or adjacent to, each cleat 1116 may be varied to, for example, permit cleats 1116 to extend outwardly relative inner cuff 1108 such that the cleats 1116 sit prouder to an exterior surface of expandable portion 1112 when expandable portion 1112 is an inflated state as compared to when expandable portion 1112 is in the neutral state.

Similar to system 800's arrangement of teeth 836 of inner cuff 808 and grooves 838 within the wall of body 802 of system 800 described above and illustrated in FIGS. 25-31, inner cuff 1108 is coupled to a proximal end of the wall of the body 1102 with teeth 1136 that fit over a proximal end of body 1102 and fit into, or engage with, grooves 1138 resident within the top and bottom (as oriented in FIG. 52) sides of the proximal end of the wall as shown in FIGS. 52-54. Body 1102 also has a distally-placed groove 1142 and a centrally-placed groove 1142 positioned on an external surface of body 1102 that are sized, configured, and positioned for acceptance of distal and proximal teeth 1140 of positioning balloon 1118, thereby allowing for attachment of positioning balloon 1118 to body 1102 as shown in FIGS. 52-54. Teeth 1136 and/or 1140 may be affixed within grooves 1138 and/or 1142 via any acceptable means including, but not limited to, chemical, mechanical, thermal, and vibrational bonding.

As may be seen in FIG. 54, system 1100 includes a first inflation media conduit 1144 and a second inflation media conduit 1146, both of which are in fluid communication with the inner cuff 1108 and the positioning balloon 1118, respectively. Inflation media conduits 1144 and 1146 are similar in structure and function to inflation media conduits 116, 216,

516, and 816 of respective systems 100, 200, 500, and 800 (see e.g., FIGS. 5 and 6, 7 and 8, 19 and 20, and 29 and 30, respectively). As shown in FIG. 54, inflation media conduits 1144 and 1146 are dedicated to corresponding cuffs 1108 and 1118, respectively, and extend within body 1102 so that a first end thereof is open to inner cuff 1108 and positioning balloon 1118 and a second end extends away from body 1102 and is resident within a tube 1148 (e.g., a multi-lumen catheter) until tube a distal end of tube 1148 terminates at a valve system 1150, which may be similar in function to valve system 826 described above and illustrated in FIGS. 29-30.

Valve system 1150 includes a first valve 1152 in communication with first conduit 1144 and a second valve 1154 in communication with second conduit 1146. First and/or second valves 1152 and/or 1154 may be, for example, a one-way valve and/or a one-way duckbill valves. Tube 1148 may be configured to have a length sufficient to extend from system 1100 a patient's cervix 101, through vagina 103, and extend out from the introitus sufficiently far (e.g., 2-24 inches) that a clinician may access and utilize valve system 1150 for the introduction and/or extraction of inflation media into/out of inner cuff 1108 and/or positioning balloon 1118 without, for example, removing or repositioning system 1100 from cervix 101 and/or vagina 103. Having first and/or second valve(s) 1152 and/or 1154 accessible outside the vagina allows for easy access to and/or use of first and/or second valve(s) 1152 and/or 1154 without requiring repositioning of the respective first and/or second conduit and/or cervical control system 1000 during use. Additionally, or alternatively, having first and/or second valve(s) 1152 and/or 1154 positioned so they may reside outside the vagina during use allows a care provider to simply break a pressure seal to release the pressure within the conduits 1144 and 1146 and cuffs 1108 and 1118, which would otherwise be trapped due to the function of the one-way valves 1152 and 1154. For example, a commonly known or commercially available device may be utilized to permit the care provided to readily break the pressure seal, such as a locking needle or syringe tip coupled with the tube 1148. The care provider may break the pressure seal by removing the valve system 1150 from the tube 1148.

Figure 55:
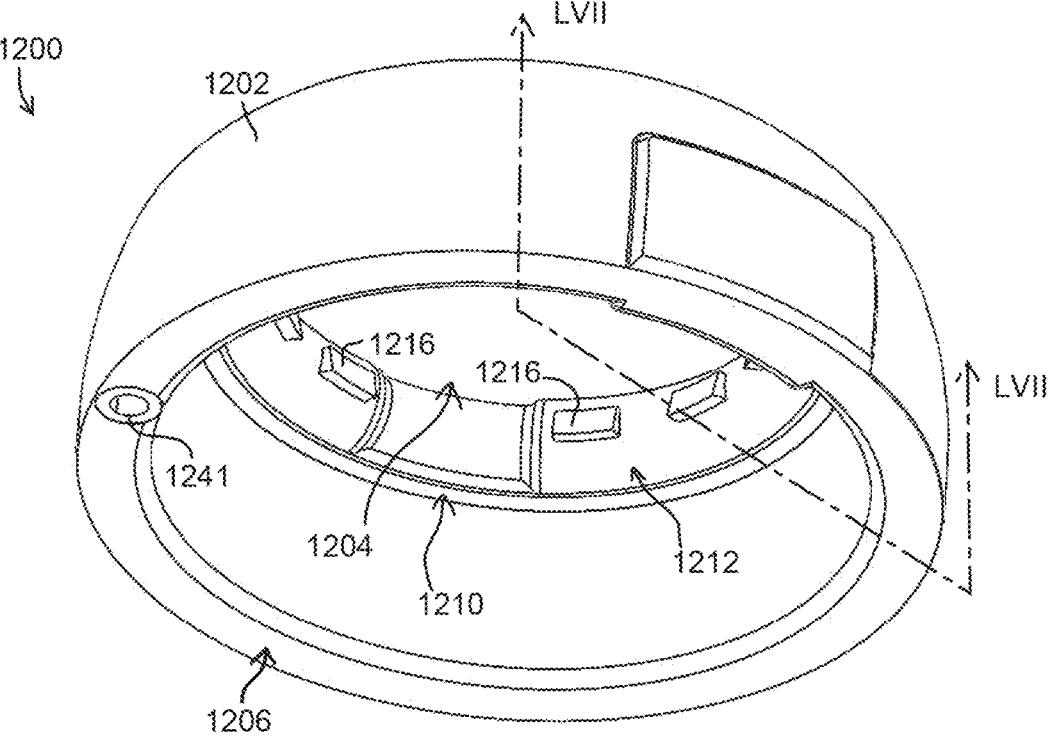
FIG. 55 illustrates a bottom side perspective view of another cervical control system depicted with an inner cuff and a positioning balloon in a deflated or neutral state, in accordance with some embodiments of the present invention.
Figure 56:
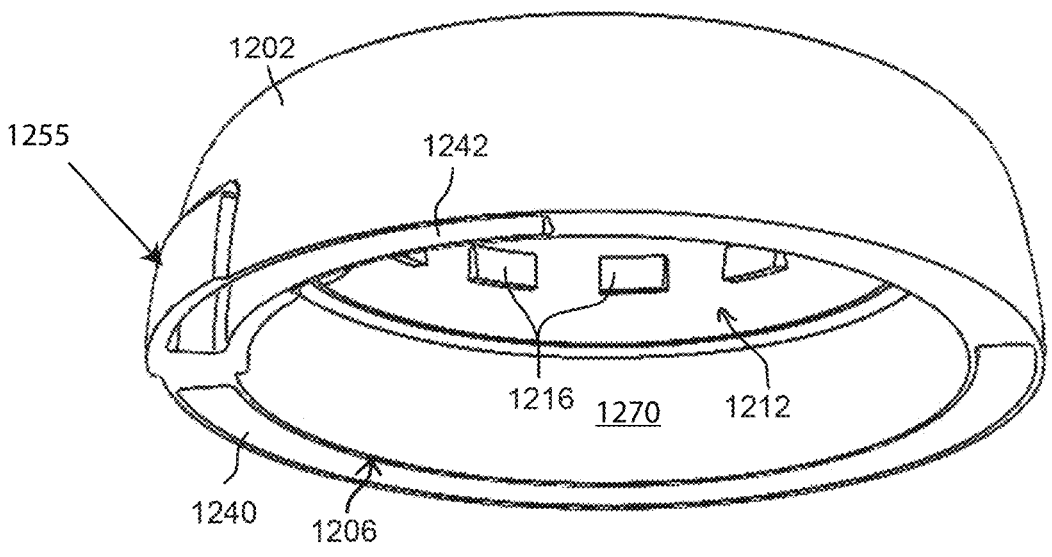
FIG. 56 illustrates a sectional bottom side perspective view of the cervical control system of FIG. 55 taken below and perpendicular to an axial center of the inner cuff of the cervical control system, in accordance with some embodiments of the present invention.
Figure 57:
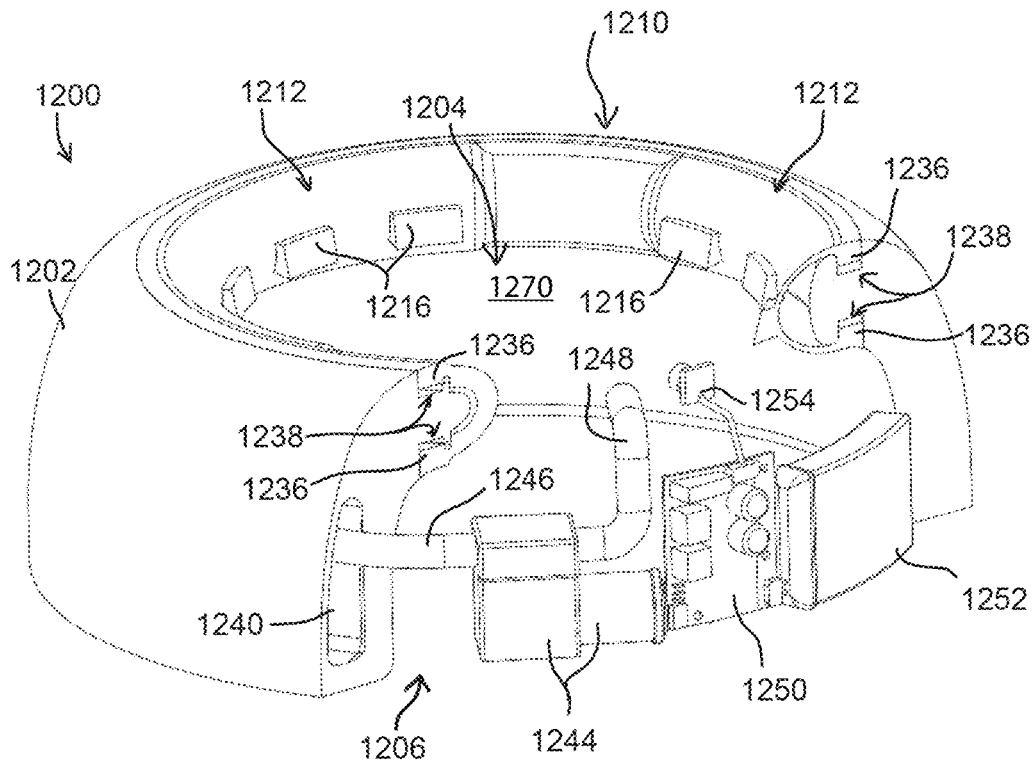
FIG. 57 illustrates a partial sectional top side perspective view taken along line LVII-LVII of FIG. 55, depicted with internal components of the cervical control system intact to show internal structure, in accordance with some embodiments of the present invention.

FIGS. 55-57 provide various views of another cervical control system 1200 (also referred to herein as "system 1200"), wherein FIG. 55 is a bottom perspective view, FIG. 56 is sectioned bottom perspective view of system 1200 with a distal edge removed thereby showing a size, shape, and position of a fluid reservoir 1240 and FIG. 57 is a cut-away view of system 1200. System 1200 includes some components that are similar to those of system 1100 and other cervical control systems disclosed herein. For example, system 1200 includes a main body 1202, a proximal opening 1204, a distal opening 1206, an interior passageway 1270, an expandable annular inner cuff 1208 (also referred to herein as "inner cuff 1208") that includes recessed portions 1210, expandable portions 1212, an array of cleats or teeth 1216 arranged and positioned on an exterior surface of expandable portions 1212 of inner cuff 1208, and teeth 1236 that are sized, configured, and positioned to fit into and engage grooves 1238 formed on the top and bottom (as oriented in FIG. 57) of a proximal end of body 1201 as shown in FIG. 57. In addition, system 1200 includes an optional distal exterior expandable element 1255 configured to receive inflationary media and expand outward to vaginal walls when system 1200 is in situ.

System 1200 further includes fluid reservoir 1240 (FIGS. 56 and 57) resident within a wall of body 1202 and in fluid communication with inner cuff 1208 and a valve system (not shown) with an inlet port 1241 (FIG. 55). Inlet port 1241 may be, for example, a one-way valve, such as described previously for systems 800 and 1100 and/or a duckbill valve configured to transfer inflation media from fluid reservoir 1240 to inner cuff 1208 and/or allow air to pass through so that equilibrium (e.g., not a vacuum) within fluid reservoir 1240 may be reached. System 1200 further includes a component cavity 1242 resident inside another portion of the wall of the body 1202 adjacent to the fluid reservoir 1240 (FIG. 56). Component cavity 1242 is sized and configured to provide space for housing an internal fluid pump 1244 that is positioned inside the wall of the body 1202 and in fluid communication with fluid reservoir 1240 via a first conduit 1246 and in fluid communication with inner cuff 1208 via a second conduit 1248 (FIG. 57). Pump 1244 may be configured and/or operable to move fluid from the fluid reservoir 1240 to one or more portions of inner cuff 1208 to inflate and/or deflate inner cuff 1208 In some embodiments, inlet port 1241 may be a vent configured to enable air transfer to counteract a vacuum forming during operation of the pump 1244.

A controller or computer 1250 is electronically coupled to pump 1244 and may be configured to execute one or more instructions to control operation (e.g., on/off, flow rate, etc.) of pump 1244. A power source, in the form of a rechargeable battery 1252, is coupled with pump 1244 and controller 1250. The controller 1250 may be enabled for wireless communication/control such that a care provider may remotely inflate/deflate inner cuff 1208 without any invasive procedure to access the system 1200, thus enabling the cervical control system 1200 to be a closed system, requiring no outside, or external, physical manipulation to adjust the cervical control system. For example, controller 1250 may include a Bluetooth® wireless communication or other remote control device. A charging cable for charging the power source may be provided for charging the battery 1252, either internally or externally of the patient. Optionally, a pressure transducer 1254 may be coupled to controller 1250 to measure pressure exerted on system 1200 and provide these measurements directly, or indirectly, to for example, a display device such as a computer screen. Information provided by pressure transducer 1254 may be used to determine, for example, the status of the system 1200, a state of inflation/deflation of internal cuff 1208, and/or and pressure being exerted on the cervix 101 or vagina 103. In some embodiments, pressure transducer 1254 may be adapted to detect a drop in pressure within acceptable bounds (as, for example, set by the care provider), and the pump 1244 may be configured to automatically add fluid to the under pressurized inner cuff 1208 to maintain the desired level of inflation. In an optional embodiment, a position and/or orientation sensing device (e.g., a solid state gyroscopic module) may be provided to detect orientation data of the cervical control system 1200 (e.g., the solid state gyroscopic module may detect and/or determine an angle of orientation for system 1800 relative to a gravity vector). Based on the position data, the device may be adapted to automatically adjust the angle of the cervical control system in the event that the cervical control system shifts beyond a desired position (as set by the care provider). Any of the devices, systems, and/or methods described herein can include one or more features disclosed in U.S. patent application Ser. No. 17/813,454 filed on Jul. 19, 2022, International Patent App. No. PCT/IB2022/056650 filed on Jul. 19, 2022, U.S. Provisional App. No. 63/237,708 filed on Aug.

27, 2021, or U.S. Provisional App. No. 63/300,263 filed on Jan. 18, 2022, each of which are incorporated by reference in their entirety.

Figure 58:
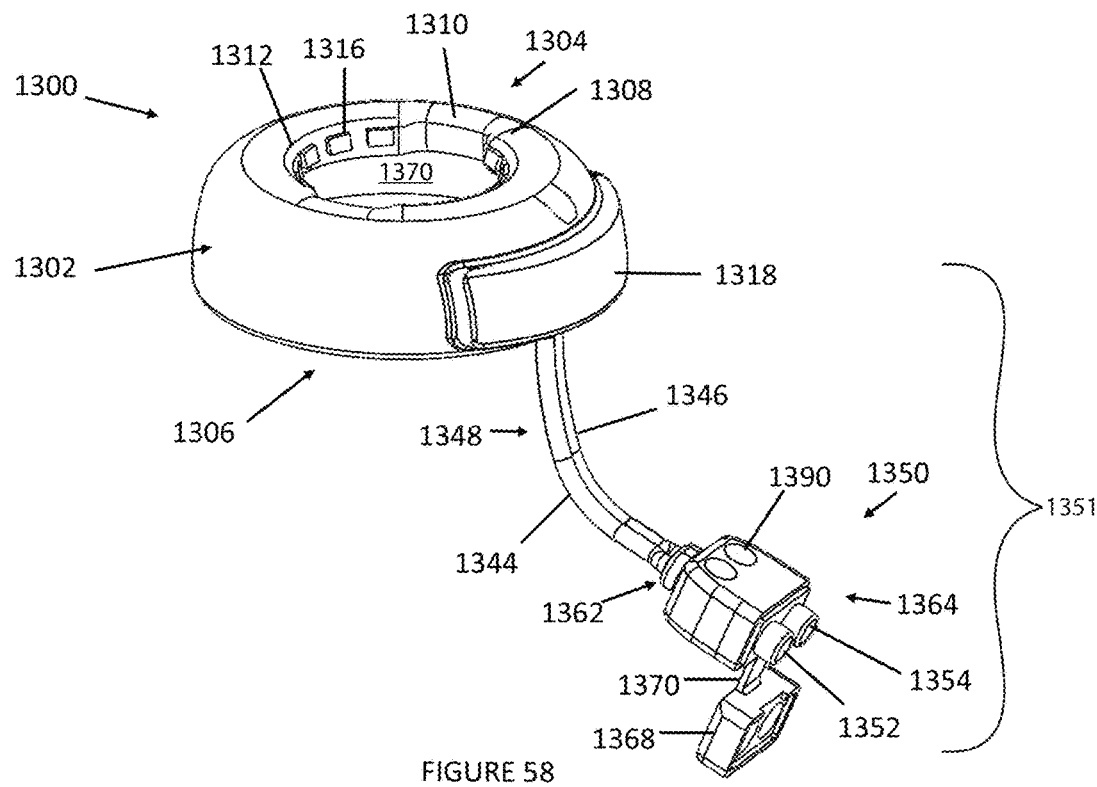
FIG. 58 illustrates a perspective view of a system including a cervical control system, tubing, and a valve system, in accordance with some embodiments of the present invention.
Figure 59:
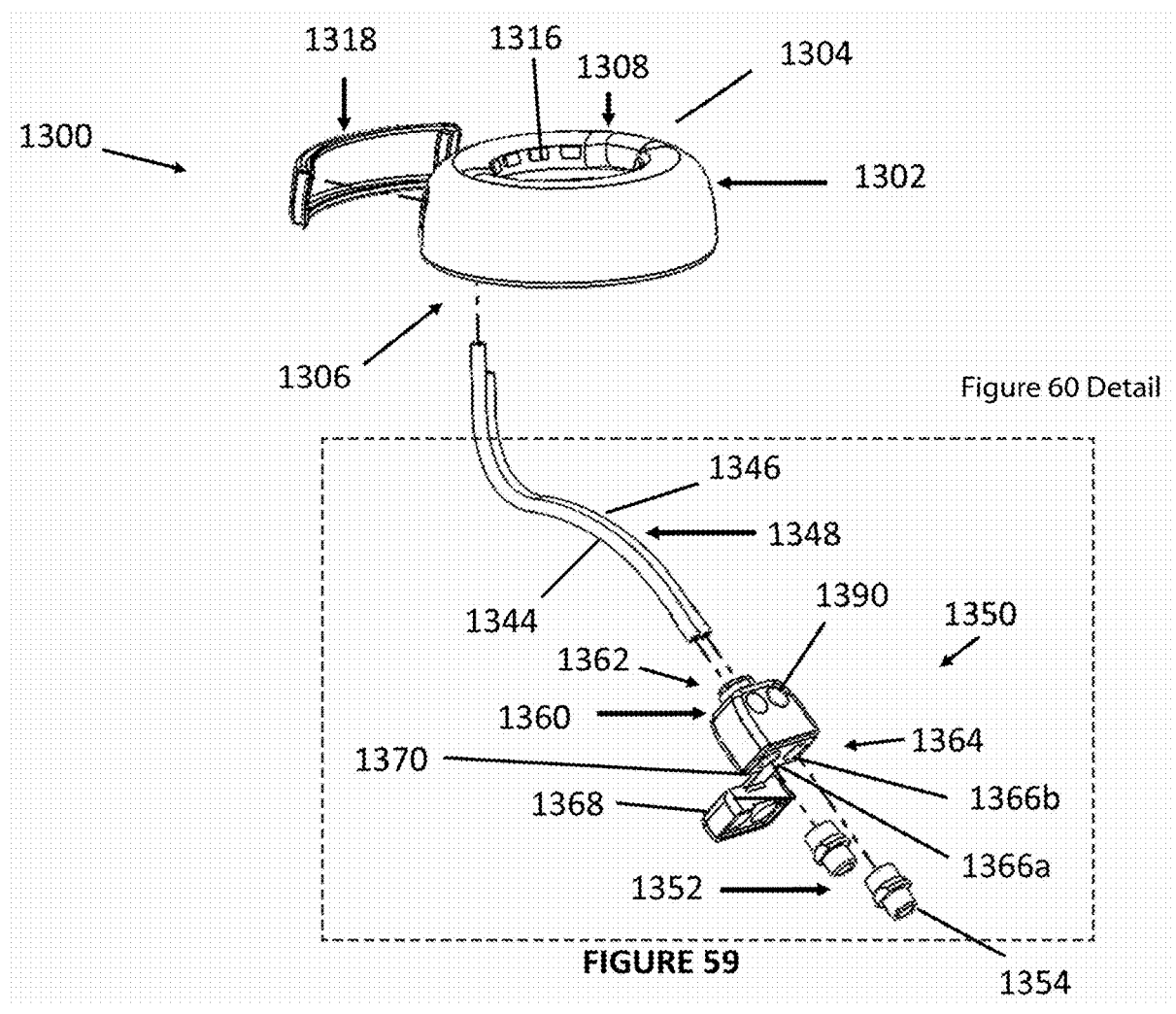
FIG. 59 illustrates an exploded perspective view of the system of FIG. 58, in accordance with some embodiments of the present invention.

FIGS. 58 and 59 illustrate embodiments of a system 1301 that includes a cervical control system 1300 (also referred to herein as "system 1300") and an inflation system 1302, wherein FIG. 58 is a perspective view of a system 1301, FIG. 59 is an exploded perspective view of system 1301. System 1300 shares some features and functionality with systems 100, 500, 1000, and 1100 described above and illustrated in FIGS. 1-6, 19-20, 36-37, and 51-54 such as a main body 1302, a proximal opening 1304, a distal opening 1306, an internal passageway 1370, and an expandable annular inner cuff 1308 with recessed portions 1310 and expandable portions 1312. In further similarity to the components of system 1100, system 1300 includes a positioning balloon 1318 positioned on an exterior surface of body 1302 proximate distal opening 1306. In further similarity to the components of system 1100, system 1300 includes an array of cleats or teeth 1316 that extend from an exterior surface of expandable portions 1312 into interior passageway 1370. In some embodiments, system 1300 may not include cleats 1316.

Positioning balloon 1318 is configured to be inflated once system 1300 is positioned within the patient and expand away from the axial center of distal opening toward, and into. the vaginal wall. Similar to system 1100, positioning balloon 1318 of cervical control system 1300 extends further up the wall of the body 1302 of the system 1300 than that of positioning balloon 518 of system 500 but, in contrast to system 1100, positioning balloon 1318 of cervical control system 1300 does not extend around the entire circumference of the body 1302. Instead, positioning balloon 1318 extends around only a portion (e.g., 20-90%) of the circumference of body 1302 as shown in FIG. 58. When in a deflated state, positioning balloon 1318 may be flush with or extend approximately 0.1-3 mm away from (e.g., interior passageway 1370), an exterior surface of body 1302. When in an inflated state, positioning balloon 1318 may extend approximately 0.5-12 mm, 6.25 mm, 4-7 mm, 7 mm, 4-6 mm, and values in between away from (e.g., interior passageway 1370), an exterior surface of body 1302

The positioning of the positioning balloon 1318 around only a portion of the circumference of body 1302 may allow for more precise positioning of the cervical control system within patient anatomy so that pressure and/or force is not exerted, for example, in a posterior direction, which may, for example, increase patient comfort and/or decrease a likelihood that an inflated positioning balloon 1318 will press on the rectum, which may cause discomfort, constipation, and/ or evacuation complications. For example, the arc shape structure of positioning balloon 1318 means that positioning balloon 1318 the distal side of system 1300 is not uniformly inflated (as may be the case with an annular positioning balloon that extends around the entire circumference of the cervical control system body) so pressure may not be extended uniformly in all directions against the vagina, which may result in pressure not being applied to organs and tissue proximate to the vagina (e.g., bladder, rectum, etc.) that may be damaged or irritated by pressure exerted thereon, which may make system 1300 more comfortable for a patient to wear, particularly for extended periods of time (e.g., days or weeks). In some cases, inflation of positioning balloon 1318 can adjust the positioning and/or orientation of the cervix to a posterior or anterior position. For example, inflation and/or expansion of positioning balloon 1318 may cause translation (e.g., forward movement)

of system 1300 and, because of system's 1300 position high on the cervix wherein positioning balloon 1318 and/or close proximity to and/or position against a patient's fornix, this translation may cause a posterior tilt of the cervix. In some cases, the cervical control system does not have a positioning balloon and only uses the inner cuff. In some embodiments, the cervical control system does not include an inner cuff and only uses the positioning balloon. In these embodiments, system 1300 may not exert compressive force on the cervix but may tilt the cervix to a preferred angle.

Inflation system 1351 includes a first inflation media conduit 1344 and a second inflation media conduit 1346 resident within a tube 1348 (which may be a multi-lumen tube including first and second conduits 1344 and 1346). System 1300 may include a first inlet (not shown) in fluid communication with inner cuff 1308 and a second inlet (not shown) in fluid communication with positioning balloon 1318 and first end of tube 1348 may be physically coupled to system 1300 via the first and/or second inlets. Additionally, or alternatively, first inflation media conduit 1344 may extend away from second inflation media conduit 1346 as shown in FIG. 59 for insertion into the first inlet so that first inflation media conduit 1344 may by in fluid communication with inner cuff 1308 as shown in FIG. 58. Additionally, or alternatively, second inflation media conduit 1346 may be configured for insertion into the second inlet so that second inflation media conduit 1346 may by in fluid communication with positioning balloon 1318 as shown in FIG. 58. In some cases, system 1301 may include more, or less, than two inflation media conduits. For example, system 1301 may include one, three, four, or more inflation media conduits.

Tube 1348 have a length (e.g., 3-24 inches) sufficient to extend away from system 1300 (when placed in the patient's vagina) and out through the vaginal opening such that a care provider may easily access the valve system 1350 without removing or repositioning system 1300 within the patient. A second, distal, end of tube 1348 and/or a second end of first and/or second inflation media conduits 1344 and/or 1346 may be coupled to a valve system 1350 that includes a valve housing 1360 (for further details see FIGS. 60-61C and their associated discussion below). Valve housing 1360 has a proximal end 1362 and a distal end 1364 and may be connected to the distal end of first and second conduits 1344 and 1346 within tube 1348. Distal end 1364 of valve housing 1360 may hold first and second valves 1352 and 1354 and may include a first opening 1366a and a second opening 1366b (shown in FIG. 59) by which a distal end of respective first and second valves 1352 and 1354 may be accessible by and/or connected to a syringe, pump, or other inflation device that can supply inflation media to inflate inner and/or positioning balloons 1308 and/or 1318. Valve housing 1360 can include a cap 1368 that may be connected to valve housing 1360 by a tether 1370 or other connector (e.g., a hinge). Cap 1368 can be removably coupled to the distal end of the valve housing 1360 and may be configured and/or arranged to cover first and/or second valves 1352 and 1354 when closed (e.g., engaged with distal end 1364) and configured to allow access to first and second valves 1352 and 1354 when open (e.g., disengaged from distal end 1364). In some embodiments, valve housing 1350 may not include cap 1368.

Valve system 1350 may be similar in function to valve system 826 and 1150 described above and illustrated in FIGS. 29-30 and FIG. 54 and may include a first valve 1352 configured to be in fluid communication with first inflation media conduit 1344 and a second valve 1352 configured to be in fluid communication with second inflation media conduit 1346. In some cases, first and second valves 1352 and 1354 may be one-way valves, duckbill valves, silicone valves, check valves, Halkey Roberts valves, luer activated check valves, check valves with polycarbonate bodies and/or combinations thereof. Use of a polycarbonate body for first and/or second valve(s) 1352 and 1354 may reduce and/or eliminate a risk that the valve can be unintentionally manipulated to break the seal and lose pressure.

In some embodiments, valve housing 1350 may house have fewer, or more, (e.g., 3-6) valves. Alternatively, in some embodiments, system 1301 may not utilize valves or valve housing 1350 and, in these embodiments, a source of inflation media may directly couple to first and/or second inflation media conduits 1344 and/or 1346 and/or tube 1348.

Figure 60:
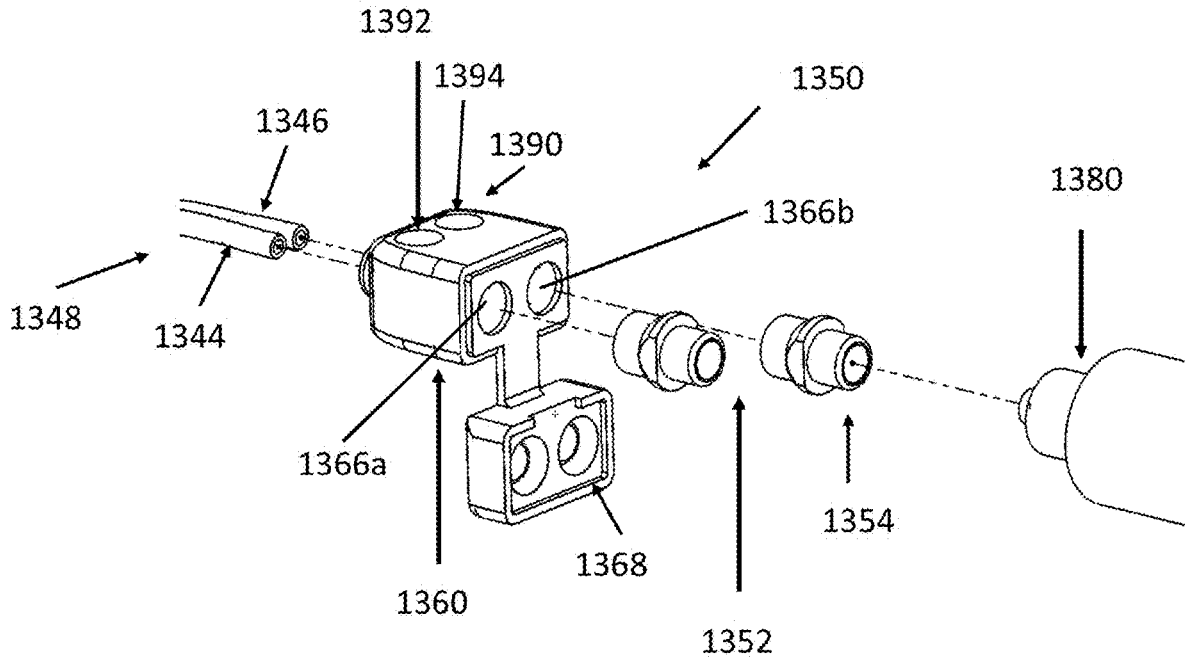
FIG. 60 illustrates a detailed exploded view of the system of FIG. 58, in accordance with some embodiments of the present invention.

FIG. 60 is a detailed exploded view of the valve system 1350 shown in FIG. 59. As may be seen in FIG. 60, first valve 1352 may be aligned with (and eventually inserted into as shown in FIG. 58) first opening 1366*a* and second valve 1354 may be aligned with (and eventually inserted into as shown in FIG. 58) second opening 1366*b*. First and/or valves 1352 and/or 1354 may be secured inside the valve housing 1360 using any appropriate means including, but not limited to, chemical, thermal, mechanical (e.g., press fit and/or friction fit), and/or vibrational bonding. A distal tip, or end, of first and/or second valves 1352 and/or 1354 may be configured to allow for coupling (e.g., leur coupling, friction fit, etc.) to and/or insertion of an inflation media source 1380 such as a syringe, pump, or squeeze bulb and communication of inflation media source 1380 into first and/or second valves 1352 and/or 1354 for communication for first and/or second inflation media conduits and/or inner cuff 1308 and/or positioning balloon 1318, respectively. Exemplary inflation media includes, but is not limited to saline, air, gas, hydrogels, water, Newtonian fluids and/or non-Newtonian fluids.

In some embodiments, valve housing 1360, tube 1348, and/or first and/or second valves 1352 and 1354 may be manufactured separately, assembled together as arranged in, for example, FIG. 60 and then permanently and/or removably bonded together. Valve housing 1360 can be formed from a flexible material such as silicone or vinyl.

During use, system 1300 may be positioned within a patient's vagina (e.g., vaginal 103) so that the patient's cervix (e.g., cervix 101) may be resident within interior passageway 1370 while a portion of tube 1348 and valve housing 1360 remains outside of the introitus and is accessible by a clinician who may insert, or otherwise engage, first and/or second valve with inflation media source 1380 and communicate inflation media to/from respective first and/or second inflation media conduit(s) for communication to/from inner cuff 1308 and/or positioning balloon 1318, respectively so that inner cuff 1308 and/or positioning balloon 1318 may be inflated and/or deflated as needed.

Since the main body 1302 is positioned within the vagina during use, it may be difficult to assess (e.g., visually, or otherwise, observe) how much pressure is being applied to patient tissue by inner cuff 1308 and/or positioning balloon 1318. To assist with this assessment, valve housing 1360 may include and/or be physically and/or communicatively coupled to one or more sensors 1390 configured to, for example, directly and/or indirectly measure and/or monitor one or more aspects of the operation of system 1301 including, but not limited to, an amount of backpressure exerted by inflation media present in first and/or second conduits 1344 and/or 1346, a flowrate of inflation media entering and/or exiting first and/or second conduits 1344 and/or 1346, a volume of inflation media entering and/or exiting first and/or second conduits 1344 and/or 1346 and/or changes thereof. In some embodiments, sensor 1390 may be and/or include a tactile or visual pressure gauge with a display provided on valve housing 1360.

Figures 61A, 61B, 61C, 61D, 61E:
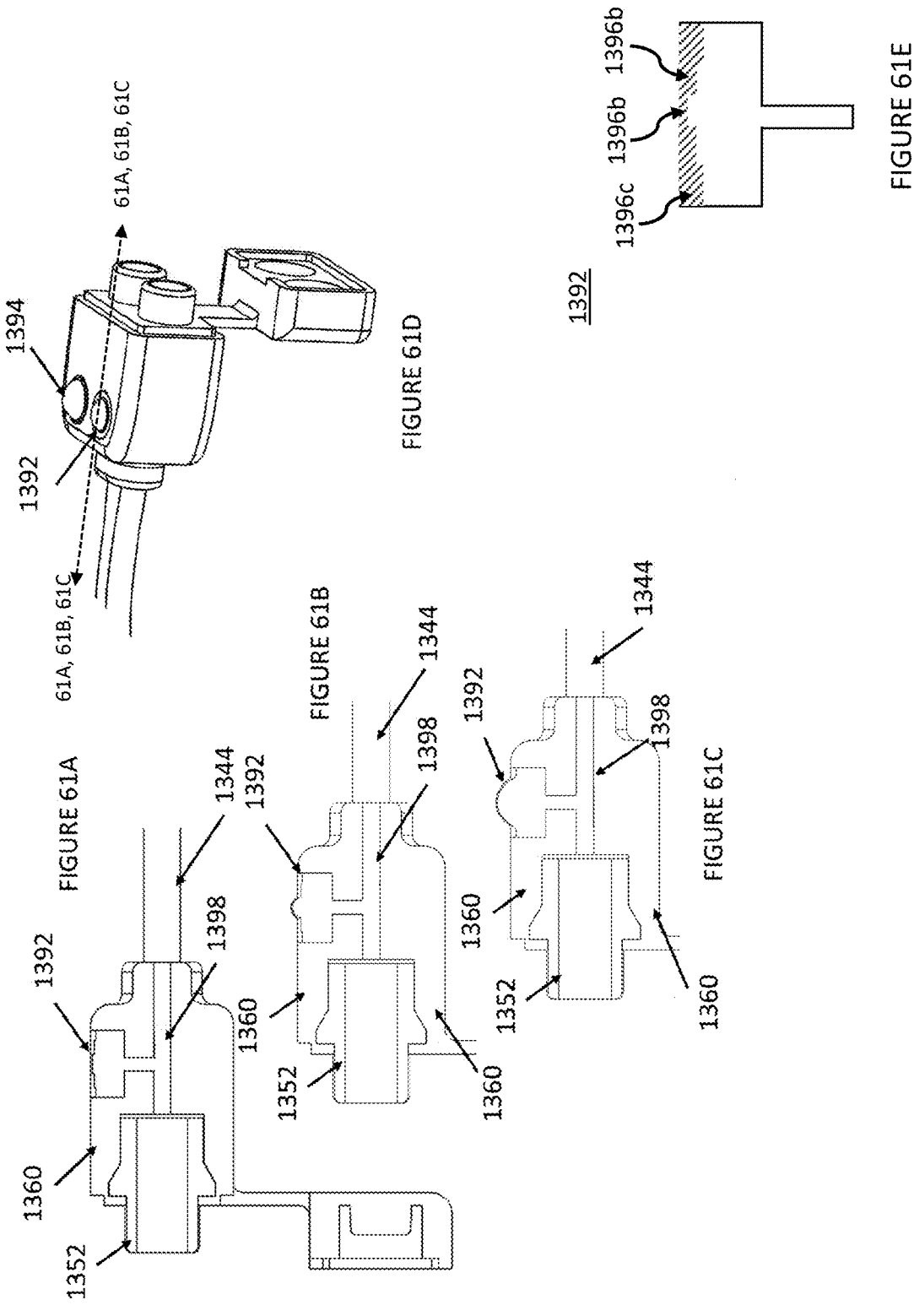
FIG. 61A illustrates a cross sectional view of a valve housing including a pressure gauge in a first position taken along sectioning line 61A, 61B, 61C of FIG. 61D, in accordance with some embodiments of the present invention.
FIG. 61B illustrates a cross sectional view of a valve housing including a pressure gauge in a second position taken along sectioning line 61A, 61B, 61C of FIG. 61D, in accordance with some embodiments of the present invention.
FIG. 61C illustrates a cross sectional view of a valve housing including a pressure gauge in a third position taken along sectioning line 61A, 61B, 61C of FIG. 61D, in accordance with some embodiments of the present invention.
FIG. 61D illustrates a perspective view of the cross sectioned valve housing with a pressure gauge of FIGS. 61A-61C, in accordance with some embodiments of the present invention.
FIG. 61E illustrates a side cross sectional view of a pressure gauge resident within the valve housing of FIG. 61D, in accordance with some embodiments of the present invention.

In some embodiments, sensor 1390 may include a first pressure gauge 1392 positioned in-line between the first valve 1352 and first inflation media conduit 1344 and a second pressure gauge 1394 positioned in-line between second valve 1354 and second inflation media conduit 1346 to measure inflation media pressure within respective first and second inflation media conduits 1344 and 1346. In some embodiments, first and/or second pressure gauges 1392 and 1394 may be a tactile pressure gauge (e.g., a pressure balloon), which can be incrementally inflated to indicate how much pressure is increased in within components of system 1300 and, on some occasions, may be configured to indicate how much the pressure has increased and/or decreased within their respective conduits in discrete increments. For example, FIG. 61E provides a cross section view of an exemplary pressure gauge 1392 having a base 1396 whose upper (as oriented in FIG. 61E) surface has varying, or stepped heights, wherein a center portion 1396*a* has a first height, a first ring 1396*b* around center portion 1396*a* has a second height, and a second ring 1396*c* surrounding first ring 1396*b* and defining an outer perimeter of pressure gauge 1392 has a third height with first center portion 1396 being higher than first ring 1396*b* and first ring 1396*a* being higher than second ring 1396*c* as shown. An upper surface of base 1396 (i.e., center portion 1396*a*, first ring 1396*b*, and second ring 1396*c*) may comprise a flexible material (e.g., silicon, latex, etc.) that expands when pressure is exerted thereon and contracts when pressure is removed therefrom. Stated differently, center portion 1396*a* may protrude from valve housing 1350 in response to a first inflated pressure, center portion 1396*a* and first ring 1396*b* may protrude from housing 1350 in response to a second inflated pressure that is higher than the first inflated pressure, and center portion 1396*a*, first ring 1396*b*, and second ring 1396*c* may protrude from housing in response to a third inflated pressure that is higher than the second inflated pressure. Accordingly, the protrusion of the thinnest first thickness in the center portion 1396*a* can be representative of the lowest first inflated pressure, the protrusion of the second thickness of the first ring 1396*b* can be representative of a second inflated pressure that is higher than the first inflated pressure, the protrusion of the third thickness of the second ring 1396*c* can be representative of a third inflated pressure that is higher than the second inflated pressure.

Additionally, or alternatively, in some embodiments, first and/or second pressure gauge 1392 and/or 1394 may include a visual color indicator. For example, center portion 1396*a*, first ring 1396*b*, and/or second ring 1396*c* may be color coded so that, for example, center portion 1396*a* is a first color, first ring 1396*b* is a second color, and second ring 1396*c* is a third color. Any color can be used for any of the portions or areas that will allow the user to visually distinguish the different portions or areas. This visual color indicator or other visual indicator can help a clinician or user determine a pressure within the pressure sensor without requiring tactile acuity that may be compromised by, for example, wearing surgical or examination gloves. In some cases, the visual indicator can be a color, pattern, symbol, number, or other indicia.

Figure 62A:
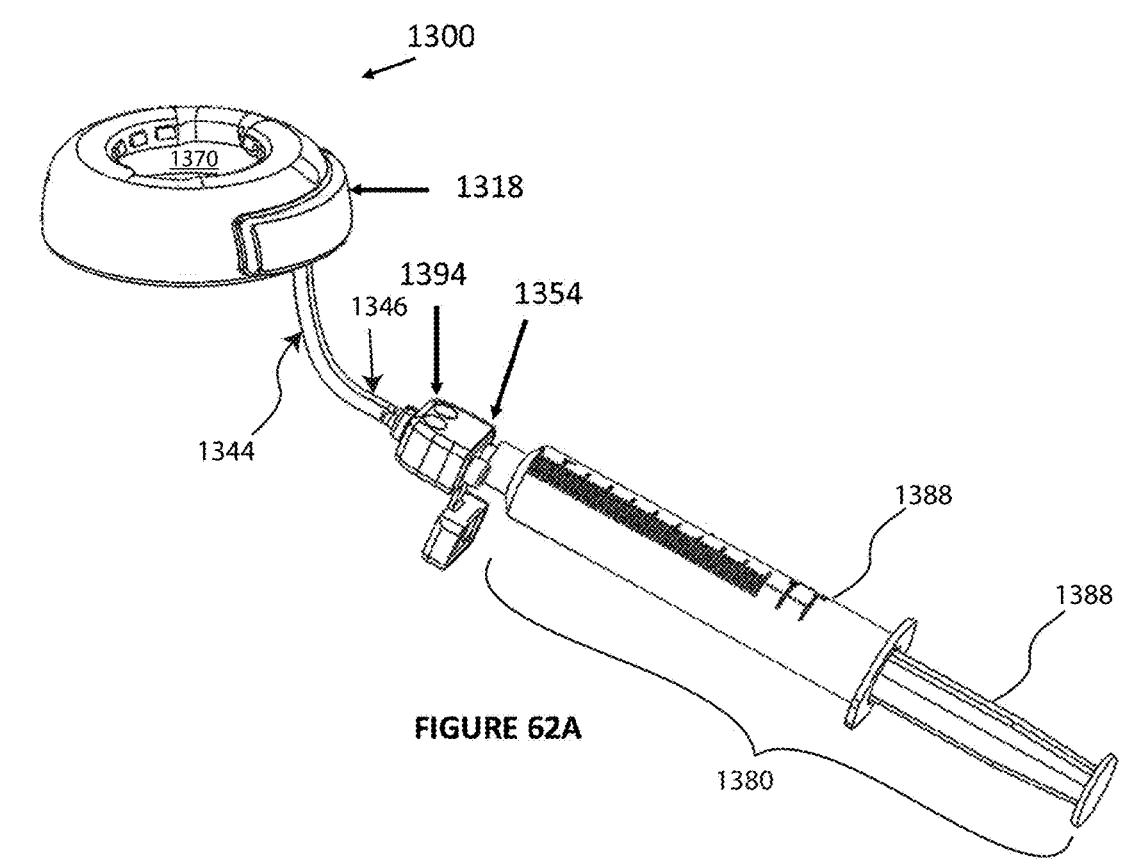
FIG. 62A illustrates a perspective view of a system including a cervical control system with an inner cuff and a positioning balloon in a neutral and deflated state and a valve housing with a syringe inserted into a valve of the valve housing, the valve being associated with the positioning balloon, in accordance with some embodiments of the present invention.
Figure 62B:
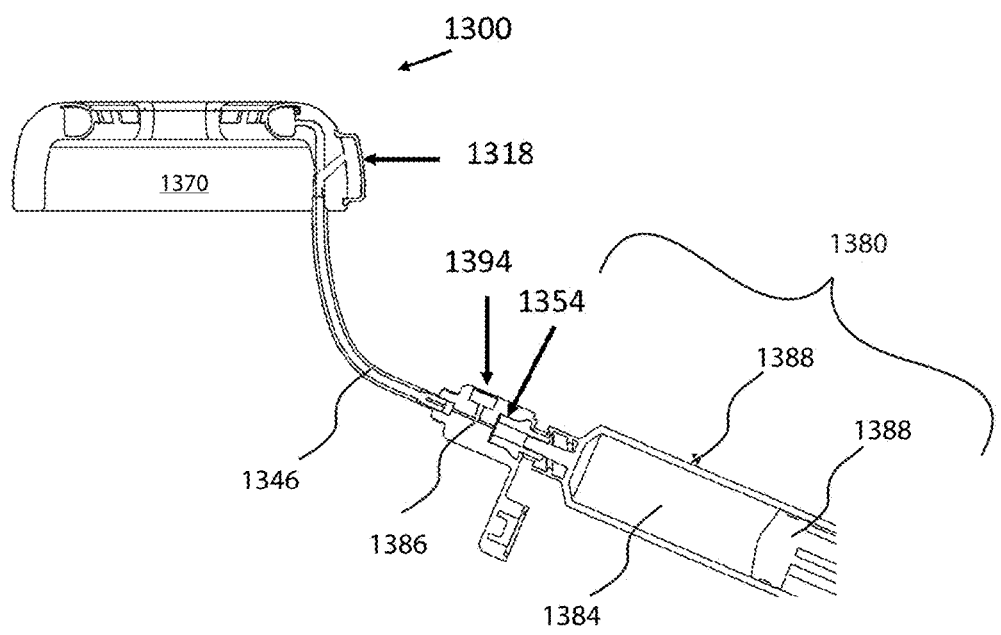
FIG. 62B illustrates a side cross sectional view of the system shown in FIG. 62A and illustrates the fluid communication pathway from the syringe to the positioning balloon, in accordance with some embodiments of the present invention.

FIG. 62A is a perspective view and FIG. 62B is a cross section view of system 1301 when inflation media source 1380 (embodied as a syringe) is positioned within second valve 1354 and in fluid communication with second inflation media conduit 1346 and positioning balloon 1318 and positioning balloon is in a deflated, or neutral, state. Positioning balloon 1318 of system 1300 is in a neutral, or deflated, state and, consequently, second pressure gauge 1394 is in a neutral state indicating there is a neutral (e.g., atmospheric) amount of pressure in positioning balloon 1318 and second inflation media conduit 1346.

The syringe of FIGS. 62A-62B includes a barrel 1382 filled with a volume of inflation media 1384, a needle 1386 in fluid communication with barrel 1382 and a plunger 1388 that fits within barrel 1382 with a fluid tight seal. As arranged in FIGS. 62A and 62B, plunger 1388 extends outward from barrel 1382 so that volume of inflation media 1384 may reside within barrel 1382 as may be the case when, for example, inflation media is to be introduced into second valve 1354 and second inflation media conduit 1346 for communication to positioning balloon 1318 (thereby inflating positioning balloon 1318) or inflation media has been extracted from positioning balloon 1318 via application of negative pressure caused by pulling plunger 1388 out of barrel 1382 (thereby deflating positioning balloon 1318).

Figure 63A:
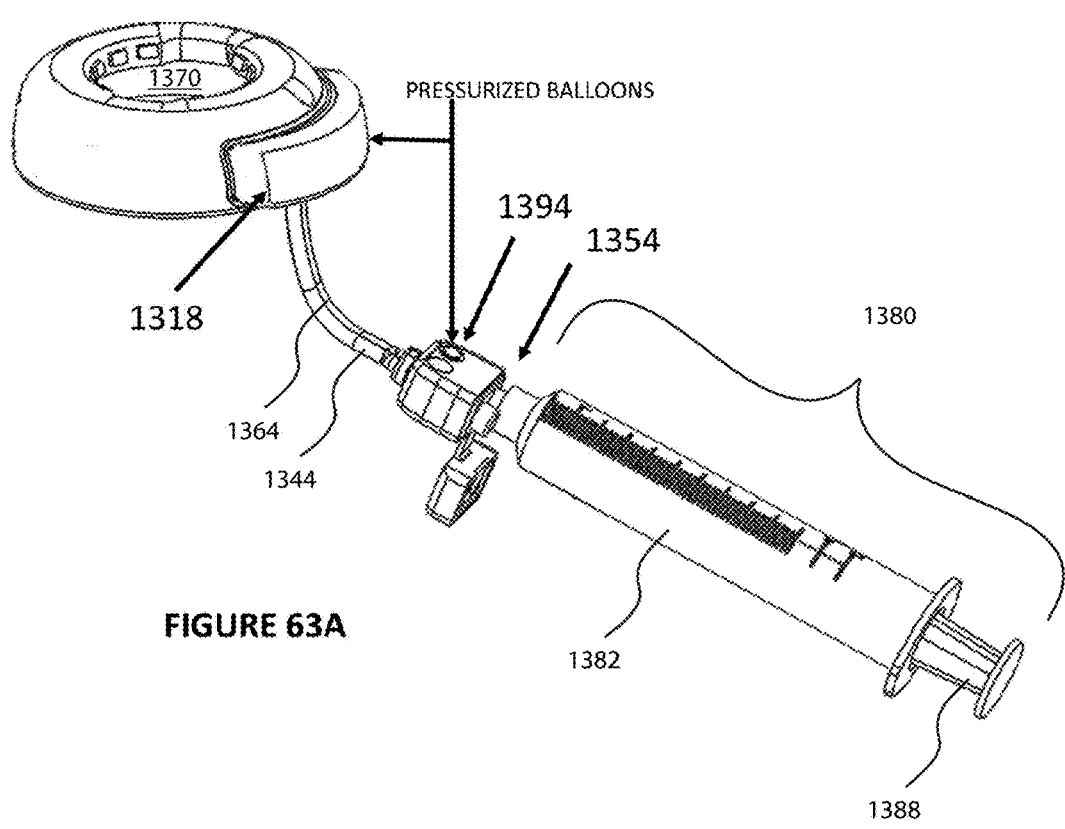
FIG. 63A illustrates a perspective view of the system of FIG. 62A with the positioning balloon in an inflated, pressurized, and/or expanded state, in accordance with some embodiments of the present invention.
Figure 63B:
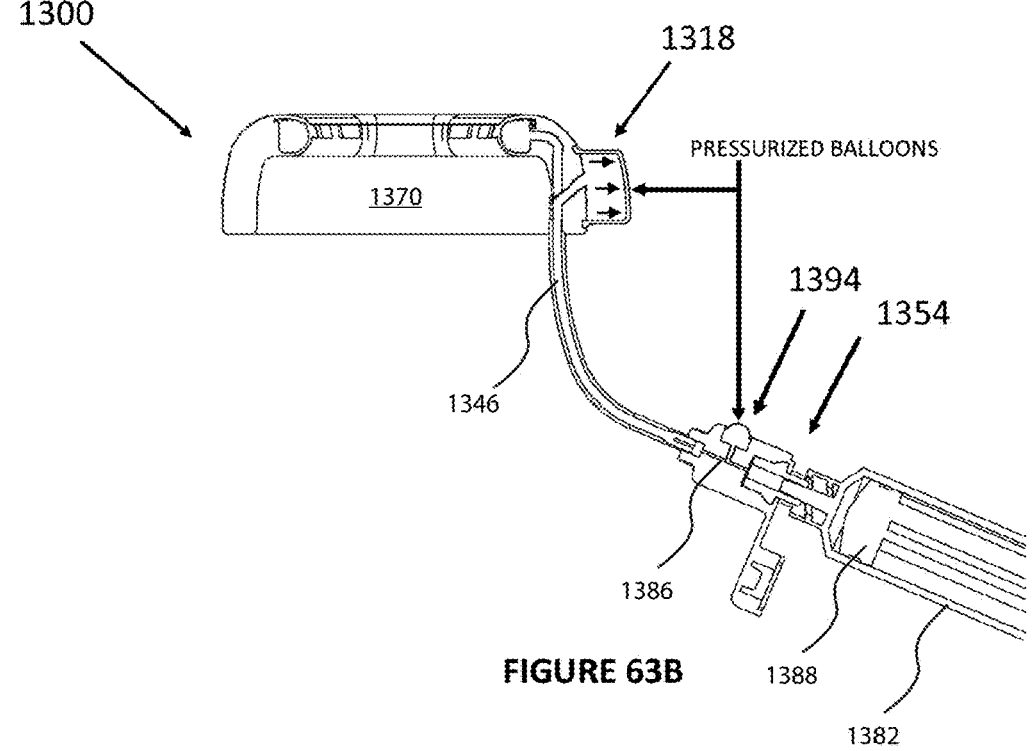
FIG. 63B illustrates a cross sectional view of the system of FIG. 63A, in accordance with some embodiments of the present invention.

FIG. 63A is a perspective view and FIG. 63B is a cross section view of system 1301 when inflation media source 1380 (embodied as a syringe) is positioned within second valve 1354 and in fluid communication with second inflation media conduit 1346 and positioning balloon 1318, wherein positioning balloon 1318 is in an inflated, or expanded, state following transfer of a portion of volume of inflation media 1384 from barrel 1382 to second valve 1354, second inflation media conduit 1346, and positioning balloon 1318, thereby inflating positioning balloon 1318 as shown. The transfer of volume of inflation media 1384 from barrel 1382 to second valve 1354, second inflation media conduit 1346, and positioning balloon 1318 may occur when plunger 1368 is depressed within barrel 1382 (i.e., pushed toward needle 1386), which may exert pressure on volume of inflation media 1384, thereby causing it to move through needle 1386 and into second valve 1354, second inflation media conduit 1346, and positioning balloon 1318, thereby inflating positioning balloon 1318 as shown. Plunger 1388 may be depressed by, for example, a clinician and/or a mechanical device (e.g., pump or robot (not shown)). When positioning balloon 1318 is inflated as shown in FIGS. 63A and 63B, pressure gauge 1394 may indicate a level of pressure in second conduit 1346 (and therefore positioning balloon 1318) by enlarging in manner similar to that discussed above with regard to FIGS. 61A-61D as shown. FIG. 63B also shows an inner chamber 1350 of inner cuff 1308. When inflation media is added to inner chamber 1350, inner cuff 1308 (or a flexible membrane comprising inner cuff or a portion thereof) may expand to accommodate an increase in a volume of inflation media present within inner chamber 1350, thereby inflating, or expanding, inner cuff 1308.

When inflation and/or deflation of inner cuff 1308 is desired, inflation media source 1380 may be extracted from second valve 1354 and inserted into first valve 1352 so that volume of inflation media 1384 may be injected into first valve 1352 for communication to first conduit 1344 and inner cuff 1308, thereby inflating inner cuff 1308. Inner cuff 1308 may be deflated by reversing this process. Additionally, or alternatively, inner cuff 1308 may be inflated by insertion of a second inflation media source 1380 (not shown) embodied as, for example, a syringe or pump into first valve 1352 so that a volume of inflation media 1384 may be injected into first valve 1352 for communication to first conduit 1344 and inner cuff 1308, thereby inflating inner cuff 1308. Inner cuff 1308 may be deflated by reversing this process.

In some embodiments, variations in wall length and wall thickness of one or more of the positioning balloons disclosed herein may serve to control a direction in which the positioning balloon expands when pressurized (i.e., inflated and/or filled with inflation media) due to, for example, properties of the material (e.g., silicon) used to make the positioning balloon and/or associated cervical control system. For example, FIG. 64A provides a cross sectional view of a portion of a cervical control system 1400 (also referred to herein as "system 1400") like, for example, cervical control system 1300 with a positioning balloon 1418 that has varied wall thicknesses when in a neutral, or deflated state and FIG. 64B is a cross sectional view of a portion of system 1400 with positioning balloon 1418 in an expanded, or inflated, state.

Positioning balloon 1418 may be similar (e.g., size, position extending from and exterior surface of system 1400, manner of inflation via an inflation media conduit, function etc.) to the positioning balloon 1318. Positioning balloon 1418 may have a proximal wall 1422, a distal wall 1424, and a vertical wall 1426 that extends from proximal wall 1422 to distal wall 1424. Vertical wall 1426, proximal wall 1422, distal wall 1424, and the outer surface of the main body 1402 form a positioning balloon chamber 1450 that can be filed with inflation media (see e.g., FIG. 64B) to inflate or expand the positioning balloon 1418. Initial proximal wall 1422 length L1 and initial distal wall 1424 length L2 may be equivalent, substantially equivalent, and/or different to adjust the expansion direction of the positioning balloon 1418. In the example of FIGS. 64A and 64B proximal wall 1422 length L1 is approximately the same as distal wall 1424 length L2, which may allow positioning balloon 1418 to expand outwardly away from the exterior surface of the main body 1402 and primarily in the direction that is perpendicular to system body 1402 and/or parallel to the transverse plane of distal opening of system 1400. Continuing with the example of FIGS. 64A and 64B, a thickness (T1) of the proximal wall 1422 and a thickness (T2) of distal wall 1424 is thinner (i.e., has a smaller magnitude) than a thickness (T3) of vertical wall 1426.

Figures 64A, 64B:
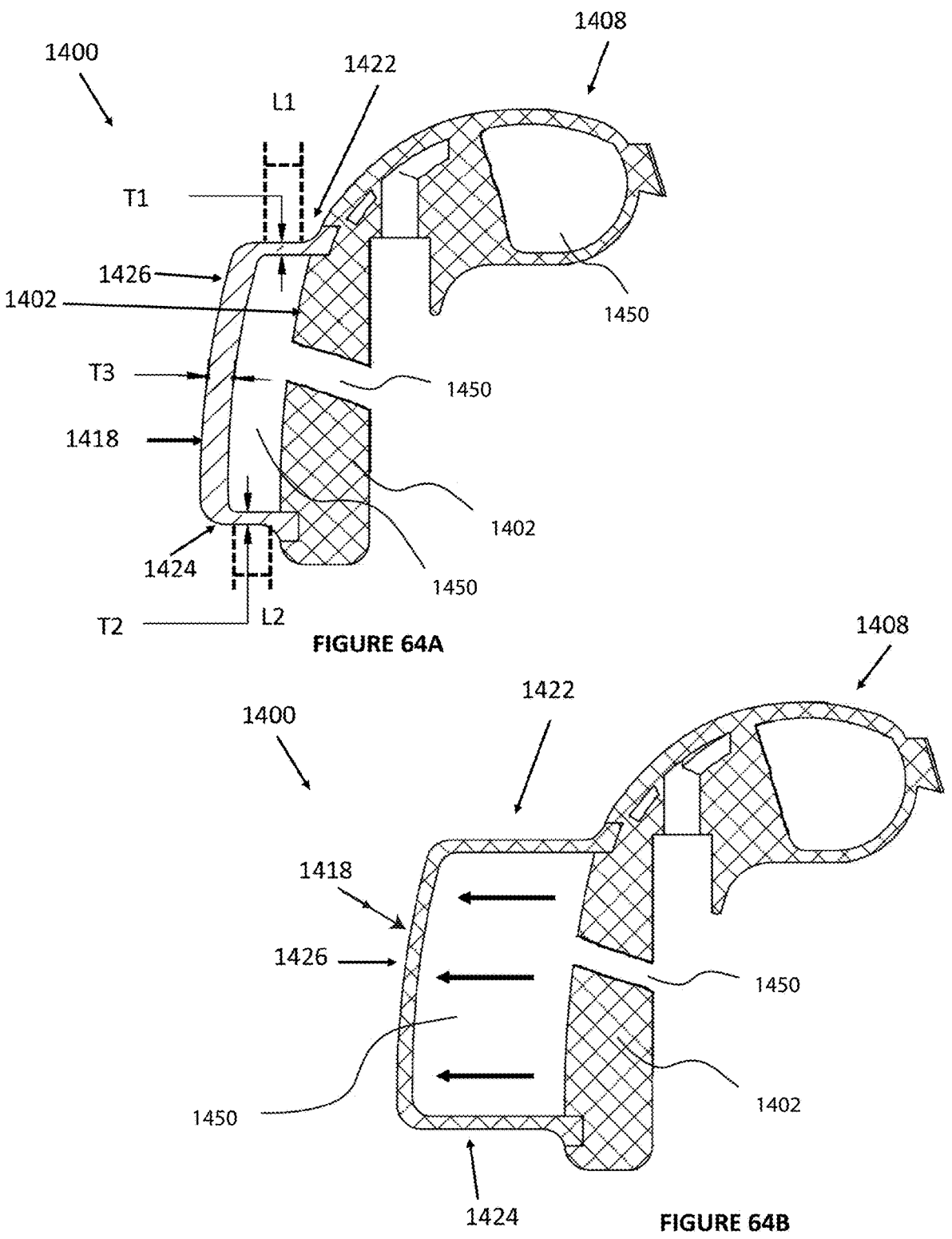
FIG. 64A illustrates a cross sectional view of a portion of a cervical control system with an inner cuff and a positioning balloon in a neutral or deflated state, in accordance with some embodiments of the present invention.
FIG. 64B illustrates a cross sectional view of the cervical control system of FIG. 64A with the inner cuff in a neutral or deflated state and the positioning balloon in an inflated state, in accordance with some embodiments of the present invention.

Due to, for example, properties of the material comprising positioning balloon 1418, differential thickness T3 of vertical wall 1426 when compared to T1 and T2 of proximal and distal walls 1422 and 1424, respectively may assist in providing expansion of positioning balloon 1418 outward (to the left as oriented in FIG. 64B) while restricting expansion in the distal and proximal directions as shown in FIG. 64B. In this way, the configuration shown in FIG. 64A allows for positioning balloon 1418 to expand outwardly from the exterior surface of the main body 1402 and away from the axial center of the distal opening in a direction substantially perpendicular to system body 1402 and/or substantially parallel to the transverse plane of the distal side of the cervical control system as illustrated by the arrows in FIG. 64B so that positioning balloon chamber 1450 has a wider rectangular shape when expanded (FIG. 64B) than when in a neutral state (FIG. 64A). While the cross section of the positioning balloon shown in FIG. 64A-64B is illustrated as rectangular or substantially rectangular, the cross section of the positioning balloon can be circular or substantially circular shaped, semi-circular or substantially semi-circular shaped, triangular or substantially triangular shaped, inverted triangular or substantially inverted triangular shaped, square or substantially square shaped, oval or substantially oval shaped, partial oval or partial substantially oval shaped, an irregular shape with a non-symmetrical cross section, or any other shape that can provide support and/or engage with the vaginal wall. In some cases, a cross sectional shape of positioning balloon 1418 may be an inverted triangular or substantially inverted triangular shaped that can expand or contract with an apex of the triangle acting as a hinge.

Exemplary thicknesses T1 and T2 of the proximal wall 1422 and/or distal wall 1424 may range from 0.3-2 mm, 0.1-1.5 mm, 0.2-1 mm, 0.4-0.8 mm, 0.3-0.6 mm, 0.1-0.5 mm, and overlapping ranges therein. The thickness T3 of the vertical wall 1426 may be 0.88 mm and/or within a range of 0.4-2 mm, 0.6-1.8 mm, 0.8-1.6 mm, 1-1.4 mm, 0.8-1 mm, and overlapping ranges therein. As described herein, in some cases, the selected wall thickness may be responsive to and/or dependent on hardness level and/or durometer of the material being used. For example, when silicone is used the selected wall thickness may be responsive to and/or dependent on the silicone's hardness level and/or durometer. As an example, when a lower durometer silicone is used (e.g., 10A) the wall thickness for T1 and/or T2 may be relatively thicker (e.g., 1-2 mm) than when higher durometer (e.g., 40A-80A on the Shore A scale) silicone and/or a more elastic/tear resistant material (e.g., a silicone dispersion material) is used, which may be relatively thinner e.g., 0.95-0.05 mm). For example, the wall thickness of T1 and/or T2 may be 0.3 mm, 0.4 mm, 0.5 mm, 0.6 mm, 0.7 mm, 0.8 mm, and overlapping ranges therein with a silicone durometer selection of 20A, 30A, 40A, or 50A. In some embodiments, the silicone durometer selection range can be 10A-70A. In some cases, the wall thickness for can be greater than or equal to 0.1 mm for expandable walls assuming the wall is stretching, and that a handle operated 10 cc syringe that is used that can output around 20 psi. In some cases, the wall thickness T1 and T2 can range from about 0.1-2 mm for a silicone durometer selection of 10A-30A hardness levels. In some embodiments, (e.g., 40A-50A hardness), the wall thickness T1 and T2 can range from 0.1 mm to 1 mm and, in other embodiments (e.g., 60A-70A hardness), wall thickness T1 and T2 can range from about 0.1-0.5 mm. While the wall thicknesses and hardness described herein are described with reference to T1 and T2, the examples of wall thicknesses and associates hardness levels can be used for any of the wall thicknesses for any expanding wall and/or membrane of the cervical control system.

Figure 65A:
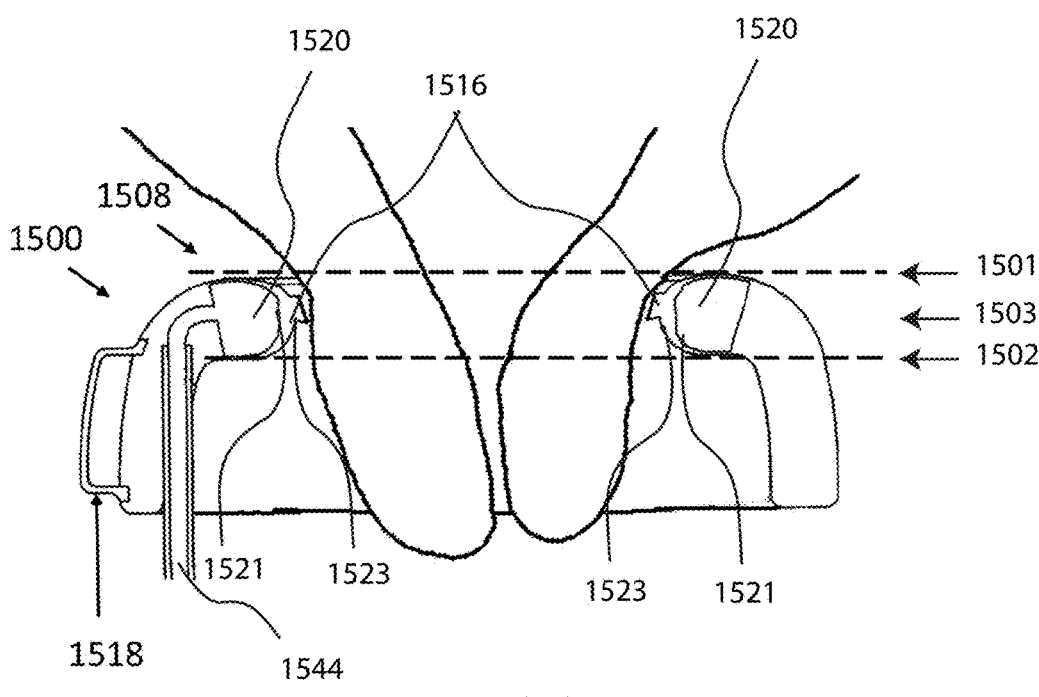
FIG. 65A illustrates a cross sectional view of add with a cervix positioned within the inner passageway thereof and an inner cuff of the cervical control system being in a neutral state, in accordance with some embodiments of the present invention.
Figure 65B:
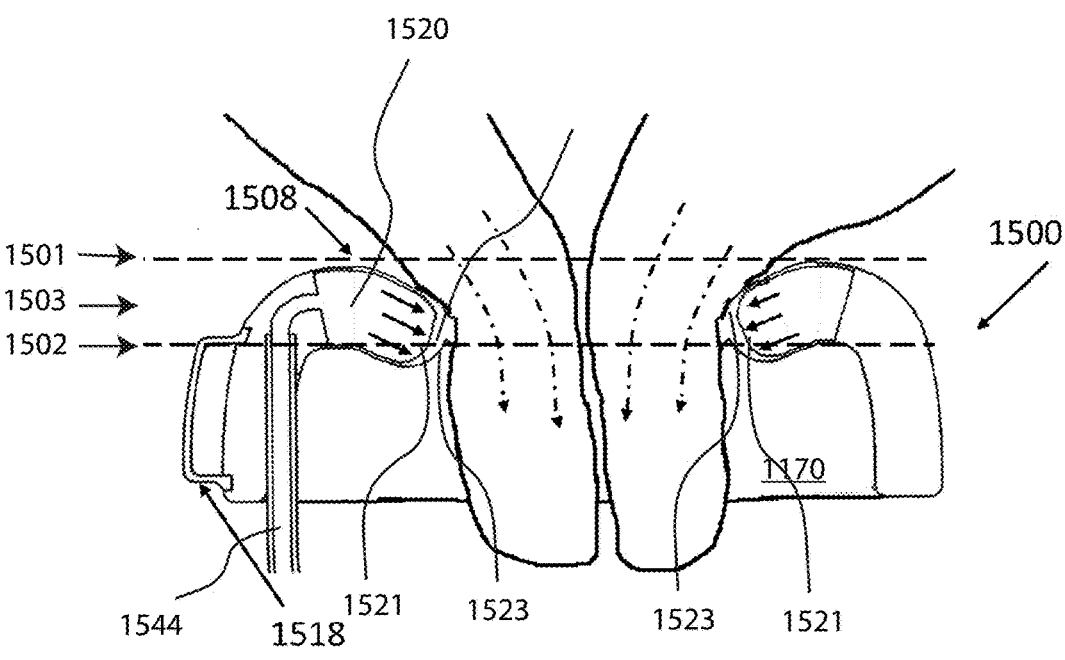
FIG. 65B illustrates a cross sectional view of the cervical control system of FIG. 65B with the cervix positioned within the inner passageway thereof and the inner cuff of the cervical control system being in an inflated, expanded, and/or pressurized state, in accordance with some embodiments of the present invention.

In some embodiments, the inner cuffs disclosed herein may also be designed and/or configured for directional expansion by, for example, leveraging material properties and/or dimensions thereof as, for example, illustrated in, for example, FIGS. 9-12, 34, and 64A, 64B described herein and, in particular, with regard to FIGS. 9-12 and 34. Another example of an inner cuff with varying wall thickness that enables directional expansion in a preferred direction is illustrated in FIGS. 65A and 65B and discussed below. In particular, FIG. 65A is a sectional view of an exemplary cervical control system 1500 (also referred to herein as "system 1500") that shows an inner cuff 1508 in a neutral state, a positioning balloon 1518 in a neutral state and cervix 101 positioned within an interior passageway 1570 of system 1500. System 1500 may be similar to, and/or have features and/or functionalities similar to, one or more of the cervical control systems disclosed herein. FIGS. 65A and 65B include a first phantom line 1501 and a second phantom line 1502 with space between first and second phantom lines 1501 and 1502 defining a proximal plane 1503 for inner cuff 1508 in the neutral state as shown in FIG. 65A.

Once cervix 101 is positioned within interior passageway 1570 as shown in FIG. 65A, inner cuff 1508 may be inflated via, for example, inflation media pushed into a first inflation media conduit 1544 in a manner similar to that described above with regard to FIGS. 58-63 and, in particular FIGS. 62A-63B. During inflation, inner cuff 1508 directionally expands toward inner passageway and downward (as oriented in the sectional view of FIG. 65B) past second phantom line 1502 so that cleats 1516 press into an exterior surface of cervix 101 and cervical tissue and push cervical tissue downward further into interior passageway, thereby elongating cervix 101 as shown in FIG. 65B.

The directional expansion of inner cuff 1508 may be enabled by varying wall thicknesses of material comprising inner cuff 1508 as disclosed herein with regard to, for example, FIGS. 9-12, 34, and 64A, 64B. As may be seen in FIGS. 65A and 65B, proximal cuff 1508 comprises a chamber 1520 in communication with first inflation media conduit 1544. When in a neutral state, chamber 1520 is bound, or defined, by an inner wall 1521 that has a shape approximating an elongated semi-circle. An exterior surface of inner cuff 1508 is defined by an outer wall 1523 that has cleats 1526 molded therein. When in a neutral state (e.g., FIG. 65A), a space between inner and outer walls 1521 and 1523 is relatively thin in a proximal wall portion and a distal wall portion and wider at an apical portion of the curve of inner cuff 1508 so that a material comprising inner cuff 1508 is thicker at apical portion (i.e., toward the apex of the approximately semi-circular curve of inner cuff 1508) than at the proximal and distal wall portions. As inner cuff 1508 is pressurized by the introduction of inflation media into chamber 1520, the apical portion stretches, or becomes thinner (e.g., 10-95% thinner), thereby expanding chamber 1520 to accommodate pressurization caused by the introduction of the inflation media into chamber 1520 in a preferred direction as shown in FIG. 65B. Expansion (e.g., radial inward expansion and/or radial downward expansion) of inner cuff 1508 acts to, for example, press cleats 1516 into cervical tissue, thereby increasing engagement between cleats 1516 and cervical tissue. Additionally, or alternatively, expansion (e.g., radial inward expansion and/or radial downward expansion) of inner cuff 1508 may act to engage cervix 101, push it closed, and/or pull it downward (relative to first and second phantom lines 1510 and 1502), thereby compressing and/or elongating cervix 101 from its original state (see. e.g., FIG. 65A) to a compressed and/or elongated state as shown in FIG. 65B, which may be helpful with, for example, preventing preterm birth and/or treating PPROM.

Stated differently, the tension, elongation, and/or compression of cervix 101 via inflation of inner cuff 1508 may create an anatomical state of cervix 101 that may control cervical function (e.g., prevent dilation and/or shorting) and, in some cases, may provide conditions conducive to replacement, enlargement, and/or regeneration of a cervical mucus plug (not shown) positioned at, or near, an internal os of cervix 101.

For example, one portion of inner cuff 1508 can inflate in a planer or more planer direction toward the axial center of the proximal opening of the cervical control system, while another portion of the inner cuff can inflate in a slight distally direction. This can allow the cervical control system to intentionally kink the cervix. In some cases, the inner cuff can be sized to provide mechanical compression to the cervix in the neutral or uninflated state by the external diameter of the inner cuff being smaller than or equal to the diameter of the cervix. In some cases, the inner cuff can expand radially inward but does not expand in a distal direction. In some cases, the inner cuff can expand distal direction but does not expand radially inward. In other cases, the inner cuff can expand only in a proximal direction or radially inward and in a proximal direction.

Figure 66:
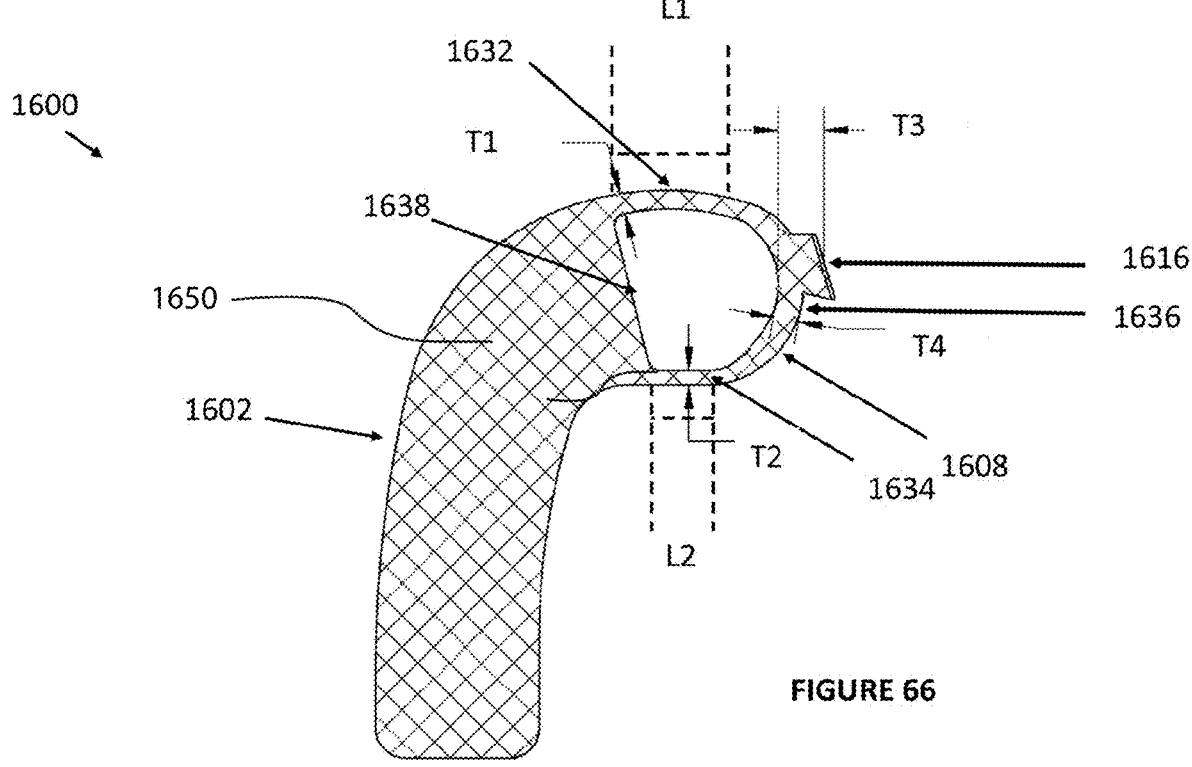
FIG. 66 illustrates a side cross sectional view of a portion of a cervical control system showing an inner cuff and an inner chamber defined by a flexible membrane of the inner cuff, in accordance with some embodiments of the present invention.

FIG. 66 illustrates a side cross sectional view of a portion of an exemplary cervical control system 1600 (also referred to herein as "system 1600"). System 1600 may be similar to and/or have features in common with, for example, systems 100, 500, 1000, 1100, 1300, 1400, and 1500 described above and illustrated in FIGS. 1-6, 19-20, 36-37, 51-54, 58-59, 64A-64B, and 65A-65B respectively. For example, system 1600 has as a main body 1602, an inner cuff 1608, and cleats 1616 that may be positioned around an interior perimeter of the inner cuff 1608 and extend therefrom in a manner similar to, for example, how cleats 1316 are positioned around and extend from an interior perimeter and/or exterior surface of inner cuff 1308 of system 1300. Inner cuff 1608 is configured and designed to have varying the wall thickness and length of portions that may facilitate expansion in a preferred (e.g., radial and/or distal direction. For example, inner cuff 1608 may have a proximal wall 1632 of a first thickness T1 and a first length L1, a distal wall 1634 of a second thickness T2 and a second length L2 and an apical section 1636 that connects proximal and distal walls 1632 and 1634 to form inner cuff 1600 to form an inner chamber 1650 as shown. Apical section 1636 may have a third thickness T3 at an apex, or center point of cleat 1616 and a remainder of apical section 1636 (i.e., without cleat 1616) may have a fourth thickness T4 as shown in FIG. 66. In some cases, proximal wall 1632 and distal wall 1634 thickness T1 and T2 may be thinner than the thicknesses T3 and T4 of apical section 1636, which may allow for expansion of the inner cuff 1608 in a radially inward direction when the inner cuff 1608 is pressurized (i.e., inflation media is added to inner chamber 1650). Exemplary first and/or second thicknesses T1 and/or T2 of the proximal wall 1632 and/or distal wall 1634 may range from about 0.5 mm-3 mm, 0.1 mm-1.5 mm, 0.2 m-1 mm, 0.4 mm-0.8 mm, 0.3 mm-0.6 mm, and overlapping ranges therein. Exemplary third thicknesses T3 of apical portion 1636 with cleat 1616 may be about 1.65 mm and/or range from 1 mm to 2 mm, 1.2 mm to 1.8 mm, 1.4 mm to 1.7 mm, 1.5 mm to 1.7 mm, 1.6 mm to 1.65 mm, and overlapping ranges therein. Exemplary thicknesses for fourth thickness T4 apical portion 1636 without the cleat 1616 are about 0.88 mm and/or may range between 0.4 mm to 2 mm, 0.6 mm to 1.8 mm, 0.8 mm to 1.6 mm, 1 mm to 1.4 mm, 0.8 mm to 1 mm, and overlapping ranges therein. Third thickness at the thickest point of the cleat 1616 can be approximately 1.9 mm and/or range between 1-3 mm, 1.5 mm to 2.5 mm, 1.8 mm to 2.2 mm or 1.9 mm and overlapping ranges therein.

As shown in FIG. 66, the inner cuff 1608 can have an inner wall 1638 that extends from the proximal wall 1632 to the distal wall 1634 and define an edge of chamber 1350 approximate opposite apical portion 1636. Inner wall 1638 can be parallel to the axial center of the cervical control system. In other cases, the inner wall 1638 can be angled up or down with respect to the axial center of the cervical control system or angled (e.g., 90-170 degrees) relative to an upper (as oriented in FIG. 66) side of distal wall 1634 as shown in FIG. 66. The angle of inner wall 1638 shown in FIG. 66 may assist with expansion of chamber 1350 and/or inner cuff 1608 in a preferred (e.g., downward) direction which may assist with, for example, elongating a cervix proximate to inner cuff 1608 and/or guiding the cervix into a desired position within system 1600. The inner cuff 1608 can be designed to have a downward bias in the neutral or deflated state so that even though the inner wall 1638 is angled up, the inner cuff 1608 can expand in the downward direction when inflated as described herein. As illustrated in FIG. 66, the cross section of inner cuff 1608 engaged on the exterior surface of the main body can be an irregular shaped cross section with a non-symmetrical cross section. While the cross section of inner cuff 1408 and inner chamber 1450 shown in FIG. 64A-64B is illustrated as having a non-symmetrical cross section roughly in the shape of a "D," a cross sectional shape of inner cuff 1408 and inner chamber 1450 may have any appropriate shape including, but not limited to, a rectangular, parallelogram, circular, substantially circular, semi-circular, substantially semi-circular shaped, triangular, substantially triangular, square, substantially square shaped, oval, substantially oval shaped, partial oval, partial substantially oval shaped, or any other shape that can assist inner chamber 1450 and/or inner cuff 1408 perform to, for example, control provide support for, and/or engage with the cervix.

Additionally, or alternatively, the length L1 of the proximal wall 1632 and the length L2 of the distal wall 1634 can be varied to control the directional expansion of the inner cuff 1608. For example, the length L1 of the proximal wall 1632 can be longer than the length L2 of the distal wall 1634 which can encourage the expansion of the inner cuff 1608 in the distal direction when the inner cuff 1608 is pressurized.

FIGS. 67A-67C and 68A-68B illustrate various views of a cervical control system 1700 in situ that may have features and/or functionally similar to, for example, systems 100, 500, 1000, 1100, 1300, 1400, 1500, and/or 1600 as described herein and illustrated in FIGS. 1-6, 19-20, 36-37, 51-54, 58-59, 64A-64B, 65A-65B, and 66, respectively. For example, system 1700 includes a main body 1702, a proximal opening 1704, a distal opening (not shown), an interior passageway 1770, an expandable annular inner cuff 1708 with recessed portions 1710 and expandable portions 1712, a positioning balloon 1718 positioned proximate to the distal opening and on an exterior surface of body 1702, a plurality of cleats 1716 arranged on an exterior surface and/or inner perimeter of inner cuff 1708, that may be similar to and/or incorporate features of the main body, proximal opening, distal opening, interior passageway, and expandable annular inner cuff with recessed portions and expandable portions, positioning balloon, and/or cleats of, for example, systems 100, 500, 1000, 1100, 1300, 1400, 1500, and/or 1600 described herein and shown in the figures.

Figures 67A, 67B, 67C:
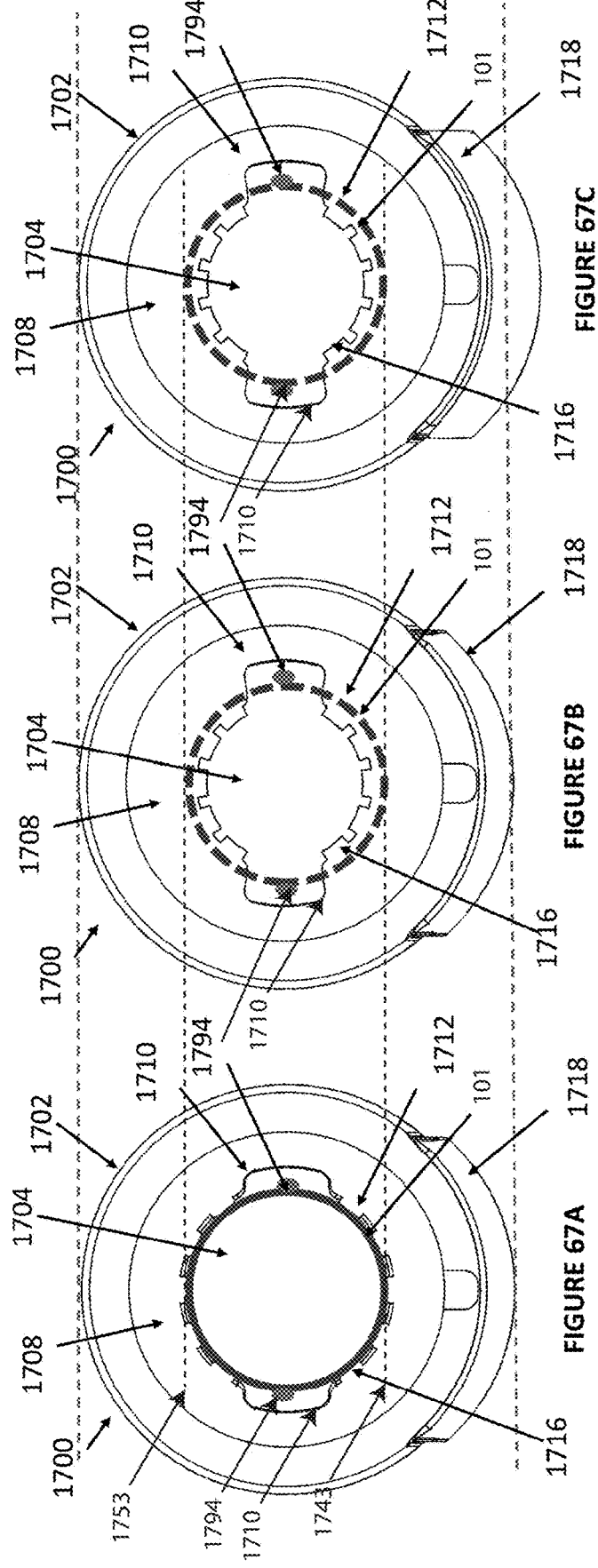
FIG. 67A illustrates a top view of a cervical control system with an inner cuff and a positioning balloon both in a neutral state and a cervix positioned within an inner passageway thereof, in accordance with some embodiments of the present invention.
FIG. 67B illustrates a top view of the cervical control system of FIG. 67A with the cervix positioned within an inner passageway thereof, the inner cuff in a pressurized, or expanded state, and a positioning balloon in a neutral state, in accordance with some embodiments of the present invention.
FIG. 67C illustrates a top view of the cervical control system of FIG. 67A with the cervix positioned within an inner passageway thereof, and both the inner cuff the positioning balloon being in a pressurized, or expanded, state, in accordance with some embodiments of the present invention.

FIGS. 67A-67C illustrate a top, or distal (when in situ) view of cervical control system 1700 in situ with cervix 101 (represented as a circle in FIG. 67A and a dashed line in FIGS. 67B and 67C) positioned within interior passageway 1770. Two major blood vessels 1794 of cervix 101 are also shown and are positioned within recessed portions 1710 of system 1700 in FIGS. 67A-67C. FIGS. 67A-67C also provide a first pair of phantom lines including a first phantom line 1751 and a second phantom line 1752 positioned above and below (as oriented in the figures) system 1700 when inner and positioning balloons 1708 and 1718 are deflated and a second pair of phantom lines including a third phantom line 1753 and fourth phantom line 1754 positioned above and below (as oriented in the figures) inner cuff 1708 when inner and positioning balloons 1708 and 1718 are deflated so that a relative changes between a size of inner cuff 1708 and outer cuff 1718 when in a neutral and inflated state may be observed.

In particular, FIG. 67A illustrates a distal view of system 1700 with both inner cuff 1708 and the positioning balloon 1718 in a neutral, or deflated, state as may be the case when system 1700 is placed within the patient's vagina 103 and cervix 101 is positioned within interior passageway 1770. FIG. 67B illustrates a distal view of system 1700 with inner cuff 1708 pressurized or inflated to apply compression around the cervix 101 and the positioning balloon 1718 is in the uninflated state (see expansion of upper and lower (as oriented in FIG. 67B) sides of inner cuff 1708 past third and fourth phantom lines 1703 and 1704, respectively). When the inner cuff 1708 is pressurized or inflated, expandable portions 1712 may expand or extend radially inward as shown in FIGS. 67B and 67C to apply compression around a circumference of cervix 101 not including blood vessels 1794 and recessed portions 1710 may remain in an uninflated, or recessed, state (i.e., do not, or only minimally, expand or extend radially inward) so that compression caused by the inflation of inner cuff 1708 is not applied (or a reduced amount is applied) to cervical blood vessels 1794. This allow expandable portion 1712 of inner cuff 1708 to compress a majority (i.e., portions proximate to extendable portions 1712) of cervix's 101 circumference areas proximate to blood vessels 1794 are relatively uncompressed while the recessed portions 1710 of the inner cuff 1708 remain uninflated or less inflated and the arteries of the cervix are not compressed (or less compressed), which allows blood flow through blood vessels 1794 to be relatively unhindered by compression caused by inner cuff 1708.

In some embodiments, inner cuff 1708 may deploy variable wall thicknesses of material (e.g., a flexible membrane) to form expandable portions 1712 and recessed portions 1710 of inner cuff 1708, with recessed portions 1710 having a greater wall thickness (and therefore more resistant to expansion) than expandable portions 1712. This arrangement can allow expandable portions 1712 to expand or inflate at a lower pressure than recessed portions 1710. Additionally, or alternatively, recessed portions 1710 may be indentations and/or recesses in the wall and/or flexible membrane of inner cuff 1701. While FIGS. 67A-67C illustrate recessed portions 1710 having a substantially rounded rectangular shape, recessed portions 1710 may be of any appropriate shape including, for example, a semi-circle, an oval, a trapezoid, a parallelogram, an irregular shape, and combinations thereof.

FIGS. 67A-67C illustrate the recessed portions 1710 of inner cuff 1708 positioned on opposite sides (e.g., approximately 180 degrees apart) of inner cuff 1708. However, recessed portions 1710 can be positioned at any position along the inner cuff 1708 that is necessary and/or preferred to prevent construction of blood vessels like blood vessels 1704 and/or restriction of blood flow to cervix 101 from arteries and/or veins. In some cases, as shown in FIG. 67A, the recessed portions 1710 are present in the inner cuff 1708 prior to inflation or expansion of the inner cuff 1708 but, this need not always be the case. In some cases, the interior volume of the recessed portions 1710 can increase as the expandable portions 1712 expand or extend radially inward when the inner cuff 1708 is pressurized.

FIG. 67C illustrates a distal view of system 1700 with inner cuff 1708 pressurized or inflated to apply compression around cervix 101 (as shown in FIG. 67B and described above) and positioning balloon 1718 in an inflated or expanded state (see expansion of lower (as oriented in FIG. 67C) edge of positioning balloon 1718 past second phantom line 1752).

Figure 68A:
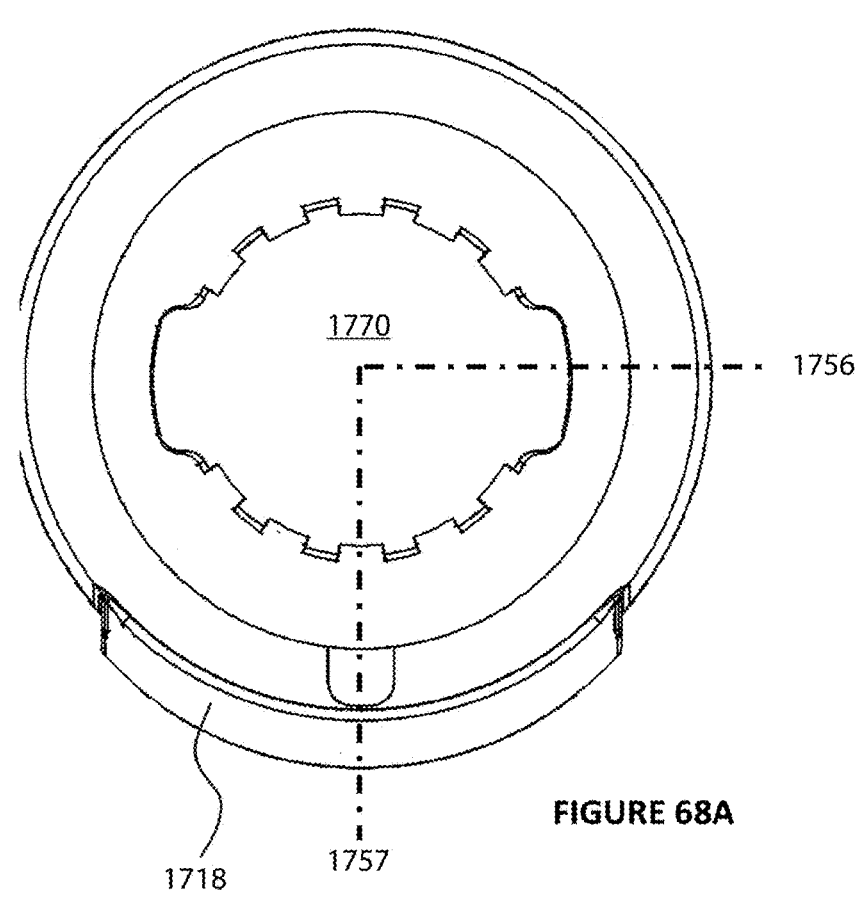
FIG. 68A illustrates a top view of the cervical control system of FIGS. 67A-67B, in accordance with some embodiments of the present invention.
Figure 68B:
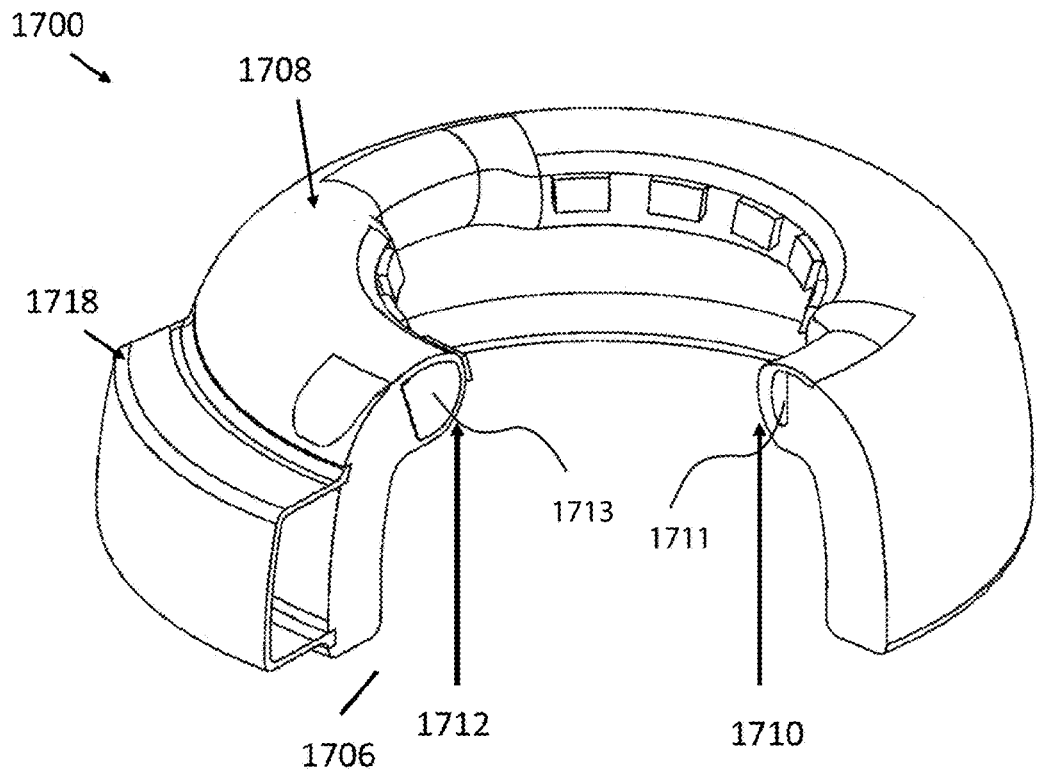
FIG. 68B illustrates a 90-degree cross section of the cervical control system of FIG. 68A, in accordance with some embodiments of the present invention.

FIG. 68A provides a top and FIG. 68B provides a 90-degree cross (along phantom lines 1756 and 1757 shown on FIG. 68A) view of system 1700 when not in situ (i.e., without cervix 101 positioned within internal passageway

1770). As shown in FIG. 68B, inner cuff 1708 can be positioned around the circumference of system 1700 at a proximal end of system 1700 and a wall thickness of recessed portion 1710 may be thicker than a wall thickness of expandable portion 1712, which may cause and/or contribute to an inner chamber 1713 of expandable portion 1712 to be larger than an inner chamber 1711 of recessed portion 1710. Larger inner chamber 1713 of expandable portion 1712 has a larger volume and can accommodate acceptance of more inflation media than inner chamber 1711 of recessed portions and this volume differential may contribute to the greater expansion capabilities of expandable portions 1712 as compared to the expansion capabilities of recessed portions 1710.

In other cases, the inner cuff can be segmented instead of running circumferentially around the cervical control system to provide for expandable portions and recessed portions. In such cases, the segments can each be supplied with a tubing or conduit assembly to provide the pressurization to each individual segment. In some cases, the inner cuff does not include recessed portions and expanded portions. In some cases, the inner cuff does not have varying wall thicknesses.

Figures 69A, 69B, 69C:
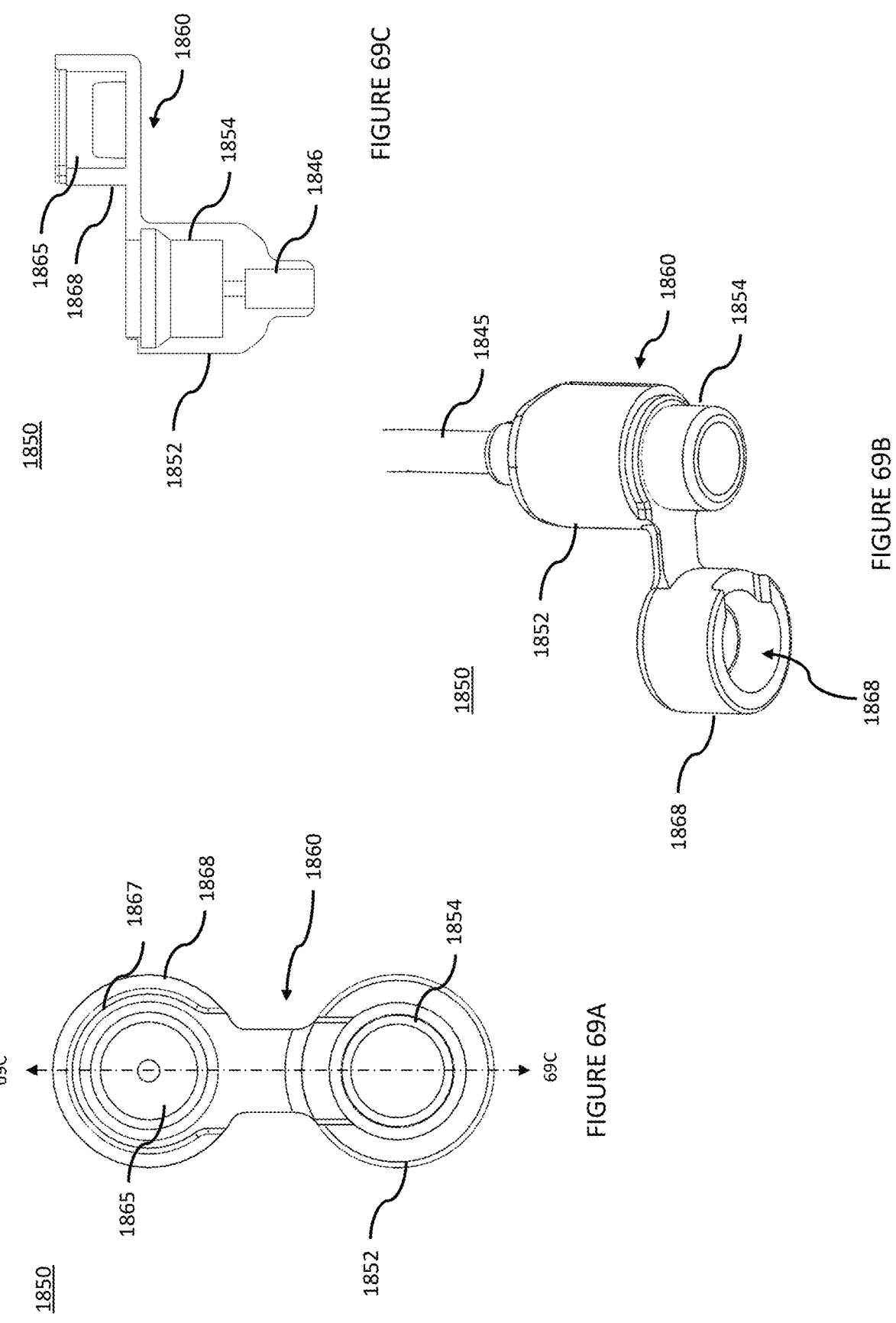
FIG. 69A illustrates a top view of a valve housing for a single valve, in accordance with some embodiments of the present invention.
FIG. 69B illustrates a bottom perspective view of the valve housing of FIG. 69A, in accordance with some embodiments of the present invention.
FIG. 69C illustrates a cross section view of the valve housing of FIG. 69A, in accordance with some embodiments of the present invention.

FIGS. 69A-69H provide various views of a system 1801 including a cervical control system configured with a single valve and components thereof. In particular, FIG. 69A provides a top view, FIG. 69B provides a perspective view and FIG. 69C provides a cross section view (take along vertical bisecting phantom line 69C of FIG. 69A) of an exemplary single valve system 1850 that includes a single port valve housing 1860, a single valve 1854, a valve base 1852, and a valve cover 1868 that includes an extension 1867 that defines a recessed area 1865. Extension 1867 may be sized, positioned, and configured to fit over and protect a portion of valve 1854 that extends from valve base 1852 and resides within recessed area 1865 when valve cover 1868 is closed by, for example, pushing it over valve 1854. Single port valve housing 1860 may be configured to hold valve 1854 in a manner similar to, for example, valve housing 1360. Valve 1854 may be, for example, a one-way valve, a duckbill valve, a silicone valve, a check valve, a Halkey Roberts valve, a luer activated check valve, or a check valve with polycarbonate bodies.

As may be seen in the cross section of FIG. 69C, single port valve housing 1860 may include a channel 1846 configured for cooperation with an inflation media conduit that may be in fluid communication with one or more components of a cervical control system, such as a cervical control system 1800A and/or 1800B as shown in, for example, FIGS. 69D-69H.

Figure 69D:
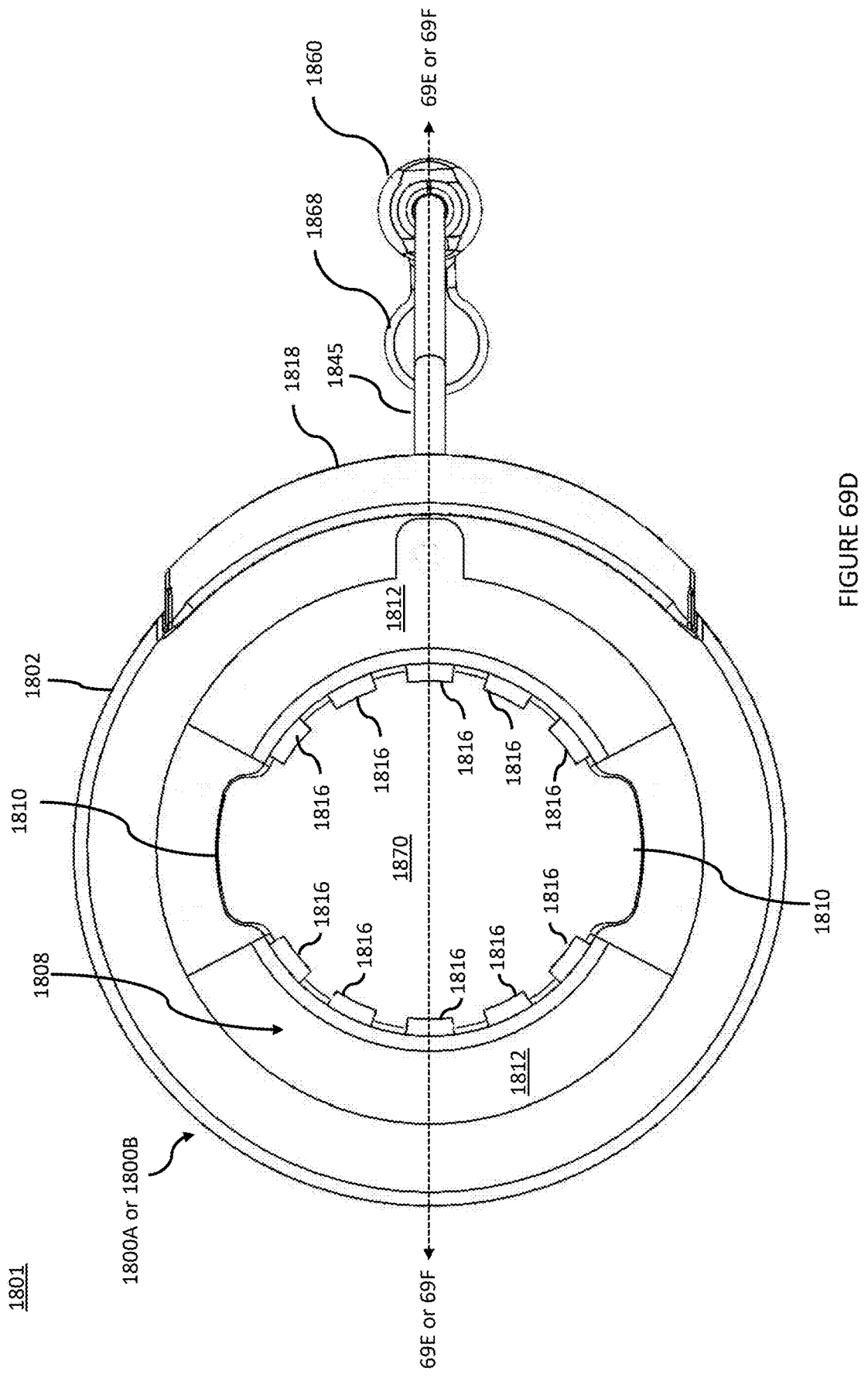
FIG. 69D illustrates a top view of system including a cervical control system and the valve housing of FIG. 69A, in accordance with some embodiments of the present invention.
Figure 69E:
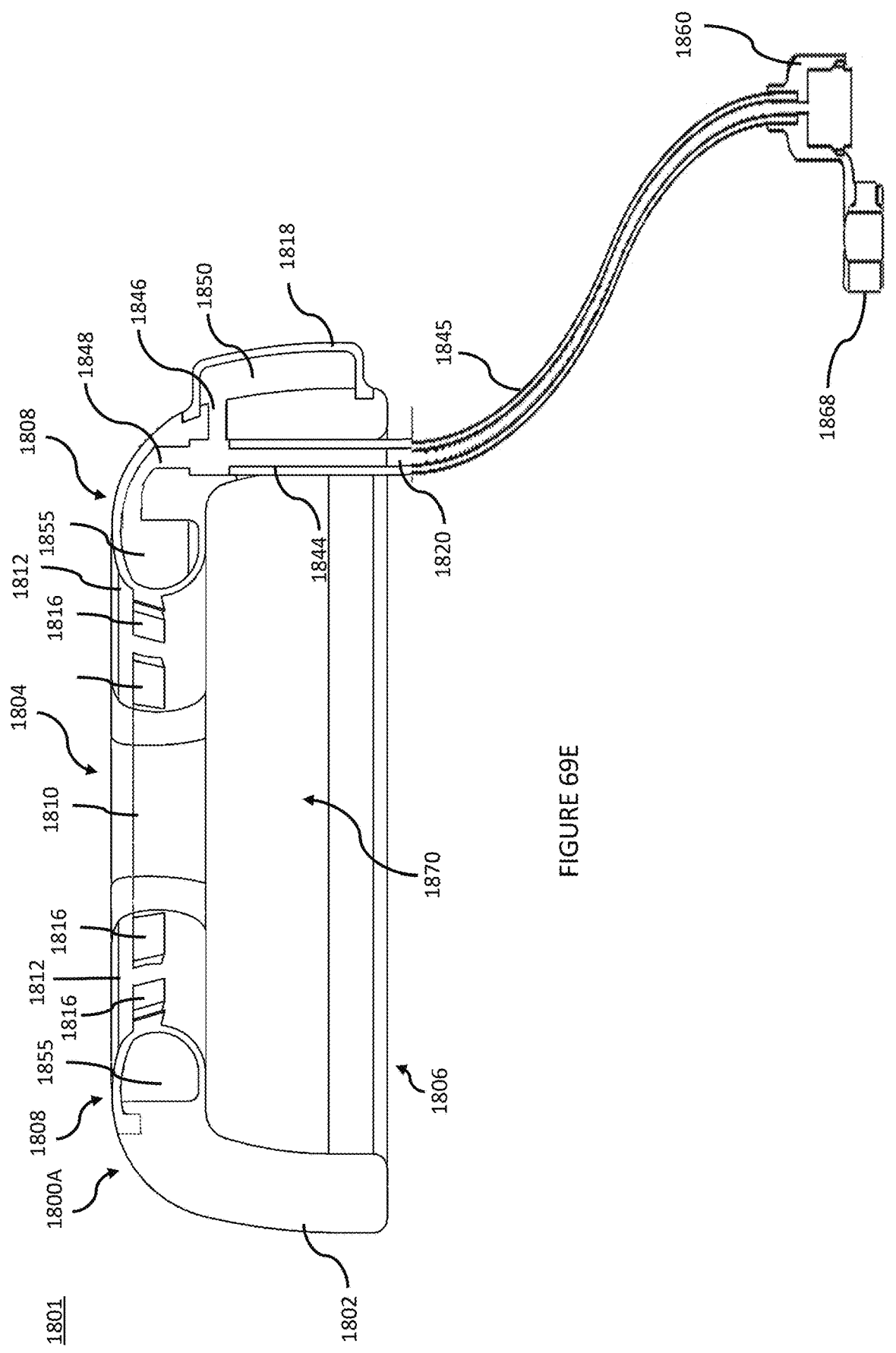
FIG. 69E illustrates a cross section of a first embodiment of the system of FIG. 69D taken along sectioning line 69E or 69F of FIG. 69D, in accordance with some embodiments of the present invention.
Figure 69F:
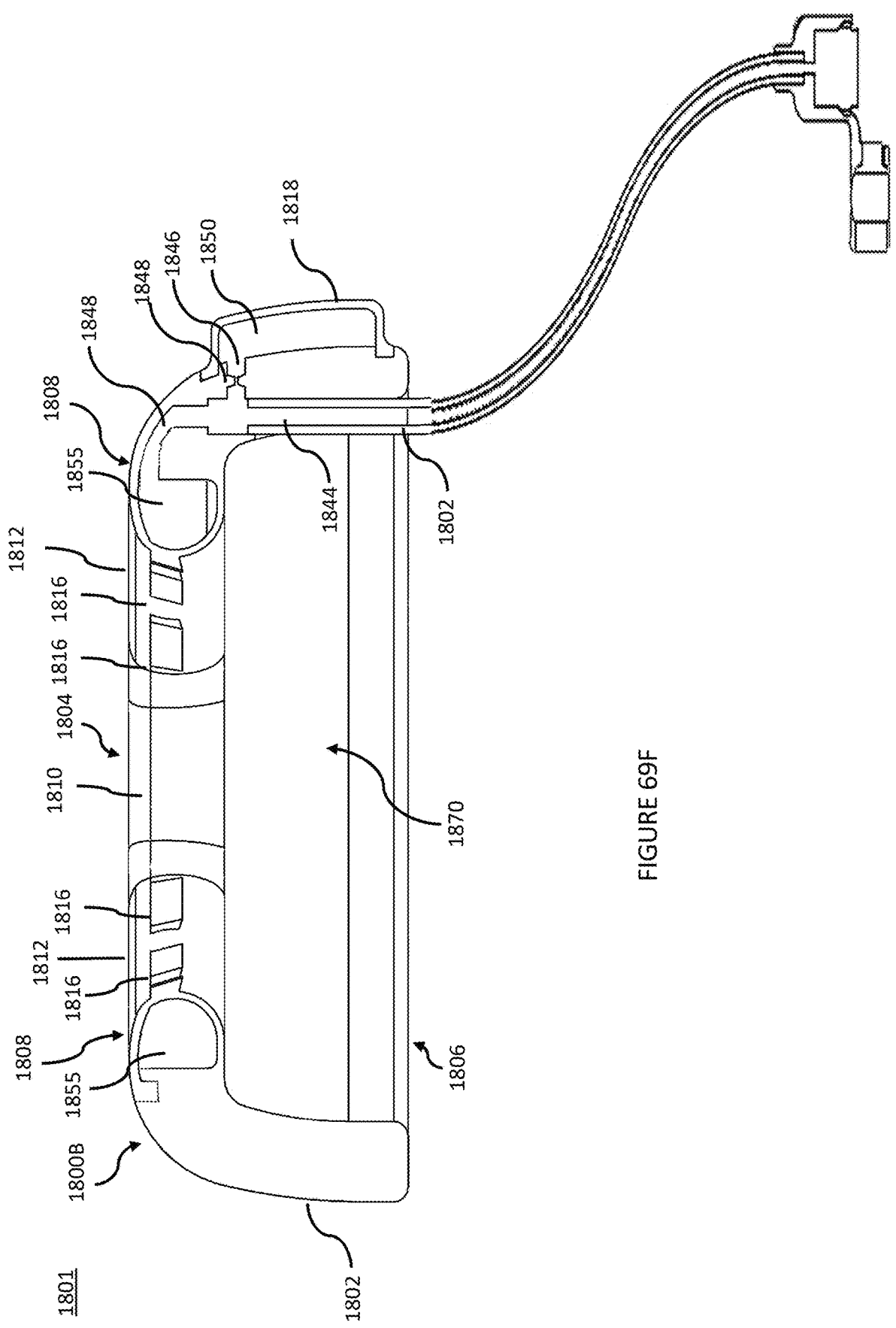
FIG. 69F illustrates a cross section of a second embodiment of the system of FIG. 69D taken along sectioning line 69E or 69F of FIG. 69D, in accordance with some embodiments of the present invention.

FIG. 69D is a top view an exemplary cervical control system 1800A or cervical control system 1800B with a single inflation media conduit; FIG. 69E is a cross section view of cervical control system 1800A (also referred to herein as system 1800A) taken along phantom bisecting line 69E69F of FIG. 69D; and FIG. 69F is a cross section view of cervical control system 1800B (also referred to herein as system 1800B) taken along phantom bisecting line 69E69F of FIG. 69D. Cervical control systems 1800A and/or 1800B may be included in system 1801 as shown in, for example, FIGS. 69G-69H. Like many of the cervical control systems disclosed herein, systems 1800A and 1800B include a main body 1802, a proximal opening 1804, a distal opening 1806, an interior passageway 1870, an expandable annular inner cuff 1808 (also referred to herein as "inner cuff 1808") with recessed portions 1810, expandable portions 1812, and a flexible membrane that defines, an inner chamber 1855 (also referred to herein as "inner cuff inner chamber 1855"), a positioning balloon 1818 positioned proximate to distal opening 1806 and on an exterior surface of body 1802, with positioning balloon 1818 include a flexible membrane that defines a positioning balloon inner chamber 1850, a plurality of cleats 1816 arranged on an exterior surface and/or inner perimeter of inner cuff 1808, that may be similar to and/or incorporate features of respective features of the main body, proximal opening, distal opening, interior passageway, and expandable annular inner cuff with recessed portions and expandable portions, positioning balloon, and/or cleats of, for example, systems 100, 500, 1000, 1100, 1300, 1400, 1500, 1600, and/or 1700 described herein and shown in the figures.

System 1800A further includes an inflation media conduit 1844 that extends from an inlet 1820 (that may be similar in form, function, and/or configuration to inlet 120) to a cross channel 1846; both of which are in fluid communication with positioning balloon inner chamber 1850 as shown. System 1800A also includes an inner cuff inflation media conduit 1848 that extends from and is in fluid communication with inflation media conduit 1844. During inflation, inflation media may be pushed into inflation media conduit 1844 via inlet 1820. From there, the inflation media may be pushed into inner cuff inflation media conduit 1848 for collection in inner chamber 1855 and cross channel 1846 for collection within positioning balloon inner chamber 1850 at a relatively uniform rate so that, for example, inner chamber 1855 and positioning balloon inner chamber 1850 fill with inflation media at approximately the same rate. For embodiments where inner chamber 1855 and positioning balloon inner chamber 1850 have the same or a similar overall volume, inner cuff 1808 and positioning balloon 1818 may expand an approximately the same rate as inflation media is added to inflation media conduit 1844. For embodiments where inner chamber 1855 has a smaller volume than positioning balloon inner chamber 1850, inner cuff 1808 may expand more quickly than positioning balloon 1818. For embodiments where inner chamber 1855 has a larger volume than positioning balloon inner chamber 1850, inner cuff 1808 may expand slower than positioning balloon 1818.

Like system 1800A, system 1800B further includes inflation media conduit 1844 that extends from inlet 1820 to cross channel 1846. However, a choke point 1846 is positioned within cross channel 1846 configured and positioned to slow a flowrate of inflation media entering positioning balloon inner chamber 1850 so that inflation media flows faster through inflation media conduit 1844 to inner cuff inflation media conduit 1848 than choke point 1848 of cross channel 1846 and inner chamber 1855 fills more quickly than positioning balloon inner chamber 1850, thereby inflating inner cuff 1808 before positioning balloon 1818. Thus, choke point 1846 may allow for the expansion of inner cuff 1808 around a cervix (e.g., cervix 101) positioned within inner passageway as, for example, shown and described herein before positioning balloon 1818 is inflated. This may allow a clinician to secure system 1800B to a patient's cervix (via expansion of inner cuff 1808) prior to repositioning (e.g., adjusting an angle) of cervix or otherwise mounting system 1800B within a patient's vagina and/or inflating positioning balloon 1818 to hold system 1800B in place.

Figures 69G, 69H:
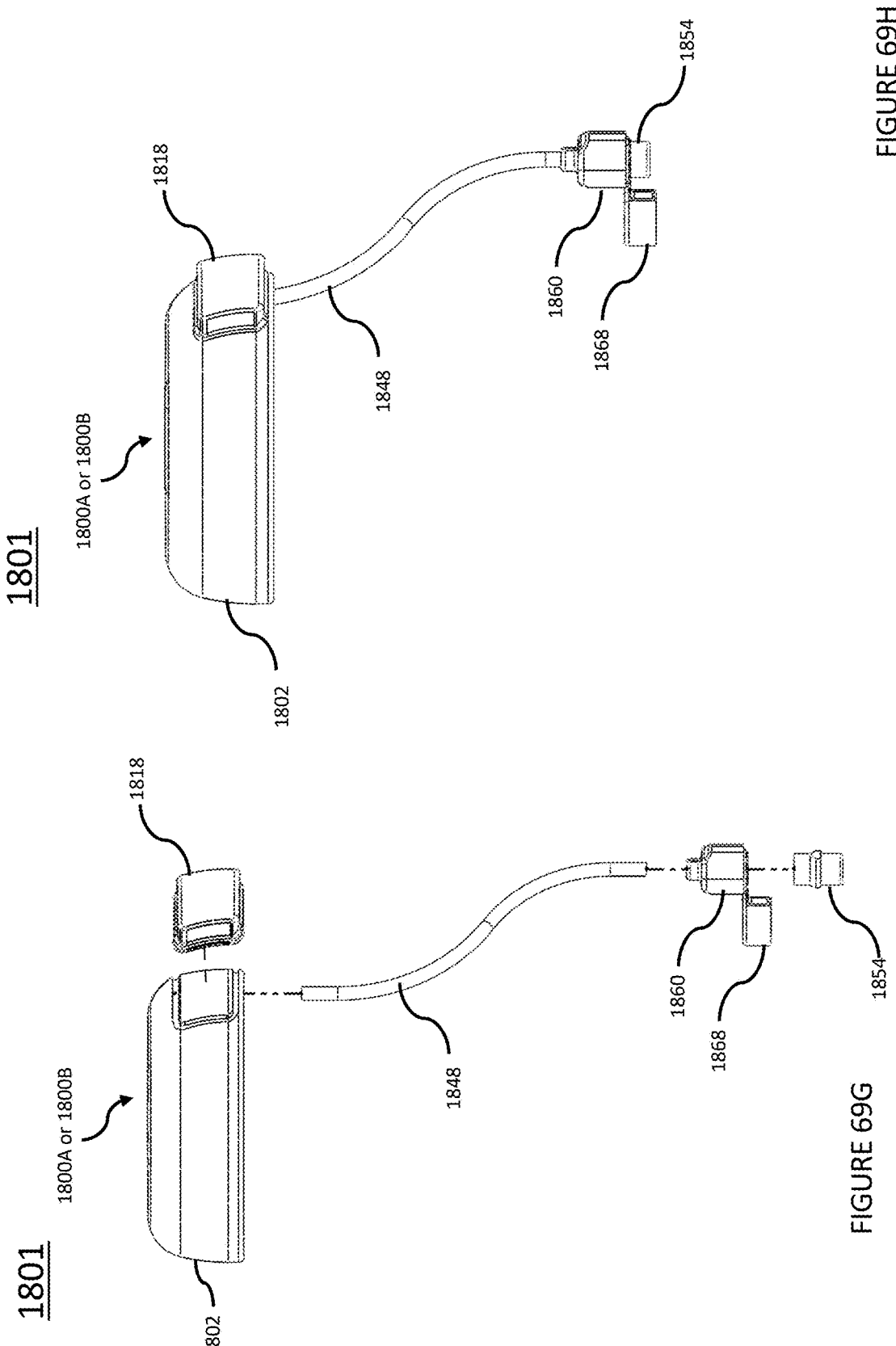
FIG. 69G illustrates an exploded side view of the system of FIG. 69E or 69F, in accordance with some embodiments of the present invention.
FIG. 69H illustrates an assembled side view of the system of FIG. 69E or 69F, in accordance with some embodiments of the present invention.
Figure 69I:
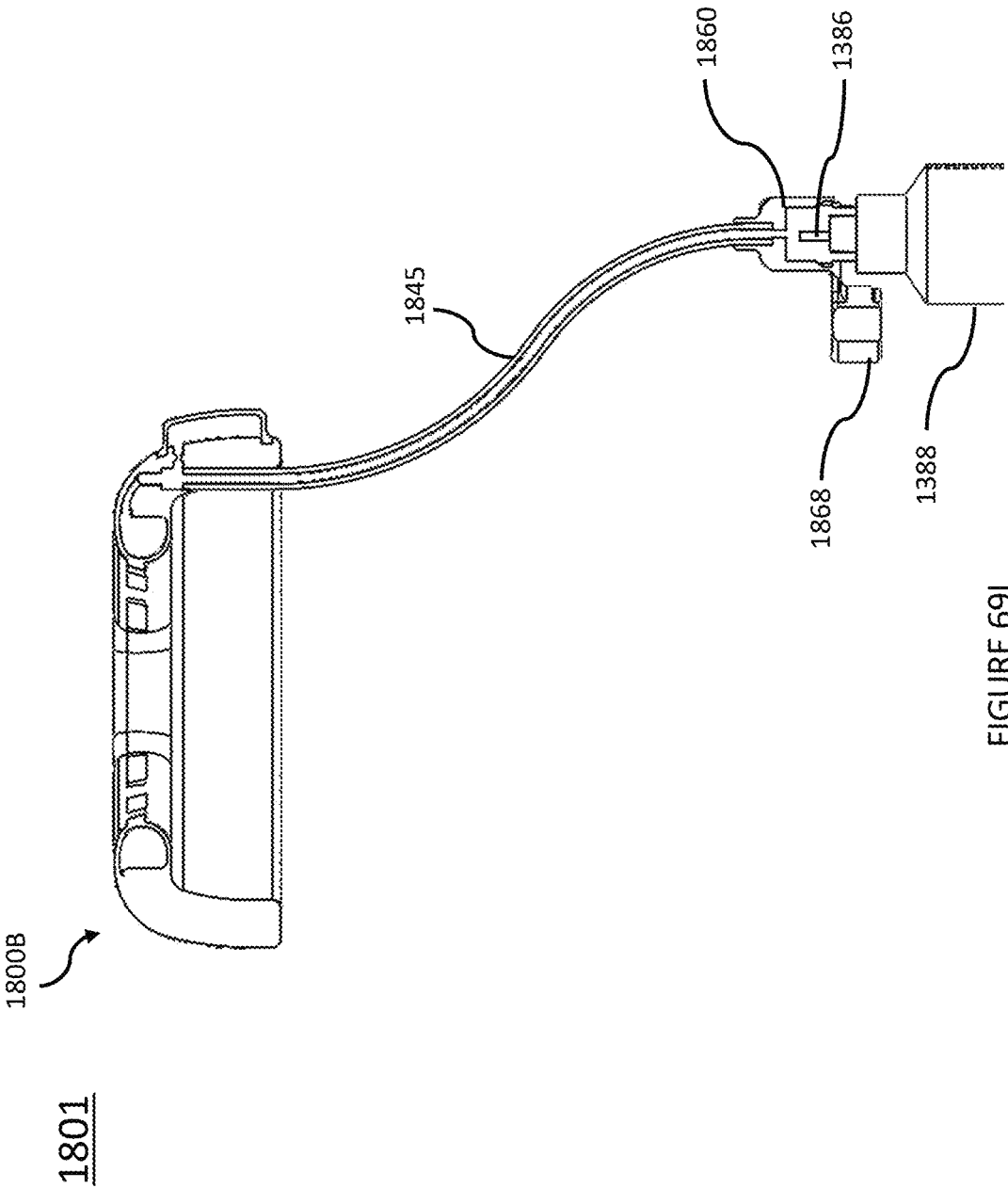
FIG. 69I illustrates bisecting cross section view of the system of FIG. 69E or 69F with an inflation source positioned with a valve of the valve housing, in accordance with some embodiments of the present invention.

FIG. 69G is an exploded view and FIG. 69H is an assembled view of system 1801. As may be seen in FIG. 69G, positioning balloon 1818 may be positioned in line with main body 1802 of system 1800A or system 1800B and affixed thereto as shown in FIG. 69H. System 1801 also includes a tube 1848 that may be positioned in line with inlet

1820 so that fluid communication between tube 1848 and inflation media conduit 1844 may be established when assembled as shown in FIG. 69H. Tube 1848 may be aligned with a first side of single port valve housing 1860 and valve 1854 may be aligned with a second side of single port valve housing 1860 as shown in FIG. 69G and assembled together as shown in FIG. 69H to form system 1801.

System 1800 also includes an inner cuff inflation media conduit 1848 that extends from and is in fluid communication with inflation media conduit 1844. During inflation, inflation media may be pushed into inflation media conduit 1844 via inlet 1820. From there, the inflation media may be pushed into inner cuff inflation media conduit 1848 for collection in inner chamber 1855 and cross channel 1846 for collection within positioning balloon inner chamber 1850 at a relatively uniform rate so that, for example, inner chamber 1855 and positioning balloon inner chamber 1850 fill with inflation media at approximately the same rate. For embodiments where inner chamber 1855 and positioning balloon inner chamber 1850 have the same or a similar overall volume, inner cuff 1808 and positioning balloon 1818 may expand an approximately the same rate as inflation media is added to inflation media conduit 1844. For embodiments where inner chamber 1855 has a smaller volume than positioning balloon inner chamber 1850, inner cuff 1808 may expand more quickly than positioning balloon 1818. For embodiments where inner chamber 1855 has a larger volume than positioning balloon inner chamber 1850, inner cuff 1808 may expand slower than positioning balloon 1818.

Figure 70B:
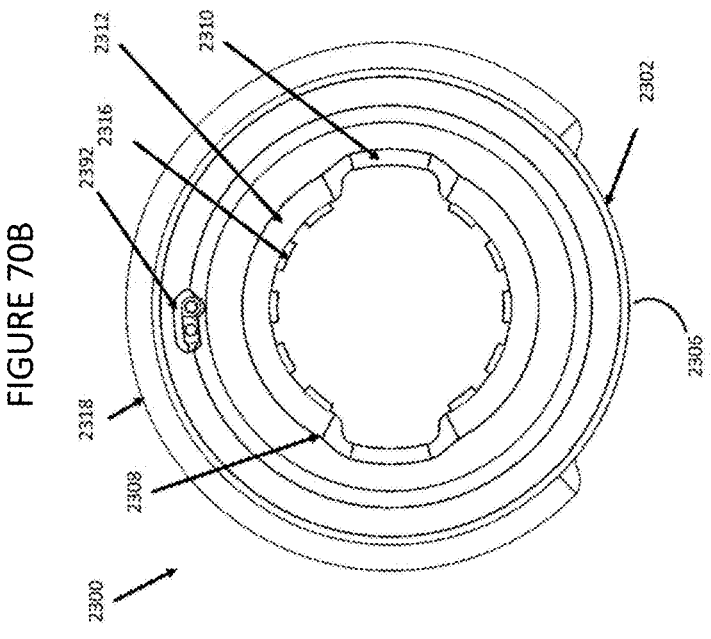
FIG. 70B illustrates a bottom, or distal side, view of the cervical control system of FIG. 70, in accordance with some embodiments of the present invention.
Figure 70A:
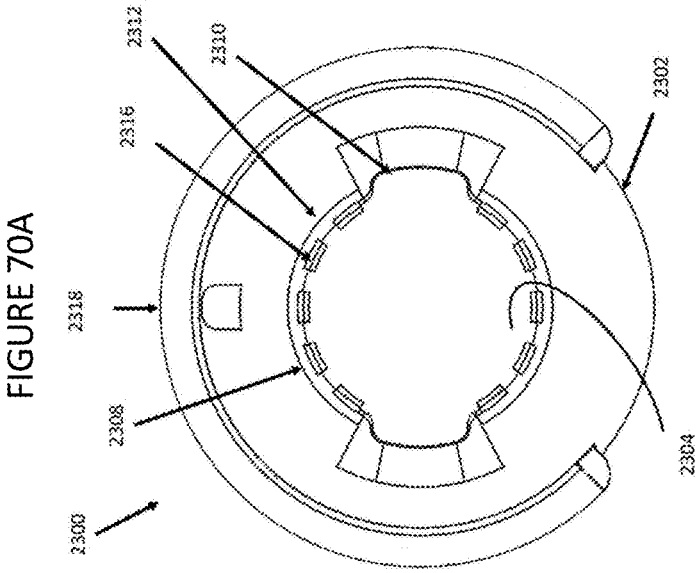
FIG. 70A illustrates a top, or proximal, side view of an exemplary cervical control system, in accordance with some embodiments of the present invention.
Figure 70C:
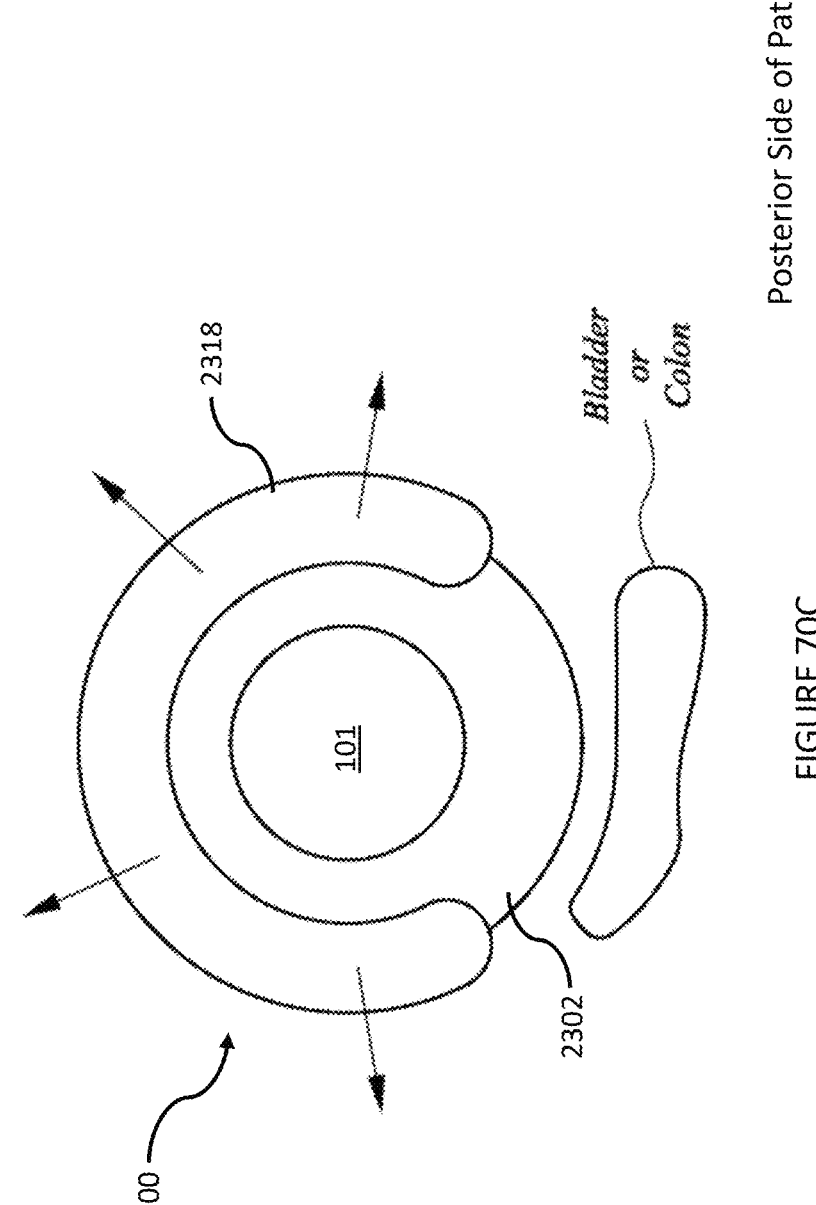
FIG. 70C illustrates a block diagram representing the cervical control system of FIGS. 70A and 70B in situ within a patient, in accordance with some embodiments of the present invention.

FIGS. 70A-70C illustrate a cervical control system 2300 configured to support a patient's pelvic organs (e.g., uterus 105, bladder, etc.) and/or hold the uterus in place to, for example, mitigate and/or prevent uterine prolapse. In particular, FIG. 70A is a top, or proximal, side view and FIG. 70B is a bottom, or distal side, view of system 2300. System 2300 is similar to, for example, systems 100, 500, 1000, 1100, 1300, 1400, 1500, 1600, 1700, and 2200 described above and illustrated in FIGS. 1-6, 19-20, 36-37, 51-54, 58-59, 64A-64B, 65A-65B, 66, 67A-67C, 68A-68B, and 82, respectively, and may include a main body 2302, a proximal opening 2304, a distal opening 2306, an expandable inner cuff 2308 with expandable portions 2312 and recessed portions 2310, an expandable positioning balloon 2318, and cleats 2316. Inner cuff 2308 and/or positioning balloon 2318 may be inflated and/or deflated using, for example, inflation media conduits, valves, valve housings, and/or inflation media sources, like the inflation media conduits valves, valve housings, and/or inflation media sources disclosed herein and may utilize the two ports 2392 shown in FIG. 70B.

Positioning balloon 2318 is configured to extend around a portion (e.g., 50-95%) of an exterior of body 2302. For example, as illustrated in FIGS. 70A and 70B, positioning balloon 2318 is similar to positioning balloon 1318 in that it only covers a portion of the circumference of an exterior surface of main body 2302. However, in the embodiment of FIGS. 70A and 70B, positioning balloon 2318 is a major arc shape (or a horseshoe shape) disposed around more than 180 degrees of the circumference of main body 2302 and extends beyond an outer perimeter of main body 2302. The larger arc shape or major arc shape of positioning balloon 2318 as compared to, for example, positioning balloon 1308 and/or the positioning balloons shown and/or described with reference to FIGS. 58-59, 62-65, and 67-68 may be particularly helpful with controlling, mitigating, and/or preventing pelvic organ prolapse as the larger arc shape of positioning balloon 2318 acts to increase the total diameter of system

2300 when inflated, which may assist with anchoring system 2300, occupying space within the vagina (thereby preventing pelvic organs from entering the vagina), and/or distribution of force within the vagina (e.g., vagina 103) so that it is not localized to one or more pressure points (as may be the case with, for example, positioning balloon 1318). In addition, system 2300, when inflated, may provide additional mechanical support to the ligaments and tissue holding pelvic organs naturally used to hold in place against a prolapsing organ.

In some cases, for use with PPROM, the supporting ligaments can be healthy and the pregnancy would be more limiting in total space in the vaginal canal. Accordingly, it can be helpful for the positioning balloon to be a smaller arc shape or minor arc shape and the positioning balloon can be used for the purpose of shifting the cervix angle rather than anchoring of the cervical control system. In some cases, the major arc shape (or horseshoe shape) allows the increase in diameter of the cervical control system to help anchor the cervical control system and provide mechanical support to a prolapsing uterus while still biasing the cervical control system towards a specific direction with just one inflating portion of inner cuff (as opposed to a cuff that extends the entire circumference of the cervical control system).

In some cases, system 2300 may be oriented within the vagina so that an area of the exterior surface of main body 2302 not covered, or occupied, but the positioning balloon 2318 is positioned proximate to and/or overlying a portion of patient anatomy in which the bladder or colon resides. Orientation in this manner prevents positioning balloon 2318 (when expanded) from pressing on the patient's bladder or colon thereby causing application of pressure to and/or irritation of these organs. As shown in FIG. 70C, when system 2300 is oriented this way, inflation of the positioning balloon 2318 can occur such that the cervical control system is anchored inside the vaginal canal but can be positioned so that the portion of the main body 2302 that is not covered by the positioning balloon 2318 can sit against the bladder and/or rectum. In this way, inflation of positioning balloon 2318 and/or use of the system may not press upon, disrupt operation of the bladder and/or rectum and/or cause patient discomfort while using system 2300.

In other cases, the system 2300 can be rotated 180 degrees from what is shown in FIG. 70C so that positioning balloon 2318 can be positioned to press up into the bladder space to, for example, prevent and/or mitigate bladder prolapse. Additionally, or alternatively, system 2300 can be rotated in any direction to accommodate patient comfort. The ability to rotate or position the system 2300 in either arrangement is beneficial to a patient because, while pressure on the bladder can benefit patients suffering from bladder prolapse, it can irritate patients who have an overactive bladder. The rotation during placement, but before inflation could allow for pressure to be applied to the anterior wall of the vaginal canal. In some cases, the increased diameter provided by the inflation of positioning balloon 2318 can help anchor the cervical control system in the vaginal canal.

Figure 71A:
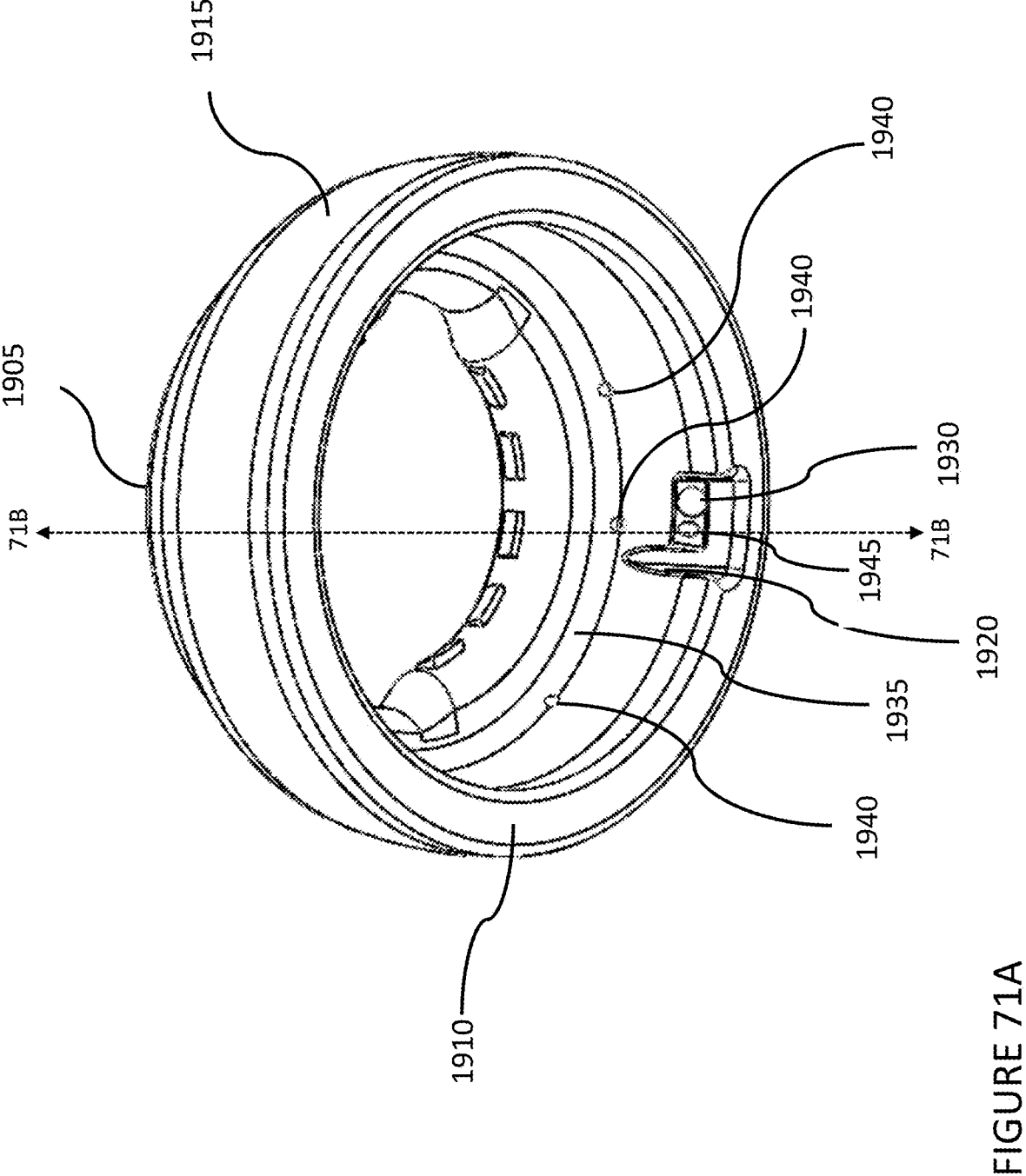
FIG. 71A illustrates a bottom perspective view of an exemplary cervical control system that includes an internal channel, in accordance with some embodiments of the present invention.
Figure 71B:
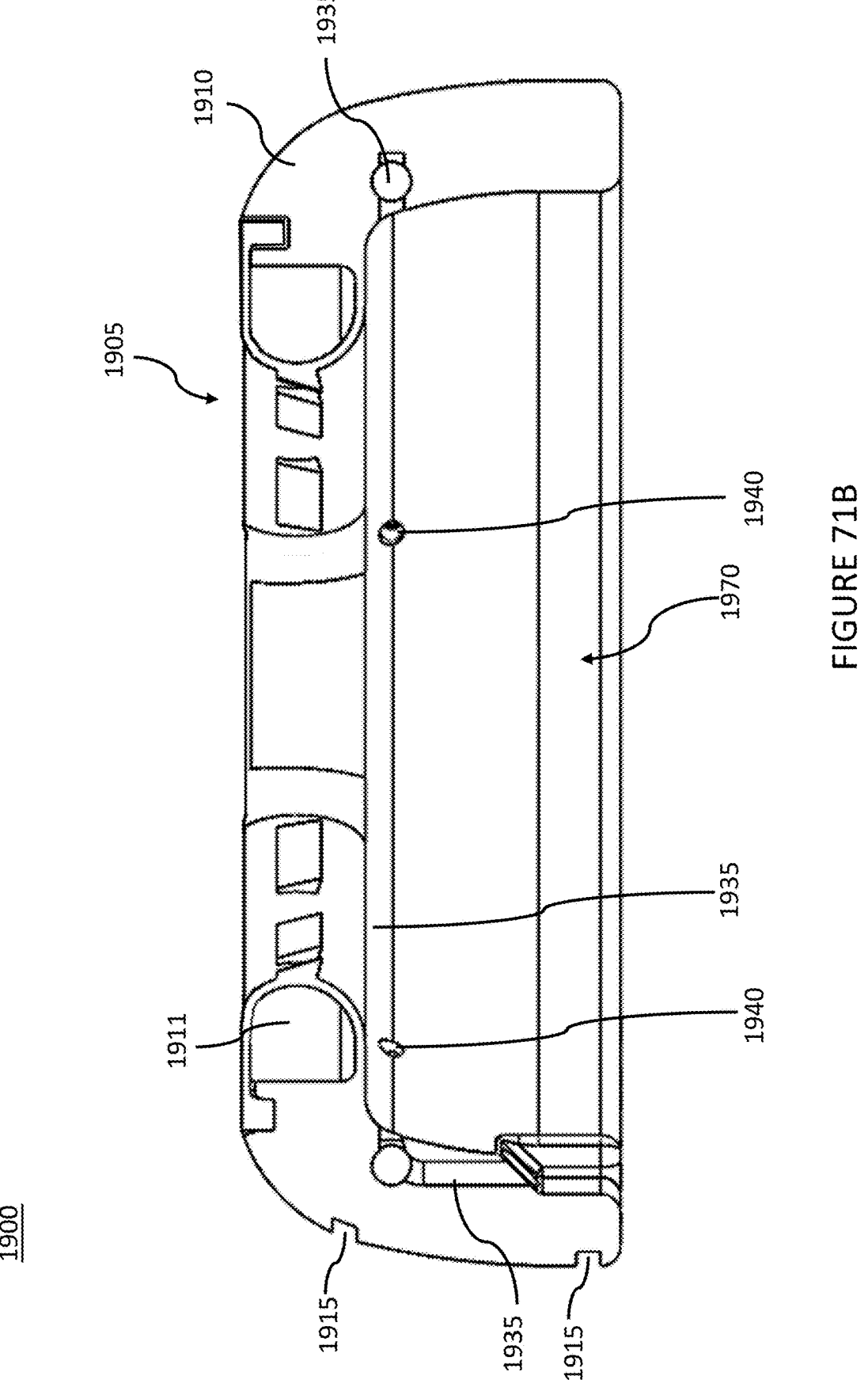
FIG. 71B illustrates a cross section view of the cervical control system of FIG. 71A, in accordance with some embodiments of the present invention.

FIG. 71A provides a bottom perspective view and FIG. 71B provides a cross section view of an exemplary cervical control system 1900 (also referred to herein as "system 1900") configured to be placed on the vaginal side of the cervix to, for example, mitigate implications of short cervix and/or prevent preterm birth.

System 1900 shares some features and functionality with the cervical control systems disclosed herein such as systems 100, 500, 1000, and 1100 described above and illustrated in FIGS. 1-6, 19-20, 36-37, and 51-54 such as a main body 1910, which includes an inner cuff 1905 that is in fluid communication with an inner cuff port 1920 and an inner cuff inflation media conduit (not shown); and an internal channel 1935 that includes a plurality of ports 1940 and is in communication with an internal channel coupling port 1945 and a channel inflation media conduit (not shown). Each port 1940 may be configured to allow for fluid (e.g., medication, antibacterial agents, etc.) to exit internal channel so that it may flow onto an interior wall of system 1900 and/or a cervix positioned within an interior passageway of system 1900 as, for example, shown and described herein. The plurality of ports 1940 may be uniformly spaced around the proximal interior of system 1900 and internal channel 1935 may be concentrically placed within main body 1910 as shown in, for example, FIG. 71B. In other embodiments, a cervical control system 1900 may include a plurality of channels on the interior or exterior of cervical control system 1900. System 1900 also includes a pair or coupling channels 1915 configured for acceptance of, and bonding to, a positioning balloon covering and/or flexible membrane as shown in, for example, FIGS. 69G and 69H.

When the flexible membrane of the positioning balloon is attached via coupling channels 1915 and system 1900 is placed proximate to a cervix, the positioning balloon and inner cuff 1905 may be inflated with inflation media as, for example, described herein. Communication between internal channel 1935, ports 1940, and internal channel coupling 1945 may be used to, for example, communicate substances (shown as small arrows in FIG. 71B) to cervical tissue via exiting one or more ports 1940 as shown in FIG. 71B. Additionally, or alternatively, negative pressure and/or a vacuum may be communicated to internal channel 1935 and ports 1940 via internal channel coupling 1945. The negative pressure and/or vacuum may evacuate substances (e.g., blood, vaginal discharge, bacteria, rinsing saline, etc.) away from the cervix and/or act to engage or hold the cervix in place.

Figures 72A, 72B:
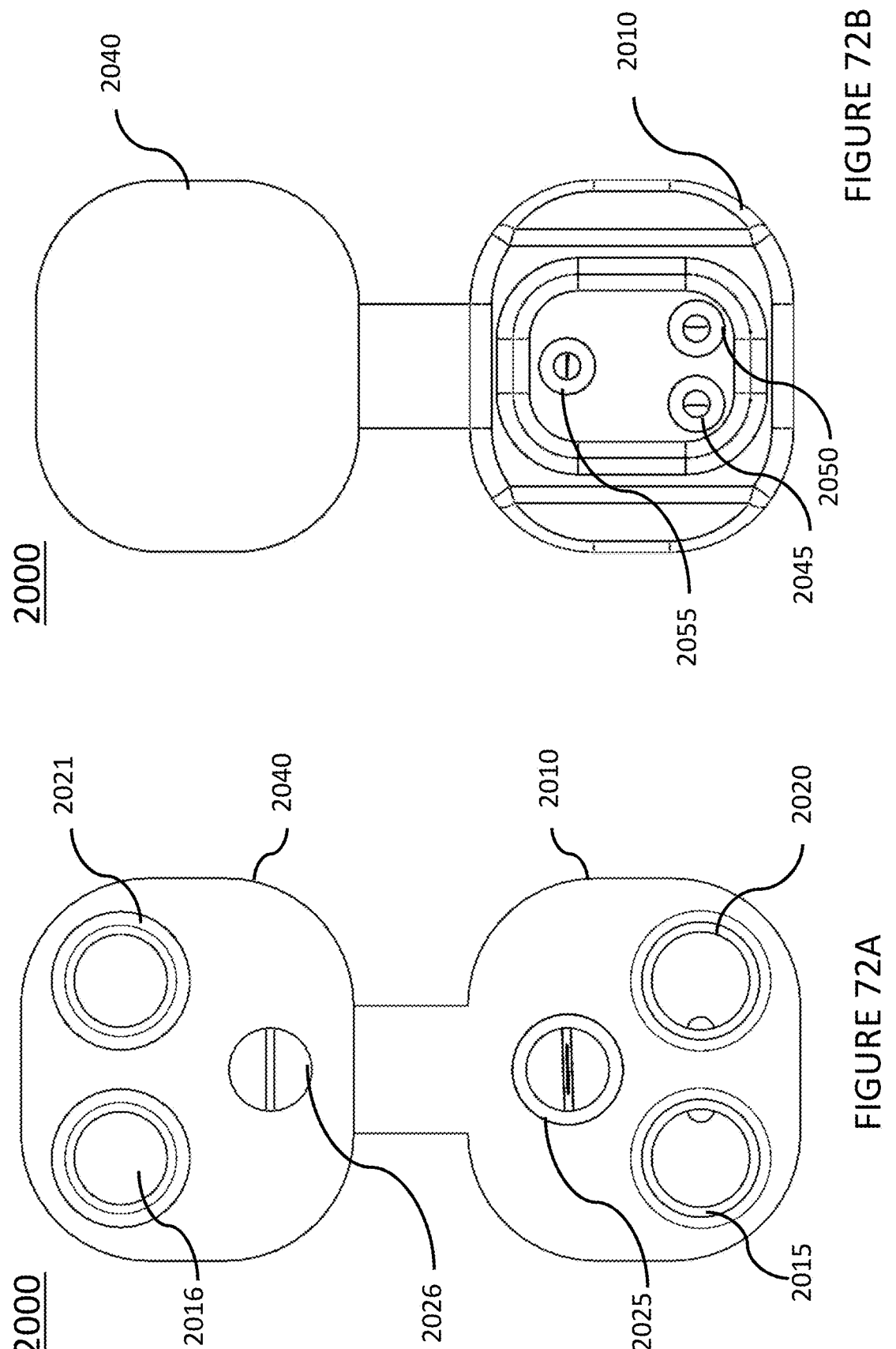
FIG. 72A illustrates a top view of a triple port valve housing, in accordance with some embodiments of the present invention.
FIG. 72B illustrates a bottom view of the triple port valve housing of FIG. 72A, in accordance with some embodiments of the present invention.
Figure 73:
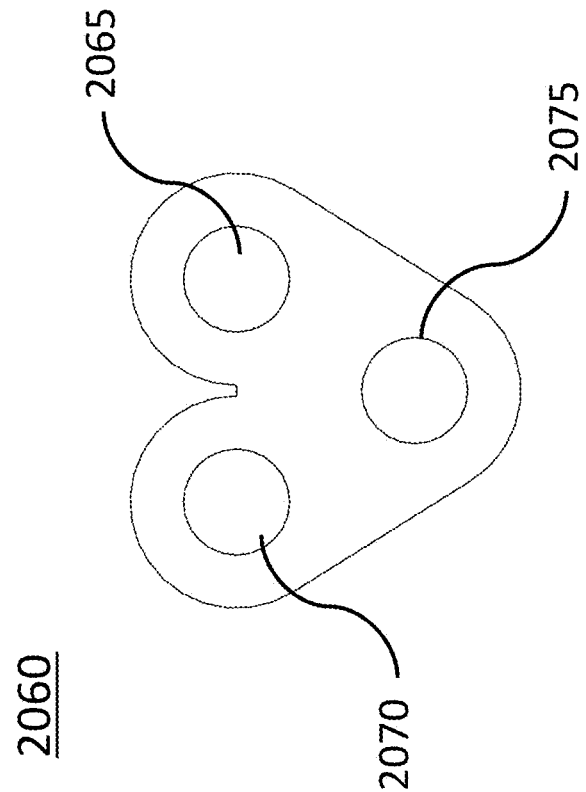
FIG. 73 illustrates a cross sectional view of tri-lumen tubing, in accordance with some embodiments of the present invention.

FIG. 72A provides a top and FIG. 72B provides a bottom view of a triple port valve housing 2000 that may be used with system 1900 and includes a base 2010 and an articulating, or folding, cover 2040. As may be seen in FIG. 72A, a first, or top, side of base 2010 includes a first port 2015, a second port 2020, and a third port 2025 and cover 2040 includes a first recess 2016 sized, positioned, and configured to cover first port 2015 when cover 2040 is folded over base 2010. Cover 2040 further includes a second recess 2021 sized, positioned, and configured to cover second port 2020 when cover 2040 is folded over base 2010 and a third recess 2026 sized, positioned, and configured to cover third port 2025 when cover 2040 is folded over base 2010. As may be seen in FIG. 72A, a second, or bottom, side of base 2010 includes a first lumen coupling 2045 sized, shaped, and configured to be inserted into and/or cooperate with a first lumen 2065 of a tri-lumen tubing 2060, a cross sectional diagram of which is provided by FIG. 73 and communicate with first port 2015. The bottom side of base 2010 further includes a second lumen coupling 2050 sized, shaped, and configured to be inserted into and/or cooperate with a second lumen 2070 of tri-lumen tubing 2060 and communicate with second port 2020 and third lumen coupling 2055 sized, shaped, and configured to be inserted into and/or cooperate with a third lumen 2075 of tri-lumen tubing 2060 and communicate with third port 2025. Cover 2040 may be folded over first, second, and third ports 2015, 2020, and 2025 to protect the ports and/or prevent foreign material from entering them when, for example, triple port valve housing is positioned within the vagina but is not coupled to another device.

Figure 74A:
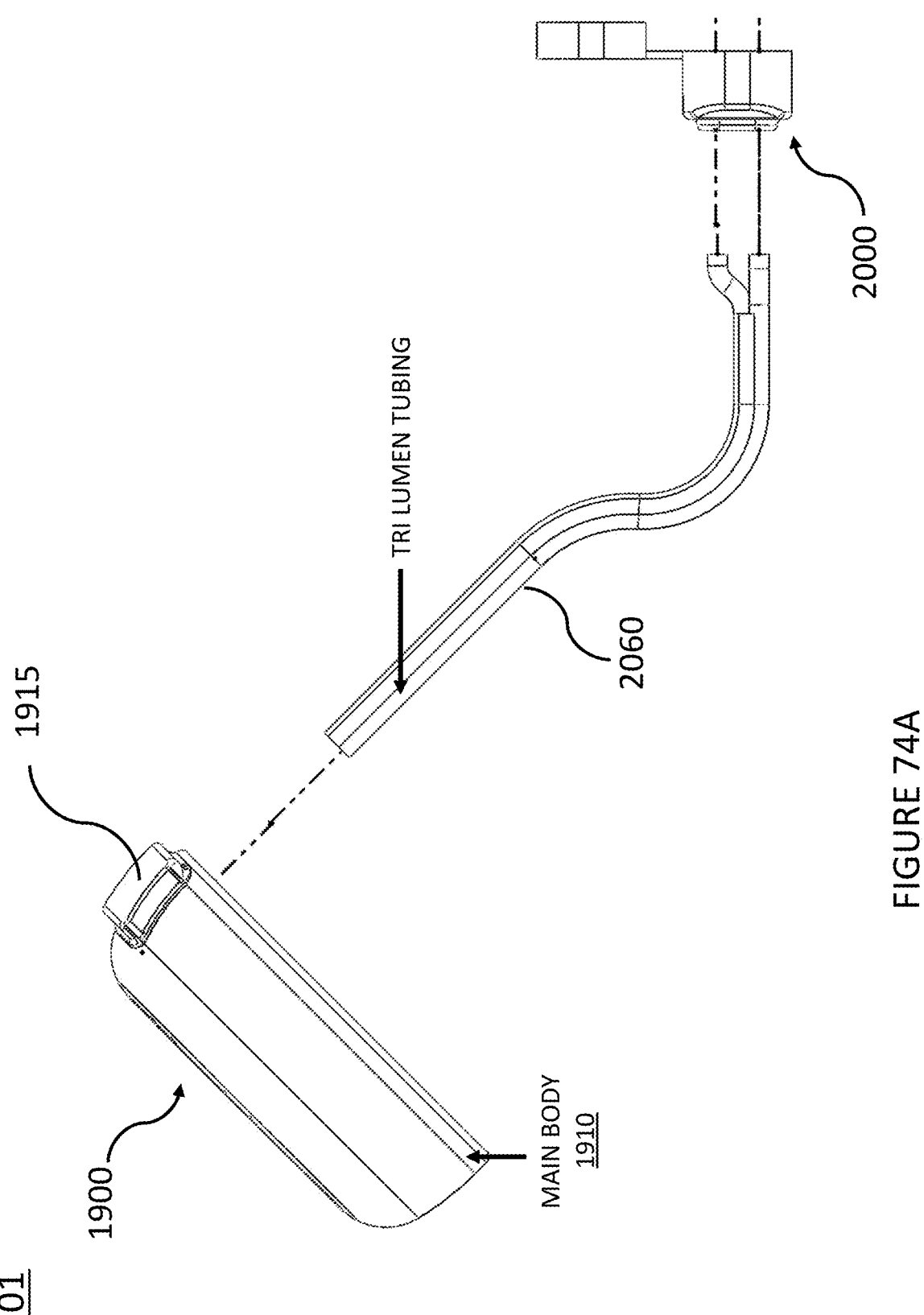
FIG. 74A illustrates an exploded view of an assembly including the cervical control system of FIGS. 71A and 71B, the triple port valve housing of FIGS. 72A and 72B, and the tri-lumen tubing of FIG. 73, in accordance with some embodiments of the present invention.
Figure 74B:
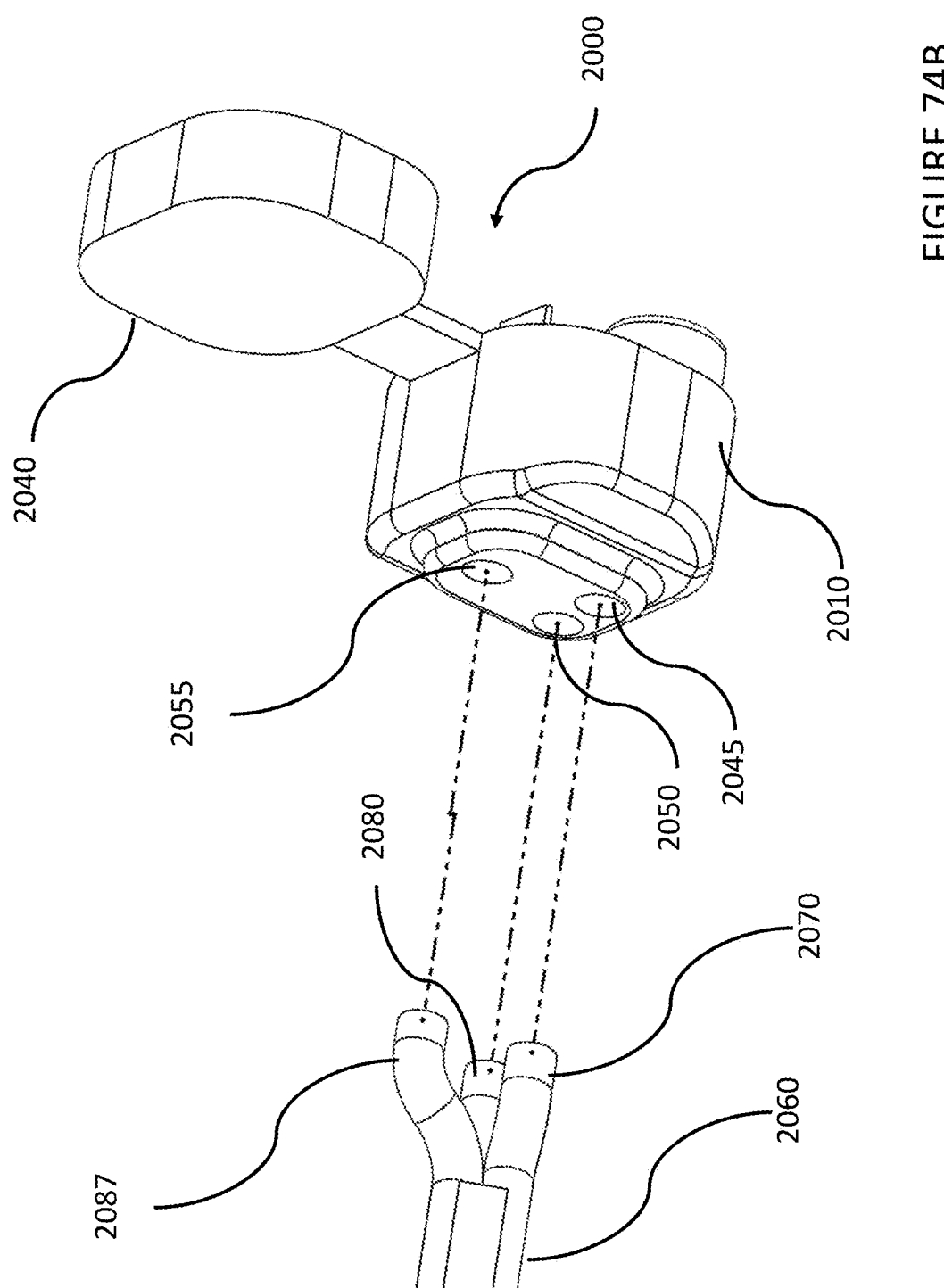
FIG. 74B illustrates a close up of a portion of the exploded view of FIG. 74A, in accordance with some embodiments of the present invention.
Figure 74C:
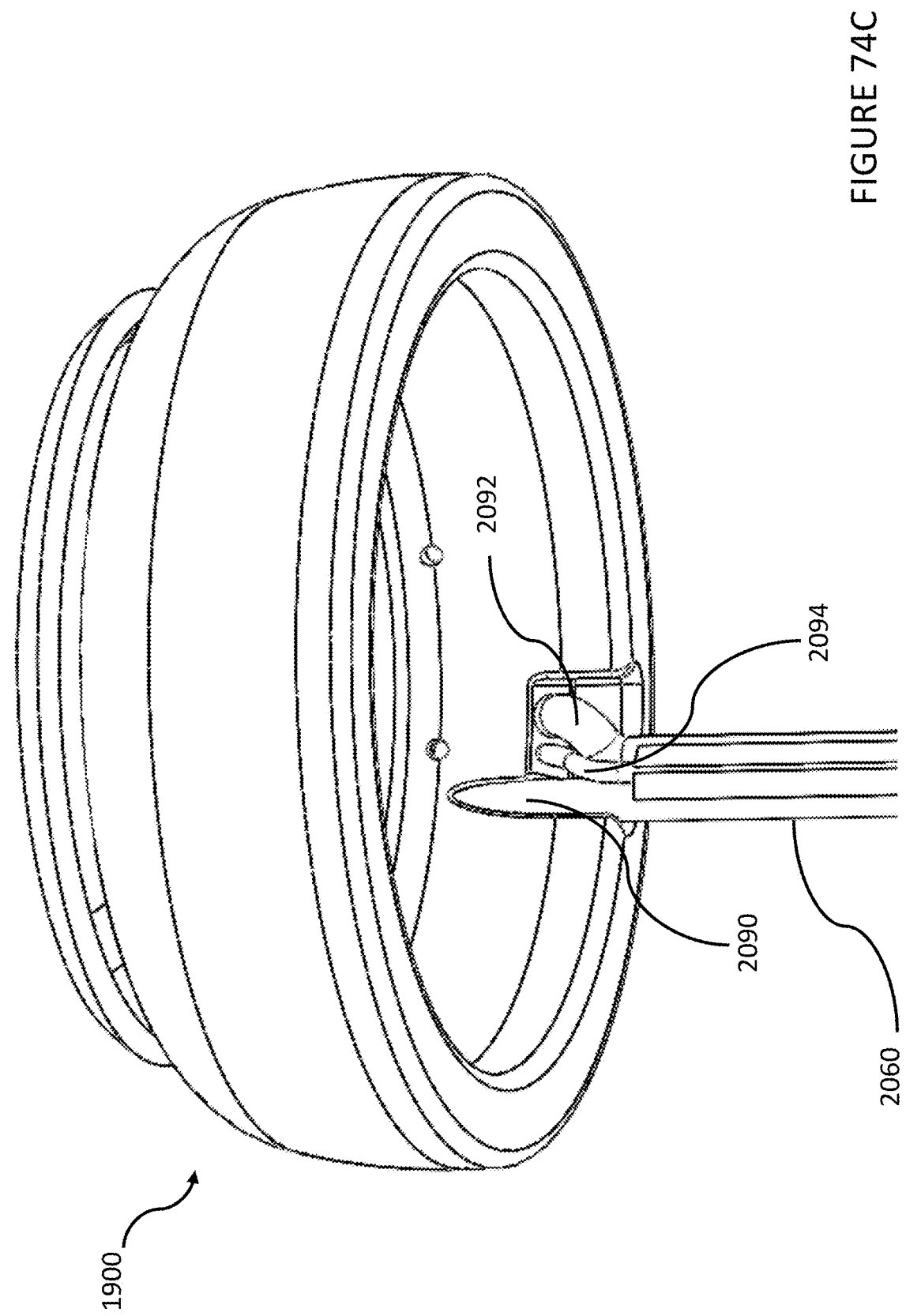
FIG. 74C illustrates the assembly of FIG. 74A when fully assembled together, in accordance with some embodiments of the present invention.

FIG. 74A provides an exploded view of an assembly 1901 of cervical control system 1900, triple port valve housing 2000, and tri-lumen tubing 2060 that shows how tri-lumen tubing 2060 is arranged between, and aligned with, cervical control system 1900 and triple port valve housing 2000 and couples them together. FIG. 74B provides a close-up view of tri-lumen tubing 2060 as it is aligned with a back side of triple port valve housing 2000, wherein an end of tri-lumen tubing 2060 has a first valve coupling extension 2070 sized and configured for insertion into and/or cooperation with first lumen coupling 2045, a second valve coupling extension 2080 sized and configured for insertion into and/or cooperation with second lumen coupling 2050, and a third valve coupling extension 2087 sized and configured for insertion into and/or cooperation with third lumen coupling 2055. FIG. 74C provides a bottom perspective close up view of an assembly of cervical control system 1900 and tri-lumen tubing 2060, wherein a fourth coupling extension 2090 of tri-lumen tubing 2060 is coupled to inner cuff port 1920, a fifth coupling extension 2092 of tri-lumen tubing 2060 is coupled to positioning balloon inflation port 1930, and a sixth coupling extension 2094 of tri-lumen tubing 2060 is coupled to internal channel coupling port 1945.

Figure 75A:
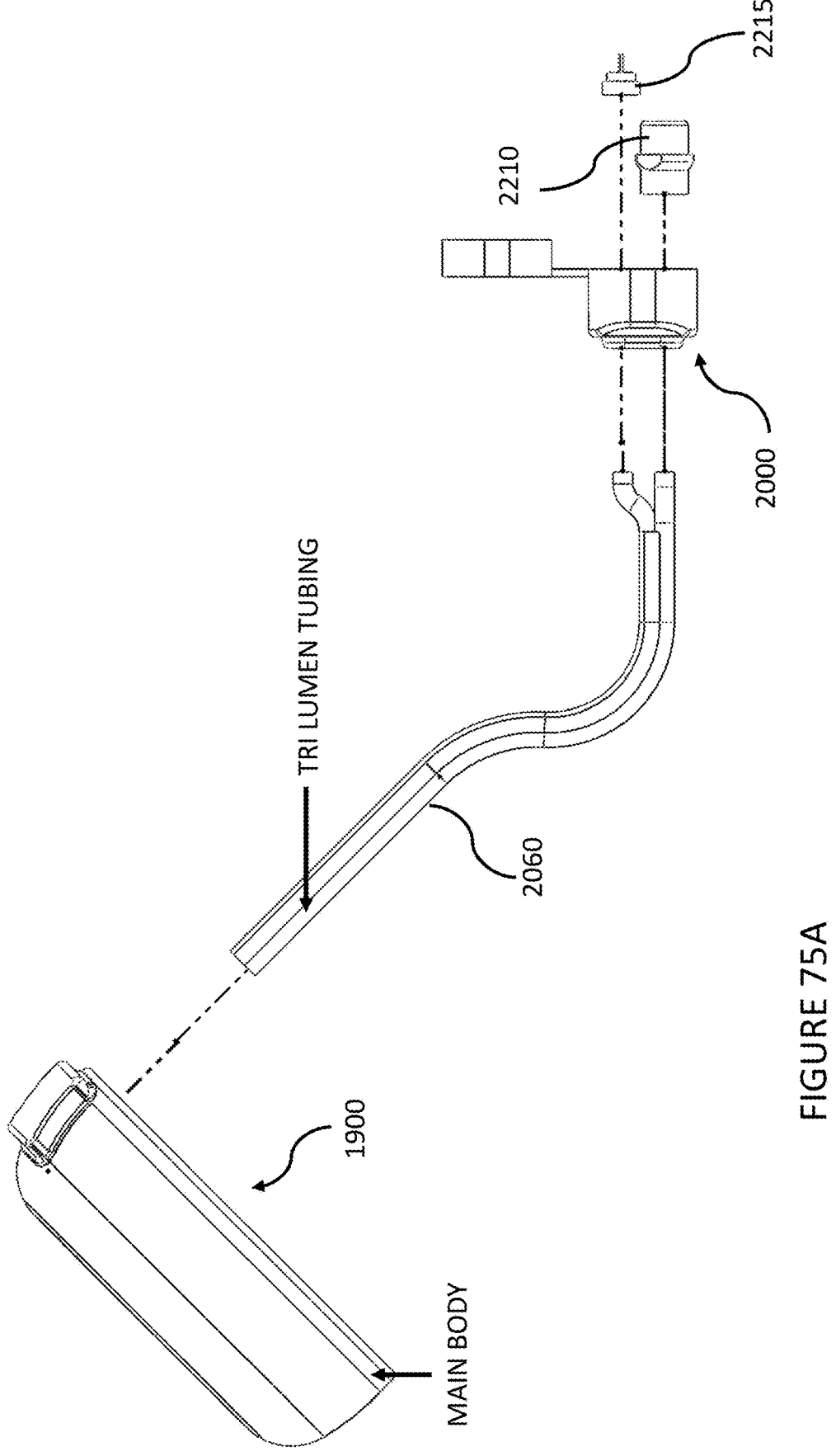
FIG. 75A illustrates a side exploded view of a system including the cervical control system of FIGS. 71A and 71B, the triple port valve housing of FIGS. 72A and 72B, and the tri-lumen tubing of FIG. 73, in accordance with some embodiments of the present invention.
Figure 75B:
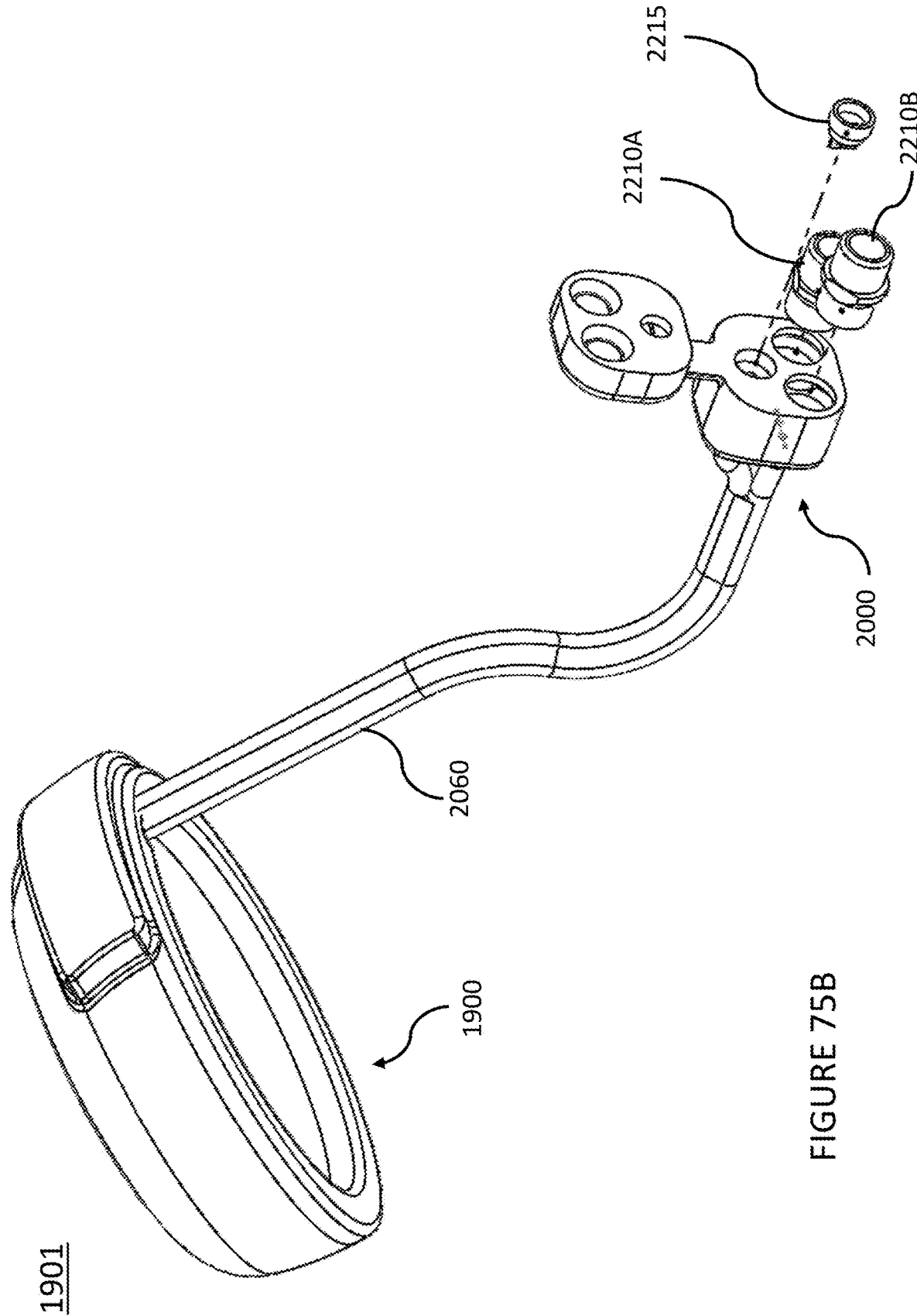
FIG. 75B illustrates a rear perspective view of the system of FIG. 75A, in accordance with some embodiments of the present invention.
Figure 75C:
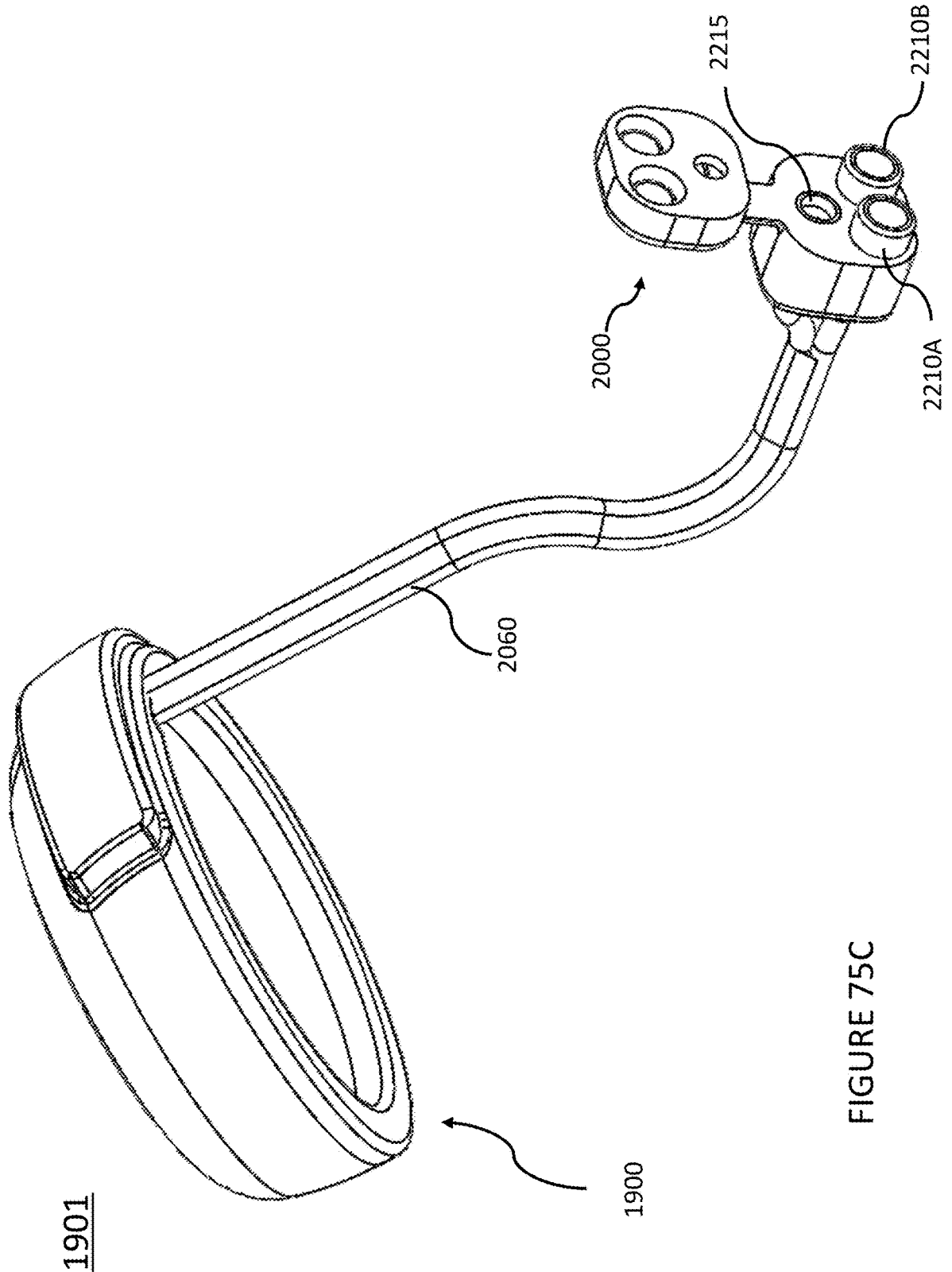
FIG. 75C illustrates a rear perspective view of the system of FIG. 75A when fully assembled with valves positioned within a valve housing, in accordance with some embodiments of the present invention.

In some embodiments, cervical control system 1900, triple port valve housing 2000, and tri-lumen tubing 2060 may be further coupled to one or more valves (e.g., check valves, duckbill valves, dome valves, and/or combination valves). For example, FIG. 75A provides a side exploded view and FIG. 75B provides a perspective exploded view of an assembly 1901 of cervical control system 1900, triple port valve housing 2000, and tri-lumen tubing 2060 along with two check valves 2110 (only one is shown) (e.g., Halkey Roberts check valves) and/or one or more duckbill valves 2215. As may be seen in FIG. 75B, a first check valve 2110A is inserted into first port 2015, a second check valve 2110B is inserted into second port 2020, and duckbill valve 2215 is inserted into third port 2025. FIG. 75B provides a rear perspective view of assembly 1901 when fully assembled with first check valve 2110A inserted into first port 2015, second check valve 2110B inserted into second port 2020, and duckbill valve 2215 inserted into third port 2025. First and second check valves 2110A and 2110B may be configured to allow passage of liquid or gas into their respective lumen and inflation media conduits and maintain pressure on the respective inner cuff 1905 and positioning balloon following their inflation. Duckbill valve 2215 may be configured to accept insertion of fluids and/or gasses into third lumen 2075 for communication to inner channel 1935.

Figure 76A:
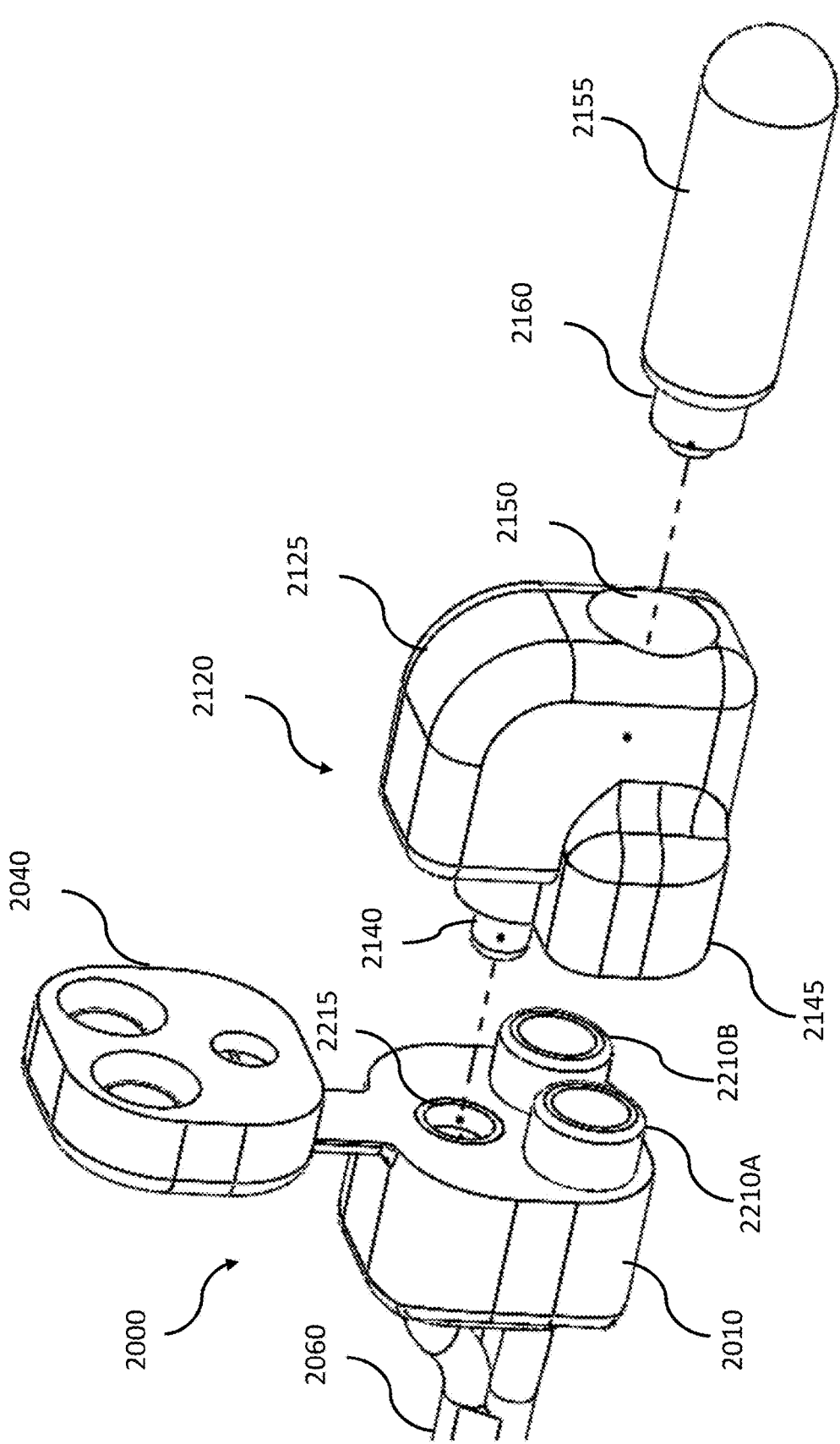
FIG. 76A illustrates a rear perspective exploded view of an assembly of the triple port valve housing of FIG. 72, a micropump assembly, and a reservoir, in accordance with some embodiments of the present invention.
Figure 76C:
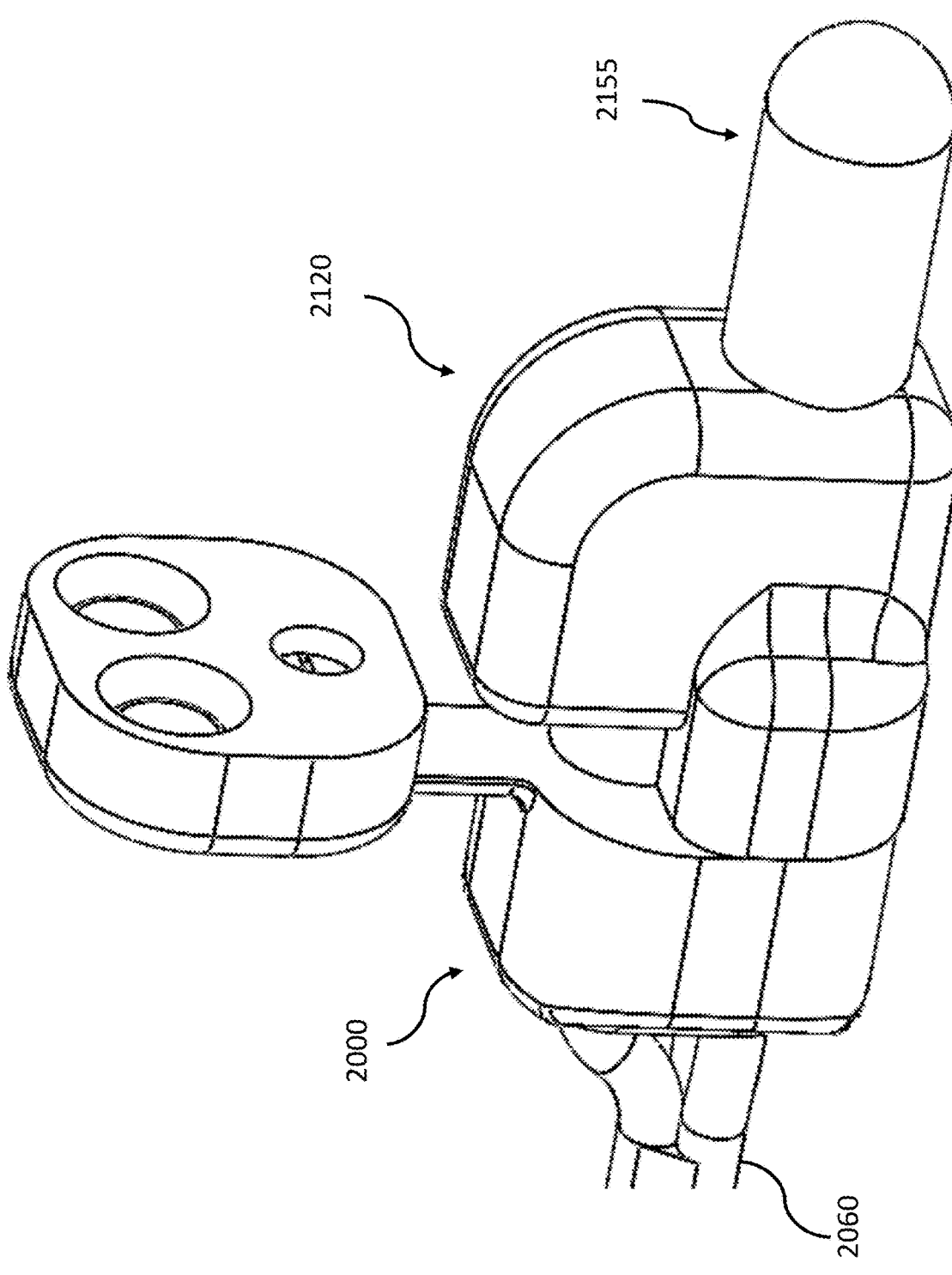
FIG. 76C illustrates a rear perspective view of an assembly of the triple port valve housing and micropump assembly of FIG. 76A with the reservoir positioned within the micropump assembly, in accordance with some embodiments of the present invention.

In some embodiments, assembly 1901 may be further coupled to a micropump assembly 2120 and a reservoir 2155 configured to hold a volume of a substance (e.g., medication, saline, alcohol, gas, etc.) to be pumped into third lumen 2075 for circulation within internal channel 1935 so that it may exit one or more of the plurality of ports 1940, as shown in FIG. 76A. In these embodiments, an extension 2160 of reservoir 2155 may be inserted into a corresponding opening 2150 in body 2125 of micropump assembly 2120 until it is fully seated therein as shown in FIG. 76C, which provides a perspective view of reservoir 2155 seated within micropump assembly 2120 and triple port valve housing 2000 engaged with micropump assembly 2120. FIGS. 76A and 76B also show how a projection, or nozzle, 2140 of micropump assembly may be inserted into duckbill valve 2215 and first and second check valves 2110A and 2110B may align with corresponding first and second openings 2130 and 2135, respectively, so that first and second check valves 2110A and 2110B may be inserted therein as shown in FIG. 76C. First and second openings 2130 and 2135 may be resident within a base 2145 and may be configured to close off first and second check valves 2110A and 501B, respectively to, for example, prevent unwanted check valve activation and/or entry of undesired materials therein. In some embodiments, first and/or second check valves 2110A and/or 2110B may be closed off by mechanical engagement via, for example, a friction fit, with a respective one of first and/or second openings 2130 and/or 2135.

Micropump assembly 2120 may be configured to pump liquid and/or gas contained within reservoir 2155 from reservoir 2155, through nozzle 2140, into duckbill valve 2215 and then onto third lumen 2075 for communication to channel 1935 and cervical tissue via one or more of the plurality of ports 1940 to, for example, provide metered, periodic, as-needed, and/or continuous dosing of the substance housed in reservoir 2155 over a period of time. In some embodiments, reservoir 2155 may hold a volume of vaginal progesterone that may be pumped from reservoir 2155 to channel 1935 to provide metered, periodic, as-needed, and/or continuous dosing of vaginal progesterone while the cervical control system and pump remain in the patient's vaginal canal.

In some embodiments, micropump assembly 2155 may be jacketed with biocompatible and compliant material (not shown) such as, but not limited to, silicone, that may serve to mitigate discomfort when micropump assembly 2120 and reservoir 2155 remains indwelling in the vaginal canal during use. After system 1900 completes the dosing regimen, the clinician can refill or replace reservoir 2155 or remove micropump assembly 2120 all together and close the cap 2040 over triple port valve housing 2000.

In some embodiments, channel 1935, third port 1945, and/or third lumen 2075 may comprise and/or be filled with and/or include an optically conductive material such as a fiber optic cable and/or silicone with a refractive index of greater than 1.4. The optically conductive material may be configured and/or selected to allow for UV light transmission therethrough that may be used for the eradication or mitigation local bacterial colonization.

Figure 77:
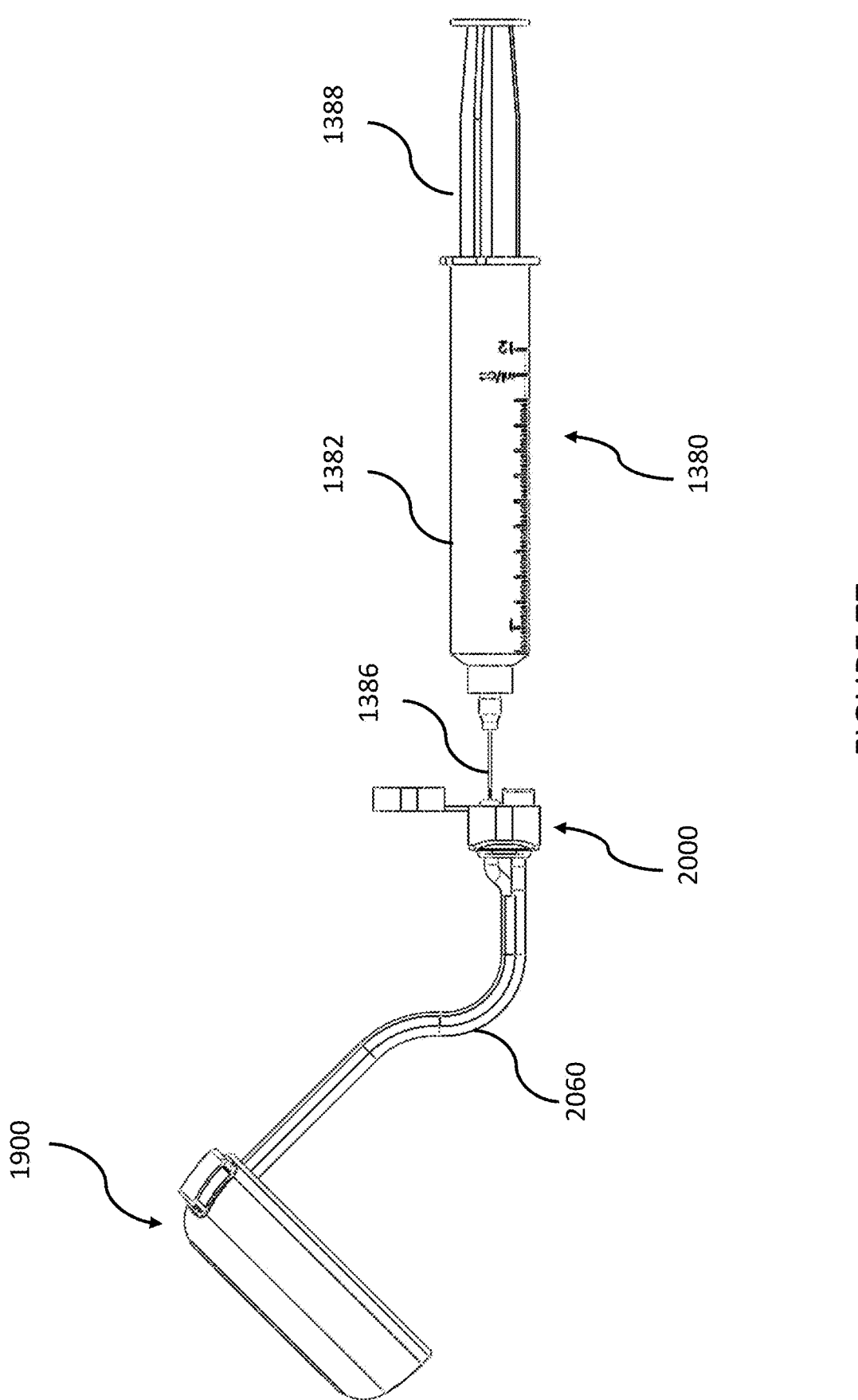
FIG. 77 illustrates a side view of an assembly including the cervical control system of FIGS. 71A and 71B, the triple port valve housing of FIGS. 72A and 72B, the tri-lumen tubing of FIG. 73 and a syringe, in accordance with some embodiments of the present invention, in accordance with some embodiments of the present invention.

FIG. 77 provides a side view of an exemplary assembly 1902 that includes syringe 1380 holding a volume of fluid in barrel 1382 thereof. Needle 1386 of syringe 1380 is inserted into duckbill valve 2215 so that the volume of fluid held in barrel 1382 may be pushed into third lumen 2075 for communication to channel 1935 and ports 1940 via depression of a plunger 1388 into barrel 1382.

Figure 78A:
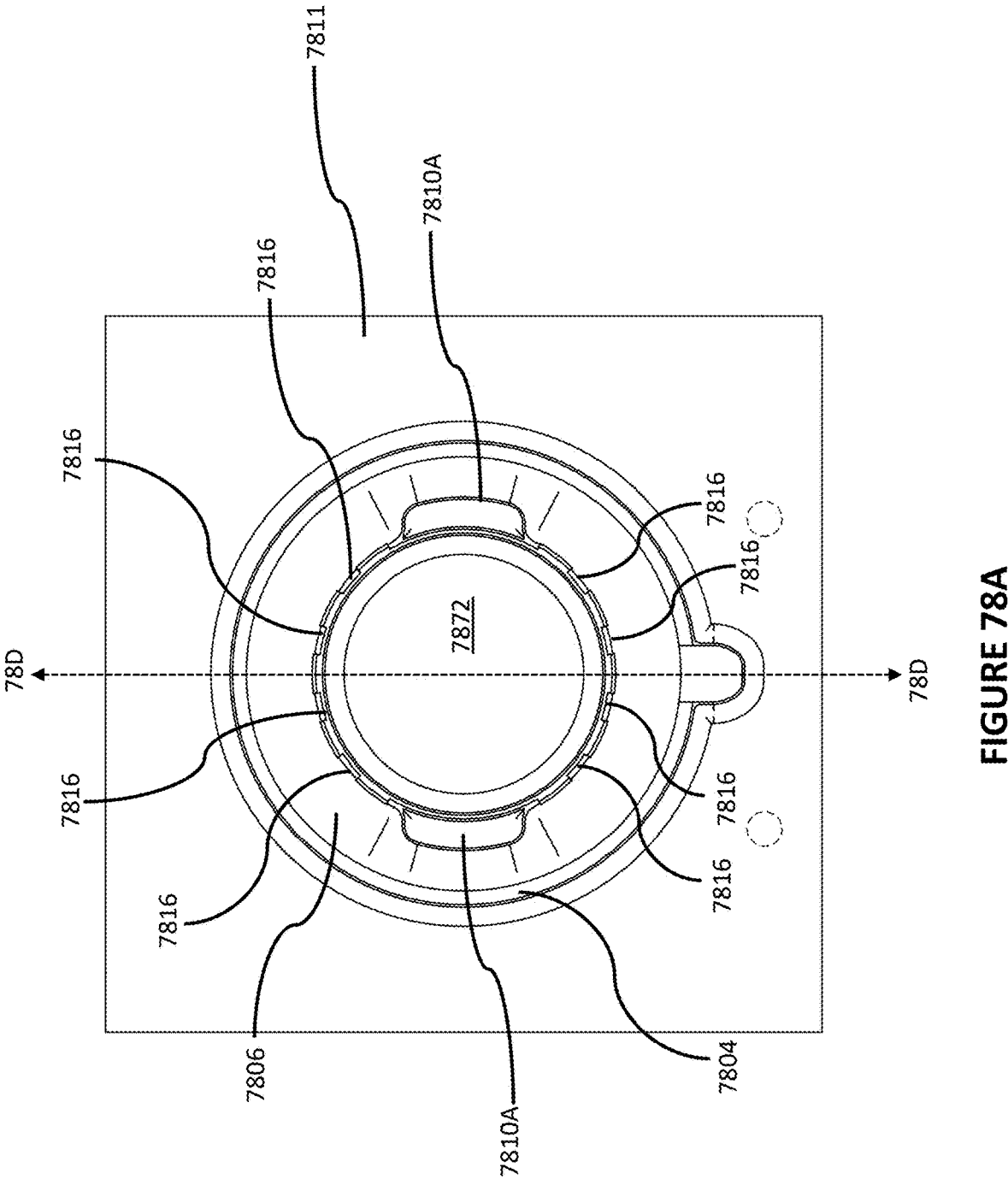
FIG. 78A illustrates a bottom view of mold top, in accordance with some embodiments of the present invention.
Figures 78B, 78C:
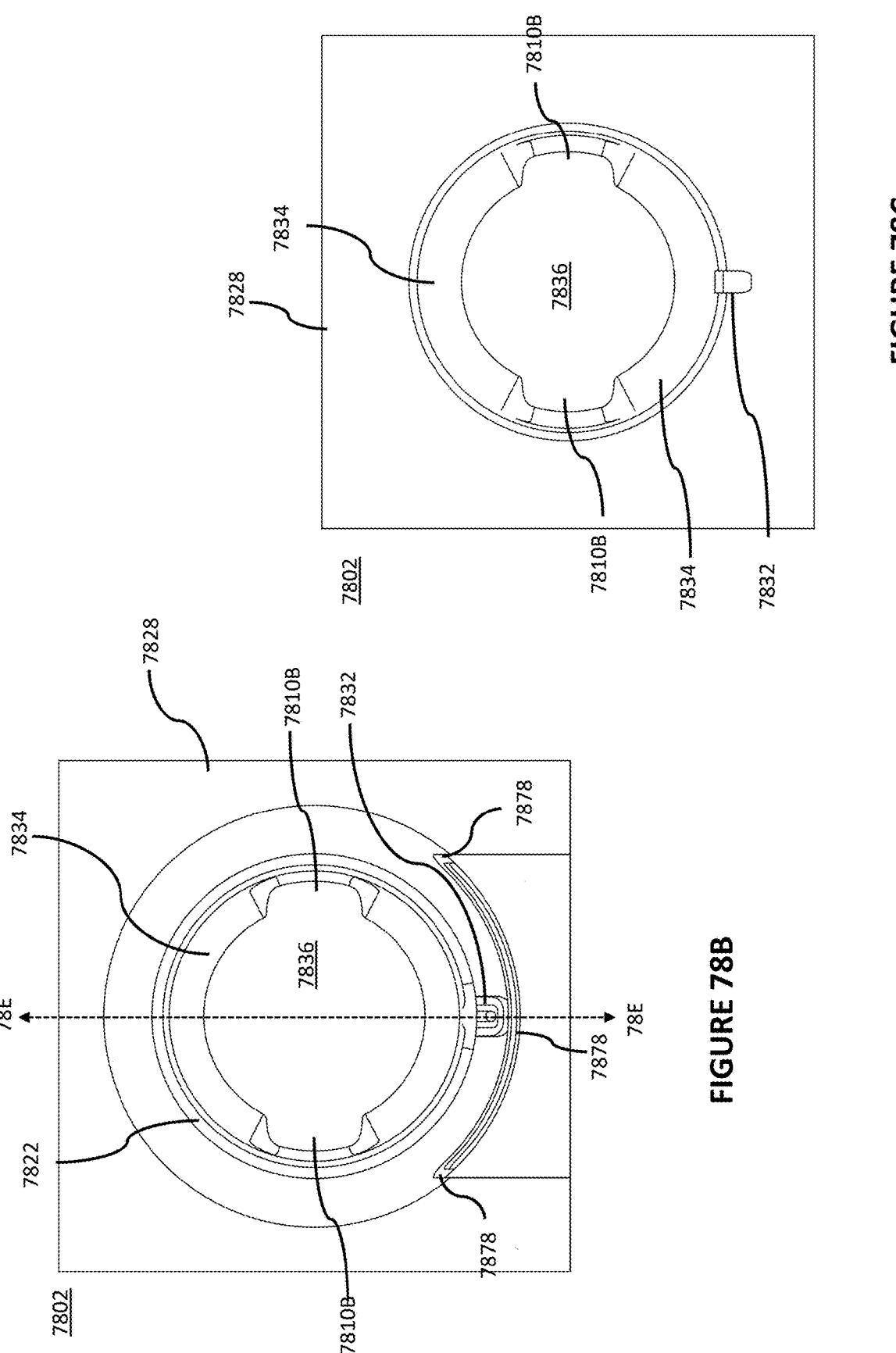
FIG. 78B illustrates a bottom view of a mold waist, in accordance with some embodiments of the present invention.
FIG. 78C illustrates a top view of mold waist, in accordance with some embodiments of the present invention.
Figures 78D, 78E:
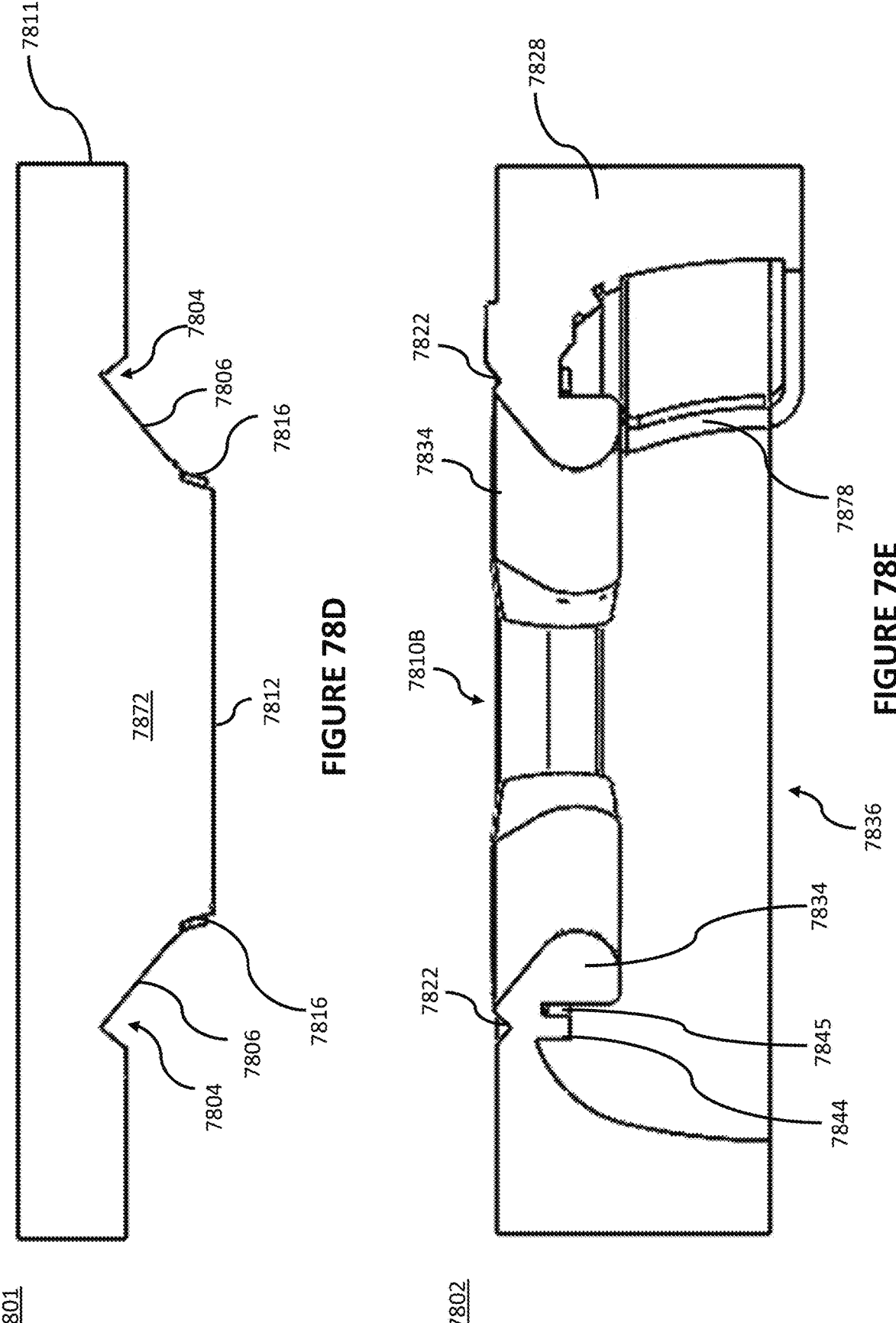
FIG. 78D illustrates a cross section view of mold top taken along bisecting line 78D of FIG. 78A, in accordance with some embodiments of the present invention.
FIG. 78E illustrates a cross section view of mold waist taken along bisecting line 78E of FIG. 78B, in accordance with some embodiments of the present invention.
Figure 78F:
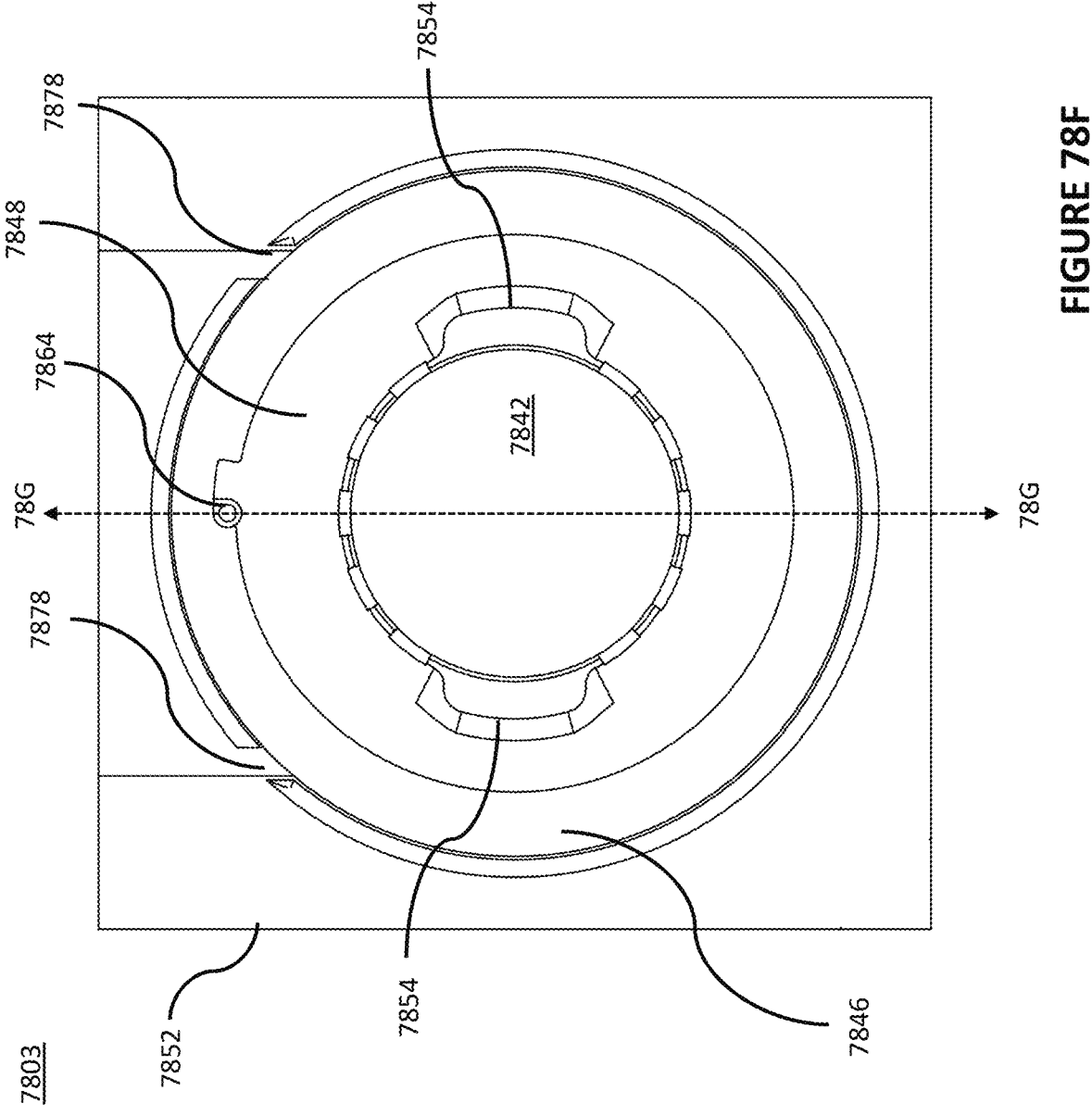
FIG. 78F illustrates a top view of a bottom mold, in accordance with some embodiments of the present invention.
Figure 78G:
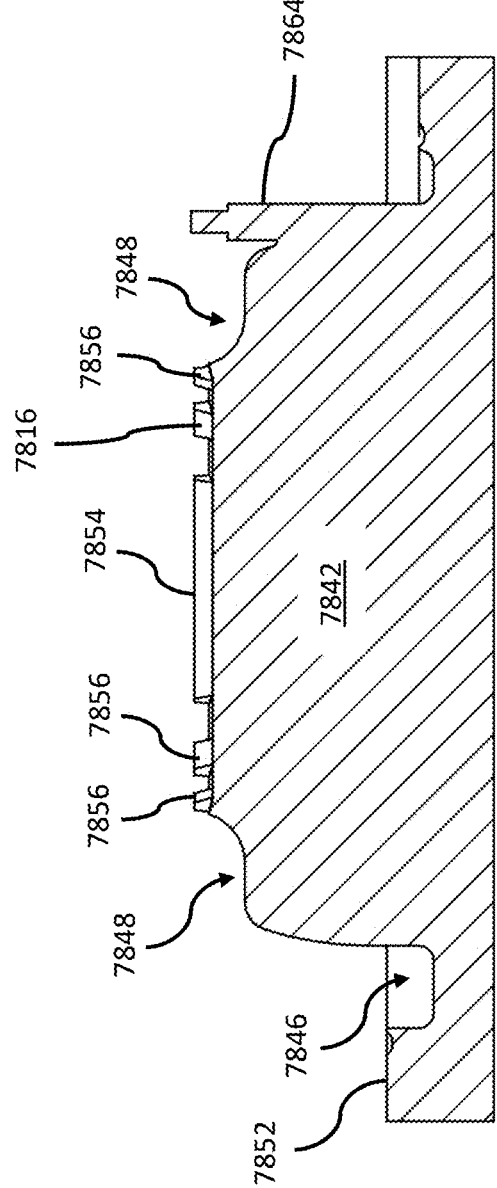
FIG. 78G illustrates a cross section view of bottom mold taken along bisecting line 78G of FIG. 78F, in accordance with some embodiments of the present invention.
Figure 78H:
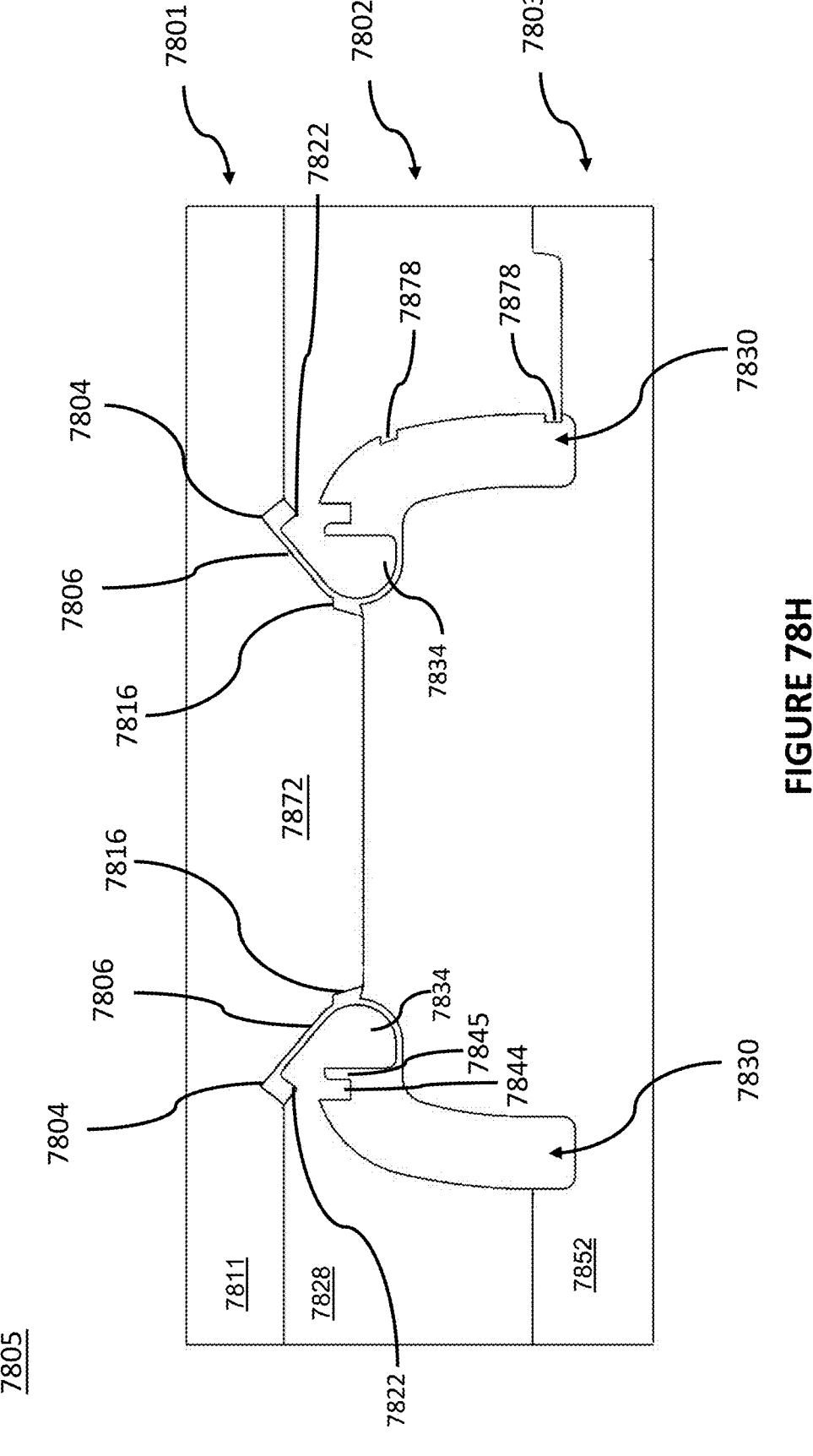
FIG. 78H is a bisecting cross section view of an assembly of the top mold of FIG. 78A, the mold waist of FIGS. 78B and 78C, and the bottom mold of FIG. 78F, in accordance with some embodiments of the present invention.
Figure 78I:
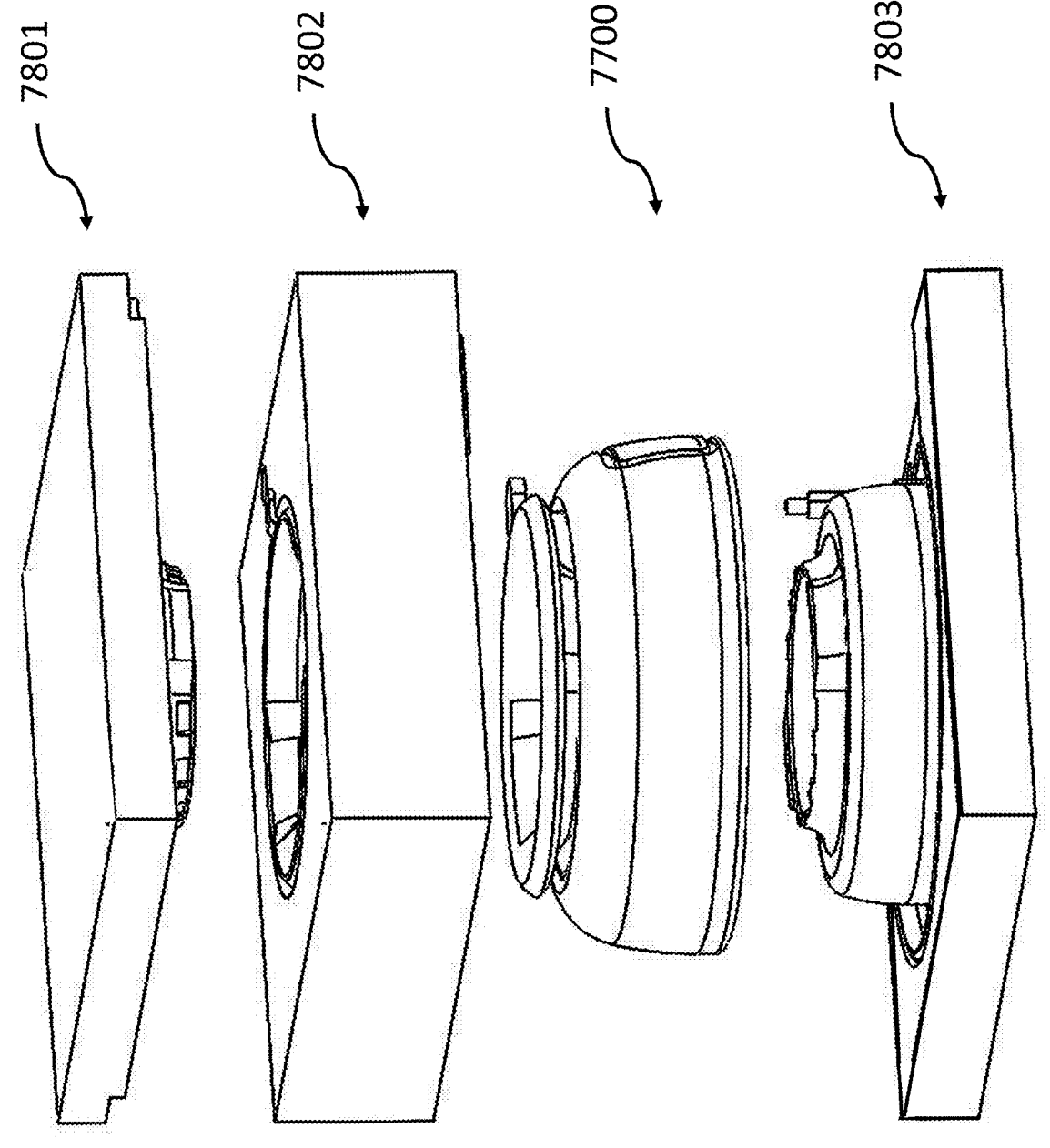
FIG. 78I Illustrates a perspective exploded view of the assembly of FIG. 78H with a molded cervical control system, in accordance with some embodiments of the present invention.
Figure 78J:
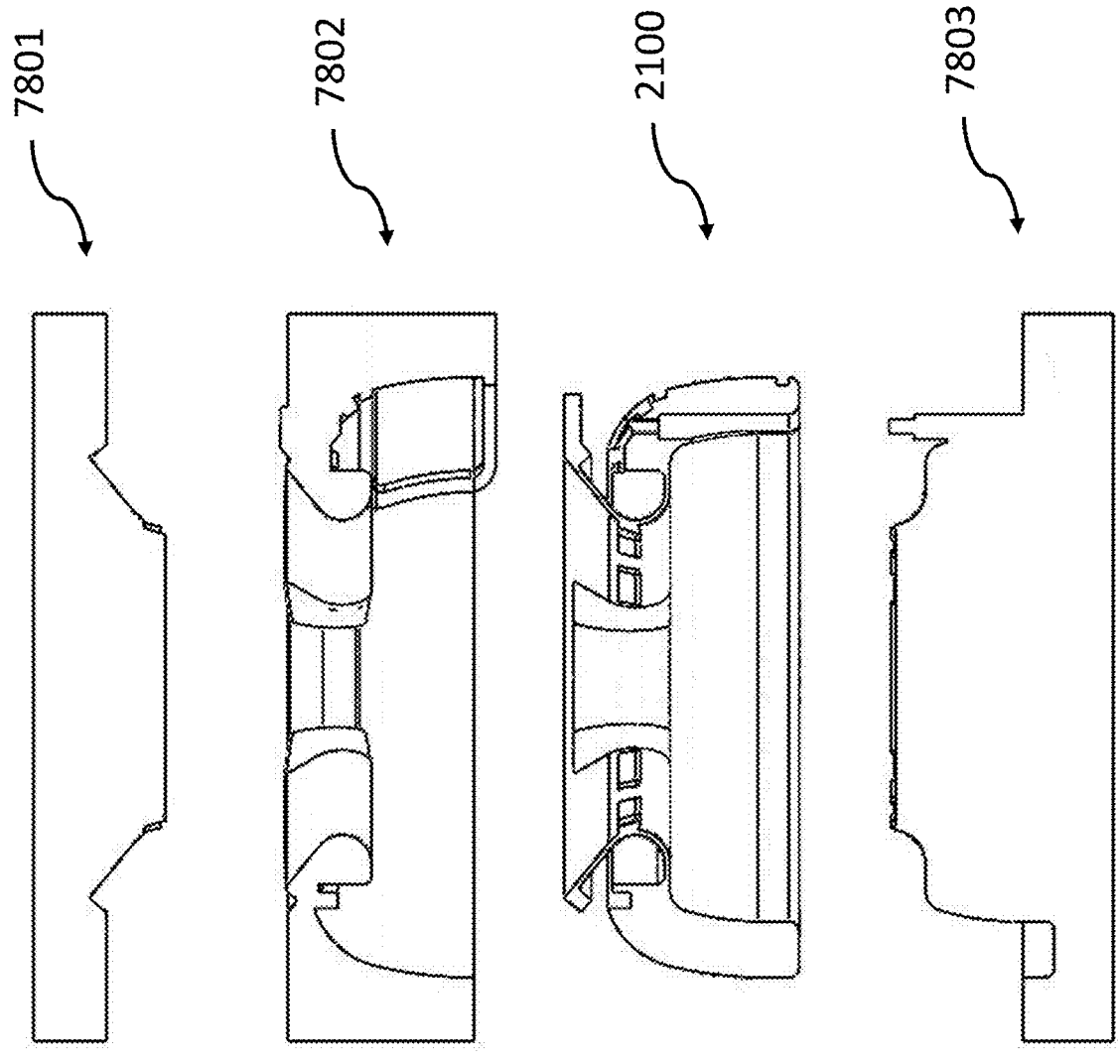
Figure 78K:
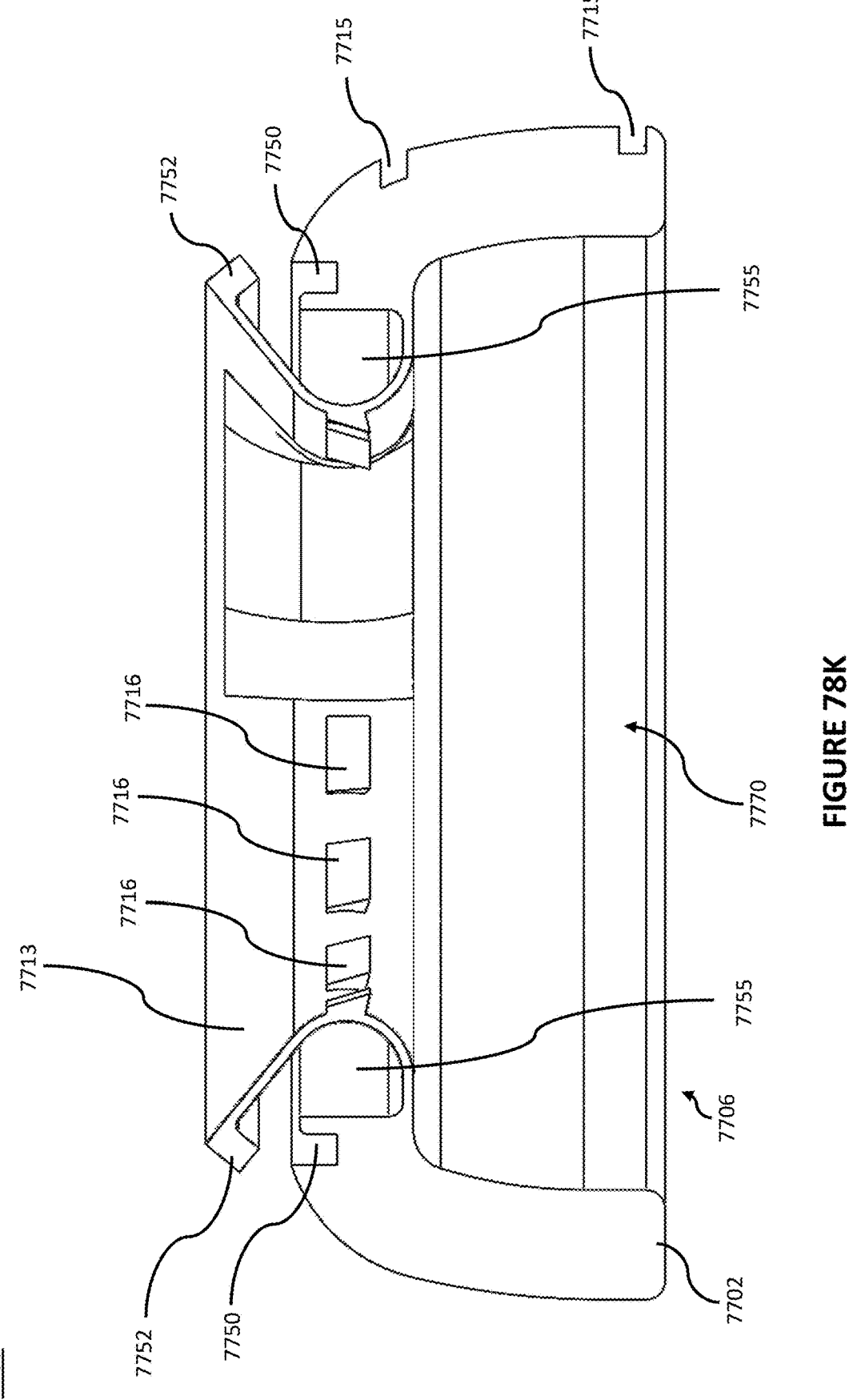
Figures 78L, 78M:
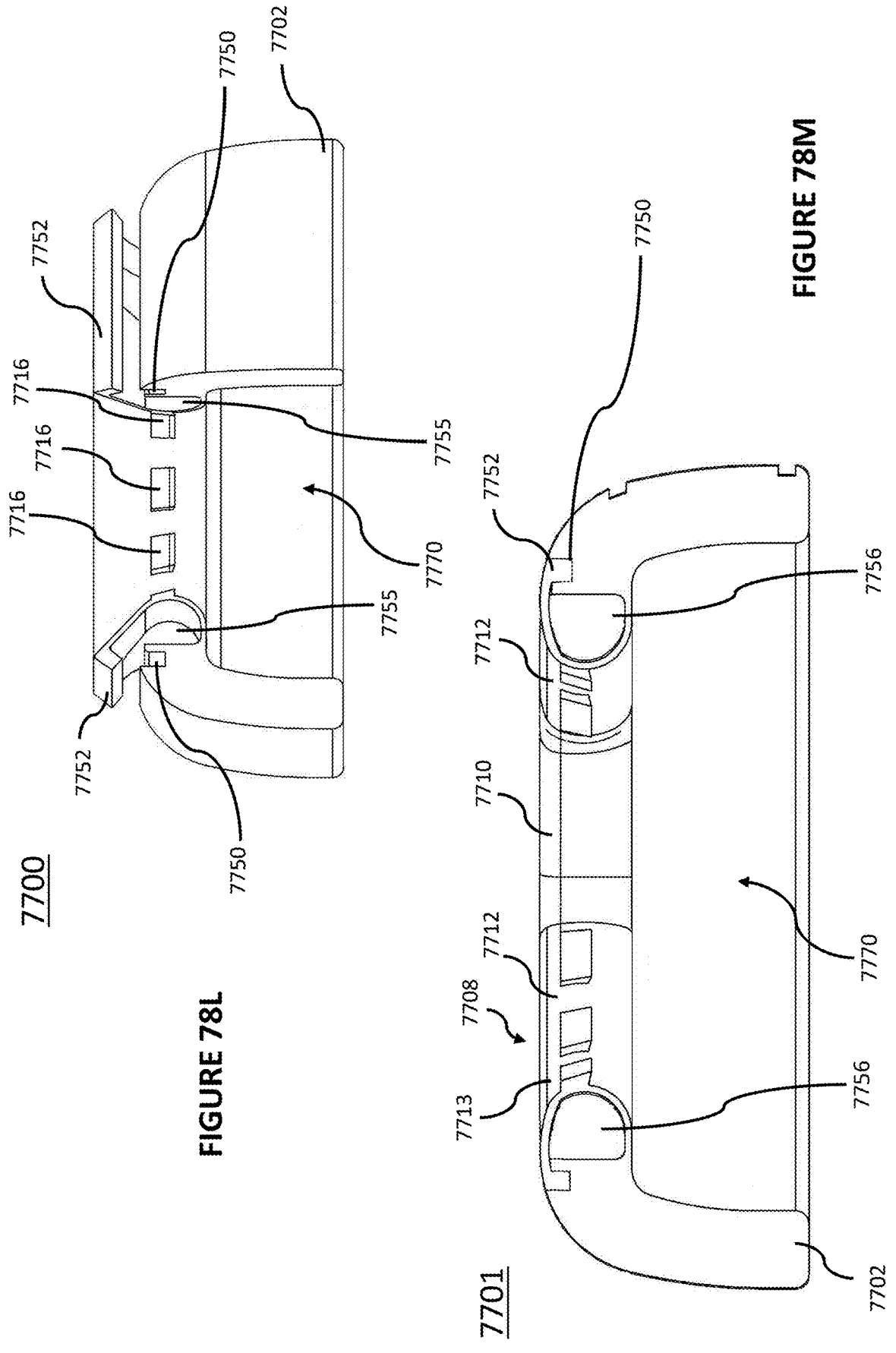

FIGS. 78A-78J provide various views of mold pieces and mold assemblies that may be used to fabricate, mold, and/or manufacture one or more of the cervical control systems described herein. In particular, FIG. 78A is a bottom view of a mold top 7801, FIG. 78B is a bottom view of a mold waist 7802, FIG. 78C is a top view of mold waist 7802, FIG. 78D is a cross section view of mold top 7801 taken along bisecting line 78D of FIG. 78A, FIG. 78E is a cross section view of mold waist 7802 taken along bisecting line 78E of FIG. 78B, FIG. 78F is a top view of bottom mold 7803, FIG. 78G is a cross section view of bottom mold 7803 taken along bisecting line 78G of FIG. 78F, FIG. 78H is a cross section view of an assembly 7805 of top mold 7801, mold waist 7802, and bottom mold 7803, FIG. 78I is an exploded perspective view of assembly 7805 with a molded cervical control system 7700, FIG. 78J is a bisecting cross sectional view of exploded assembly 7805 cervical control system 7700, FIG. 78K is a bisecting cross sectional view of cervical control system 7700, FIG. 78L is an angled sectional view of cervical control system 7700, and FIG. 78M is a bisecting cross sectional view of a cervical control system 7701, which is cervical control system 7700 with the inner cuff fully assembled (i.e., a flange of the flexible membrane comprising the inner cuff is inserted into and bonded to a corresponding groove residing in the main body of the system). All directional reference terms (e.g., top, bottom, upper, lower, etc.) used in the following discussion of FIGS. 78A-78M are made with reference to the orientations shown in FIGS. 78H-78J. Use of the term "distal" refers to the side of the system in opposition to the inner cuff and generally configured for use proximate to the fornix (toward the uterus) and use of the term "proximal" generally refers to the side of the system that is furthest away from the uterus when in situ.

Mold top 7801, mold waist 7802, and/or mold bottom 7803 may be aligned with one another and/or compressed together to generate one or more of the cervical control systems disclosed herein using any appropriate device, tool, mechanism, and/or system including, but not limited to, alignment pins, alignment holes, alignment grooves, alignment extensions, clamps, presses, alignment blocks, and the like. Material (e.g., silicon) may be injected or otherwise (e.g., pressed) added to/used with mold top 7801, mold waist 7802, and/or mold bottom 7803 to fabricate one or more of the cervical control systems disclosed herein.

As may be seen in the bottom view and the cross section view of mold top 7801 provided by FIGS. 78A and 78D, respectively, mold top 7801 includes a proximal opening extension 7872 sized, configured, and positioned to mold, or manufacture, a proximal opening of a cervical control system like the proximal openings disclosed herein. Top mold 7801 further includes a pair of upper recessed portion notches 7810A sized, configured, and positioned to mold, or manufacture, an upper surface of the recessed portions of a flexible membrane like the recessed portions disclosed herein. Mold top 7801 also includes a plurality of cleat notches 7816 sized, configured, and positioned to mold, or manufacture a corresponding plurality of cleats that extend from an exterior surface of a flexible membrane of an inner cuff like the cleats disclosed herein. Mold top 7801 further includes an angled plane 7806 sized, configured, and positioned to mold, or manufacture an upper surface of a flexible membrane of an inner cuff like the flexible membranes and inner cuffs disclosed herein. Mold top 7801 further includes an extension notch 7804 sized, configured, and positioned to mold, or manufacture an upper surface of a groove extending from an outer perimeter of a flexible membrane of an inner cuff.

As may be seen in FIGS. 78B, 78C, and 78E, mold waist 7802 includes mold waist base 7828 and a center aperture 7836 sized, configured, and positioned, to allow for the manufacture of an internal passageway via insertion of an internal passageway extension 7842 provided by a bottom mold 7803 (see e.g., FIGS. 78F and 78G) and a pair of a lower recessed portion notches 7810B sized, configured, and positioned to mold, or manufacture, a lower surface of the recessed portions of a flexible membrane like the recessed portions disclosed herein. Mold waist 7801 further includes a flexible membrane surface 7834 sized and configured to be positioned proximate to angled plane 7806 of top mold 7801 (see e.g., FIG. 78H) so that negative space between top mold 7801 and waist mold 7802 forms the inner cuff flexible membrane, an inner chamber of inner cuff, and a flexible membrane extension. Mold waist 7801 further includes a lower extension groove 7822 sized, configured, and positioned to cooperate with extension notch 7804 to form an underside of an extension of a flexible membrane configured to fit within a groove of a cervical control system formed by groove extension 7844 (see e.g., FIG. 78H). Mold waist 7802 further includes a positioning balloon groove 7878 sized, configured, and positioned to mold a groove into which a flexible membrane of a positioning balloon may be attached as shown in, for example, FIGS. 59 and/or 69G. Mold waist 7902 further includes a fluid conduit feature 7832 configured to cooperate with a fluid conduit extension 7864 of bottom mold 7803 to form a cavity for one or more fluid conduits like the fluid conduits disclosed herein. As may be seen in the cross section of FIG. 78E, flexible membrane surface 7834 may wrap around and include material used to create an inner chamber of an inner cuff like the inner chambers disclosed herein.

FIG. 78F provides a top view of bottom mold 7803 and FIG. 78G provides a cross section view of bottom mold 7803. Bottom mold 7803 includes a bottom mold base 7852 with an inner passageway extension 7842 that has cleat projections 7856 and recessed portion projections 7854 extending therefrom. Cleat projections 7856 may be sized, positioned, and configured to cooperate with cleat notches 7816 of top mold 7801 to form cleats that extend from an exterior surface of a flexible membrane of an inner cuff like the cleats, flexible membranes, and inner cuffs disclosed herein. Recessed portion projections 7854 may be sized, positioned, and configured to cooperate with upper recessed portion notches 7810A and lower recessed portion notches 7810B to form recessed portions of an inner cuff of a cervical control system like the recessed portions of inner cuffs disclosed herein. Bottom mold base 7852 further includes a cervical control system distal edge groove 7846 sized, positioned, and configured to form the lower, or distal, edge of a cervical control system like the cervical control systems disclosed herein. In addition, bottom mold base 7852 a curved groove 7848 size, positioned, and configured to form the lower, or distal, edge of the flexible membrane that forms an inner cuff like the inner cuffs disclosed herein.

When molding, or manufacturing, a cervical control system like the cervical control systems disclosed herein bottom mold 7803 may be placed on a surface and mold waist 7802 may be aligned with bottom mold 7803 prior to use. Then, mold top 7801 may be aligned with and fit over mold waste 7802. Mold top, waist, and base 7801, 7802, and 7803 may be compressed (e.g., clamped) together or otherwise assembled so that a likelihood of movement between the mold pieces is reduced and/or eliminated. A cross section view of an exemplary assembly 7805 of top mold 7801, mold waist 7802, and bottom mold 7803 is provided by FIG. 78H, wherein negative space between top mold 7801, mold waist 7802, or bottom mold 7803 (i.e., space not occupied by top mold 7801, mold waist 7802, or bottom mold 7803) may define the shape and configuration of a molded cervical control system like the cervical control systems disclosed herein.

Next, material (e.g., silicone, plastic, etc.) with which to manufacture the cervical control system may be injected into the mold assembly (e.g., mold assembly 7805) to form a cervical control system like the cervical control systems disclosed herein. Once the material has cured, the mold assembly may be disassembled so that the molded cervical control system may be released therefrom. FIG. 78I provides an exploded perspective view and FIG. 78J provides a cross section view of assembly 7805 after a cervical control system 7700 has been molded therein. Using assembly 7805, a cervical control system may be molded in substantially one piece, with the exception of the attachment of a flexible membrane to form a positioning balloon. This simplifies the manufacturing process and leads fewer junction points for additional pieces, which leads to improved durability and performance while lowering manufacturing costs.

FIGS. 78K and 78L provide a cross section and a sectional view, respectively of cervical control system 7700 (also referred to herein as system 7700) after it comes out of assembly 7805 before an inner cuff 7708 is assembled. System 7700 includes many of the components of the cervical control systems disclosed herein including a main body 7702, a distal opening 7706, an internal passageway 7770, a flexible membrane 7713, and a plurality of cleats 7716. Flexible membrane 7713 further includes indentations 7715 formed by positioning balloon groove 7878, positioned on an exterior surface of main body 7702, and configured for acceptance of a flexible membrane (not shown) of a positioning balloon may be attached as shown in, for example, FIGS. 59 and/or 69G.

System 7700 further includes an open area 7755 sized shaped and configured to provide an inner chamber 7756 for the system once extension 7752 is positioned within and/or bonded within groove 7750, there by forming a fully assembled inner cuff 7708 of a cervical control system 7701 as shown in the cross section of FIG. 78M. Inner cuff 7708 further includes recessed portions 7710 and expandable portions 7712 that may be configured and/or function in a manner similar to the inner cuff recessed and expandable portions disclosed herein.

Figure 79:
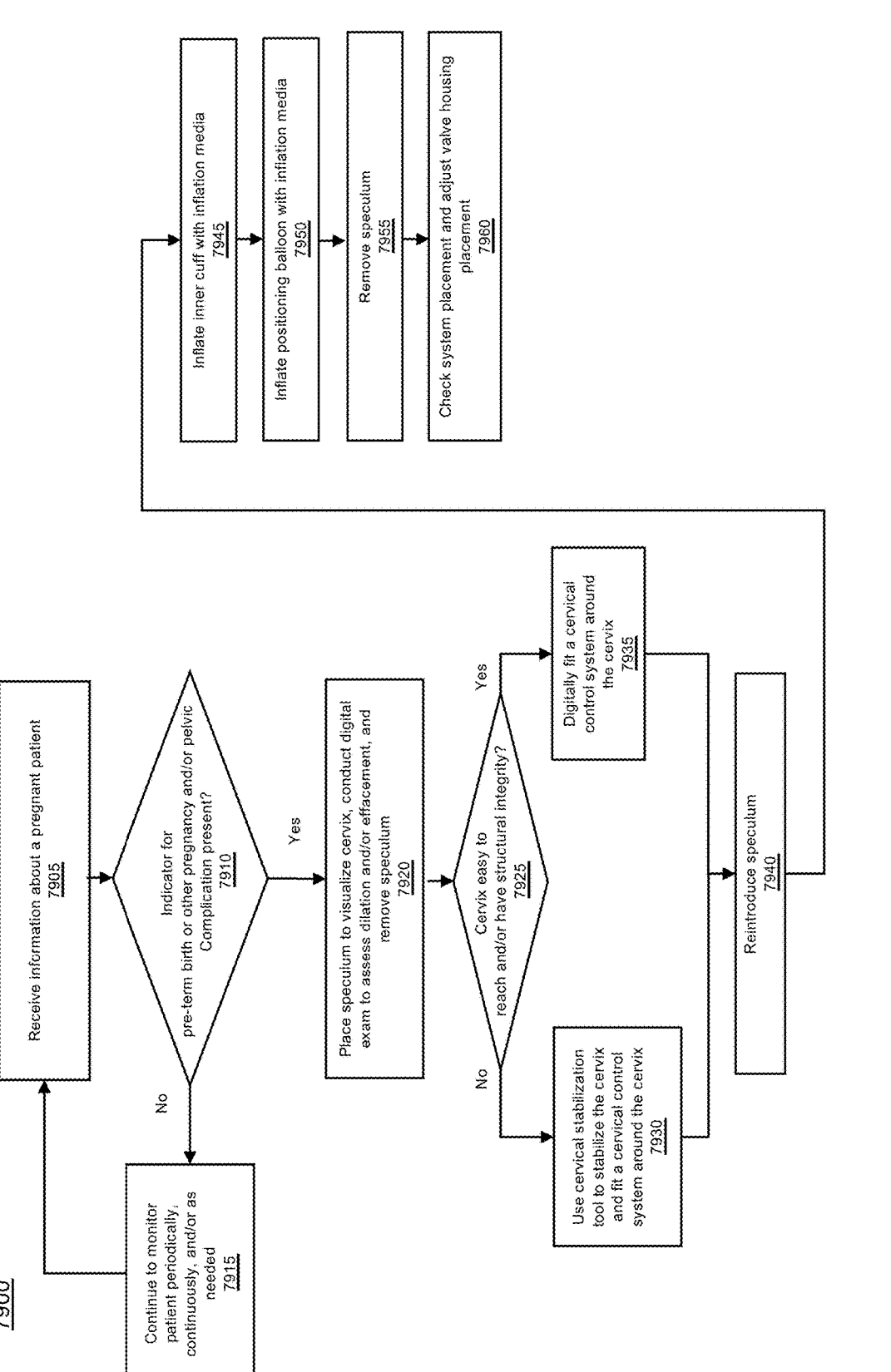

FIG. 79 is a flowchart that illustrates an exemplary process 7900 for deciding whether or not to insert and/or use a cervical control system like the cervical control systems disclosed herein for a patient and/or how to insert and/or use the cervical control system to, for example, foster regeneration and/or restoration of a cervical mucus plug, prevent pre-term labor and/or delivery, extend gestation of a fetus, and/or treat short cervix, PROM, PPROM, pregnancy complications, and/or prolapse of pelvic organs and/or tissue. Process 7900 may be executed by, for example, a clinician, care provider, doctor, surgeon, nurse, or other technician providing medical care to a patient. In some embodiments, one or more steps of process 7900 may be executed by and/or with the assistance of a computer or software running on a computer and/or a database such as an electronic medical record database. Process 7900 will be concurrently discussed with figures (e.g., FIGS. 80-80L depicting how various steps of process may be executed and/or a result thereof.

Optionally, in step 7905, information about a pregnant patient may be received. The information may include, for example, lab testing results for the patient, the patient's medical history, images of the patient's anatomy (e.g., pelvic and/or uterine ultrasound images) from which a cervical length and/or dilation may be determined, visual examination of the patient's anatomy (e.g., vagina and/or cervix), and/or digital examination of the patient's anatomy. Exemplary lab testing results include, but are not limited to, hormone (e.g., estrogen, progesterone, oxytocin, etc.) levels and/or fetal fibronectin (fFN) levels present in, for example, the cervicovaginal fluid. Exemplary medical historical information that may be received includes, but is not limited to, age, how many fetuses (e.g., single, twins, triplets, etc.) are present in the patient's uterus, history of preterm birth for the patient and/or within the patient's family, history of pregnancy complications for the patient and/or within the patient's family, history of a short cervix, PROM, and/or PPROM for the patient and/or within the patient's, family, whether the patient has undergone a cervical procedure (e.g., surgery, a cerclage, electrosurgical excision procedure (LEEP), and/or whether the patient has one or more risk factors for pregnancy complications and/or a high risk pregnancy such as advanced age, chronic inflammation, diabetes, and/or high blood pressure. Exemplary examination information that may be received and/or determined via execution of step 7905 includes, but is not limited to, a PROM and/or PPROM diagnosis and/or a determination that the cervix is of a particular (e.g., shortened) length that may be less than 25 mm, and/or within the range of lengths that includes between 17-39 mm, 15-40 mm, or 10-45 mm.

When step 7905 is performed, it may be determined (using some, or all, of the information received and/or determined at step 7905) in step 7910 whether the pregnant patient is at risk for and/or has an indication for pre-term birth, pregnancy complications, pelvic (e.g., prolapse) complications, and/or is otherwise a good candidate for use of a cervical control system like the cervical control systems disclosed herein and, if not, process 7900 may proceed to step 7915 and the patient may be monitored periodically, continuously, and/or as-needed to, for example, reassess whether or not use of a cervical control system may be beneficial to the patient (e.g., execution of step 7910 may be repeated).

When it is determined in step 7910 or is otherwise determined (e.g., by a clinician when steps 7905 and/or 7910 are not performed) that the pregnant patient is at risk for and/or has an indication for pre-term birth, pregnancy complications, pelvic (e.g., prolapse) complications, and/or is otherwise a good candidate for use of a cervical control system, execution of process 7900 may advance to (or initially start with) step 7920, wherein a speculum may be placed within the patient's vagina so that the cervix may be visually observed, measured, and/or digitally examined to, for example, assess dilation, effacement, integrity, sufficiently, length, structural integrity. FIG. 80A provides a sagittal view of an exemplary patient 8000 illustrating the patient's vaginal canal 1992, introitus (vaginal opening) 1994, short cervix 1996, and external os (distal opening of the cervix) 1998 and FIG. 80B provides a sagittal view of patient 8000 illustrating a speculum positioned within vaginal canal 1992 (as may occur during execution of step 7920) so that, for example, cervix 1996 may be visually observed and/or swabbed to obtain a sample for laboratory testing. After the speculum is placed, the cervix may be digitally examined to, for example, assess dilation, integrity, length, and/or effacement When the cervix (e.g., cervix 1996) is easy to reach and/or has structural integrity (determination of step 7925), the speculum may be removed from the vaginal canal and a cervical control system such as the cervical control systems disclosed herein may be digitally inserted into the vaginal canal (e.g., vaginal canal 1992) and fit around the cervix (e.g., cervix 1996) by, for example, inserting the cervix into an internal passageway of the cervical control system as, for example, shown and described herein (step 7935). An example of how step 7935 may be performed is shown in FIG. 80C, which shows the hand of a clinician digitally inserting the cervical control system by performing step 7025.

Alternatively, in step 7925, the clinician may determine that the cervix is hard to reach and display's a higher degree of softness such that it may be better/more effective to use a cervical stabilization system (e.g., forceps) to first stabilize the cervix and then place the cervical control system and/or use the cervical stabilization system to pull the cervix through the internal passageway of the cervical control system (step 7930) as shown in, for example, FIG. 80D. Step 7930 may be performed after the speculum inserted in step 7920 has been removed.

Once the cervical control system is in place around the cervix following execution of steps 7930 or 7935, at step 7940 the clinician may reintroduce the speculum as shown in FIG. 80E and inflate the inner cuff with inflation media (e.g., saline) (step 7945) as shown in, for example, FIG. 80F, which illustrates how the inner cuff may expand or extend downward so that the inflation of the inner cuff pulls the cervix down and/or does not push the uterus up, which could cause the cervix to be pulled out of the inner cuff 1908 or the system.

Once inner cuff is inflated (step 7945), a positioning balloon of the cervical control system may be inflated (step 7950) with inflation media (for example, saline) to position the positioning balloon, the cervical control system, and/or cervix as desired, an example of which is shown in FIG. 80G. As illustrated in FIG. 80G, the positioning balloon can be inflated to tilt the cervix at angle to, for example, decrease pressure exerted thereon by the uterus. FIG. 80G also illustrates the positioning of the cervix before the tilt with dash line 2032 and illustrates the positioning of the cervix after the tilt with dashed line 2034. As noted by the arrow in FIG. 80G, the cervix can be more posterior after the positioning balloon is inflated. FIG. 80G also illustrates the system with the positioning balloon positioned posteriorly. In this orientation, by inflating the positioning balloon, the cervical control system can push at the top of the posterior portion of the cervix in order to lever the remainder of the cervix posterior as shown in FIG. 80G, which may be done by pressing on the top of the posterior side of the cervix or, in other cases, by rotating the system 180 degrees and pressing on the lower portion of the anterior side of the cervix (to tilt the cervix posteriorly). While FIG. 80G illustrates the system with the positioning balloon placed posteriorly, the positioning balloon 1918 can be placed in any orientation to tilt the cervix to provide the best support for the cervix and/or based on the physician discretion. In the next step 7955, the clinician can remove the speculum and check placement digitally and then tuck the valve housing 1960 (similar to the valves and valve housing 1360 described with reference to FIGS. 58-63) into the vaginal canal (step 7960) and shown in, for example, FIG. 80H.

In some embodiments, the cervical control system may be placed via execution of some, or all, of the steps of process 7900 to treat and/or mitigate symptoms associated with prolapse, such as pelvic organ prolapse (e.g., uterine prolapse). In these cases, the cervical control systems disclosed herein may be used to treat symptoms of prolapse including, but not limited to bleeding, pressure, pain, incontinence (e.g., urinary incontinence), and so on. Such symptoms may also be treated herein without the underlying condition of pelvic organ prolapse. As an example, FIG. 80I illustrates a sagittal view of a patient 8001 with a cervical control system 2200 positioned around the patient's cervix and used to support uterine prolapse. System 2200 may be similar to, for example, systems 100, 500, 1000, 1100, 1300, 1400, 1500, 1600, and 1700 described above and illustrated in FIGS. 1-6, 19-20, 36-37, 51-54, 58-59, 64A-64B, 65A-65B, 66, 67A-67C, and 68A-68B. Similar to the components of systems 100, 500, 1000, 1100, 1300, 1400, 1500, 1600, and 1700 described above, system 2200 of FIG. 80I includes a main body 2202, a proximal opening 2204, a distal opening 2206, and an expandable positioning balloon 2218. As illustrated in FIG. 80I, system 2200 can be placed in an inverted orientation compared to the orientations described with reference to FIGS. 1-6, 19-20, 36-37, 51-54, 58-59, 64A-64B, 65A-65B, 66, 67A-67C, and 68A-68B. The inverted orientation of the system 2200 orients the system 2200 so that the cervix can be cupped inside the larger distal opening 2206 of the system 2200 and closed in via inflation of the cervical control system's inner cuff. The distal opening can have a cushioning layer such as a silicone gel to increase surface area contact and provide the user with more comfort. Positioning balloon 2218 can be placed in an anterior position as shown in FIG. 80I. However, the positioning balloon 2218 can be placed in any orientation that best facilitates uterine support. Once the cervical control system is placed within the patient, the clinician or user can inflate the positioning balloon 2218 to provide mechanical support to the uterus, thereby treating uterine prolapse. In some cases, positioning balloon 2218 can be deflated before removal. System 2200 can provide structurally semi-rigid support while also offering an expandable portion (for example, the positioning balloon) to accommodate anatomical variety. When used to treat and/or mitigate symptoms of prolapse, process steps 7905-7960 may be performed however, in some cases, inner cuff may not be inflated (step 7945).

Additionally, or alternatively, process 7900 and/or steps thereof may be executed to mitigate the effects of and/or treat PPROM or PROM. In these cases, positioning of the cervical control system around the patient's cervix may act to hold the cervix closed and prevent further escape, or leaking, of amniotic fluid from the ruptured amniotic sac.

FIG. 80J illustrates a sagittal view of a pregnant patient, illustrating an intact membrane 1802 of an amniotic sac filled with a normal, or clinically acceptable, level of amniotic fluid 1804. FIG. 80K illustrates a sagittal view of a pregnant patient that has experienced PPROM and has a ruptured membrane 1802 and a low level of amniotic fluid 1804 due to leaking of the amniotic fluid from ruptured membrane 180. FIG. 80L illustrates a sagittal view of a pregnant patient with her cervix 101 positioned within, and being compressed by, a cervical control system 1800, which may be similar to one or more of the cervical control systems described herein. Cervical control system 1800 may be placed within the patient via execution of one or more steps of process 7900. Compression of cervix 101 may act to stop, or decrease a flow rate, of amniotic fluid leakage from ruptured membrane 1802, thereby allowing replenishment of amniotic fluid within ruptured membrane 1802. In some embodiments, the main body of one or more of the cervical control systems disclosed herein may be a partial cube shape, a pyramid shape, a partial egg shape with an oval or partially oval cross section, an irregular three-dimensional shape with non-symmetrical cross section, or any other shape suitable for placement around the cervix and for engaging the vaginal wall.

In some cases, multiple layers of material (for example, multiple layers of silicone) can be used to create the proximal and/or positioning balloon and/or the cervical control system(s) and/or devices themselves. For example, embodiments such as those shown in FIG. 26-27 can utilize multiple layers of material (for example, silicone) that would be joined. In such cases, a plasma bonding process can be used to join the layers of material. For example, plasma could be applied which alters the surface energy/chemistry of the material to promote adhesion to fully cured silicone. In other cases, a silicone glue can be used. In some cases, the glue could pose a risk to occluding the channels for inflation and can result in poor sealing characteristics. Accordingly, in some cases, a plasma bonding process can be used and no glue and/or other adhesive or limited glue and/or other adhesive is used. In some embodiments, one, two, three or more layers are used, and the layers can be joined using a plasma bonding process.

In some embodiments, the various different components, and functions of the embodiments of the cervical control systems described and illustrated herein may be adapted for use with any of the other embodiments disclosed herein. Thus, the cervical control systems of the various illustrative embodiments detailed above provide selectively adjustable cervical control system for controlling and/or supporting an insufficient cervix, mitigating leaks of amniotic fluid due to ruptured amniotic sac membranes, fostering growth and/or regeneration of cervical mucus plugs, and/or supporting pelvic organs to, for example, promote extended gestation of pre-term pregnancies, reduce pregnancy complications, and improve patient (pregnant woman and baby) outcomes. The cervical control systems include an upper or inner cuff for supporting, elongating, and/or constricting a patient's cervix in an attempt to impede the cervix from further dilating, opening, or further shortening.

The inner cuffs disclosed herein may comprise a flexible membrane of fixed or varying width that define one or more inner chambers open to and/or configured for acceptance of inflation media therein. As inflation media is inserted and/or pushed into the inner chambers of the inner cuffs, their corresponding flexible membranes may expand in size to, for example, engage and/or constrict a cervix positioned therein. The expansion of the flexible membranes/inner cuffs may be radial and/or distal directions. At times, the inner cuffs disclosed herein may include multiple expandable bladders which may be independently addressable (e.g., inflatable or deflatable) to provide customizable support for the cervix based on the specific needs of the patient. In a preferred embodiment, the inner cuffs disclosed herein provide a transverse force as well as a downward force (e.g., away from the uterus) to the cervix, which may promote retention of the cervix within the inner cuff, elongation of the cervix, and/or compression of the cervix (which may reverse and/or prevent dilation of the cervix). In several embodiments, the inner cuff is shaped and dimensioned to permit blood flow from the upper cervix to the lower cervix protruding through the inner cuff.

The cervical control systems disclosed herein may include a lower or positioning balloon of the cervical control systems disclosed herein may be provided to seat or secure the body of the corresponding cervical control system on the patient's vaginal wall during use. The positioning balloon may include one or more expandable bladders that may be independently addressable to provide customizable support for and/or control of the cervix.

Also disclosed herein are kits that include one or more of the cervical control systems described herein. FIG. 81 provides a block diagram of the contents of an exemplary kit 8100 with exemplary components, pieces, devices and/or apparatus including, but not limited to, one or more cervical control system(s) and/or system(s) 8105 like the cervical control systems disclosed herein, a container of inflation media 8110, an inflation media delivery device 8115, one or more cervical stabilization devices 8120, one or more measurement devices 8125, one or more valve housings 8130, one or tubes and/or catheters 8135, a speculum 8140, and a container of lubricant 8140. Importantly, not all embodiments of kit 8100 will include all of the components, pieces, devices and/or apparatus shown in FIG. 81.

In some embodiments, kit 8100 may include a plurality of different cervical control systems with different features that may be tailored for certain situations and/or patient anatomical features. For example, cervical control device(s) and/or system(s) 8105 may include a small, medium, and large cervical control system. Additionally, or alternatively, cervical control device(s) and/or system(s) 8105 may include a cervical control system adapted to treat PPROM and a cervical control system adapted to treat short cervix. Additionally, or alternatively, cervical control device(s) and/or system(s) 8105 may include cervical control systems with differing inner cuff and/or positioning balloon features (e.g., size, number and/or type of cleats, etc.).

In some embodiments, inflation media delivery device may be a pump or syringe that, on some occasions, may be pre-filled with inflation media. On these occasions, kit 8100 may not include inflation media container 8110. Exemplary cervical stabilization devices 8120 include, but are not limited to, forceps and a tenaculum. Exemplary measurement devices 8125 may be configured to measure a length or dilation of a cervix and include, but are not limited to, rulers. On some occasions, tubes and/or catheters 8135 may include tubes and/or catheters of varying lengths so that, for example, a clinician may select a particular length of tube that, for example, enables easy access to an end of the tube/catheter extending from the introitus when the cervical control system is in situ. In this way, the selected tube and/or catheter may accommodate patient anatomy and/or clinician preference. In some embodiments, the tubes and/or catheters 8135 may include tubes and/or catheters with one, two, three, or four lumens and the type of tube and/or catheter 8135 selected may be responsive to the type of cervical control system(s) and/or system(s) 8105 selected and/or how many fluid conduits and/or inlets the selected cervical control system(s) and/or system(s) 8105 has. Valve housing 8130 may be any of the valve housings disclosed herein and, in some cases a plurality of valve housings may be provided by kit 8100 so that the valve housing 8130 used may be responsive to and/or configured to cooperate with a selected tube and/or catheter 8135 or cervical control system(s) and/or system(s) 8105.

Container of lubricant 8140 may hold any appropriate lubricating material that may make use of one or more components of kit 8100 easier and/or more comfortable for a patient. In some cases, the lubricant may include an active agent such as an anti-microbial and/or pharmacological agent.

Changes and modifications in the specifically described embodiments can be carried out without departing from the principles of the present disclosure. Each of the disclosed aspects and examples of the present disclosure may be considered individually or in combination with other aspects, examples, and variations of the disclosure. In addition, unless otherwise specified, none of the steps of the methods of the present disclosure are confined to any particular order of performance.

While the methods and devices and systems described herein may be susceptible to various modifications and alternative forms, specific examples thereof have been shown in the drawings and are herein described in detail. It should be understood, however, that the embodiments are not to be limited to the particular forms or methods disclosed, but rather intended is to cover modifications, equivalents, and alternatives falling within the spirit and scope of the various examples and embodiments described and the appended claims. Further, the disclosure herein of any particular feature, aspect, method, property, characteristic, quality, attribute, element, or the like in connection with an example can be used in all other examples set forth herein. Any methods disclosed herein need not be performed in the order recited. The use of sequential, or time-ordered language, such as "then," "next," "after," "subsequently," and the like, unless specifically stated otherwise, or otherwise understood within the context as used, is generally intended to facilitate the flow of the text and is not intended to limit the sequence of operations performed. Thus, some examples may be performed using the sequence of operations described herein, while other examples may be performed following a different sequence of operations.

Conditional language used herein, such as, among others, "can," "might," "may," "e.g.," and the like, unless specifically stated otherwise, or otherwise understood within the context as used, is generally intended to convey that some examples include, while other examples do not include, certain features, elements, and/or states. Thus, such conditional language is not generally intended to imply that features, elements, blocks, and/or states are in any way required for one or more examples or that one or more examples necessarily include logic for deciding, with or without author input or prompting, whether these features, elements and/or states are included or are to be performed in any particular example. Where devices, systems, and/or methods "comprise" certain features or steps, such devices, systems, and/or methods may also "consist essentially of" such features or steps if identified as such in the claims.

The methods disclosed herein may include certain actions taken by a practitioner; however, the methods can also include any user or third-party instruction of those actions, either expressly or by implication. For example, actions such as "positioning a device" include "instructing positioning of a device."

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonable under the circumstances, for example ±5%, ±10%, ±15%, etc.). For example, "about 4 inches" includes "4 inches." Phrases preceded by a term such as "substantially" include the recited phrase and should be interpreted based on the circumstances (e.g., as much as reasonably possible under the circumstances). For example, "substantially linear" includes "linear." Unless stated otherwise, all measurements are at standard conditions including temperature and pressure.

The phrase "at least one of" is intended to require at least one item from the subsequent listing, not one type of each item from each item in the subsequent listing. For example, "at least one of A, B, and C" can include A; B; C; A and B; A and C; B and C; or A, B, and C.

What is claimed is:
1. A method to compress a cervix, comprising:
positioning a cervix of a patient within an internal passageway of a cervical control system, the cervical control system comprising:
an expandable cuff configured to surround at least a portion of the cervix of the patient;
a positioning balloon disposed at an exterior surface of the cervical control system, wherein the positioning balloon surrounds a portion of a circumference of the exterior surface;

a first inflation media conduit comprising a first end in fluid communication with the expandable cuff and a second end opposite the first end configured to receive inflation media;
a second inflation media conduit comprising a first end in fluid communication with the positioning balloon and a second end opposite the first end configured to receive inflation media; and
a bi-lumen tube configured to extend the patient's vaginal canal and exit the introitus when the cervical control system is in position within the patient, wherein a first end of a first lumen of the bi-lumen tube is in fluid communication with the second end of the first inflation media conduit and a second opposing end of the first lumen is configured to receive inflation media, and wherein a first end of a second lumen of the bi-lumen tube is in fluid communication with the second end of the second inflation media conduit and a second opposing end of the second lumen is configured to receive inflation media;
accessing the second end of each of the first and second lumens of the bi-lumen tube outside the patient's body; and
adding inflation media to each of the second ends of the first and second lumens of the bi-lumen tube for communication to the respective first and second inflation media conduits; and
adding inflation media to the second end of each of the first and second inflation media conduits thereby expanding the expandable cuff and the positioning balloon respectively.

2. The method of claim 1, wherein the second end of the first inflation media conduit or the second inflation media conduit is in fluid communication with a valve, the method further comprising:
opening the valve to add inflation media to the respective first or second inflation media conduit and closing the valve to hold inflation media within the respective first or second inflation media conduit.

3. The method of claim 1, wherein the second end of the first inflation media conduit is in fluid communication with a first valve and the second end of the second inflation media conduit is in fluid communication with a second valve, the method further comprising:
opening the first valve to add inflation media to the first inflation media conduit;
closing the valve to hold inflation media within the first inflation media conduit;
opening the second valve to add inflation media to the second inflation media conduit;
closing the second valve to hold inflation media within the second inflation media conduit.

4. The method of claim 1, wherein the expansion of the expandable cuff compresses the cervix.

5. The method of claim 1, further comprising:
adjusting a volume of inflation media in the expandable cuff to adjust a degree of traction applied to the cervix.

6. The method of claim 1, wherein the expansion of the expandable cuff compresses the cervix and slows or stops a flow of amniotic fluid from the cervix.

7. The method of claim 1, further comprising:
adjusting a volume of inflation media in the expandable cuff to treat premature rupture of membranes (PROM) or preterm premature rupture of membranes (PPROM).

8. The method of claim 1, further comprising:

adjusting a volume of inflation media in the expandable cuff to treat short cervix.

9. The method of claim 1, further comprising:

adjusting a volume of inflation media in the positioning balloon to adjust the angle of orientation of the cervix.

10. The method of claim 1, further comprising:

adjusting a volume of inflation media in the expandable cuff and/or the positioning balloon to prevent onset of labor and delivery of a fetus.

11. The method of claim 1, further comprising:

adjusting a volume of inflation media in the positioning balloon to anchor the cervical control system within the patient's vagina.

12. The method of claim 1, wherein the cervical control system is placed responsively to the patient being associated with a risk factor for pre-term labor.

13. The method of claim 1, wherein the cervical control system is placed responsively to the patient being diagnosed with a short cervix.

14. The method of claim 1, wherein the cervical control system is placed responsively to the patient being diagnosed with premature rupture of membranes (PROM) or preterm premature rupture of membranes (PPROM).

15. The method of claim 1, wherein a degree of expansion or contraction of the expandable cuff and/or the positioning balloon is responsive to at least one of a clinical need, an orientation of the cervix, an orientation of the patient's uterus, a degree of dilation of the cervix, a length of the cervix, a degree of softness of the cervix, a level of amniotic fluid present in the patient's uterus, or an indication of a status of the patient's amniotic sac membrane.

16. The method of claim 1, wherein the expansion of the positioning balloon adjusts an angle of orientation of the cervix.

17. A method to compress a cervix, comprising:

positioning a cervix of a patient within an internal passageway of a cervical control system, the cervical control system comprising:

a cuff comprising:

an exterior surface defining an internal passageway configured to accept insertion of the cervix of the patient therein;

an interior surface; and a first inner chamber disposed between the inner surface and the exterior surface;

an expandable positioning balloon disposed on an exterior surface of the cervical control system and including a second inner chamber;

a first inflation media conduit, the first inflation media conduit comprising:

a first end in fluid communication with the first inner chamber; and a second end configured to receive inflation media;

a second inflation media conduit, the second inflation media conduit comprising:

a first end in fluid communication with the second inner chamber; and a second end configured to receive inflation media; and a bi-lumen tube configured to extend through the patient's vaginal canal and exit the introitus when the cervical control system is in position within the patient, wherein a first end of a first lumen of the bi-lumen tube is in fluid communication with the second end of the first inflation media conduit and a second opposing end of the first lumen is configured to receive inflation media, and wherein a first end of a second lumen of the bi-lumen tube is in fluid communication with the second end of the second inflation media conduit and a second opposing end of the second lumen is configured to receive inflation media;

accessing the second end of each of the first and second lumens of the bi-lumen tube outside the patient's body;

adding inflation media to the second end of each of the first and second lumens of the bi-lumen tube for communication to the respective first and second inflation media conduits;

adding inflation media to the second end of the first inflation media conduit, thereby expanding the cuff; and adding inflation media to the second end of the second inflation media conduit, thereby expanding the expandable positioning balloon.

18. The method of claim 17, wherein the second end of the first inflation media conduit is in fluid communication with a first valve and the second end of the second inflation media conduit is in fluid communication with a second valve, the method further comprising:

opening the first valve to add inflation media to the first inflation media conduit;

closing the valve to hold inflation media within the first inflation media conduit;

opening the second valve to add inflation media to the second inflation media conduit;

closing the second valve to hold inflation media within the second inflation media conduit.

19. The method of claim 17, wherein the expansion of the cuff compresses the cervix.

20. The method of claim 17, further comprising:

adjusting a volume of inflation media in the cuff to adjust a degree of traction applied to the cervix.

21. The method of claim 17, further comprising:

adjusting a volume of inflation media in the cuff to slow or stop a flow of amniotic fluid from the cervix.

22. The method of claim 17, further comprising:

adjusting a volume of inflation media in the cuff to treat premature rupture of membranes (PROM) or preterm premature rupture of membranes (PPROM).

23. The method of claim 17, further comprising:

adjusting a volume of inflation media in the cuff to treat short cervix.

24. The method of claim 17, further comprising:

adjusting a volume of inflation media in the expandable positioning balloon to adjust the angle of orientation of the cervix.

25. The method of claim 17, further comprising:

adjusting a volume of inflation media in the cuff and/or the expandable positioning balloon to prevent onset of labor and delivery of a fetus.

26. The method of claim 17, further comprising:

adjusting a volume of inflation media in the expandable positioning balloon to anchor the cervical control system within the patient's vagina.

27. The method of claim 17, wherein the cervical control system is placed responsively to the patient being associated with a risk factor for pre-term labor.

28. The method of claim 17, wherein the cervical control system is placed responsively to the patient being diagnosed with a short cervix.

29. The method of claim 17, wherein the cervical control system is placed responsively to the patient being diagnosed with premature rupture of membranes (PROM) or preterm premature rupture of membranes (PPROM).

30. The method of claim 17, wherein a degree of expansion or contraction of the cuff and/or the expandable positioning balloon is responsive to at least one of a clinical need, an orientation of the cervix, an orientation of the patient's uterus, a degree of dilation of the cervix, a length of the cervix, a degree of softness of the cervix, a level of amniotic fluid present in the patient's uterus, and/or an indication of a status of the patient's amniotic sac membrane.

\* \* \* \* \*